United States Patent
Wang et al.

(10) Patent No.: US 7,968,734 B2
(45) Date of Patent: Jun. 28, 2011

(54) ORGANOCATALYSTS AND METHODS OF USE IN CHEMICAL SYNTHESIS

(75) Inventors: Wei Wang, Albuquerque, NM (US); Jian Wang, Albuquerque, NM (US); Hao Li, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 253 days.

(21) Appl. No.: 11/628,818

(22) PCT Filed: Jun. 30, 2005

(86) PCT No.: PCT/US2005/023691
§ 371 (c)(1),
(2), (4) Date: Dec. 7, 2006

(87) PCT Pub. No.: WO2006/007586
PCT Pub. Date: Jan. 19, 2006

(65) Prior Publication Data
US 2007/0244328 A1    Oct. 18, 2007

Related U.S. Application Data

(60) Provisional application No. 60/584,939, filed on Jul. 1, 2004, provisional application No. 60/584,940, filed on Jul. 1, 2004, provisional application No. 60/585,973, filed on Jul. 6, 2004, provisional application No. 60/585,974, filed on Jul. 6, 2004, provisional application No. 60/586,057, filed on Jul. 6, 2004, provisional application No. 60/608,321, filed on Sep. 9, 2004, provisional application No. 60/608,334, filed on Sep. 9, 2004, provisional application No. 60/634,169, filed on Dec. 8, 2004, provisional application No. 60/657,856, filed on Mar. 2, 2005, provisional application No. 60/669,561, filed on Apr. 8, 2005.

(51) Int. Cl.
*C07D 207/16* (2006.01)
*C07D 207/04* (2006.01)

(52) U.S. Cl. ...................................... 548/537; 548/566

(58) Field of Classification Search .................. 548/537, 548/558, 566, 568
See application file for complete search history.

(56) References Cited

U.S. PATENT DOCUMENTS

| 4,533,656 A * | 8/1985 | Walker ............................ 514/19 |
| 5,194,624 A | 3/1993 | Murata et al. |
| 6,552,226 B1 | 4/2003 | MacMillan |
| 6,784,323 B2 | 8/2004 | MacMillan |
| 6,861,535 B2 | 3/2005 | Bulliard et al. |
| 6,900,322 B1 | 5/2005 | Reggelin et al. |

FOREIGN PATENT DOCUMENTS

| FR | 2765220 A1 * | 12/1998 |
| WO | WO 01/44179 A1 * | 6/2001 |
| WO | WO 02/090355 A1 * | 11/2002 |
| WO | WO 03047740 | 6/2003 |

OTHER PUBLICATIONS

Wang et al., Selective benzoylation of primary amines in the presence of secondary amines, 1999, Tetrahedron Letters, 40, 6745-6747.*
Sunden et al., Novel organic catalysts for the direct enantioselective alpha-oxidation of carbonyl compounds, 2005, Tetrahedron Letters, 46, 3385-3389.*
Ryan et al., A radioassay for aminoacylproline hydrolase (aminopeptidase P) activity, 1992, Biochimica et Biophysica Acta, 1119, 133-139.*
Wang, GT, et al. "Design, Synthesis and Structural Analysis of Influenza Neuraminidase Inhibitors Containing Pyrrolidine Cores" *J.Med. Chem.* 2001, 44, 1192-1201.
Yi, X, et al. "Study on Molecular Mechanism and 3D-QSAR of Influenza Neuraminidase Inhibitors" *Bioorganic & Medicinal Chemistry* 2003, 11, 1465-1474.
Kettle, JG et al. "N-Benzylindole-2-carboxylic acids: potent functional antagonists of the CCR2b chemokine receptor" *Bioorganic & Medicinal Chemistry Letters* 2004, 14, 405-408.
Jansen, M et al. "Variations of acidic functions at position 2 and substituents at positions 4, 5 and 6 of the indole moiety and their effect on NMDA-glycine site affinity" *European Journal of Medicinal Chemistry* 2003, 38, 855-865.

* cited by examiner

*Primary Examiner* — Kamal A Saeed
*Assistant Examiner* — Kristin Bianchi
(74) *Attorney, Agent, or Firm* — Henry D. Coleman; R. Neil Sudol; William J. Sapone

(57) ABSTRACT

The present invention pertains generally to compositions comprising organocatalysts that facilitate stereo-selective reactions and the method of their synthesis and use. Particularly, the invention relates to metal-free organocatalysts for facilitation of stereo-selective reactions, and the method of their synthesis and use.

25 Claims, 16 Drawing Sheets

Pyrrolidine amide/sulfonamide/imide-based organocatalyst.

Figure 3. Pyrrolidine amides/sulfonamides-catalyzed organic reactions through an enamine intermediate.

Proposed transition-state model for α-aminoxylation reactions.

Pyrrolidine sulfonamide V-catalyzed highly enantio- and diastereoselective Michael addition reaction.

FIGURE 7A
Intermolecular Michael addition reaction:
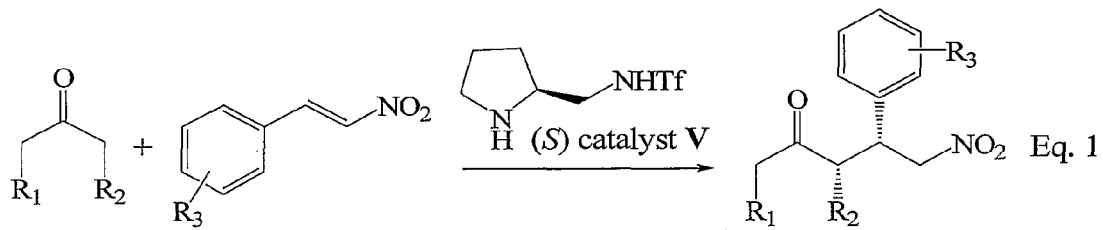
Intramolecular Michael addition reaction:
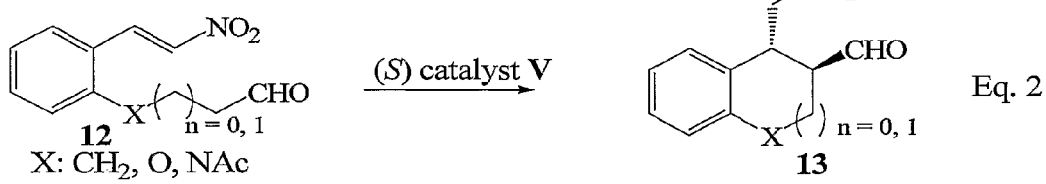
Organocatalyst V catalyzed asymmetirc Michael addition reactions

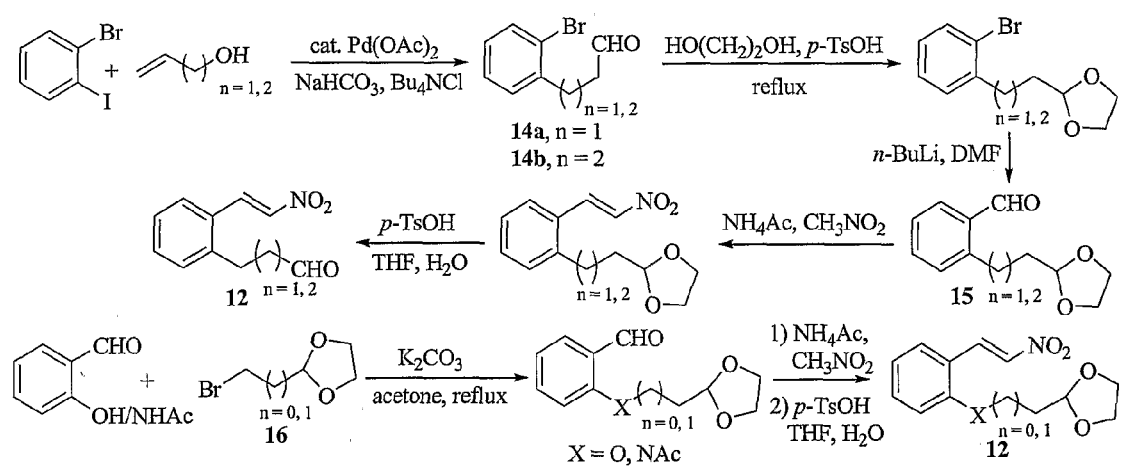
Figure 7B. Synthesis of *trans*-β-nitrostyrene aldehyde substrates.

Organocatalyst catalyzed asymmetric aldol reactions.

Pyrrolidine sulfonamide V catalyzed enolization of α, α–dialkyl aldehydes.

A novel pyrrolidine imide IV-catalyzed tandem Mannich-elimination reaction.

Three-component Mannich reactions

Catalyst V catalyzed direct three-component Mannich reactions

Three Component Mannich reaction

Sequential Mannich-type, tandem Mukaiyama Aldol-cyclization reaction

Chiral Amine Organocatalysts

Two-step synthesis of Sch 50971

Three-step synthesis of rigid GABA analogues.

Three-step synthesis of pyrrolidine core 29 of CCR5 antagonists.

Four-step synthesis of Ro 15-8081

Three-step synthesis of benzopyrano[3,4-c]pyrrole derivatives.

Two-step synthesis of key intermediate 37.

Synthesis of (+)-polyoxamic acid (42), the key component of polyoxins

Synthesis of key component amino lactone 46 in (-)-funebrine and (-)-funebral

Efficient synthesis of azasugars *via* Mannich-type, tandem Mukaiyama aldol-cyclization reactions

ORGANOCATALYSTS AND METHODS OF USE IN CHEMICAL SYNTHESIS

RELATED APPLICATIONS

This application claims the benefit of priority of U.S. application No. 60/584,939, filed Jul. 1, 2004; 60/584,940, filed Jul. 1, 2004; 60/585,973, filed Jul. 6, 2004; 60/585,974, filed Jul. 6, 2004; 60/586,057, filed Jul. 6, 2004; 60/608,321, filed Sep. 9, 2004; 60/608,334, filed Sep. 9, 2004; 60/634,169, filed Dec. 8, 2004; 60/657,856, filed Mar. 2, 2005; 60/669,561, filed Apr. 8, 2005; all of which disclosures are incorporated by reference in their entirety herein.

FIELD OF THE INVENTION

The present invention pertains generally to compositions comprising organocatalysts that facilitate stereo-selective reactions and the method of their synthesis and use. Particularly, the invention relates to metal-free organocatalysts for facilitation of stereo-selective reactions, and the method of their synthesis and use.

BACKGROUND OF THE INVENTION

The growing demand for chiral non-racemic compounds and drugs in the pharmaceutical industry has created a formidable synthetic challenge for chemists to find cost-effective and highly stereoselective means to assemble these molecules. Of the various methods available for the preparation of enantiomerically pure compounds, asymmetric catalytic processes are the most attractive. Over the past several decades, the main body of research in catalysis has been focused on transition metal-based organometallic catalysts and significant progress has been made. Surprisingly, however, relatively few asymmetric transformations have been reported which employ organic molecules as reaction catalysts (organocatalysts) despite their enormous potential in asymmetric transformations and widespread availability in optically pure forms.

A chiral molecule is one that is not superimposable on its mirror image. Often referred to as "handedness," (in fact the term "chirality" derives from the Greek word for "hand") since the property can be demonstrated by examining one's hands, which are mirror images of each other, but which are not superimposable one on the other. A chiral molecule is also observable for having the property of rotating the plane of polarization of plane-polarized monochromatic light passed through it—a phenomenon called "optical activity." Pure solutions of a single stereoisomer (the chiral molecule and its mirror image are called "stereoisomers" or "enantiomers") will rotate the plane of plane polarized light in one direction, and the other enantiomer will rotate polarized light the same number of degrees, but in the opposite direction. For this reason, stereoisomers are often called "optical isomers." A solution that contains an equal mixture of the two optical isomers (a "racemic" mixture) will not change the plane of plane polarized light, because the effects of the two isomers cancel each other out. Pairs of stereoisomers are sometimes indistinguishable one from another in chemical reactions, but can be distinguished by examining a physical property (usually optical) of the molecule.

It has long been known, particularly in the pharmaceutical industry, that often one enantiomer is more effective in a reaction (or in a therapeutic treatment) than its mirror-image counterpart. In fact, in one well documented case of the importance of chirality, the use of a racemic mixture of thalidomide in pregnant women caused severe birth defects in their children. It was determined that one enantiomer was a powerful sedative while the other was toxic. As a result, obtaining a substantially pure form of a single enantiomer is often very desirable.

Given the Laws of Thermodynamics, this proves initially difficult. The left- and right-handed forms have identical free energy (G), so the free energy difference ($\Delta G$) is zero. The equilibrium constant for any reaction (K) is the equilibrium ratio of the concentration of products to reactants. The relationship between these quantities at any Kelvin temperature (T) is given by the standard equation:

$$K = \exp(-\Delta G/RT)$$

wherein R is the universal gas constant (Avogadro's number×Boltzmann's constant k)=8.314 J/K·mol.

For the reaction of changing left-handed to right-handed amino acids (L→R), or the reverse (R→L), $\Delta G=0$, so K=1. That is, the reaction reaches equilibrium when the concentrations of R and L are equal; that is, a racemate is produced.

For separation of or "resolving" a racemate (i.e., separate the two enantiomers), another homochiral substance is usually introduced. The idea is that right-handed and left-handed substances have identical properties, except when interacting with other chiral phenomena. The analogy is that our left and right hands grip an achiral (non-chiral) object like a stick equally, but they fit differently into a chiral object like a left-handed glove. Thus to resolve a racemate, an organic chemist will usually use a ready-made homochiral substance from a living organism. The reaction products of the R and L enantiomers with an exclusively right-handed substance R', that is R-R' and L-R' (called diastereomers), are not mirror images. So they have different physical properties, e.g. solubility in water, and thus they can be separated.

The trick here is that you have to have the homo-chiral substance to separate the enantiomers and be able to separate the substance from the desired enantiomer. While available for separation of some chiral substances, such substances are certainly not readily available for all. Chemists have tried other ways to reach their goal of substantially pure enantiomers, including asymmetric synthesis, wherein only one enantiomer is produced in synthesis of the compound, thereby eliminating the need to resolve a racemate.

In particular, asymmetric synthesis of optically active natural and unnatural α-amino acids has been of long-standing interest to organic chemists since these substances are versatile synthetic building blocks for the preparation of an assortment of biologically important molecules. In this regard, the enantioselective Mannich-type reaction of an enolate or enolate equivalent with α-imino ester constitutes a powerful approach to the synthesis of novel functionalized γ-keto-α-amino acid derivatives. S. E. Denmark, O. J.-C. Nicaise In *Comprehensive Asymmetric Catalysis*, (Eds.; E. N. Jacobsen, A. Pfaltz, H. Yamamoto), Springer, Heidelberg, 1999, pp 926; b) D. Arend, B. Westermann, N. Risch, *Angew. Chem.* 1998, 110, 1096-1122; D. Arend, B. Westermann, N. Risch, *Angew. Chem. Int. Ed.* 1998, 37, 1044-1070.

Over the past few years, catalytic, enantioselective versions of this process have received great attention with emphasis being given to the development of organometallic catalysis. S. E. Denmark, O. J.-C. Nicaise In *Comprehensive Asymmetric Catalysis*, (Eds.; E. N. Jacobsen, A. Pfaltz, H. Yamamoto), Springer, Heidelberg, 1999, pp 926; b) D. Arend, B. Westermann, N. Risch, *Angew. Chem.* 1998, 110, 1096-1122; D. Arend, B. Westermann, N. Risch, *Angew. Chem. Int. Ed.* 1998, 37, 1044-1070; H. Ishitani, M. Ueno, S. Kobayashi, *J. Am. Chem. Soc.* 1997, 119, 7153-7154; b) S. Kobayashi, T.

Hamada, K. Manabe, *J. Am. Chem. Soc.* 2002, 124, 5640-5641; c) H. Ishitani, S. Ueno, S. Kobayashi, *J. Am. Chem. Soc.* 2000, 122, 8180-8186; E. Hagiwara, A. Fujii, M. Sodeoka, *J. Am. Chem. Soc.* 1998, 120, 2474-2475; b) A. Fujii, E. Hagiwara, M. Sodeoka, *J. Am. Chem. Soc.* 1999, 121, 545-556; D. Ferraris, B. Young, T. Dudding, T. Lectka, *J. Am. Chem. Soc.* 1998, 120, 2474-2475; b) D. Ferraris, B. Young, C. Cox, T. Dudding, W. J. Drury, III, L. Ryzhkov, T. Taggi, T. Lectka, *J. Am. Chem. Soc.* 2002, 124, 67-77.

However, these metal-based catalysis methods rely on the use of pre-formed enolates or enolate equivalents. An effective, atom-economic asymmetric version of this reaction, employing unmodified carbonyl compounds would be more attractive from a synthesis standpoint. The examples of such reactions catalyzed by organometallic-based chiral catalysts have been described by Shibasaki, Trost and Jørgensen. S. Yamasaki, T. Iida, M. Shibasaki, *Tetrahedron Lett.* 1999, 40, 307-310; B. M. Trost, L. M. Terrell, *J. Am. Chem. Soc.* 2003, 125, 338-339; K. Juhl, N. Gathergood, K. A. Jørgensen, *Angew. Chem.* 2001, 113, 3083-3085; K. Juhl, N. Gathergood, K. A. Jørgensen, *Angew. Chem. Int. Ed.* 2001, 40, 2995-2997.

The development of metal-free organo-catalysts has emerged as a new frontier in asymmetric catalysis, pioneered by List, Barbas III, and MacMillan. P. I. Dalko, L. Moisan, *Angew. Chem.* 2001, 113, 3840-3864; P. I. Dalko, L. Moisan, *Angew. Chem. Int. Ed.* 2001, 40, 3726-3748; b) a review of proline catalyzed reactions: B. List, *Tetrahedron* 2002, 58, 5573-5590; B. List, R. A. Lerner, C. F. Barbas III, *J. Am. Chem. Soc.* 2000, 122, 2395-2396; K. A. Ahrendt, C. J. Borths, D. W. C. MacMillan, *J. Am. Chem. Soc.* 2000, 122, 4243-4244.

Several catalytic systems including L-proline, peptides and small organic molecules have been reported for the Mannich reactions. B. List *J. Am. Chem. Soc.* 2000, 122, 9336-9337; B. List, P. Pojarliev, W. T. Biller, H. J. Martin, *J. Am. Chem. Soc.* 2002, 124, 827-833; Y. Hayashi, W. Tsuboi, M. Shoji, N. Suzuki, *J. Am. Chem. Soc.* 2003, 125, 11208-11209; Y. Hayashi, W. Tsuboi, I. Ashimine, T. Urushima, M. Shoji, K. Sakai, *Angew. Chem.* 2003, 115, 3805-3808; Y. Hayashi, W. Tsuboi, I. Ashimine, T. Urushima, M. Shoji, K. Sakai, *Angew. Chem. Ed. Engl.* 2003, 42, 3677-3680; A. Córdova, W. Notz, G. Zhong, J. M. Betancort, C. F. Barbas III, *J. Am. Chem. Soc.* 2002, 124, 1842-1843; b) A. Córdova, S. Watanabe, F. Tanaka, W. Notz, C. F., Barbas III, *J. Am. Chem. Soc.* 2002, 124, 1866-1867; c) A. Córdova, C. F. Barbas III, *Tetrahedron Lett.* 2003, 44, 1923-1926; P. Vachal, E. N. Jacobsen, *J. Am. Chem. Soc.* 2002, 124, 10012-10013; b) A. G. Wenzel, E. N. Jacobsen, *J. Am. Chem. Soc.* 2002, 124, 12964-12965. Only the L-proline catalyzed process described by Barbas III (referenced above) and his co-workers promotes direct Mannich-type reactions of ketones and aldehydes with α-imino esters.

Compared with traditional metal-ligand complex catalysts, it is surprisingly found that metal-free organo-catalysts are less expensive, benign to the environment, easy to prepare and handle, and are air-stable, and non-sensitive to moisture. Therefore, the field would be greatly enhanced with the development of novel metal-free organo-catalysts which reduce time, effort, and amount of reactant necessary to arrive at a single enantiomer product. In turn, industries such as the pharmaceutical industry which require such purified forms can reduce the cost of and improve the quality of their ultimate product.

Over 50 percent of all drugs on the world market are based on chiral molecules and their sales exceeded $159 billion in 2002.[1-3] The Food and Drug Administration requires that both enantiomers of new chiral drugs are fully characterized separately with respect to pharmacological activity, iii vitro and in vivo pharmacokinetic profile, and toxicology. Consequently, most chiral pharmaceuticals will be sold as enantiomerically pure forms. This has created a great demand for chemists to develop new methodologies and strategies for efficient and enantioselective synthesis of chiral non-racemic compounds and drugs. Of the various methods available for the preparation of enantiomerically pure compounds, asymmetric catalytic processes are the most attractive.[4, 5] New and effective catalytic reactions have been discovered at an explosive rate. While the field is progressing rapidly, many challenges remain in asymmetric catalysis. Developing highly active catalysts that feature broad substrate scope and that can function under mild and simple reaction conditions remains a critical issue. Moreover, with the increasing environmental concerns associated with massive production of chemical wastes and hazards, the synthesis of chemicals, therapeutic agents and materials in an efficient, practical, economical, and environmentally benign fashion poses a paramount challenge to organic chemists.[6] It is especially important to identify reactions that are based on readily available starting materials and reagents utilizing environmentally benign chemical processes. [7-9]

Over the past 30 years, the major focus in catalysis has been directed towards the development of organometallics, which consist of metal complexes with chiral ligands and tremendous progress has been made.[4, 5] However, surprisingly, purely organic compounds, despite their enormous potential and broad availability in optically pure forms, are rarely used in asymmetric catalysis. In recent years, with the realization of this deficiency and inspired by enzyme-catalyzed reactions in biological systems, small organic molecule-based organo-catalysts have gradually been recognized and emerged as a new frontier in asymmetric catalysis. [10-16] It has been demonstrated that, in many cases, these small molecule catalysts display high catalytic activities for organic reactions that proceed with excellent enantio- and/or diastereoselectivities. Compared with their counterpart organometallic catalysts, these substances afford distinguishable benefits. First, they are easily prepared, more environmentally benign and cheaper since they do not rely on expensive and toxic metals. Second, generally organocatalysts catalyzed reactions can be performed under an aerobic condition in common, even water-containing organic solvents. Third, they are more robust and can be stored and handled in an air atmosphere, thus providing operational simplicity. Fourth, these small organic molecules can be immobilized on a solid support and reused more conveniently than are organometallic/bioorganic analogues. Consequently, they show promising adaptability to high-throughput screening and process chemistry. Other advantages associated with the use of organocatalysts, especially compared with enzymes and other bioorganic catalysts, are that they are more stable and less expensive and that they are capable of catalyzing a variety of organic reactions with a diverse range of different substrates.

Despite early successes in study of asymmetric organic transformations catalyzed by amino acid proline as a representative organocatalyst, relatively few efficient organocatalysts other than amino acid have been developed.[10, 12, 13, 17-19] Therefore, in the new emerging field, there are many opportunities for innovation and considerable challenges exist for the development of novel organocatalysts. In this proposal, we describe a novel "privileged" structure-based approach for catalyst design that should lead to a new class of organocatalysts. Such catalysts can provide high levels of asymmetric induction across a broad spectrum of chemical processes. This strategy has been very successfully employed in drug design and development by utilization of a "privileged" structure as a platform to which different functionality is added to produce a number of potent and specific drugs or drug candidates towards different therapeutic targets.[20-22] Such an approach can be employed in both the conceptual and practical development of new organocatalysts. The benefits of this strategy are not only found in a new paradigm for catalyst development, but also in the realization of high catalytic efficiencies that afford broad substrate scopes for a variety of organic transformations.

In the design of novel organocatalysts by using a "privileged" structure-based approach, the selection of the "privileged" core scaffolds is critical to the success of catalyst development. A careful survey of successful organocatalysts, including the amino acid proline,[12-14] MacMillan[23-29] and Jorgenson's catalysts[30-33] and others,[15, 34-41] reveal that a five-membered ring system containing a nitrogen atom is essential for catalytic activity.

The advantages, objects and features of such stereo-selective catalysts will become apparent to those skilled in the art when read in conjunction with the accompanying following description and drawing figures. As those skilled in the art will appreciate, the conception on which this disclosure is based readily may be used as a basis for designing other structures, methods, and systems for carrying out the purposes of the present invention. The abstract associated with this disclosure is neither intended to define the invention, nor intended to be limiting as to the scope of the invention in any way.

BRIEF DESCRIPTION OF THE FIGURES

FIG. 7A shows an intermolecular Michael addition reaction.

FIG. 7B shows the synthesis of nitrostyrene aldehyde compounds.

BRIEF DESCRIPTION OF THE INVENTION

Figure 1:
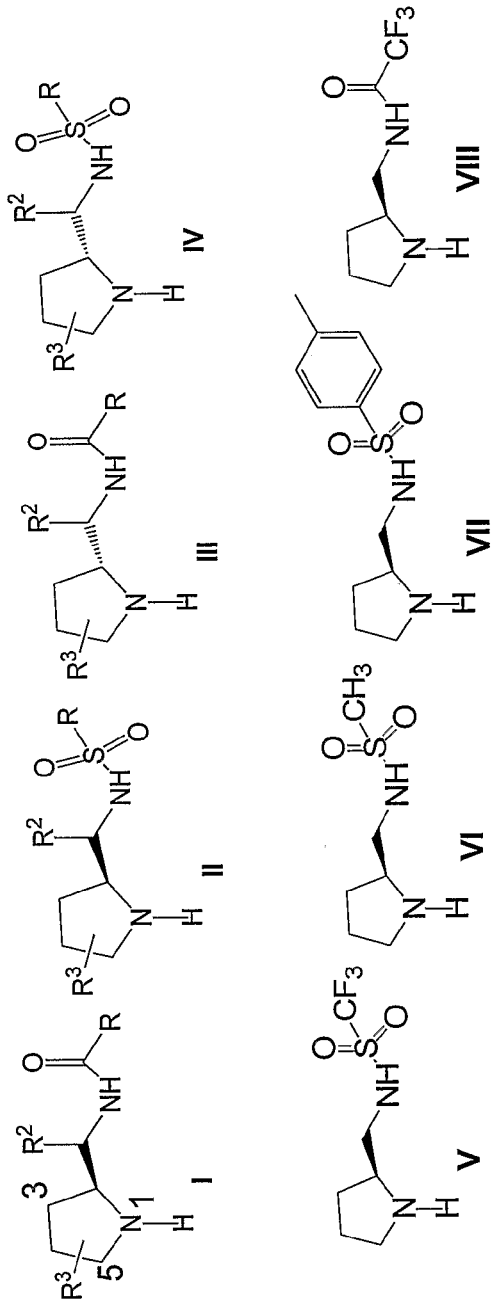
FIGS. 1 and 2 depict a number of organocatalysts according to the present invention.

The present invention relates to chiral catalytic compounds according to the general structure(s):

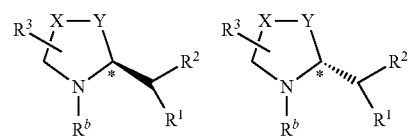

Where X is independently selected from $CH_2$, $N-R^a$, O, S or $C=O$;

Y is $CH_2$, $N-R^a$, O, S or $C=O$, with the proviso that at least one of X or Y is $CH_2$, and preferably both of X and Y are $CH_2$;

$R^a$ is H, an optionally substituted $C_1$-$C_{12}$ alkyl, preferably an optionally substituted $C_1$-$C_6$ alkyl including a $C_3$-$C_6$ cyclic alkyl, or an optionally substituted aryl group, preferably an optionally substituted phenyl group;

$R^b$ is H, an optionally substituted $C_1$-$C_{12}$ alkyl, preferably an optionally substituted $C_1$-$C_6$ acyclic or cyclic alkyl group, CHO, N(Me)O, $CO(S)R^a$ or the group:

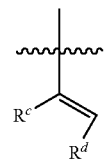

Where $R^c$ and $R^d$ are each independently H, F, Cl, an optionally substituted $C_1$-$C_{20}$ alkyl, preferably an optionally substituted $C_1$-$C_{12}$ alkyl, more preferably a $C_1$-$C_6$ alkyl, and an optionally substituted aryl group, or together $R^c$ and $R^d$ form an optionally substituted carbocyclic or optionally substituted heterocyclic ring, preferably an optionally substituted 5 to 7 membered cyclic ring;

$R^1$ is OH, OR, NR'R'', $NHC(=O)R$, $NHSO_2R$;

$R^2$ is H, F, Cl, an optionally substituted $C_1$-$C_{20}$ alkyl, preferably an optionally substituted $C_1$-$C_6$ alkyl, an optionally substituted aryl group or a =O group (which establishes a carbonyl group with the carbon to which =O is attached;

$R^3$ is H, OH, F, Cl, Br, I, Cl, an optionally substituted $C_1$-$C_{20}$ alkyl, alkenyl or alkynyl ("hydrocarbyl") group, preferably an optionally substituted $C_1$-$C_6$ alkyl, or an optionally substituted aryl, such that the carbon to which $R^3$ is attached has an R or S configuration;

R is H, an optionally substituted $C_1$-$C_{20}$ alkyl, preferably an optionally substituted $C_1$-$C_6$ alkyl, or an optionally substituted aryl group, R' and R'' are each independently H, an optionally substituted $C_1$-$C_{20}$ alkyl group, preferably an optionally substituted $C_1$-$C_6$ alkyl, or an optionally substituted aryl group; or together R' and R'' form an optionally substituted heterocyclic, preferably a 4 to 7 membered optionally substituted heterocyclic group or an optionally substituted heteroaryl ring with the nitrogen to which R' and R'' are attached; and wherein said organocatalyst is free from a metal catalyst.

Preferably, both X and Y are $CH_2$ groups.

Compounds according to the present invention are organocatalysts and exhibit catalytic activity in a number of synthetic methods free from an accompanying metal catalyst. This is an unexpected result and allows the present catalysts to be used in a more environmentally friendly manor, while exhibiting high synthetic efficiencies. In preferred aspects, the present invention relates to a single enantiomer, diastereomer or isomer. Note that carbon atoms designated * are chiral centers. Note that compounds which are simple derivatives of proline (proline with attachments on the amino group and in which the $CO_2H$ group on the carbon a to the amino group) are preferred in many aspects of the present invention.

In preferred aspects of the organocatalyst compounds X and Y are both $CH_2$, $R_b$ is H, $R^1$ is NHC(=O)R or $NHSO_2R$, wherein R is an optionally substituted $C_1$-$C_4$ alkyl group, preferably a $CF_3$ group, an alkyl group such as a t-butyl group containing fluoride or other electron withdrawing substituents, or an optionally substituted aryl group, preferably a p-methylphenyl group, a p-nitrophenyl group, a p-trifluoromethylphenylgroup, a 2,6-di($C_1$-$C_4$)alkylphenyl or a 2,4,6-tri ($C_1$-$C_4$)alkylphenyl group where the alkyl group, if substituted, is preferably a $CF_3$ group, $R^2$ is H or =O and $R^3$ is H. In certain compounds where $R^1$ is NR'R", preferably R' and R" form an optionally substituted pyrrolidine or piperidine ring, or other saturated heterocyclic ring.

Preferred compounds according to the present invention also include compounds according to the chemical formula:

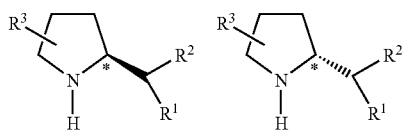

Where $R^1$, $R^2$ and $R^3$ are the same as those groups which are described above. Preferably, $R^1$ is NHC(=O)R or $NHSO_2R$, wherein R is an optionally substituted $C_1$-$C_4$ alkyl group, preferably a $CF_3$ group, an alkyl group such as a t-butyl group containing fluoride or other electron withdrawing substituents, or an optionally substituted aryl group, preferably a p-methylphenyl group, a p-nitrophenyl group, a p-trifluoromethylphenylgroup, a 2,6-di($C_1$-$C_4$)alkylphenyl or a 2,4,6-tri ($C_1$-$C_4$)alkylphenyl group where the alkyl group, if substituted, is preferably a $CF_3$ group. Preferably, $R^2$ is H or =O and $R^3$ is H. Preferably, when $R^1$ is NR'R", R' and R" form an optionally substituted pyrrolidine or piperidine ring, or other saturated heterocyclic ring.

Catalytic compounds according to the invention may be used to catalyze the following reactions, in many instances with high stereo- and/or enantiomeric selectivity in good to excellent yield:
   The direct α-aminoxylation reactions of ketones and aldehydes;
   Mannich-type reactions of ketones and aldehydes with α-imino esters—synthesis of unnatural α-amino acids;
   Michael addition reactions of aldehydes and ketones to nitrostyrenes;
   α-Selenylation reactions of aldehydes and ketones;
   α-Sulfenylation reactions of aldehydes and ketones;
   Aldol condensation reactions of ketones with aldehydes, aldehydes with aldehydes and ketones with ketones;
   Dehydration Reactions of ketones and aldehydes to produce alpha, beta unsaturated ketones;
   Mannich reactions of ketones, amines and aldehydes;
   Mukaiyama-Michael Addition of Silyl Enol Ethers to alpha,beta-unsaturated Aldehydes to produce 1,5-dicarbonyl compounds;

In general in the above methods, the organocatalyst is used in an amount ranging from about 0.01% to about 30 mol % (based upon the amount in moles of the reactant included in greatest amount), preferably about 0.5 mol % to about 25 mol %, preferably about 1% to about 20 mol %, also about 2 mol % to about 20 mol %. These methods are presented in greater detail in the sections which follow.

Particularly preferred organocatalysts according to the present include the following compounds:

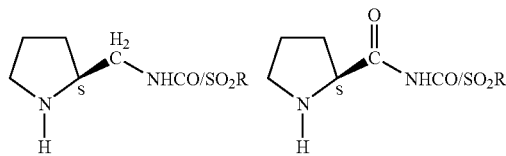

Where R is H, an optionally substituted $C_1$-$C_4$ alkyl group, preferably including a $CF_3$ group, an optionally substituted aryl group, preferably a phenyl group which is optionally substituted with from 1 to 3 substituents (preferably at the ortho and/or para positions of the phenyl group) which include $C_1$-$C_4$ alkyl groups which are optionally substituted with electron withdrawing substituents such as fluoro groups or nitro groups.

DETAILED DESCRIPTION OF THE INVENTION

As used herein, the following terms are used to describe the present invention. The definitions provided below, within context, may be used exclusively, or may be used to supplement definitions which are generally known to those of ordinary skill in the art.

Unless otherwise indicated, the present invention is not limited to particular molecular structures, substituents, synthetic methods, reaction conditions, or the like, and accordingly, these may vary. It is also to be understood that the terminology used herein is for the purpose of describing particular embodiments only and is not intended to be limiting.

As used in the specification and the attached claims, the use of "a," "an" and "the" include references to plural subject matter referred to unless the context clearly dictates otherwise. Thus, for example, reference to "a catalyst" includes a single catalyst as well as a combination or mixture of two or more catalysts, reference to "a reactant" encompasses a combination or mixture of different reactants as well as a single reactant, and the like.

A term which is subsumed under another term may be embraced by the broader term or by the more narrow specific term as appropriate within the context of the use of that term. All terms used to describe the present invention are used within context.

In this specification and in the claims that follow, reference will be made to a number of terms, which shall be defined to have the following meanings:

As used herein, the phrase "according to the formula", "having the formula" or "having the structure" is not intended to be limiting and is used in the same way that the term "comprising" is commonly used. The term "independently" is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the term "optionally substituted" means that a non-hydrogen substituent may or may not be present on a given atom, and, thus, the description includes structures where a non-hydrogen substituent is present and structures where a non-hydrogen substituent is not present.

The term "compound" is used herein to refer to any specific chemical compound disclosed herein. Within its use in context, the term generally refers to a single compound, such as a single enantiomer or diastereomer, but in certain instances may also refer to stereoisomers and/or optical isomers (including racemic mixtures) of disclosed compounds.

The term "effective" is used in context to describe an amount of a compound, component, condition or other aspect of the invention which occurs in an amount or at a level which is sufficient to effect an intended result, whether that compound, component or condition is an organocatalyst according to the present invention, a solvent, a reactant, an amount of heat or other aspect of the invention.

The term "alkyl" as used herein refers to a branched or unbranched saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl ("carbocyclic") groups such as cyclopentyl, cyclohexyl and the like. Generally, although again not necessarily, alkyl groups herein contain 1 to about 20 carbon atoms, preferably 1 to about 12 carbon atoms, more preferably about 1 to 6 carbon atoms ("lower alkyl"). "Substituted alkyl" refers to alkyl substituted with one or more substituent groups as otherwise described herein, and subsumes the terms "heteroatom-containing alkyl" or "heteroalkyl" which, in context, refer to an alkyl substituent in which at least one carbon atom is replaced with a heteroatom, such as an ether group, thioether group, a pyrrole or piperidine, as described in further detail infra. If not otherwise indicated, the terms "alkyl" and "lower alkyl" include linear, branched, cyclic, unsubstituted, substituted alkyl groups, respectively.

The term "alkenyl" as used herein refers to a linear, branched or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 20 carbon atoms, preferably 2 to 6 carbon atoms. The term "lower alkenyl" describes an alkenyl group of 2 to 6 carbon atoms. The term "substituted alkelnyl" refers to alkenyl substituted with one or more substituent groups, and subsumes the term "heteroatom-containing alkenyl" and "heteroalkenyl" which refer to alkenyl in which at least one carbon atom is replaced with a heteroatom. If not otherwise indicated, the terms "alkenyl" and "lower alkenyl" include linear, branched, cyclic and unsubstituted or substituted alkenyl and lower alkenyl, respectively. Note that alkenyl groups are used within context and not where a reaction scheme would dictate that its use is unfavorable.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively. Note that alkynyl groups are used within context and not where a reaction scheme would dictate that its use is unfavorable.

The term "alkoxy" as used herein intends an alkyl group bound through a single, terminal ether linkage; that is, an "alkoxy" group may be represented as —O-alkyl where alkyl is as defined above. A "lower alkoxy" group describes an alkoxy group containing 1 to 6 carbon atoms, and includes, for example, methoxy, ethoxy, n-propoxy, isopropoxy, t-butyloxy, etc. Preferred substituents falling within "$C_1$-$C_6$ alkoxy" or "lower alkoxy" herein contain 1 to 4 carbon atoms, and additionally preferred such substituents contain 1 or 2 carbon atoms (i.e., methoxy and ethoxy).

The term "aryl" as used herein, and unless otherwise specified, refers to an aromatic group generally containing 5 to 30 carbon atoms and containing a single aromatic ring (phenyl) or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" are subsumed under the term aryl, in which at least one carbon atom of a carbocyclic aryl group is replaced with a heteroatom, as will be described in further detail infra. If not otherwise indicated, the term "aryl" includes unsubstituted, substituted, and/or heteroatom-containing aromatic groups.

The term "carbocyclic" refers to a cyclic ring structure, which, in context, is saturated or unsaturated and contains exclusively carbon atoms within the ring structure. The term "heterocyclic" refers to a cyclic ring structure, which, in context, is either saturated or unsaturated and may contain one or more atoms other than carbon atoms (e.g., N, O, S, etc.) within the ring structure.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms, while preferred aralkyl and alkaryl groups contain 6 to 20 carbon atoms, and particularly preferred such groups contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof, as otherwise specifically described in the specification.

The terms "halogen" and related terms such as "halo" are used in the conventional sense to refer to a chloro, bromo, fluoro or iodo substituent.

The term "heteroatom-containing" as in a "heteroatom-containing alkyl group", (also termed a "heteroalkyl" group), "heterocyclic" group or a "heteroatom-containing aryl group" (also termed a "heteroaryl" group) refers to a molecule, group, linkage or substituent in which one or more carbon atoms are replaced with an atom other than carbon, e.g., nitrogen, oxygen, sulfur, phosphorus or silicon, preferably from 1 to 3 nitrogen, oxygen or sulfur atoms. Similarly, the term "heteroalkyl" refers to an alkyl group that is heteroatom-containing, the term "heterocyclic" more broadly refers to a cyclic group that is heteroatom-containing (thus, also potentially containing unsaturated groups), the terms "heteroaryl" and heteroaromatic" respectively refer to "aryl" and "aromatic" groups that are heteroatom-containing, and the like. Examples of heteroalkyl groups include alkoxyaryl, alkylsulfanyl-substituted alkyl, N-alkylated amino alkyl, and the like. Examples of heterocyclic groups, include heteroaryl groups such as pyrrolyl, pyrrolidinyl, pyridinyl, quinolinyl, indolyl, pyrimidinyl, imidazolyl, 1,2,4-triazolyl, tetrazolyl, thiazole, etc., and heteroatom-containing alicyclic groups such as pyrrolidino, morpholino, piperazino, piperidino, etc.

"Hydrocarbyl" refers to univalent hydrocarbyl radicals containing 1 to about 30 carbon atoms, preferably 1 to about 20 carbon atoms, preferably about 1 to 12 carbon atoms, preferably about 1 to 6 carbon atoms, including linear, branched, cyclic, saturated and unsaturated species, such as alkyl groups, alkenyl groups, aryl groups, and the like. "Substituted hydrocarbyl" or "optionally substituted hydrocarbyl" refers to hydrocarbyl substituted with one or more substituent groups, and the term "heteroatom-containing hydrocarbyl" is subsumed under the term hydrocarbyl in which at least one carbon atom is replaced with a heteroatom. Unless otherwise indicated in context, the term "substituted hydrocarbyl" is to be interpreted as including substituted and/or heteroatom-containing hydrocarbyl moieties, including heterocyclic moieties.

The term "substituted" as in "substituted alkyl," "substituted aryl," "substituted hydrocarbyl", etc. and the like, as described hereinabove, refers to a carbon-containing or other moiety used in context, such as hydrocarbyl, alkyl, aryl, including cyclic versions of same, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl(—CO-alkyl) and $C_6$-$C_{20}$ arylcarbonyl(—CO-aryl)), acyloxy(—O-acyl), $C_2$-$C_{24}$ alkoxycarbonyl(—(CO)—O-alkyl), $C_6$-$C_{20}$ aryloxycarbonyl(—(CO)—O-aryl), halocarbonyl(—CO)—X where X is halo), $C_2$-$C_{24}$ alkylcarbonato(—O—(CO)—O-alkyl), $C_6$-$C_{20}$ arylcarbonato(—O—(CO)—O-aryl), carboxy(—COOH), carboxylato(—COO$^-$), carbamoyl(—(CO)—NH$_2$), mono-substituted $C_1$-$C_{24}$ alkylcarbamoyl(—(CO)—NH($C_1$-$C_{24}$ alkyl)), di-substituted alkylcarbamoyl(—(CO)—N($C_1$-$C_{24}$ alkyl)$_2$), mono-substituted arylcarbamoyl(—(CO)—NH-aryl), thiocarbamoyl(—(CS)—NH$_2$), carbamido(—NH—(CO)—NH$_2$), cyano(—C≡N), isocyano(—N$^+$≡C—), cyanato(—O—C≡N), isocyanato(—O—N$^{+}$≡C$^-$), isothiocyanato(—S—C≡N), azido(—N=N$^+$=N$^-$), formyl(—(CO)—H), thioformyl(—(CS)—H), amino(—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido(—NH—(CO)-alkyl), $C_5$-$C_{20}$ arylamido(—NH—(CO)-aryl), imino(—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino(—CR=N(alkyl), where R=hydrogen, alkyl, aryl, alkaryl, etc.), arylimino(—CR=N(aryl), where R=hydrogen, alkyl, aryl, alkaryl, etc.), nitro(—NO$_2$), nitroso(—NO), sulfo(—SO$_2$—OH), sulfonato(—SO$_2$O—), $C_1$-$C_{24}$ alkylsulfanyl (—S-alkyl; also termed "alkylthio"), arylsulfanyl(—S-aryl; also termed "arylthio"), $C_1$-$C_{24}$ alkylsulfinyl —(SO)-alkyl), $C_5$-$C_{20}$ arylsulfinyl (—(SO)-aryl), $C_1$-$C_{24}$ alkylsulfonyl(—SO$_2$-alkyl), $C_5$-$C_{20}$ arylsulfonyl(—SO$_2$-aryl), phosphono(—P(O)(OH)$_2$), phosphonato(—P(O)(O$^-$)$_2$), phosphinato(—P(O)(O$^-$)), phospho(—PO$_2$), and phosphino(—PH$_2$); and the hydrocarbyl moieties $C_1$-$C_{24}$ alkyl (preferably, $C_1$-$C_{20}$ alkyl, more preferably $C_1$-$C_{12}$ alkyl, most preferably $C_1$-$C_6$ alkyl), $C_2$-$C_{24}$ alkenyl (preferably $C_2$-$C_{20}$ alkenyl, more preferably $C_2$-$C_{12}$ alkenyl, most preferably $C_2$-$C_6$ alkenyl), $C_2$-$C_{24}$ alkynyl (preferably $C_2$-$C_{20}$ alkynyl, more preferably $C_2$-$C_{12}$ alkynyl, most preferably $C_2$-$C_6$ alkynyl), $C_5$-$C_{30}$ aryl (preferably $C_5$-$C_{20}$ aryl, more preferably $C_5$-$C_{12}$ aryl), and $C_6$-$C_{30}$ aralkyl (preferably $C_6$-$C_{20}$ aralkyl, more preferably $C_6$-$C_{12}$ aralkyl). In addition, the aforementioned functional groups may, if a particular group permits within the context of a reaction pathway or synthesis, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated. Substitutions which are cyclic groups may be bonded to a single atom within a moiety or more than one substituent may be joined to form a cyclic ring, thus forming for example, bi- or tricyclic groups.

When the term "substituted" appears prior to a list of possible substituted groups, it is intended that the term apply to every member of that group. For example, the phrase "substituted alkyl and aryl" or "substituted alkyl or aryl" is to be interpreted as "substituted alkyl and substituted aryl" or "substituted alkyl or substituted aryl."

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % (95% ee) of the composition in which it is contained, more preferably at least about 99 wt. % (99% ee) of that composition, more preferably about 99+ wt. % (99+% ee) of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 65 wt. % (65% enantiomeric enrichment or "ee") of the product, preferably at least about 75 wt. % (75% ee), at least about 85 wt. % (85% ee), at least about 95 wt. % (95% ee), at least 99 wt. % (99% ee) and at least 99+ st. % (99+% ee) of the product.

The term "temperature" is generally used to describe the temperature at which a reaction takes place. In general, reactions according to the present invention may take place at a temperature ranging from significantly below room temperature (e.g., −78° C.) or above temperature (for example, at reflux temperatures which, depending on the boiling point of the solvent used, can be several hundred degrees celcius), but preferably reactions proceed at or about ambient or room temperature (i.e., the temperature of the surrounding laboratory or manufacturing facility).

The term "solvent" is used to describe a medium (typically, but not necessarily inert) in which a reaction takes place using the organocatalysts according to the present invention. Solvents may include polar and non-polar solvents, including, for example, $H_2O$, pyridine, triethanolamine, tetrahydrofuran, 1,4-dioxane, acetonitrile, dimethylacetamide (DMA), dimethylformamide (DMF), dimethylsulfoxide (DMSO), acetonitrile, methylene chloride, nitromethane, chloroform, methanol, ethanol, isopropanol, etc., aqueous alcohol (methanol, ethanol, isopropanol, N-methylpyrrolidone (NMP), ethylacetate, benzene, toluene, etc. and mixtures, thereof.

The term "acid" is used (within the context of its use) as it is typically understood by those of ordinary skill in the art to describe a protic acid (proton donor) or Lewis acid for use in the present invention and may include strong acids, such as hydrochloric acid, sulfuric acid, phosphoric acid, sulfamic acid, etc., organic acids, such as acetic acid, benzoic acid, mandelic acid, propionic acid and butyric acid, etc. and a number of Lewis acids well-known in the art, such as $AlX_3$, $BX_3$, $FeX_3$, $GaX_3$, $SbX_3$, $SnX4$, $ZnX_3$, where X is a halogen atom or an inorganic radical, among numerous others.

The term "base" is used (within the context of its use) as it is typically understood by those of ordinary skill in the art to describe a proton acceptor or Lewis base. Typical bases include sodium or potassium hydroxide, various carbonates, various amines and related typical bases such as pyridine, triethylamine, etc. Lewis bases are electron acceptors which are well-known in the art and include such bases as $NH_3$, $PF_3$, $PCl_3$, $H_2S$, $H_2O$, $HOCH_2CH_2CH_2OH$, $Cl^-$, $OH^-$, $O_2CCO_2^{2-}$; and any negatively charged ion.

The term "protecting group" refers to a chemical moiety or group which protects or prevents an active moiety or group from participating with or interfering with one or more chemical synthetic steps and its removal restores the moiety to its original active state. The term protecting group as used herein refers to those groups intended to protect against undesirable reactions during synthetic procedures. Such protecting groups are well known to those skilled in the art and are exemplified in U.S. Pat. No. 5,288,709, as well a large number of other references. Protecting groups can be removed with inter alia acid, base, fluoride ions, hydrogenation, metals such as zinc as well as by numerous other methods which are well known in the art. One of ordinary skill in the art can readily choose an appropriate protecting group to facilitate synthetic reactions according to method aspects of the present invention without engaging in undue experimentation. t-butyl carbamate (BOC), 9-fuorenylmethyl carbamate (FMOC), benzyl carbamate (CBz) and ortho-nitrobenzyl carbamate groups may be used in the present invention. P-methoxyanisidine group (PMP) group is a preferred group for the protection of a nitrogen. The benzyl carbamate (CBz)group is preferred for the protection of hydroxyl groups. Numerous addition groups including acyl groups, benzyl groups, silyl groups, etc. may be used as acceptable protecting groups for synthetic purposes according to the present invention.

The term "isolation" or "isolating" refers to the process or method by which a product compound or composition is isolated from a reaction mixture. These methods may include various forms of chromatography, including those which employ chiral packing or support in columns, including standard column chromatography, medium and high pressure liquid chromatography, crystallization, precipitation, etc., countercurrent distribution, etc. All methods for isolating compounds according to the present invention are well know in the art.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

The present invention preferably relates to chiral catalytic compounds according to the general structure(s):

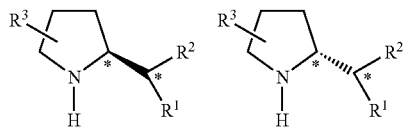

Where $R^1$ is OH, OR, NR'R", NHC(=O)R, $NHSO_2R$;
$R^2$ is H, F, Cl, an optionally substituted $C_1$-$C_{20}$ alkyl, preferably an optionally substituted $C_1$-$C_6$ alkyl, an optionally substituted aryl group or a =O group (which establishes a carbonyl group with the carbon to which =O is attached;
$R^3$ is H, OH, F, Cl, Br, I, Cl, an optionally substituted $C_1$-$C_{20}$ alkyl, alkenyl or alkynyl ("hydrocarbyl") group, preferably an optionally substituted $C_1$-$C_6$ alkyl, or an optionally substituted aryl, such that the carbon to which $R^3$ is attached has an R or S configuration;
R is H, an optionally substituted $C_1$-$C_{20}$ alkyl, preferably an optionally substituted $C_1$-$C_6$ alkyl, or an optionally substituted aryl group,
R' and R" are independently H, an optionally substituted $C_1$-$C_{20}$ alkyl group, preferably an optionally substituted $C_1$-$C_6$ alkyl, or an optionally substituted aryl group; or together R' and R" form an optionally substituted heterocyclic, preferably a 4 to 7 membered optionally substituted heterocyclic group or an optionally substituted heteroaryl ring with the nitrogen to which R' and R" are attached; and wherein said organocatalyst is free from a metal catalyst.

In preferred aspects of the organocatalyst compounds, R' is NHC(=O)R or $NHSO_2R$, wherein R is an optionally substituted $C_1$-$C_4$ alkyl group, preferably a $CF_3$ group, an alkyl group such as a t-butyl group containing fluoride or other electron withdrawing substituents, or an optionally substituted aryl group, preferably a p-nitrophenyl group, a p-trifluoromethylphenylgroup, a 2,6-di($C_1$-$C_4$) alkylphenyl or a 2,4,6-tri($C_1$-$C_4$)alkylphenyl group where the alkyl group, where substituted, is a $CF_3$ group, $R^2$ is H or =O and $R^3$ is H. Preferably, R' and R" form an optionally substituted pyrrolidine or piperidine ring, or other saturated heterocyclic ring.

In the present invention, in an aminoxylation method, a compound of the formula:

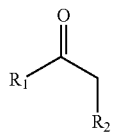

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group, is reacted with a compound according to the structure:

Where Ar is an optionally substituted aryl group, in the presence of an effective amount of an organocatalyst according to the present invention in a solvent at a temperature which is optionally above or below ambient temperature to produce a compound according to the structure:

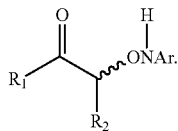

In preferred aspects, the compound produced is:

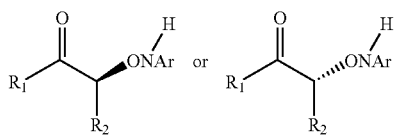

Having an enantiomeric enrichment of at least about 65%.

In a method for effecting Mannich-type reaction to form an amino acid, an aldehyde or a ketone according to the structure:

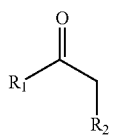

is reacted in a solvent at ambient temperature or optionally at a temperature above or below ambient temperature in the presence of an effective amount of an organocatalyst according to the present invention with a compound according to the structure:

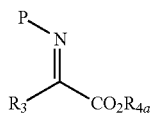

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group, where P is a blocking or protecting group (preferably, a PMP group), $R_3$ is H or an optionally substituted alkyl or aryl group and $R_{4a}$ is an alkyl or aryl group, preferably a $C_1$-$C_6$ alkyl group (more preferably, a $C_1$-$C_3$ alkyl group) with an effective amount of a catalyst according to the present invention to produce an amino acid compound of the structure:

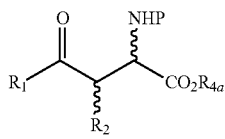

In a subsequent step, the protecting group is removed to produce a compound according to the structure:

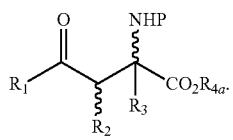

In preferred aspects, the amino acid which is produced is an enatiomerically enriched compound according to the structure:

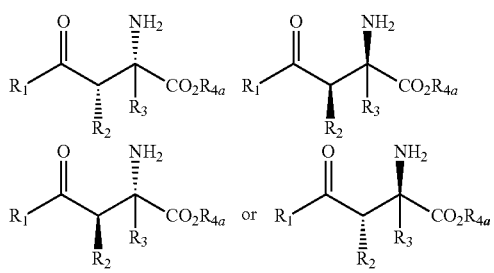

having an enantiomeric enrichment of at least about 65%.

In a Michael addition reaction, a compound of the formula:

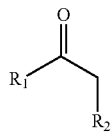

in a solvent at ambient temperature or optionally at a temperature above or below ambient temperature in the presence of an effective amount of an organocatalyst according to the present invention with a compound according to the structure:

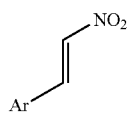

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group and Ar is an optionally substituted aryl group with an effective amount of a catalyst according to the present invention to produce a compound according to the structure:

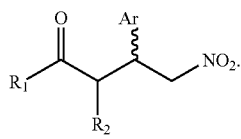

In preferred aspects the amino acid is an enantiomerically enriched product having the structure:

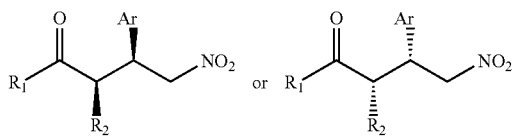

having an enantiomeric enrichment of at least about 65%.

In a method aspect of the present invention for introducing a selenyl group into an aldehyde or ketone, an aldehyde or a ketone according to the structure:

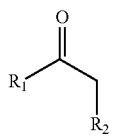

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group, is reacted in a solvent at ambient temperature or optionally at a temperature above or below ambient temperature in the presence of an effective amount of an organocatalyst according to the present invention with a selenylation reagent to produce a compound according to the structure:

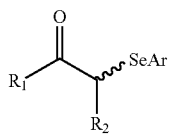

Where $R_1$ and $R_2$ are the same as above and Ar is an optionally substituted aryl group, preferably a phenyl group.

In preferred aspects, the selenylated compound is

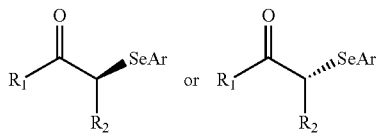

having an enantiomeric enrichment of at least about 65%.

In a method aspect of the present invention for introducing a sulfenyl group into an aldehyde or ketone, an aldehyde or a ketone according to the structure:

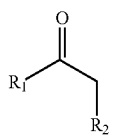

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group, is reacted in a solvent at ambient temperature or optionally at a temperature above or below ambient temperature in the presence of an effective amount of an organocatalyst according to the present invention with a sulfenylation reagent to produce a compound according to the structure:

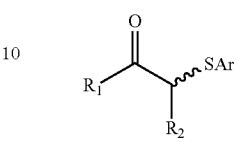

Where $R_1$ and $R_2$ are the same as above and Ar is an optionally substituted aryl group, preferably a phenyl group.

In preferred aspects, the selenylated compound is

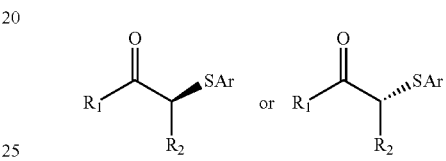

having an enantiomeric enrichment of at least about 65%.

In an aldol reaction according to the present invention, an aldehyde or a ketone according to the structure:

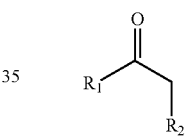

is reacted in a solvent at ambient temperature or optionally at a temperature above or below ambient temperature in the presence of an effective amount of an organocatalyst according to the present invention with a compound according to the structure:

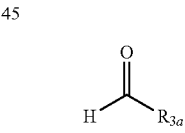

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group and $R_{3a}$ is an optionally substituted hydrocarbyl group including an optionally substituted aryl group to produce a condensation product according to the structure:

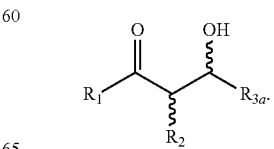

In preferred aspects, the aldol condensation compound is

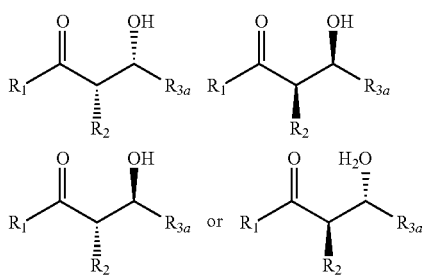

having an enantiomeric enrichment of at least about 65%.

In a dehydration reaction according to the present invention, an aldehyde or a ketone according to the structure:

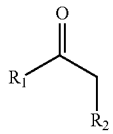

is reacted in a solvent at ambient temperature or optionally at a temperature above or below ambient temperature in the presence of an effective amount of an organocatalyst according to the present invention with a compound according to the structure:

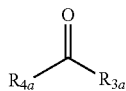

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group;

$R_{3a}$ is an optionally substituted hydrocarbyl group including an optionally substituted aryl group and $R_{4a}$ is H, an optionally substituted hydrocarbyl group including an optionally substituted aryl group and dehydrated (in a subsequent dehydration step) to produce a condensation product according to the structure:

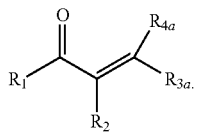

The dehydration step may be effected using any standard dehydration conditions, including in the presence of base.

In a modified Mannich reaction according to the present invention, an aldehyde or a ketone according to the structure:

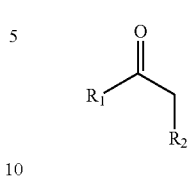

is reacted in a solvent at ambient temperature or optionally at a temperature above or below ambient temperature in the presence of an effective amount of an organocatalyst according to the present invention with a compound according to the structure:

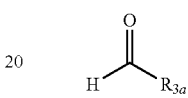

and a compound according to the structure:

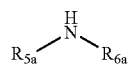

Where $R_1$ and $R_2$ are independently H, an optionally substituted $C_1$-$C_{20}$ hydrocarbyl group, including an optionally substituted aryl group or together $R_1$ and $R_2$ can form an optionally substituted carbocyclic or heterocyclic group;

$R_{3a}$ is an optionally substituted hydrocarbyl group including an optionally substituted aryl group;

$R_{5a}$ and $R_{6a}$ are independently H or an optionally substituted hydrocarbyl group including an optionally substituted aryl group to produce a product according to the structure:

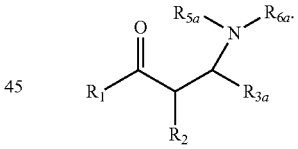

In preferred aspects, the modified Mannich reaction product is

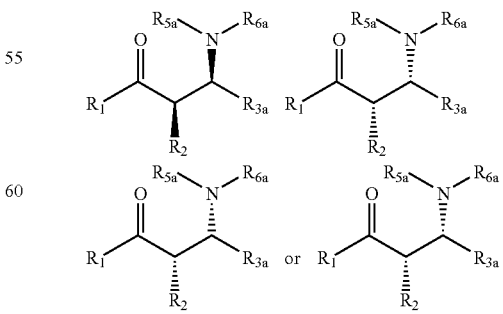

having an enantiomeric enrichment of at least about 65%.

In an asymmetric Mukaiyama-Michael addition reaction, a compound according to the structure:

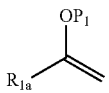

is reacted with a compound according to the structure:

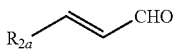

where $R_{1a}$ and $R_{2a}$ are independently an optionally substituted hydrocarbyl group, including an optionally substituted aryl group;

$P_1$ is a protecting group, preferably a silyl protecting group, more preferably a tert-butyldimethyl silyl group or a trimethylsilyl group, more preferably a trimethylsilyl group, in the presence of an effective amount of organocatalyst according to the present invention and an acid additive, preferably a Lewis acid, in a solvent at room temperature or optionally at a temperature above or below room temperature to produce a compound according to the structure:

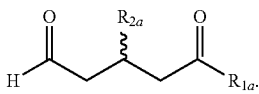

In preferred aspects, the product compound is

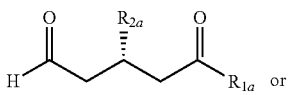

or

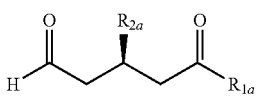

having an enantiomeric enrichment of at least about 65%.

Synthesis of Organocatalytic Compounds

A number of organocatalysts according to the present invention may be synthesized pursuant to the following synthetic description. The first general group to be presented are those set forth in FIG. 1.

The first generation of catalysts as shown above, were designed and prepared according to scheme 1 set forth below. They were efficiently synthesized from N-Cbz-proline 1 in six steps. It is noted that the key intermediate 5 is commercially available. The catalysts I-VIII can alternately be prepared in three steps as shown below with minor variation. Alternative steps may be used to synthesize the other catalysts set forth above.

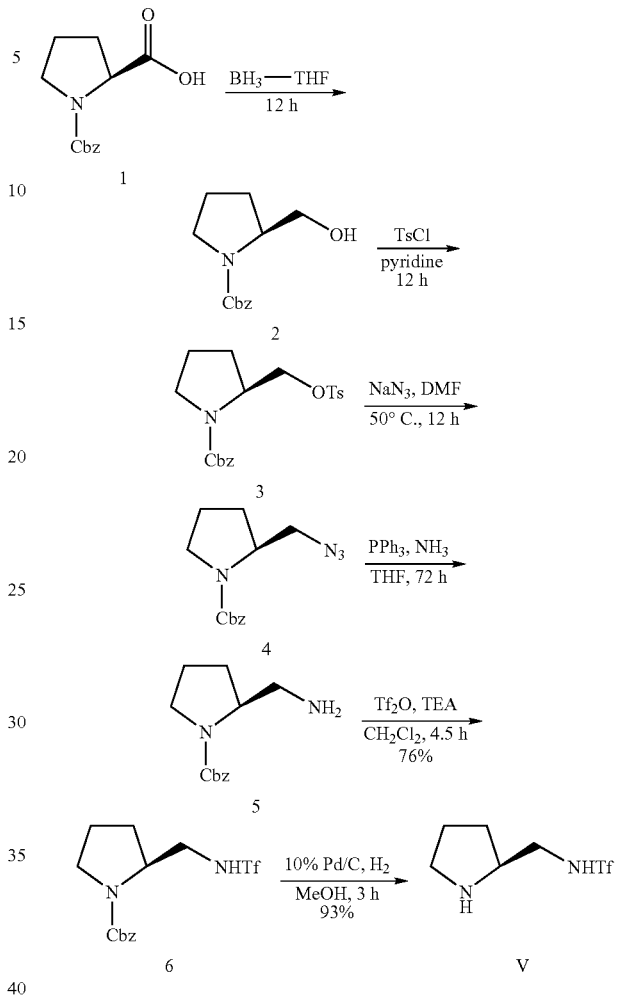

Scheme 1. Synthesis of organocatalyst pyrrolidine sulfonamide V.

However, it was found that a one-step synthesis of the amine (labeled "5" in the above and below reaction schemes) in a much improved yield of about 74% was possible by utilizing commercially available (and much less expensive) (S)-2-carbamoyl-1-N-CBz-pyrrolidine to arrive at the desire N-Cbz amine (labeled "6" in the above and below reaction schemes). It had been reported in prior art literature that there was a method for the reduction of an amide to an amine by use of borane ($BH_3$). Surprisingly, the amide in (S)-2-carbamoyl-1-N-CBz-pyrrolidine (labeled "6" in the reaction scheme below) was selectively reduced to amine by $BH_3$ without affecting the Cbz protecting group. Optimization of reaction conditions and work-up procedures gave a yield of 74%, without racemization.

A typical procedure for the reduction is as follows: starting with a solution of (S)-2-carbamoyl-1-N-CBz-pyrrolidine (0.5 g, 2 mmol) in THF (10 ml), borane $BH_3$ (12 ml, 12 mmol, 1.0M THF solution) was added slowly at 0° C. under $N_2$. The resulting solution was heated to reflux for 7 hours, then cooled to 0° C., followed by slow addition of 4.5 mL of 12N HCl to destroy the B—N complex. The mixture was heated to reflux for 6 hours, cooled to roomed temperature (RT), then was neutralized to ph8 by a 1N NaOH aqueous solution. After THF and water were removed under reduced pressure, the crude product was purified by use of flash silica gel column chromatography (1/10=MeOH/CH$_2$Cl$_2$) to afford a clear, slightly yellow oil in 74% yield (348 mg).

The inventive reaction scheme follows:

Scheme 2. One step synthesis of N-Cbz-pyrrolidine amine 5.

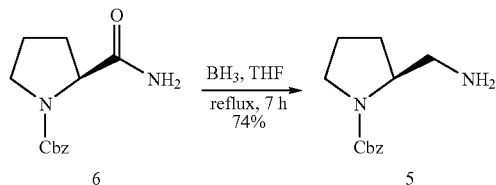

With the N-Cbz amine (labeled "5" in the above reaction schemes) derived, the synthesis of the pyrrolidine sulfonamide Catalyst V was carried out in the remaining two steps (as in the earlier prior art process), as shown below:

Scheme 3. Synthesis of organo-catalyst pyrrolidine sulfonamide V.

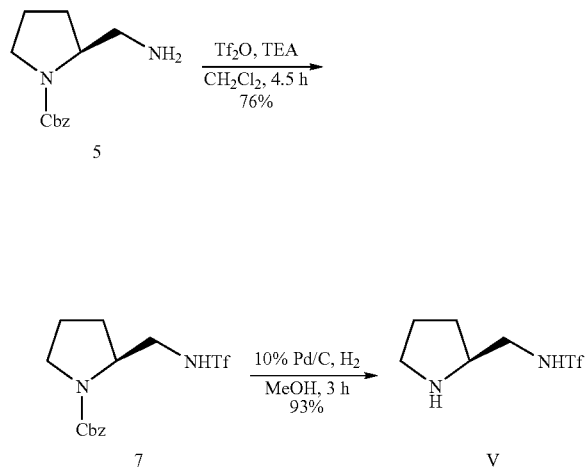

An acylation of the amine group in the compound 5 was done with triflic acid anhydride (Tf$_2$O) in the presence of TEA to give a sulfonamide (labeled "7" above) and achieved a 76% yield. Slow addition of the Tf$_2$O (over 1 hour) was necessary at 0° C. to reduce a bis-acylation of the product. Finally, the Cbz protecting group was removed by Pd catalyzed hydrogenation. The crude product was recrystallized in MeOH to give a crystal used for catalysis.

Other catalysts according to the present invention may be readily synthesized in a straightforward manner in two steps. This synthesis is presented in scheme 4, below. Acylation of the amine group 1 with acid activating conditions such as DCC/HOBt as an activating agent or with activating acid derivatives such as an acid anhydride, or an acid or sulfonyl chloride in the presence of a base such as triethylamine (TEA) will provide an amide or sulfonamide 3. As a final step, the carbobenzyloxy (Cbz) protecting group is removed by Pd catalyzed hydrogenation. Using this method, the corresponding (R) enantiomers can be prepared as well from (R)-2-carbamoyl-1-N-Cbz-pyrrolidone. These synthetic steps may be generalized over a broad range of organocatalysts according to the present invention. R can be any number of groups, including those which are presented in FIG. 1, V-VIII.

Scheme 4. Synthesis of organocatalyst pyrrolidine sulfonamides I-II of FIG 2.

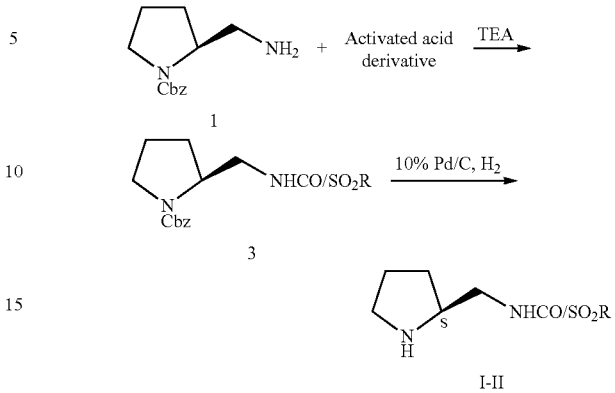

The carboxylic acid proton in proline plays a critical role in enhancing the reactivity and the stereoselectivity of proline-based catalysts. In contrast, L-prolinamide is known to be much less effective in catalyzing reactions. The acidity of NH protons in L-prolinamide is much less than that of a carboxyl group in proline and, as a result, the significant difference in catalytic activity between these two substances is likely due to their different acidity. Based upon this reactivity it was hypothesized that increasing the acidity of the NH amide protons would lead to a significant enhancement in the catalytic activity of L-prolinamides. It is known that the pKa of trifluorosulfonamide in water is 6.3, which is comparable to that of acetic acid (pKa of 4.76). However, in DMSO, trifluorosulfonamides have an even greater acidity (pKa of 9.7) which approaches that of acetic acid pKa of 12.3). With these observations in mind, we envisioned that incorporation of trifluorosulfonamide moiety into a pyrrolidine system would create a new class of amine-sulfonamide bifunctional organocatalysts that could function in the same way as proline in catalyzing organic reactions.

The catalysts of the present invention labeled "V-VIII", described above, contains a primary trifluoromethanesulfonamide group linked to a chiral pyrrolidine backbone. Catalyst V, as an example, is readily prepared from (S)-2-amino-1-N-Cbz-pyrrolidine by using a known reaction sequence. Burch, R. M. et al., WO Patent 9203415, 1992. As will be described in more detail hereinbelow, catalyst V effectively catalyzes nitrosobenzene induced α-aminoxylation reactions of aldehydes and ketones with comparable and, in some cases, even greater activity and efficiency than proline.

Other approaches for the synthesis of organocatalysts according to the present invention follow the general scheme above or by alternative schemes by analogy, with modifications to accommodate the varying substituents on the organocatalyst.

Figure 2:
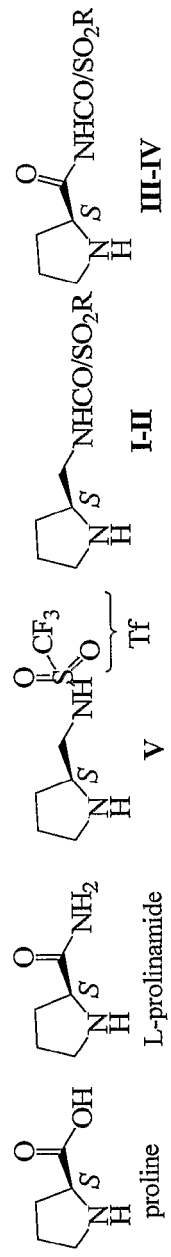

In the design of new organocatalysts according to the present invention, the catalytic activities and the reaction stereoselectivities of proline and its derivatives, which have demonstrated high catalytic activity and euntioselectivity for reactions is studied. The carboxylic acid proton in proline plays a critical role in enhancing the reactivity and stereoselectivity of proline based catalysts.[41-43] In contrast, L-prolinamide is known to be ineffective in catalyzing reactions such as the aldol reaction (FIG. 2). The acidity of NH protons in L-prolinamide is much less than that of a carboxyl group in proline. Thus, it appears that the significant difference in catalytic activity between these two substances is likely due to their different acidities. We hypothesize that increasing the acidity of the NH amide proton would lead to a significant enhancement in the catalytic activity of L-prolinamides. It is known that the pKa value of trifluoromethanesulfonamide in water is 6.3, which is comparable to that of acetic acid (pKa of 4.76).[44-46] However, in DMSO, trifluoromethanesulfonamide has an even greater acidity (pKa of 9.7) than that of acetic acid (pKa 12.3).[44, 45] With the above observations in mind, incorporation of trifluoromethanesulfonamide moiety into a pyrrolidine privileged system create a new class of amine-amide/sulfonamide bifunctional organocatalysts (V of FIG. 2) that function in the same way as proline does in catalyzing organic reactions (see FIG. 2).

Figure 3:
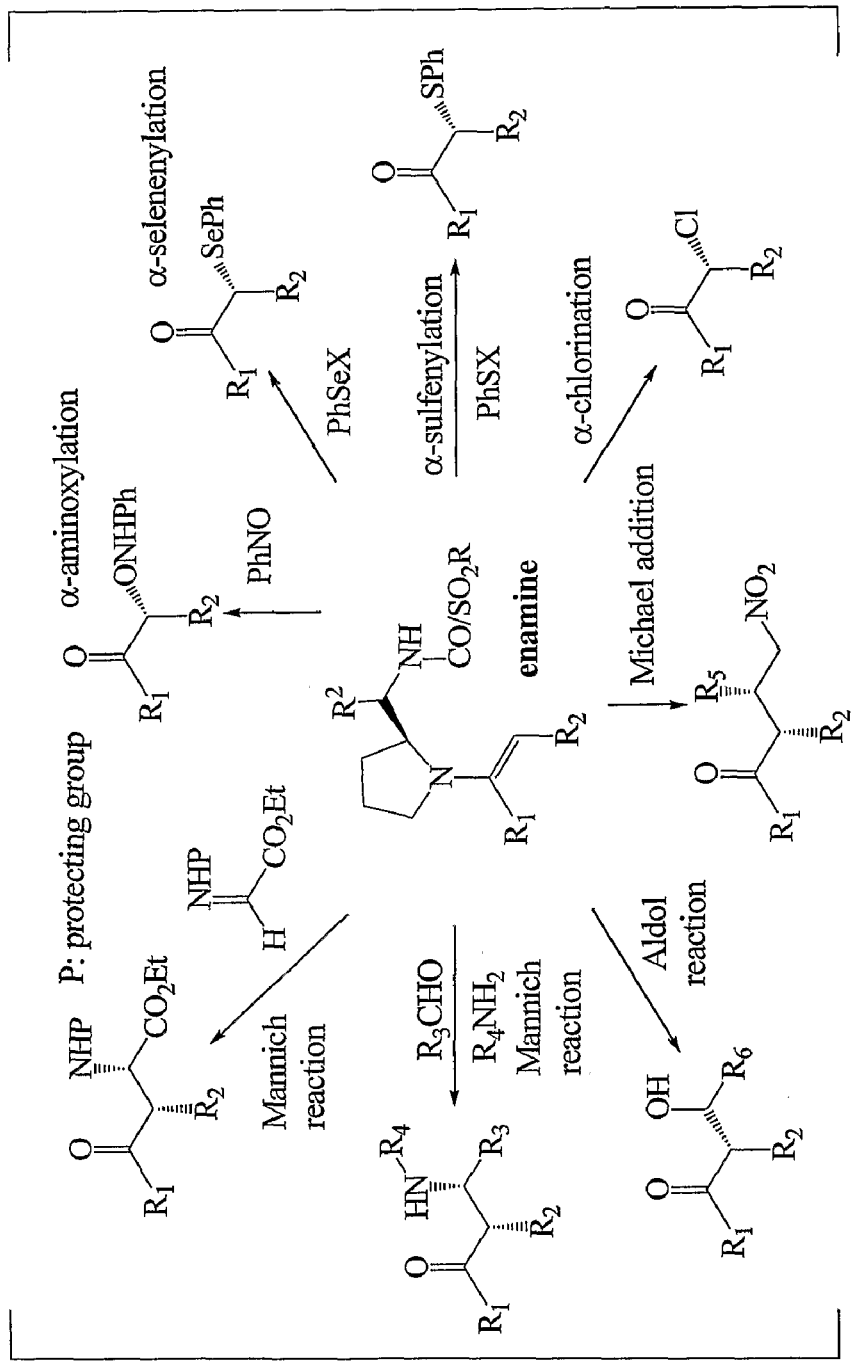
FIG. 3 depicts a general flow chart of a number of reactions which may be catalyzed by organocatalysts according to the present invention.
Figure 4:
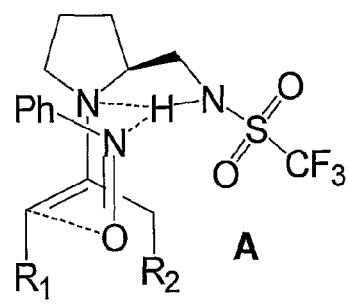
FIG. 4 shows a proposed transition state model for aminoxylation reactions according to the present invention.
Figure 5:
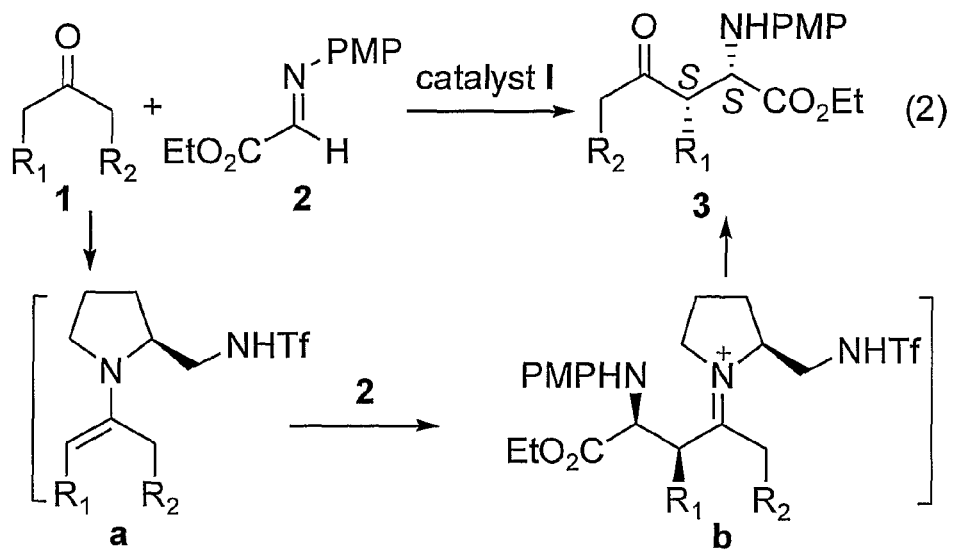
FIG. 5 depicts a Mannich reaction of ketones with alpha-imino esters.
Figure 6:
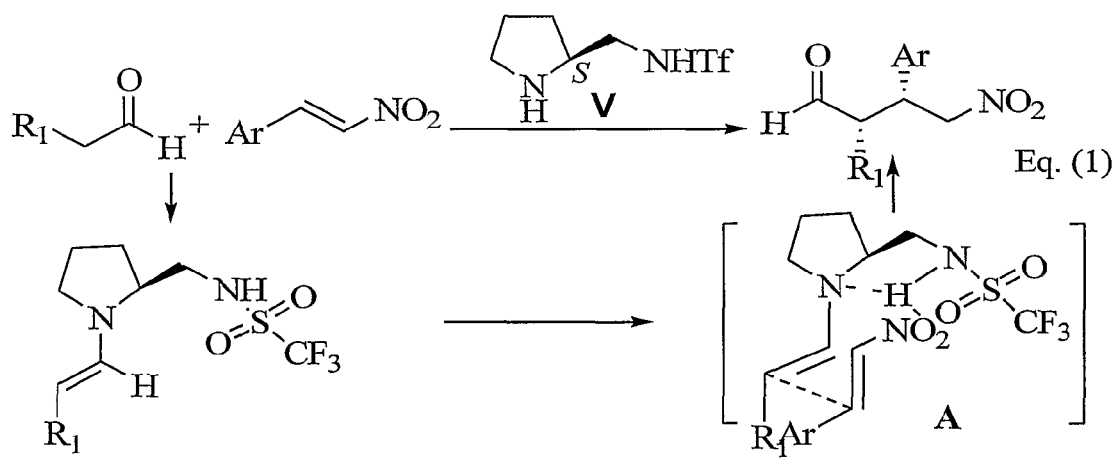
FIG. 6 depicts a catalyzed Michael addition reaction.

The other way to enhance the acidity of L-prolinamide is to convert the amide to an imide by introducing an electron-withdrawing $CO/SO_2R$ moiety as in III-IV (FIG. 2). The pKa value of $CF_3CONH_2$ in DMSO is about 17.2, while succinimide is about 14.7.[44] We believe the pKa of the imide in III-IV could be even smaller with a much stronger electron-withdrawing R group (such as $CF_3$). The new pyrrolidine amide/sulfonamide/imide organocatalysts I-IV of FIG. 2 not only provide highly catalytic activity for activating substrates, but also improve the enantio- and/or diastereoselectivity of the reaction.[47-49] The larger $CO/SO_2R$ effectively shields one side of an enamine double bond of a reaction intermediate, derived from an aldehyde or ketone (FIG. 3). Thus the attack of an electrophile proceeds from the non-shielded side to give a product in high enantio- and/or diastereoselectivity. The hypothesis has been proved by using (S) pyrrolidine trifluoromethanesulfonamide V as catalyst for the high stereoselective Michael addition reactions.[49]

The reactions promoted by the new organocatalysts can share a similar reaction mechanism through an enamine intermediate (FIG. 3). In the enamine process, the catalysts activate an enolizable aldehyde or ketone by generating an enamine, which then reacts with various electrophiles to afford different reaction products (FIG. 3). Following this pattern, the reactions of interest according to the present invention include the Mannich-type reactions of α-imino ester, the three-component Mannich reaction, aldol condensation reaction, sequential Mannich-type, tandem Mukaiyama Aldol-cyclization reaction, tandem Mannich-elimination reaction and Michael addition reaction. These reactions are useful for α-aminoxylation reactions, Mannich-type reactions of α-imino ester with aldehydes, α-selenenylation and α-sulfenylation reactions of aldehydes and ketones and the Michael addition reaction of aldehydes to nitroolefins.

Generally, high yields and excellent enantio- and/or diastereoselectivities have been achieved. In many cases, these organocatalysts display higher catalytic activity and better enantio- and/or diastereoselectivities than proline and other catalysts. It should be noted that this new class of bifunctional pyrrolidine amide/sulfonamide/imide catalysts can promote reactions without the need for an additive (e.g., acid) to activate the substrate. Furthermore, their catalytic activity can potentially be further manipulated by controlling their acidity and steric bulk through variations in the amide/sulfonamide/imide groups. In this way, it may be possible to tailor the catalytic activity to the optimum for a variety of organic reactions. All of these proposed processes represent powerful methods for constructing interesting, diversely functionalized organic molecules, which can be used as versatile building blocks for the synthesis of a variety of natural and non-natural biologically active substances.

In the above referenced FIG. 3, in general terms it is noted that $R_1$, $R_2$, $R_3$, $R_4$ and $R_5$ within context are independently selected from H, an optionally substituted $C_1-C_{20}$ hydrocarbyl group, preferably an alkyl group, more preferably a $C_1-C_6$ alkyl group, an optionally substituted aryl group, preferably an optionally substituted phenyl group, such as a benzyl group or together $R_1$ and $R_2$ form a cyclic (carbocyclic or heterocyclic) group, preferably a carbocyclic group, preferably a fully saturated carbocyclic group having from 5 to 7 members in the carbcyclic ring.

α-Aminoxylation Reactions of Aldehydes and Ketones

Optically active α-hydroxy carbonyl compounds are found in a large number of therapeutic agents, natural products, and other chemicals. Although a number of enantioselective methods for the synthesis of these substances have been reported, most employ indirect approaches, requiring preformation of enolates and enolate equivalents from the corresponding ketones and aldehydes. From the viewpoint of economy, direct α-aminoxylation reactions of aldehydes and ketones, which give α-hydroxy carbonyl molecules, are more attractive. Recently, organometallic and proline-catalyzed direct enantioselective α-aminoxylation reactions of unmodified aldehydes and ketones with nitrosobenzene have been achieved.[53-60] Small organic molecules other than proline for catalyzing this reaction have not yet been developed.[35] Therefore we tested the utility of pyrrolidine trifluoromethanesulfonamide (catalyst V) for the reaction. The studies showed that catalyst V effectively catalyzed nitrosobenzene induced α-aminoxylation reactions of ketones and aldehydes with comparable and, in some cases even greater activity and efficiency than does proline (Tables 1 and 2). Excellent levels of enantioselectivities ($\geq 97\%$ ee) were achieved in high yields (66-84%). Only O-addition products at the nitrobenzene were observed.[47]

The reaction of cyclohexanone with nitrosobenzene in the presence of a catalytic 20% mol of Catalyst V at room temperature was carried out in different solvents. The results revealed that Catalyst V exhibited a high catalytic efficiency in its promotion of high yielding (greater than about 60%) α-aminoxylation reactions. These also yielded excellent enantioselectivities (greater than about 90% enantiomeric excess (ee)) and high regioselectivities as shown below in Table 1.

TABLE 1

Effect of Solvents on the Asymmetric α-Aminoxylation Reactions[a]

| entry 1 | solvent | % yield[b] | % ee[c] |
|---|---|---|---|
| 1 | DMSO | 84 | >99 |
| 2 | $CHCl_3$ | 85 | >99 |
| 3 | DMF | 62 | >99 |
| 4 | THF | 77 | >99 |
| 5 | $CH_3CN$ | 66 | >99 |
| 6 | EtOAc | 76 | >99 |

[a]Reaction conditions: A solution of 2 (2 equiv.) in DMSO was added by a syringe pump over 10 min to a solution of 1a (1 equiv.) and I (0.2 equiv.) in DMSO and the reaction was continued for an additional 10 min (see Supporting Information).
[b]Isolated yields
[c]Enantiomeric excess determined by chiral HPLC analysis (Chiralpak AD).

Independant used, the reactions were completed in 20 minutes and afforded O-addition products (labeled above as "3a"). In contrast, solvents have a significant effect on proline-catalzyed α-aminoxylation reaction yields and enantioselectivities. Based on this exploratory study, DMSO was selected for further study.

To demonstrate the generality of direct α-aminoxylations catalyzed by Catalyst V, reactions of a varietey of ketone substrates with nitrosobenzene in DMSO (at room temperature were explored. The results of reactions of four cyclic and acyclic ketones promoted by 20 mol % of Catalyst V are given in Table 2 below.

TABLE 2

Catalyst I Catalyzed Direct α-Aminoxylation Reactions of Different Ketones

| entry | Ketone | % yield[a] | % ee[b] |
|---|---|---|---|
| 1 | 1a (cyclohexanone) | 84 | >99 |
| 2 | 1b (tetrahydropyranone) | 86 | >99 |
| 3 | 1c (1,4-cyclohexanedione monoethylene ketal) | 94 | 98 |
| 4 | 1d (3-pentanone) | 71 | 97 |

[a]Isolated yields.
[b]Enantiomeric excess determined by chiral HPLC analysis (Chiralpak AD or AS-H).

These processes take place smoothly to give O-addition products exclusively in good yields and with high enantioselectivities as described above. As with cyclohexanone, tetrahydro-4H-pyran-4-one and 1,4-cyclohexanedione monoethylene ketal gave adducts 3b,c in high yields (86% and 94%, respectively). with excellent enantioselectivities (greater than 99% and 98% respectively). A good yield and high level of enantioselectivity (97% ee) was also observed for the α-aminoxylation reaction of 3-pentanone (labeled as "1d"). The effect of catalyst loading on reaction efficiency was also examined and is shown in Table 3 below.

TABLE 3

Effect of Catalyst Loading on α-Aminoxylation Reactions

| entry | mol % I | time | % yield[a] | % ee[b] |
|---|---|---|---|---|
| 1 | 20 | 15 min | 84 | >99 |
| 2 | 10 | 30 min | 80 | >99 |
| 3 | 5 | 50 min | 72 | >99 |
| 4 | 2 | 2.5 h | 70 | >99 |
| 5 | 1 | 6.5 h | 64 | >99 |

[a]Isolated yields.
[b]Enantiomeric excess determined by chiral HPLC analysis (Chiralpak AD or AS-H).

Remarkably, a catalyst loading as low as 1.0 mol % still yields to significantly fast reaction without any loss of enantioselectivity (greater than 99% ee).

Alpha-aminoxylation reactions of nitrosobenzene with aldehydes, catalyzed by Catalyst V were probed next. Under the same reaction conditions described above (20 mol % of Catalyst V in DMSO at room temperature), efficient reaction occurs within 0.5 hours following slow addition of nitrosobenzene over a 30-60 minute period as shown in Table 4 below.

TABLE 4

Catalyst I Catalyzed Direct α-Aminoxylation of Different Aldehydes

| entry | $R_1$ | % yield[a] | % ee[b] |
|---|---|---|---|
| 1 | i-Pr, 1e | 81 | >99 |
| 2 | $CH_3$, 1f | 66 | >99 |
| 3 | n-Pr, 1g | 73 | >99 |
| 4 | n-Bu, 1h | 74 | >99 |
| 5 | $PhCH_2$, 1i | 79 | >99 |

[a]Isolated yields.
[b]Enantiomeric excess determined by chiral HPLC analysis (Chiralpak AD or AS-H).

Owing to their instability, the aldehyde O-addition products were reduced by $NaBH_4$ in situ to produce the more stable 2-aminoxy alcohols, labeled 3e-I, prior to purification and characterization. Again, the reactions result in efficient (66-81%), highly enantioselective (greater than 99% ee) and highly regioselective formation of O-additon products also as shown in Table 4.

A similar transition state model (labeled "A") to that used to rationalize the prior art proline-catalyzed α-aminoxylation reactions of ketones and aldehydes can be used to explain the regiochemical and steriochemical courses of the processes catalyzed by Catalyst V, as shown in the proposed transition state model for α-aminoxylation reaction states below.

In this model, the enamine formed by reaction of (S)-pyrrolidine sulfonamide Catalyst V with the enolizable ketone or aldehyde is attacked by nitrosobenzene from the less hindered Si face through a chair transition state to afford the O-addition product enantioselectively. The trifluoromethylsulfonamide group may also play a role in controlling the stereochemistry of the process by offering further interference for attack at the Re face.

It should be noted that the catalytic activity of the new organo-catalyst family can be manipulated by controlling acidity and steric bulk through variations in the sulfonamide group. In this way, it may be possible to tailor its catalytic activity to a variety of organic reactions.

Mannich-Type Reactions of Ketones and Aldehydes with α-Imino Esters-Synthesis of Unnatural α-Amino Acids Asymmetric synthesis of optically active natural and unnatural α-amino acids has been of long-standing interest to organic chemists since these substances are versatile synthetic building blocks for the preparation of an assortment of biologically important molecules.[61-66] In this regard, the enantioselective Mannich-type reactions of enolates or enolate equivalents with α-imino esters constitute a powerful approach to the synthesis of novel functionalized γ-keto-α-amino acid derivatives.[67, 68] Over the past few years, catalytic, enantioselective versions of this process have received great attention with a major emphasis being given to the development of organometallic catalysis.[69-77] These metal-based catalytic methods rely on the use of preformed enolates or enolate equivalents. An effective, atom-economic asymmetric version of this reaction, employing unmodified carbonyl compounds would be more attractive.[78-85] Along this line, we discovered that the catalyst V exhibited high catalytic activity for facilitating the reactions of unmodified ketones with α-imino ester with excellent regio-, diastereo-, and enantioselectivities. [48]

We envisioned that enamines formed from ketones and catalyst V would also add to electrophilic α-imino ester in Mannich-type reactions to provide novel functionalized α-keto-γ-amino acids as shown in the following equation:

We also explored the reaction of cyclohexanone 1f with α-imino ethyl glyoxylate 2 in the presence of 20 mol % of catalyst I in DMSO (Table 5, entry 1). The study revealed that the Mannich-type reaction done just use 2 h at room temperature and provide an excellent enantioselectivity (>99% ee). This new catalyst V displayed a higher level of catalytic activity and higher yield (90% vs 81%) than L-proline. According to $^1$H NMR analysis, Syn-diastereomer was formed predominantly (dr>95:5). The stereochemistry of compound 3f is (S, S) configuration, consistent with the result of L-proline-catalyzed Mannich-type reactions.

TABLE 5

Effect of solvent on Mannich-type reaction of cyclohexanone 1f with α-imino ethyl glyoxylate 2

| Entry | Reaction Time (h) | Solvent | % Yield$^a$ | % ee$^b$ | dr$^c$ |
|---|---|---|---|---|---|
| 1 | 2.0 | DMSO | 90 | >99 | >95:5 |
| 2 | 7.0 | CHCl$_3$ | 86 | 95 | >95:5 |
| 3 | 2.5 | DMF | 82 | 97 | >95:5 |

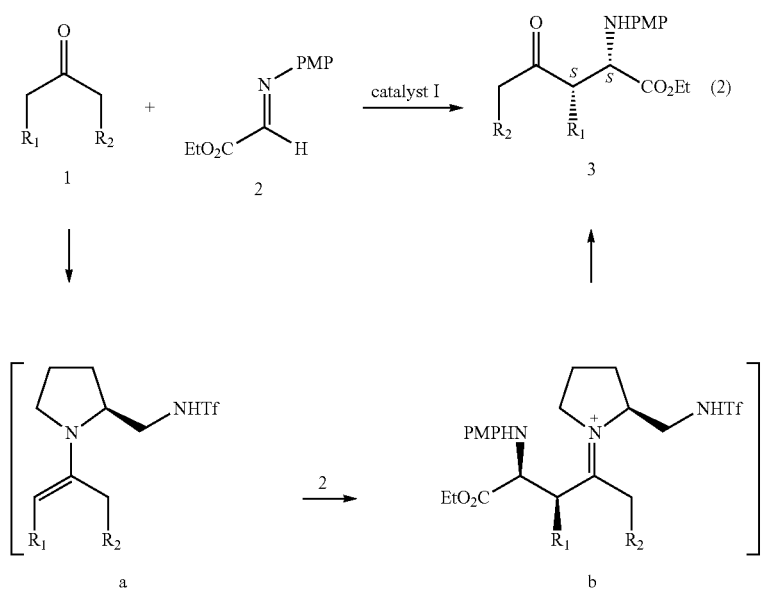

Figure 5

TABLE 5-continued

Effect of solvent on Mannich-type reaction of cyclohexanone 1f with α-imino ethyl glyoxylate 2

| Entry | Reaction Time (h) | Solvent | % Yield[a] | % ee[b] | dr[c] |
|---|---|---|---|---|---|
| 4 | 4.5 | THF | 89 | 97 | >95:5 |
| 5 | 3.5 | $CH_3CN$ | 88 | 98 | >95:5 |
| 6 | 5.5 | $CH_3NO_2$ | 76 | 98 | >95:5 |
| 7 | 5.5 | EtOAc | 84 | 98 | >95:5 |
| 8 | 2.0 | 1,4-Dioxane | 89 | 97 | >95:5 |

[a]Isolated yields.
[b]Enantiomeric excess (ee) determined by chiral HPLC analysis (Chiralpak S-H).
[c]dr = syn/anti As determined by $^1$H NMR after column chromatography.

above). Eight type of solvents already been used in this study. Catalyst V exhibited high activities in all of selected solvents; in every case, good to high yields (76-90%), high enantioselectivities (95% to >99% ee), and high diastereoselectivities (≧95:5 syn/anti) were observed. Finally, DMSO was selected as fantastic solvent to further examine the process. Then, a variety of catalyst loadings were probed for testing the reaction efficiency. Different catalyst loadings (2-20 mol %) were respectively employed to catalyze the reaction of cyclohexanone 1f with α-imino ethyl ester 2 in DMSO (Table 6a). As a decrease in catalyst loading happened, the reaction time was increased (2 h to 50 h). However, the results of the reaction yields (81-90%), enantio- and diastereoselectivities remained high or only slightly decrease (91% to >99% ee, and >95:5 dr) when the catalyst loading was lowered. Based on this study, 10 mol % of catalyst I was finally selected to ensure high levels of enantio-and stereoselectivities (96% ee, >95:5 dr) and efficiency (90% yield) while maintaining a reasonable reaction time (3.5 h, Table 6a, entry 2).

TABLE 6a

Effect of catalyst loadings on Mannich-type reaction of cyclohexanone 1f with α-imino ethyl glyoxylate 2

| Entry | Mol % V | Reaction Time (h) | % yield[a] | % ee[b] | dr[c] |
|---|---|---|---|---|---|
| 1 | 20 | 2.0 | 90 | >99 | >95:5 |
| 2 | 10 | 3.5 | 90 | 96 | >95:5 |
| 3 | 5 | 14 | 86 | 96 | >95:5 |
| 4 | 2 | 50 | 81 | 91 | >95:5 |

[a]Isolated yields.
[b]Enantiomeric excess (ee) determined by chiral HPLC analysis (Chiralpak AS-H).
[c]dr = syn/anti As determined by $^1$H NMR.

After establishment of reaction conditions was completed, we next explored the scope of the Mannich-type reactions between α-imino ester 2 and a variety of ketones (Table 6b). Significantly, we observed that catalyst V can catalyze α-imino ester 2 reacting with both acyclic (entries 1-5) and cyclic ketones (entries 6-8) to afford products (3a-3e) in good yields (74-91%) with high diastereo-and enantioselectivities (>95:5 dr and 96% to >99% ee). In the case of ketones 2-8 (Table 6b, entries 2-8), two adjacent stereochiral centers were generated simultaneously with complete (S,S)-stereocontrol. More importantly, reactions of unsymmetric ketones (entries 2, 4, and 5) resulted in the highly regioselective production of adducts 3b,d,e resulting from reaction at the more substituted a-sites with excellent stereoselectivities as well (≧96% ee and ≧95/5 dr syn/anti). Studies with differently α-substituted carbonyl substrates (entries 2, 4, and 5) reveal that methyl, allyl, and hydroxyl substituents provided the greatest degree of stereochemical control (96% to >99% ee and dr P95:5 (syn/anti)). Finally, changes in the electronic properties of ketones (Table 6b, entries 5, 7, and 8) had only a small effect on the process.

TABLE 6b

Pyrrolidine Sulfonamide I catalyzed Mannich-type reaction of various ketones with α-imino ethyl glyoxylate 2

| Entry | Product | % Yield[a] | % ee[b] | dr[c] |
|---|---|---|---|---|
| 1 | 3a | 91 | >99 | — |
| 2 | 3b | 84 | 97 | >95:5 |
| 3 | 3c | 83 | 97 | >95:5 |

TABLE 6b-continued

Pyrrolidine Sulfonamide I catalyzed Mannich-type reaction of various ketones with α-imino ethyl glyoxylate 2

[Scheme: ketone 1 (R$_1$, R$_2$ substituted) + PMP-N=CH-CO$_2$Et (2) → with catalyst V (pyrrolidine-CH$_2$-NHTf, 10 mol %), RT, DMSO, 2-20 h → product 3 (ketone with NHPMP and CO$_2$Et substituted stereocenter)]

| Entry | Product | % Yield[a] | % ee[b] | dr[c] |
|---|---|---|---|---|
| 4 | 3d (allyl, CO$_2$Et, NHPMP) | 88 | 96 | >95:5 |
| 5 | 3e (OH, CO$_2$Et, NHPMP) | 74 | >99 | >95:5 |
| 6 | 3f (cyclohexanone derivative) | 90 | 96 | >95:5 |
| 7 | 3g (tetrahydropyranone derivative) | 83 | >99 | >95:5 |
| 8 | 3h (dioxolane-spiro cyclohexanone derivative) | 78 | 96 | >95:5 |

[a] Isolated yields.
[b] Enantiomeric excess (ee) determined by chiral HPLC analysis (Chiralpak AS-H or AD).
[c] dr = syn/anti As determined by $^1$H NMR.

Catalyst V catalyzed reactions are tolerant of both acyclic ketones (entries 1-5) and cyclic ketones (entries 6-8). As shown in entries 2-8 in Table 6b, above, two adjacent stereogenic centers with (S, S) configurations were generated selectively in this carbon-carbon bond forming process. More importantly, the use of unsymmetric ketones (entries 2, 4, and 5) resulted in regioselective formation of adducts resulting from reaction at the more substituted α-sites with excellent stereoselectivities (≧96% ee and ≧95/5 dr syn/anti). Variations in the alkyl group (entries 2, 4 and 5) revealed that methyl, allyl and hydroxyl substituents provided great levels of stereocontrol (96->99% ee and dr≧95:5 (syn/anti). Changes in electronic properties of the ketones (Table 6b, entries 5, 7 and 8) had a limited effect on the reaction rates and stereoselectivities. In these cases, good yields and high enantio- and diastereoselectivities were achieved.

L-Pyrrolidine-sulfonamide organocatalyst V catalyzed Mannich-type reactions were extended to unmodified aldehydes and α-imino ester. In this method, isovaleraldehyde was used as a model compound to examine the effect of Solvents in the presence of 10 mol % catalyst V (Table 6c). A variety of solvents were used in this research. Catalyst V exhibited excellent activities in most of selected solvents. After comparing both of yield and stereoselectivity, DMSO and 1,4-Dioxane were found to provide the best yields (89%, 87%), high enantioselectivities (97%, 98% ee), and high diastereoselectivities (>95:5, >95:5 syn/anti) respectively. Finally, DMSO and 1,4-Dioxane were selected as fantastic solvent to further examine the process. Then, different type of catalyst loading was examined to this model reaction in these two solvents. When DMSO used as solvent in this catalytic system, enantioselectivity has an obvious decrease (97% ee to 87% ee) as catalyst loading decreased from 10 mol % to 2.5 mol % (Table 6d). In this case, reaction time also has a huge increase (2.5 h to 14 h). Yield has a little decrease (89% to 83%) and diastereoselectivity also has a decrease (>95:5 to 10:1) (Table 6e). Fortunately, when 1,4-Dioxane used in this catalytic reaction, no big difference in yield (87% to 82%) and enantioselectivity (98% to 96%) was found comparing with DMSO as a solvent. When catalyst loading decreased to 2.5 mol %, diastereoselectivity has a huge decrease. After full consideration, 1,4-Dioxane was picked up as a final solvent, and 5 mol % catalyst loading was selected as best one.

After full reaction conditions established, next step was to evaluate the generality of the Mannich reactions between α-imino ester 2 and a variety of aldehydes (Table 6f). The reaction is tolerant of a variety of aldehydes. Regardless of the length of the side chains (C$_4$-C$_{10}$) (entries 1-7, Table 6f), the reactions of all aldehydes tested were completed between 6 h and 8.5 h in high yields (81% to 91%), excellent enantioselectivites (96% to 97% ee), and high diastereoselectivites (>95:5). Under the reaction conditions, aromatic aldehyde (entry 7) also gave an excellent result.

TABLE 6c

Effect of solvent on Mannich-type reaction of isovaleraldehyde 4a with α-imino ethyl glyoxylate 2

| Entry | Solvent | Reaction time (h) | % Yield[a] | % ee[b] | dr[c] |
|---|---|---|---|---|---|
| 1 | DMSO | 2.5 | 89 | 97 | >19:1 |
| 2 | CHCl$_3$ | 10 | 59 | 83 | 1:1 |
| 3 | DMF | 3.0 | 84 | 97 | >19:1 |
| 4 | CH$_3$CN | 6.0 | 74 | 98 | 12:1 |
| 5 | Toluene | 16 | 47 | 52 | 1:3 |
| 6 | EtOAc | 10 | 52 | 95 | 6:1 |
| 7 | 1,4-Dioxane | 2.5 | 87 | 98 | >19:1 |
| 8 | THF | 12 | 48 | 92 | 3.5:1 |

[a]Isolated yields.
[b]Enantiomeric excess (ee) determined by chiral HPLC analysis (Chiralpak AS-H).
[c]dr = syn/anti As determined by $^1$H NMR.

TABLE 6D

Effect of catalyst loadings on Mannich-type reaction of isovaleraldehyde 4a with α-imino ethyl glyoxylate 2 when DMSO as solvent.

| Entry | Mol % V | Reaction Time (h) | % yield[a] | % ee[b] | dr[c] |
|---|---|---|---|---|---|
| 1 | 10 | 2.5 | 89 | 97 | >95:5 |
| 2 | 5 | 5.5 | 88 | 91 | 95:5 |
| 3 | 2.5 | 14 | 83 | 87 | 10:1 |

[a]Isolated yields.
[b]Enantiomeric excess (ee) determined by chiral HPLC analysis (Chiralpak AS-H).
[c]dr = syn/anti As determined by $^1$H NMR.

TABLE 6E

Effect of catalyst loadings on Mannich-type reaction of isovaleraldehyde 4a with α-imino ethyl glyoxylate 2 when 1,4-Dioxane as solvent.

| Entry | Mol % I | Reaction Time (h) | % yield[a] | % ee[b] | dr[c] |
|---|---|---|---|---|---|
| 1 | 10 | 2.5 | 87 | 98 | >95:5 |
| 2 | 5 | 6.5 | 86 | 97 | >95:5 |
| 3 | 2.5 | 18 | 82 | 96 | 12:1 |

[a]Isolated yields.
[b]Enantiomeric excess (ee) determined by chiral HPLC analysis (Chiralpak AS-H).
[c]dr = syn/anti As determined by $^1$H NMR.

TABLE 6f

Pyrrolidine Sulfonamide I catalyzed Mannich-type reaction of various aldehydes with α-imino ethyl glyoxylate 2

| Entry | Product | Reaction time (h) | % Yield[a] | % ee[b] | dr[c] |
|---|---|---|---|---|---|
| 1 | 5a (R=iPr) | 6.5 | 86 | 97 | >95:5 |
| 2 | 5b (R=n-C$_3$H$_7$) | 6.0 | 88 | 97 | >95:5 |
| 3 | 5c (R=n-C$_4$H$_9$) | 6.5 | 85 | 96 | >95:5 |
| 4 | 5d (R=n-C$_5$H$_{11}$) | 7.5 | 87 | 96 | >95:5 |
| 5 | 5e (R=n-C$_6$H$_{13}$) | 7.0 | 84 | 96 | >95:5 |

TABLE 6f-continued

Pyrrolidine Sulfonamide I catalyzed Mannich-type reaction of various aldehydes with α-imino ethyl glyoxylate 2

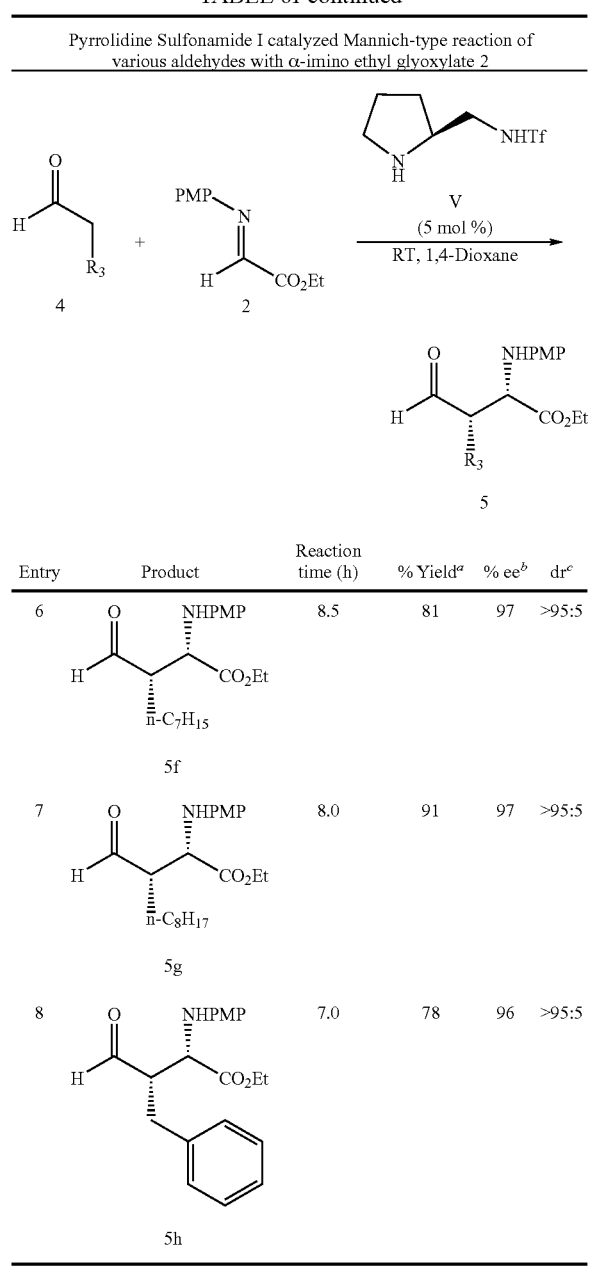

| Entry | Product | Reaction time (h) | % Yield[a] | % ee[b] | dr[c] |
|---|---|---|---|---|---|
| 6 | 5f (n-C7H15) | 8.5 | 81 | 97 | >95:5 |
| 7 | 5g (n-C8H17) | 8.0 | 91 | 97 | >95:5 |
| 8 | 5h (benzyl) | 7.0 | 78 | 96 | >95:5 |

[a]Isolated yields.
[b]Enantiomeric excess (ee) determined by chiral HPLC analysis (Chiralpak AS-H).
[c]dr = syn/anti As determined by $^1$H NMR.

Michael Addition Reactions of Aldehydes and Ketones to Nitrostyrenes

The Michael addition reaction is one of the most general and versatile methods for formation of C—C bonds in organic synthesis.[5, 86] Thus, it is not surprising that the development of enantioselective catalytic protocols for this cornerstone reaction has received much attention.[15, 87, 88] Efforts aimed at achieving asymmetric versions of the process by using chiral organocatalysts have been an intensively explored in recent years. L-Proline and other pyrrolidine-based catalytic systems for asymmetric Michael reactions have been described, but only moderate enantioselectivities are typically observed.[37, 40, 89-96] As a result, the design and development of new and efficient chiral organocatalysts to achieve high levels of enantio- and/or diastereo-selectivity of Michael conjugate addition remains a major challenge in synthetic organic chemistry.[25, 27, 30, 31, 97-101] Recently, Kotsuki and his coworkers described a chiral pyrrolidine-pyridine catalyst that promotes highly enantio- and diastereoselective Michael addition reactions of ketones with nitrostyrenes.[102] However, poor enantioselectivity (ca. 22% ee) is obtained when an aldehyde is used as the substrate.

We envisioned that the (S)-pyrrolidine sulfonamide (catalyst V) may form a chiral enamine with an aldehyde, which can serve as a Michael donor in reactions with a nitroolefin. In addition, model inspection suggested that the process would take place by preferential enamine addition to the less hindered Si face of the nitroolefin (FIG. 7). Unlike L-proline, the larger $CF_3SO_2$— group in V should effectively block the Re face in transition state A. Consequently, high levels of enantio- and/or diastereoselectivity may occur. In addition, the bifunctional nature of catalyst V, possessing an acidic sulfonamide and a basic pyrrolidine group, might lead to high catalytic activities even in the absence of an acidic additive. Indeed, high enantio- (89-99% ee) and diastereoselectivity (≧20:1 dr) of the asymmetric Michael addition reactions were achieved in reactions, promoted by the chiral pyrrolidine sulfonamide V (Table 7).[49]

A survey of the reaction media and temperature using the model reaction of iso-butyraldehyde with trans-β-nitrostyrene in the presence of the pyrrolidine trifluoromethanesulfonamide V (20 mol %) revealed that the use of i-PrOH as a solvent at 0° C. led to the highest enantioselectivity (90% ee). These results are presented in Table 7 below.

TABLE 7

Effect of solvents on the asymmetric Michael addition reaction of iso-butyraldehyde to trans-β-nitrostyrene.[a]

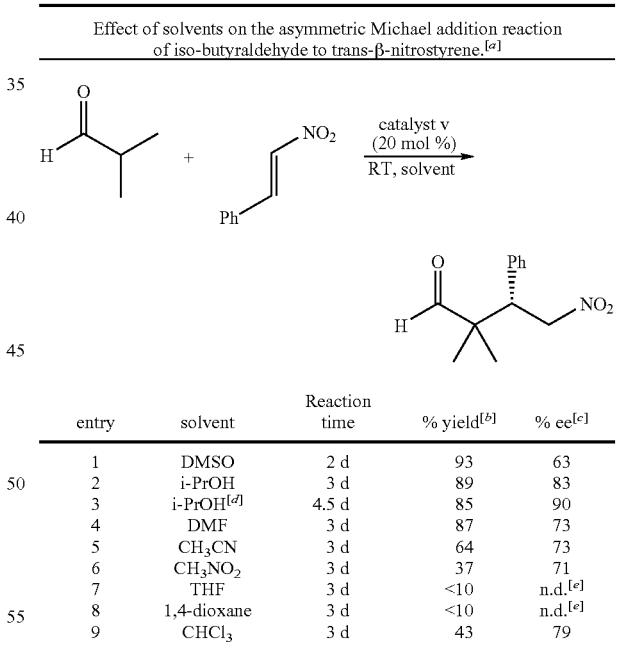

| entry | solvent | Reaction time | % yield[b] | % ee[c] |
|---|---|---|---|---|
| 1 | DMSO | 2 d | 93 | 63 |
| 2 | i-PrOH | 3 d | 89 | 83 |
| 3 | i-PrOH[d] | 4.5 d | 85 | 90 |
| 4 | DMF | 3 d | 87 | 73 |
| 5 | CH3CN | 3 d | 64 | 73 |
| 6 | CH3NO2 | 3 d | 37 | 71 |
| 7 | THF | 3 d | <10 | n.d.[e] |
| 8 | 1,4-dioxane | 3 d | <10 | n.d.[e] |
| 9 | CHCl3 | 3 d | 43 | 79 |

[a]Reaction condition: see Experimental Section.
[b]Isolated yields.
[c]Enantiomeric excess (ee) determined by chiral HPLC analysis (Chiralpak AS-H).
[d]at 0° C.
[e]not determined.

Encouraged by the results set forth in Table 7, we next probed the scope of the reaction with a variety of aldehydes and nitroolefins (Table 8). All reactions were conducted in i-PrOH at 0° C. in the presence of 20 mol % of I. In each case, smooth reactions occurred to generate Michael adducts in high yields (63-99%), high enantioselectivities (89-99% ee)

and excellent diastereoselectivities (dr≧20:1). Variations in the nitrostyrenes used in reaction with iso-butyraldehyde had no effect on enantioselectivities (Table 8, entries 1-3) and we therefore conclude that the reaction is general in this regard. Reaction of the more bulky cyclopentanecarboxaldehyde gave an even higher ee (93%) and yield (89%) (Table 8, entry 4). More significant is the observation that catalyst V catalyzed reactions of mono-substituted aldehydes yielded adducts with excellent enantio- (94-99% ee) and diastereoselectivities (≧20:1 dr) and high yields (63-99%) (Table 8, entries 5-9). In these processes, two adjacent stereogenic centers were generated with complete stereocontrol. Again changes in the electronic properties of the nitroolefins (Table 8, entries 5-8) and steric demands of the aldehydes (Table 8, entries 5, 8, and 9) had only a small effect on the stereoselectivities and reaction efficiencies of these reactions.

TABLE 8

Catalyst V catalyzed Michael addition reactions of aldehydes to trans-β-nitrostyrenes.

| Entry | product | time | % yield[a] | % ee[b] | dr[c] |
|---|---|---|---|---|---|
| 1 | | 4.5 d | 85 | 90 | — |
| 2 | | 6 d | 67 | 90 | — |
| 3 | | 6 d | 75 | 89 | — |
| 4 | | 42 h | 89 | 93 | — |
| 5 | | 20 h | 99 | 96 | 50:1 |
| 6 | | 28 h | 63 | 94 | 22:1 |
| 7 | | 24 h | 86 | 99 | 20:1 |

TABLE 8-continued

Catalyst V catalyzed Michael addition reactions of aldehydes to trans-β-nitrostyrenes.

![Reaction scheme: aldehyde with R1, R2 + Ar-CH=CH-NO2, catalyst V (pyrrolidine-CH2-NHTf), 20 mol%, 0°C, i-PrOH, giving product with aldehyde, R1, R2, Ar, CH2NO2]

| entry | product | time | % yield | % ee | dr |
|---|---|---|---|---|---|
| 8 | aldehyde with Ph and n-C4H9 substituents, CH2NO2 | 24 h | 94 | 99 | 30:1 |
| 9 | aldehyde with Ph and n-C5H11 substituents, CH2NO2 | 26 h | 91 | 97 | 50:1 |
| 10 | cyclohexanone with Ph, CH2NO2 | 10 h | 96 | 97 | 50:1 |

*a* Isolated yields.
*b* Determined by chiral HPLC analysis (Chiralpak AS-H, or AD and Chiralcel OD-H).
*c* Determined by ¹H NMR.

The results presented in the table above also demonstrated that V also catalyzed Michael addition reactions of ketones (Table 8, entry 10 and table 8b). Under the reaction conditions described above, addition of cyclohexanone to trans-β-nitrostyrene resulted in the formation of the adduct in 96% yield, 97% ee and 50:1 dr.

TABLE 8b

Catalyst 15 catalyzed Michael addition reactions of ketones to trans-□-nitrostyrenes.

![Reaction scheme: ketone with R1, R2 + Ar-CH=CH-NO2, catalyst 15 (pyrrolidine-CH2-NHTf), 20 mol%, 0°C, i-PrOH, giving product]

| entry | product | time | % yield$^a$ | % ee$^b$ | dr$^c$ |
|---|---|---|---|---|---|
| 1 | cyclohexanone-Ph-CH2NO2 | 10 h | 96 | 97 | 50:1 |
| 2 | cyclohexanone-C6H4-Me-p-CH2NO2 | 24 h | 84 | 96 | 50:1 |
| 3 | cyclohexanone-C6H4-OMe-CH2NO2 | 16 h | 92 | 98 | 50:1 |
| 4 | cyclohexanone-C6H4-CF3-CH2NO2 | 34 h | 70 | 88 | 50:1 |
| 5 | cyclohexanone-C6H4-Cl-p-CH2NO2 | 24 h | 83 | 99 | 50:1 |
| 6 | cyclohexanone-thiophene-CH2NO2 | 36 h | 79 | 86 | 30:1 |

TABLE 8b-continued

Catalyst 15 catalyzed Michael addition reactions of ketones to trans-β-nitrostyrenes.

| entry | product | time | % yield[a] | % ee[b] | dr[c] |
|---|---|---|---|---|---|
| 7 | (tetrahydropyran-3-yl with CH₂CH₂NO₂ and Ph) | 24 h | 87 | 98 | 50:1 |
| 8 | (tetrahydrothiopyran-3-yl with CH₂CH₂NO₂ and Ph) | 12 h | 95 | 97 | 30:1 |
| 9 | (cyclohexanone with CH₂CH₂NO₂ and C₆H₄—Cl-p) | 24 h | 83 | 99 | 50:1 |
| 10 | (acetone adduct with Ph, NO₂) | 8 h | 96 | 55 | — |
| 11 | (ethyl ketone adduct with Ph, NO₂) | 36 h | 85 | 93 | 50:1 |
| 12 | (β-hydroxy ketone with Ph, NO₂, OH) | 48 h | 46 | 46 | 3:1 |
| 13 | (β-OTBDMS ketone with Ph, NO₂) | 18 h | 89 | 86 | 14:1 |
| 14 | (isopropyl ketone with Ph, NO₂) | 48 h | 72 | 77 | 50:1 |

[a]Isolated yields.
[b]Determined by chiral HPLC analysis (Chiralpak AS-H, or AD and Chiralcel OD-H).
[c]Determined by ¹H NMR.

In a preliminary study, it was shown that the reaction of cyclohexanone with trans-β-nitrostyrene in the presence of 20 mol % V gave a Michael addition product with full stereocontrol (96% yield, 97% ee, 50:1 dr).[49] This promising result promotes us to study other ketone substrates including cyclic and acyclic systems (FIG. 7A Eq. 1). It is anticipated that other highly stereocontrolled reactions catalyzed by V can be achieved. We are also interested in exploring the intramolecular version of the asymmetric Michael addition reactions, which can provide highly functionalized five or six-membered ring structures 13 (FIG. 7A, Eq. 2). Interestingly, to the best of our knowledge, no asymmetric intramolecular version of the Michael reaction has been reported.[86, 159] The asymmetric inter- and intramolecular Michael addition reaction can be utilized for the synthesis of a wide range of molecules with diversified structures and biological activities.

The synthesis of the trans-β-nitrostyrene aldehyde substrates 12 used for the intramolecular Michael reactions is described in FIG. 7B. The conversion of 1-bromo-2-iodobenzene to bromoaldehyde 14a,b has been established in the literature using Pd-catalyzed coupling with the three and four carbon units allyl alcohol and 3-buten-1-ol in 82 and 87% yield, respectively.[160] Protection of the aldehydes in 14 as the ethylene glycol acetals, then lithiation/formylation can afford the new formed aldehydes 15 in good yields, according to literature procedures.[161] The final products 12 can be obtained by the known synthetic sequence of converting the aldehyde into a nitrostyrene[162] and deprotection of the acetal.[163]

The preparation of heteroatom (e.g., O and NAc) containing substrates 12 can be achieved starting from 2-hydroxyl or 2-acetamide aldehydes in 3 steps: O or N-alkylation with acetal bromides 16 under a basic condition[164], and then followed by two more steps, the same procedures used above (FIG. 8B).[162, 163]

α-Selenylation and α-Sulfenylation Reactions of Aldehydes and Ketones

α-Seleno and α-sulfenylated carbonyl compounds are useful synthetic intermediates.[103-106] For example, syn-elimination reaction of these substances is a powerful, mild method for the preparation of α,β-unsaturated aldehydes and ketones.[107, 108] Several methods for their preparation have been reported,[107-126] including the most commonly used one, acid or base promoted α-oxidation of aldehydes and ketones. However, generally these methods require the use of stoichiometric amounts of acid and base and, in many cases, the preformation of enamines and enolates from their corresponding carbonyl precursors is necessary. To our knowledge, no direct, catalytic procedure for α-selenenylation and α-sulfenylation of unmodified aldehydes and ketones has been described. Our recent investigations in organocatalysis have resulted in simple, direct and efficient methods for the preparation of α-seleno and α-sulfenylated aldehydes and ketones.[50-52] These α-oxidation reactions are promoted by the respective oragnocatalysts L-prolinamide and pyrrolidine trifluoromethanesulfonamide, V.

In the study of α-selenenylation reactions of aldehydes, after screening 8 organocatalysts, we found L-prolinamide was the most effective one for this process. Under the optimal reaction conditions using N-phenylselenophthalimide as selenenylation reagent in $CH_2Cl_2$, the α-selenenylation reactions proceeded rapidly using 2 mol % of L-prolinamide within 10-60 min to afford α-phenylselenoaldehydes in high yields (76-95%) (Table 9).[50]

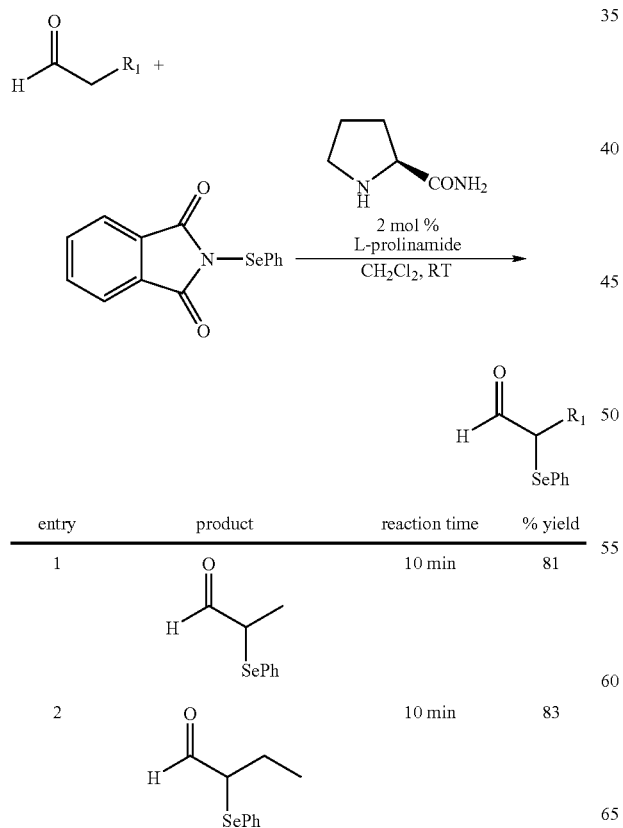

TABLE 9

L-Prolinamide catalyzed α-selenenylation reactions of aldehydes.

| entry | product | reaction time | % yield |
|---|---|---|---|
| 1 | (CH(CH₃), SePh) | 10 min | 81 |
| 2 | (CH(C₂H₅), SePh) | 10 min | 83 |
| 3 | (CH(n-C₃H₇), SePh) | 10 min | 85 |
| 4 | (CH(i-Pr), SePh) | 10 min | 88 |
| 5 | n-C₄H, SePh | 10 min | 78 |
| 6 | n-C₅H, SePh | 10 min | 86 |
| 7 | n-C₆H₁₃, SePh | 10 min | 95 |
| 8 | n-C₇H₁₅, SePh | 10 min | 91 |
| 9 | n-C₈H₁₇, SePh | 10 min | 84 |

TABLE 9-continued

L-Prolinamide catalyzed α-selenenylation reactions of aldehydes.

[Reaction scheme: aldehyde + N-SePh phthalimide with 2 mol% L-prolinamide (pyrrolidine-CONH₂) in CH₂Cl₂, RT, giving α-SePh aldehyde product]

| entry | product | reaction time | % yield |
|-------|---------|---------------|---------|
| 10 | [PhCH₂-CH(SePh)-CHO] | 10 min | 80 |
| 11 | [(CH₃)₂C(SePh)-CHO] | 1 h | 76 |
| 12 | [1-(SePh)cyclohexane-CHO] | 1 h | 81 |

In an attempt to extend the L-prolinamide-catalyzed α-selenenylation method to ketones, we found that, under the similar reaction conditions using 30 mol % L-prolinamide only moderate reaction yield (61%) of the selenenylation product was obtained and much longer reaction time (12 h) was required for cyclohexanone. Interestingly, in addition to forming the mono α-selenenylation adduct, bis α,α- and α,α'-selenenylation products were also produced. However, we found the pyrrolidine trifluoromethanesulfonamide V, exhibited the most promising catalytic activity on this reaction on a variety of ketones (Table 10).[51]

α-Selenenylation reactions of ketones catalyzed by the pyrrolidine sulfonamide I proved to be general (Table 10). In each case, high yields of predominantly mono-addition products were obtained for α-selenenylation reactions of a wide range of acyclic and cyclic ketones. The mild reaction conditions were tolerant of a variety of substrate functionalities (Table 10, entries 5, 12, and 13). We also observed that I catalyzed reactions of various ring-sized cyclic ketones (Table 10, entries 7-14).

TABLE 10

Pyrrolidine sulfonamide V catalyzed α-selenenylation reactions of ketones.

[Reaction scheme: R₁-CH₂-C(O)-CH₂-R₂ ketone + N-SePh phthalimide with 10 mol% pyrrolidine-CH₂-NHTf catalyst V in CH₂Cl₂, RT, giving α-SePh ketone product]

| entry | product | reaction time | % yield[a] |
|-------|---------|---------------|------------|
| 1 | CH₃-C(O)-CH₂-SePh | 24 h | 69 |
| 2 | CH₃CH₂-C(O)-CH(CH₃)-SePh | 24 h | 61 |
| 3 | n-Pr-C(O)-C(Et)(SePh) | 48 h | 58 |
| 4 | i-Pr-CH₂-C(O)-CH₂-SeF | 17 h | 62 |
| 5[b] | CH₂=CH-CH₂CH₂CH₂-C(O)-CH₂-SePh | 24 h | 63 |
| 6 | Ph-C(O)-CH₂-SePh | 24 h | 81 |
| 7 | 2-(SePh)-cyclopentanone | 24 h | 78 |

TABLE 10-continued

Pyrrolidine sulfonamide V catalyzed
α-selenenylation reactions of ketones.

| entry | product | reaction time | % yield[a] |
|---|---|---|---|
| 8 | (2,2-dimethylcyclopentanone with SePh) | 24 h | 67 |
| 9 | (cyclohexanone with SePh) | 16 h | 80 |
| 10 | (tetrahydropyran-4-one with SePh) | 24 h | 79 |
| 11 | (N-methylpiperidin-4-one with SePh) | 24 h | 76 |
| 12 | (1,4-dioxaspiro[4.5]decan-8-one with SePh) | 26 h | 85 |
| 13 | (cyclohex-2-enone with SePh) | 24 h | 72 |
| 14 | (cycloheptanone with SePh) | 48 h | 59 |

[a]Isolated yield.
[b]Two regioisomers at less substituted (structure shown) and more substituted site observed by $^1$H NMR of with ratio of 10:1.

The pyrrolidine trifluoromethanesulfonamide organocatalyst V also displayed the most effective catalytic activity on α-sulfenylation reactions of aldehydes and ketones (Table 11). Using 20-30 mol % catalyst I, N-(phenylthio)phthalimide as a sulfenylation reagent in CH$_3$CH provided α-sulfenylation products in good yields (42-88%).[52]

Generally, high yields (60-88%) were obtained for reactions of cyclic ketones (Table 11, entries 1-3). Unfortunately, α-sulfenylation reactions of acyclic ketone substrates were sluggish and complex product mixtures were produced. This direct, catalytic α-sulfenylation reaction is not restricted to cyclic ketones since it also is applicable to aldehydes (Table 11, entries 4-11). Variations in the steric demand of aldehydes had only a minor effect on the α-sulfenylation reaction efficiency. Generally, high reaction yields were obtained regardless of the length and degree of branching of the aldehyde chain. Interestingly, in some cases (Table 11, entries 5-7, and 10), bis-addition products were formed in variable, minor amounts (by $^1$H NMR analysis of the crude product mixtures), however the mono- and bis-products cannot be separated by silica gel column chromatography.

TABLE 11

Pyrrolidine sulfonamide V catalyzed α-sulfenylation reactions of ketones and aldehydes.

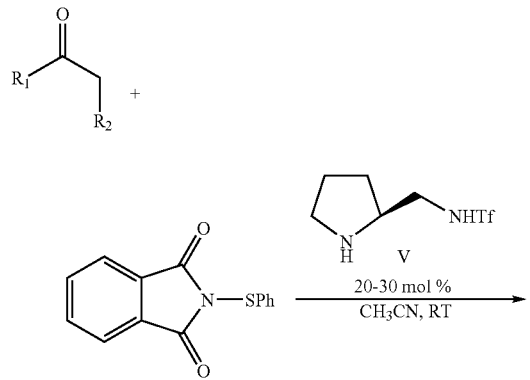
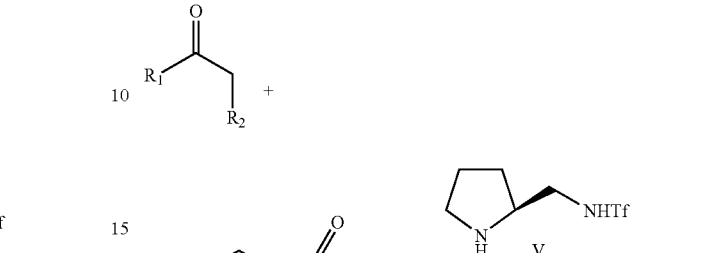

| entry | product | t (h) | % yield[a] |
|---|---|---|---|
| 1 | (2-SPh cyclohexanone) | 4 | 83[b] |
| 2 | (3-SPh tetrahydropyran-4-one) | 6 | 88[b] |
| 3 | (3-SPh N-methylpiperidin-4-one) | 24 | 60[b] |
| 4 | (α-SPh isovaleraldehyde) | 24 | 56[b] |
| 5 | (α-SPh butyraldehyde + bis-SPh) 7.4:1 | 36 | 56[c,d] |
| 6 | (α-SPh hexanal + bis-SPh, n-Bu) 20:1 | 36 | 42[c,d] |
| 7 | (α-SPh heptanal + bis-SPh, n-C5H11) 23:1 | 36 h | 52[c,d] |
| 8 | (α-SPh octanal, n-C6H13) | 30 h | 66[c] |
| 9 | (α-SPh nonanal, n-C7H15) | 36 h | 63[c] |
| 10 | (α-SPh decanal + bis-SPh, n-C8H17 / n-C8H18) 7.4:1 | 36 h | 57[c,d] |

TABLE 11-continued

Pyrrolidine sulfonamide V catalyzed α-sulfenylation
reactions of ketones and aldehydes.

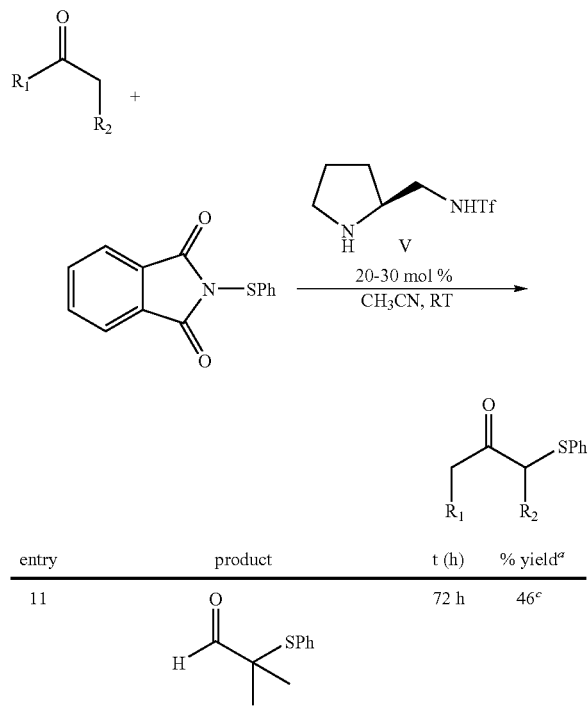

| entry | product | t (h) | % yield$^a$ |
|---|---|---|---|
| 11 | 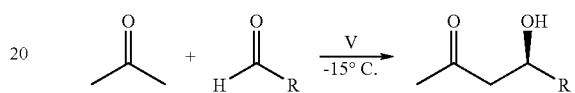 | 72 h | 46$^c$ |

$^a$Isolated yield.
$^b$20 mol % I used.
$^c$30 mol % I used.
$^d$Molar ratio determined by $^1$H NMR.

Aldol Reactions

The aldol condensation reaction is a useful synthetic step for construction/synthesis of β-hydroxy carbonyl compounds, which are versatile building blocks for preparation of a wide range of pharmaceuticals and natural products. Since the pioneering finding by List and Barbas III, and their co-workers, that L-proline could work as a catalyst in the intermolecular, direct aldol reaction,[42] the concept of small organic molecules as catalysts has received great attention. Recently, several organocatalyst systems have been developed including those which employ L-proline,[39, 42, 43, 137-142] aminoalcohols,[41, 143-145] diamines,[38, 146] and pyrrolidine tetrazole.[36] Based on these observations and our studies, the basic/acidic bifunctional pyrrolidine amide/sulfonamide/imide-based catalysts I-IV and V are used for promoting the reaction (FIGS. 2 and 7).

Figure 8:
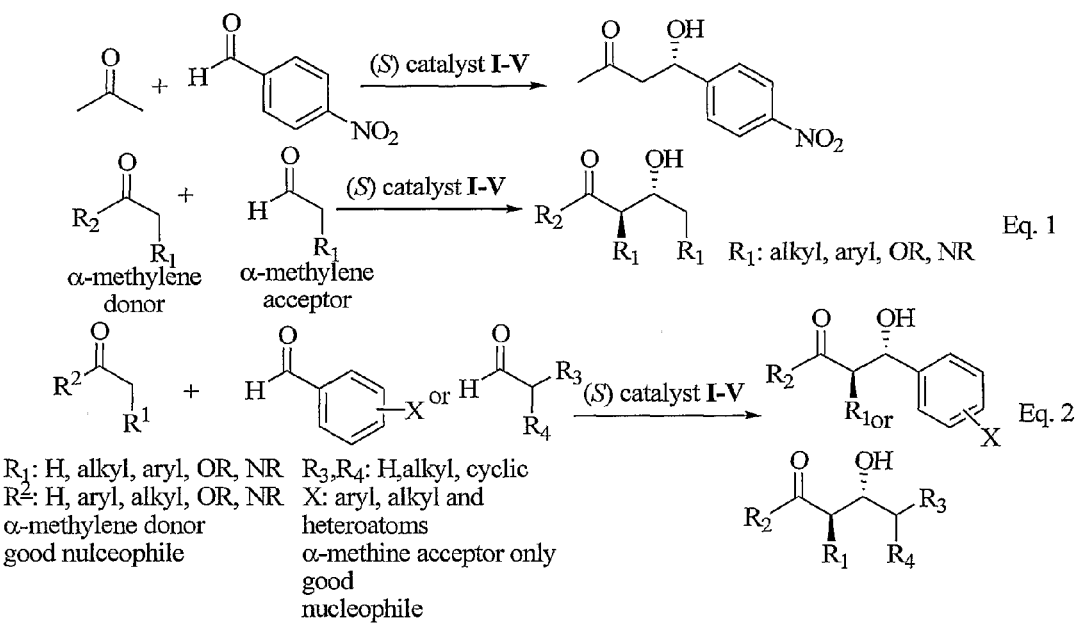
FIG. 8 shows organocatalyst catalyzed asymmetric aldol reactions.

A typical reaction between acetone and p-nitrobenzaldehyde in DMSO is used (FIG. 8). The pyrrolidine amide/sulfonamide/imide organocatalysts, with 30 mol % loading, will be employed in the reaction to screen for catalytic activity and efficiency. The enantioselectivity and/or diastereoselectivity of the reaction is determined by using chiral HPLC and $^1$H NMR. Variations in the aldehydes and ketones are examined to probe the generality of the reaction. In selecting suitable pairs of aldehydes and ketones for study, care is necessary in order to achieve good levels of chemo-differentiations. It is generally true that aldehydes containing a methylene unit (CH$_2$R$_2$) adjacent to the carbonyl have a strong propensity to dimerize, via participation as both nucleophile and electrophile (FIG. 8, Eq. 1). In contrast, aldehydes that incorporate an α-methine carbon (CHR$_3$) generally do not homo-dimerize when exposed to an organocatalyst, instead behaving as electrophilic acceptors exclusively. In the latter case, it is presumed that the kinetic inaccessibility of the α-methine proton and the thermodynamic instability of the corresponding enamine effectively prohibit nucleophile formation (FIG. 8, Eq. 2).

Aldol Condensation Reactions of Ketones with Aldehydes

The above-listed four catalysts V-VIII of FIG. 1 were screened for stereo-selectivity of desired compounds in Aldol reactions. The screenings were performed at room temperature (RT). It was observed that catalyst V gave the best results in terms of reaction yields and enantio-selectivity, however the remaining catalysts also showed promising results, utilizing the reaction scheme below.

Aldol Condensation Reaction

As a consequence of its high yields and selectivity, catalyst V was screened for enantioselective Aldol condensation on several molecules as shown in Table 12 below. The screening were carried out with reaction temperatures at room temperature (RT), 0° C. and −15° C. and using acetone. The screening with p-nitrobenzaldehyde led to the highest enantiomeric excess (ee) at −15° C. (84%) compared with 46% at RT and 78% at 0° C., respectively. Product yield was also not sacrificed at any temperature. Given such, the remaining reactions of a variety of aromatic aldehydes with acetone were conducted in the presence of 20% mole catalyst V at −15° C. for 7-24 hours and the results of these screenings are summarized in Table I. The reaction yields for screenings of these compounds ranged from 66% to 75% with 84-86% ee. Aliphatic aldehydes with acetone are under investigation and expected to give an even higher ee.

Aldol Condensation Reaction

TABLE 12

| R | Yield (%) | ee (%) |
|---|---|---|
| O$_2$N-C$_6$H$_4$- | 71 | 84 |
| Br-C$_6$H$_4$- | 67 | 86 |

TABLE 12-continued

![reaction scheme: acetone + H-C(O)-R →(V, -15°C) product with OH]

| R | Yield (%) | ee (%) |
|---|---|---|
| 4-chlorophenyl | 66 | 85 |
| 2-chlorophenyl | 71 | 83 |
| 2-naphthyl | 75 | 80 |

Figure 9:
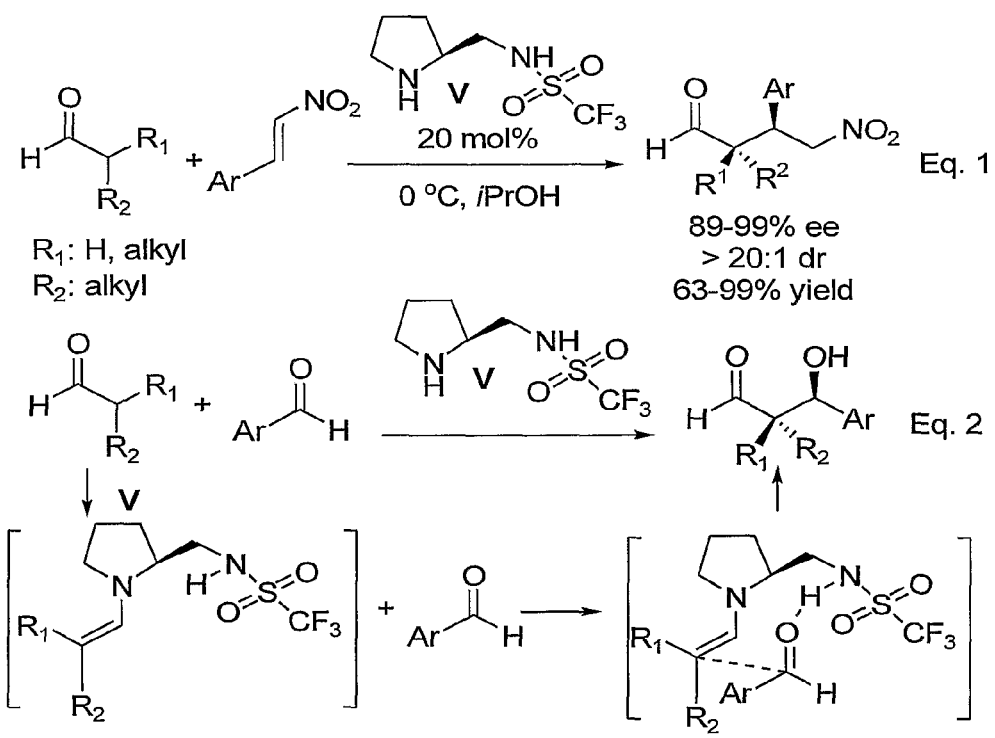
FIG. 9 shows organocatalyst reactions forming dialkly aldehydes.

Additional studies related to the aldol reaction came from the utility of pyrrolidine sulfonamide V to catalyze highly efficient Michael addition reactions of α,α-dialkyl aldehydes with β-nitrostyrenes (FIG. 9, Eq. 1).[12] In this process, catalyst V effectively catalyzes enolization of an α,α-dialkyl aldehyde to form electron rich enamines, which then add to the nitro-olefin electrophile. Intrigued by the possibility this mechanistic scenario might be expanded to encompass other electrophiles such as aldehydes, we postulated that organocatalyst V promoted aldol reactions of α,α-dialkyl aldehydes as donors with aldehyde acceptors, would generate products containing quaternary carbon centers (FIG. 9, Eq. 2).[13] The results of efforts exploring this proposal have demonstrated that the asymmetric aldol reactions using 20 mol % of (S)-pyrrolidine sulfonamide V take place to form β-hydroxyaldehydes in high yields (81-97%) and enantioselectivities (91-97% ee).

Initial studies, testing the feasibility of this catalytic process, focused on the reaction of iso-butyraldehyde 1a as an aldol donor and p-nitrobenaldehyde 2a as an acceptor in the presence of 20 mol % V in DMSO at room temperature. The reaction took place smoothly and afforded the aldol adduct 3a in a good yield (83%) and a high enantioselectivity (91% ee) (Table 1, entry 1). The absolute configurations at the chiral center in aldol product 3a was determined to be S by comparison of the $^1$H NMR and optical rotation data for 3a with those of the known compound.[6a] A poor reaction rate, yield and enantioselectivity were observed when other solvents were used for this process (Table 1, entries 2-6). Thus, DMSO was selected as reaction medium for reactions probing the scope of this asymmetric aldol reaction.

TABLE 12A

Effect of solvents on the asymmetric aldol reaction of iso-butyraldehyde 1a with p-nitrobenzaldehyde 2a by pyrrolidine sulfonamide I.[a]

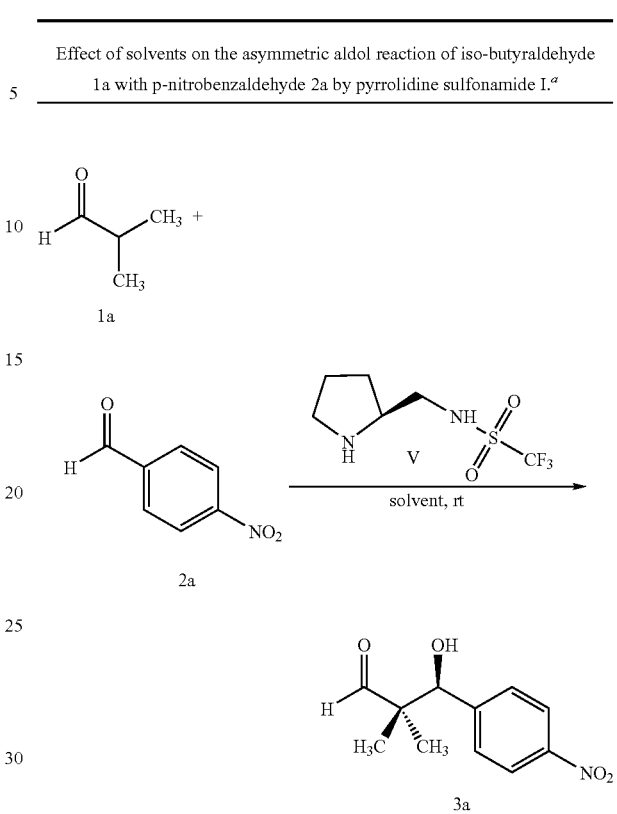

| Entry | Solvent | t (h) | % yield[b] | % ee[c] |
|---|---|---|---|---|
| 1 | DMSO | 43 | 83 | 91 |
| 2 | DMF | 72 | 77 | 81 |
| 3 | 1,4-dioxane | 72 | 41 | 80 |
| 4 | CH$_3$CN | 72 | 63 | 48 |
| 5 | THF | 72 | 68 | 79 |
| 6 | MeOH | 72 | 37 | 18 |

[a]Unless otherwise specified, the reaction was carried out using 1a (4.0 mmol) and 2a (0.4 mmol) in the presence of 20 mol % I in 1.0 mL of solvent at rt for a certain period of time.
[b]Isolated yields after chromatographic purification.
[c]Determined by chiral HPLC analysis (Chiralpak AS-H).

A number of aldol reactions were carried out under the reaction conditions described above in the presence of 20 mol % V in DMSO. Examination of the results reveals that the (S)-pyrrolidine sulfonamide V promoted aldol processes is generally applicable to a variously functionalized aldehyde acceptors (Table 13, entries 1-10). In all cases, high levels of enantioselectivities (91-97%) and high reaction yields (81-96%) are observed. Interestingly, only one of the aldehyde groups in terephthalaldehyde participated in reaction with iso-butyraldehyde 1a to give the mono-aldol addition product exclusively in excellent yield (97%) and enantioselectivity (97% ee), even when an excess of 1a (10 equiv.) was used (Table 13, entry 9). Moreover, two stereogenic centers were formed simultaneously in a high diastereo-controlled manner (93% ee, 6/1 anti/syn) when unsymmetric dialkyl aldehyde α-ethyl α-methyl aldehyde was used (Table 13, entry 10).

TABLE 13

Synthesis of aldol products with forming quaternary carbon centers catalyzed by pyrrolidine sulfonamide V.[a]

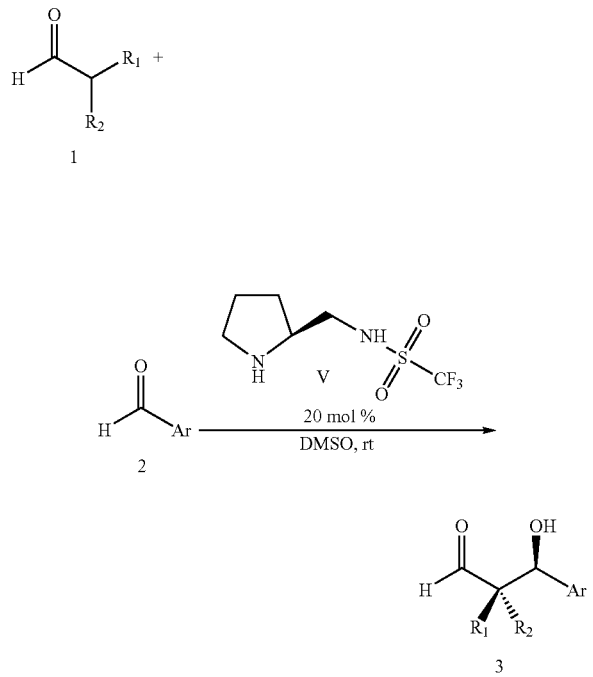

| Entry | $R_1$, $R_2$ | Ar | t (h) | % yield[b] | % ee[c] |
|---|---|---|---|---|---|
| 1 | Me, Me | 4-$NO_2$—$C_6H_4$ | 43 | 83 | 91 |
| 2 | Me, Me | 4-$CF_3$—$C_6H_4$ | 24 | 83 | 95 |
| 3 | Me, Me | 4-Br—$C_6H_4$ | 84 | 94 | 94 |
| 4 | Me, Me | 4-Cl—$C_6H_4$ | 96 | 96 | 94 |
| 5 | Me, Me | 4-F—$C_6H_4$ | 96 | 81 | 93 |
| 6 | Me, Me | 4-CN—$C_6H_4$ | 72 | 95 | 95 |
| 7 | Me, Me | 2-$NO_2$—$C_6H_4$ | 72 | 81 | 93 |
| 8[d] | Me, Me | 4-$CH_3O_2C$—$C_6H_4$ | 144 | 93 | 94 |
| 9 | Me, Me | 4-CHO—$C_6H_4$ | 72 | 97 | 97 |
| 10[e] | Me, Et | 4-$NO_2$—$C_6H_4$ | 168 | 85 | 93 |

[a]See footnote a in Table 1 and the supporting information.
[b]Isolated yield after chromatographic purification.
[c]Determined by chiral HPLC analysis (Chiralpak AS-H or Chialcel OJ-H).
[d]The reaction was run at 0° C.
[e]dr determined by $^1$H NMR with a ratio of 6/1 anti/syn.

The results evidence that the bifunctional (S)-pyrrolidine trifluoromethanesulfonamide V, as well as other organocatalysts according to the present invention, is an effective organocatalyst for promoting direct asymmetric aldol reactions of α,α-dialkyl aldehydes. These processes, which lead to formation of quaternary carbon centers, take place in high yields and exceptionally high enantioselectivities.

Dehydration Reactions to Product α,β-Unsaturated Unsaturated Ketones

Figure 10:
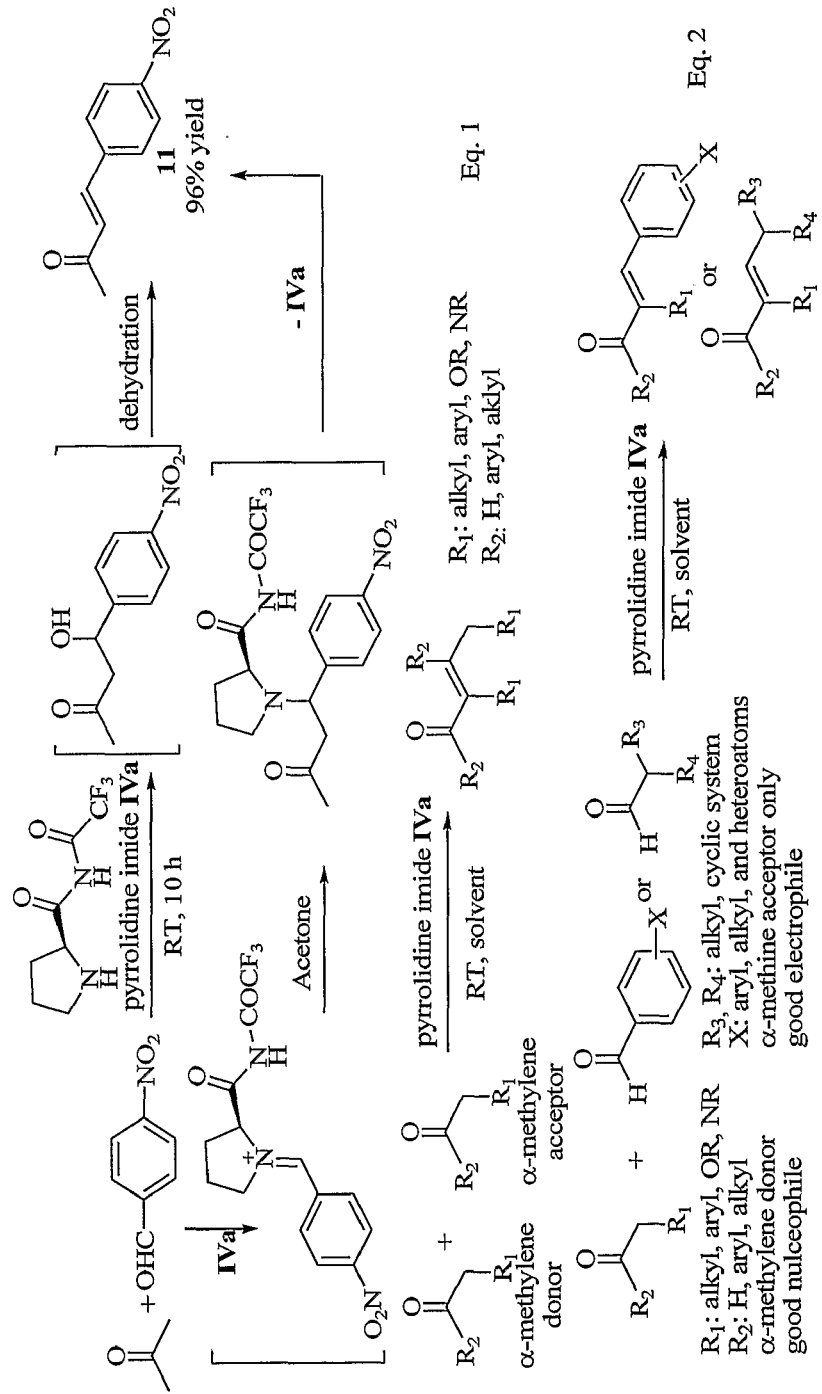
FIG. 10 shows tandem Mannich-elimination reactions using the present catalysts.

During the research of seeking new small organic molecules having structural diversity for catalyzing aldol reactions, we have designed and prepared a novel pyrrolidine imide IVa as an organocatalyst (FIG. 10). This bifunctional molecule having basic pyrrolidine and significantly acidic imide moieties could function the same way as L-proline does for promoting reactions. The proton of the imide is even more acidic than that of the carboxylic acid in proline. In an initial study using 20 mol % of IVa for an aldol reaction, the reaction of acetone with p-nitrobenzaldehyde in DMSO, surprisingly, did not result in the desired condensation product (FIG. 10). Instead, interestingly, the dehydration product α,β-unsaturated ketone 11 was obtained exclusively and in an almost quantitative yield (96%) (FIG. 10). A careful monitoring the course of the reaction by TLC revealed that under the reaction condition in the presence of the catalyst IVa, the aldol condensation product was not observed. On the basis of the results, we propose α,β-unsaturated ketone 11 are formed through a Mannich-elimination sequence.[42, 137, 139, 140, 158] In this case, the stronger acidic imide in IVa may play a critical role in facilitating the tandam reaction over the aldol reaction. However, we cannot exclude an aldol-dehydration reaction. Based on our observation, we conceived that the catalyst IVa could be used for a one-pot synthesis of α,β-unsaturated aldehydes and ketones via a novel tandem Mannich-elimination reaction. To our knowledge, no such study has been described employing a direct organocatalytic method for the preparation of versatile α,β-unsaturated aldehydes and ketones from simple aldehydes and ketones (FIG. 10, Eq. 1 and 2). In the proposed study, we plan to explore the novel oganocatalytic tandem Mannich-elimination reactions on a variety of aldehydes and keton. The reaction conditions will be optimized with a focus on the reaction media and the catalyst loading. The scope of the reaction using a variety of appropriate aldehydes and ketons will be examined under the optimal reaction conditions as set forth in FIG. 10.

An initial investigation of a variety of reaction media on the process revealed that reaction solvents played a significant role in the formation of α,β-unsaturated ketone a and aldol condensation product b. It is noted that in DMSO exclusively dehydration product a was produced in a 93% yield. However, in the 8 other solvents tested, both products were formed and in many cases the aldol product b was the major product (entry 3-9). The results of the study caused us to select DMSO as reaction medium for further reactions.

TABLE 14A

Effect of Solvent on Yield of Dehydrated Product and Aldol Product

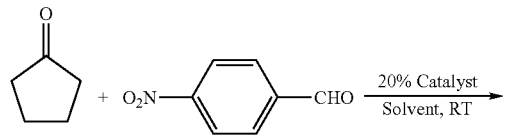

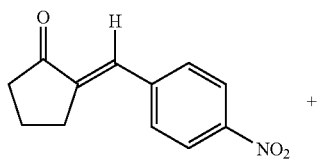

a

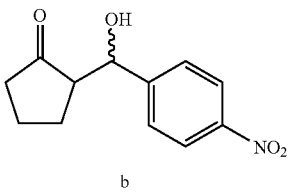

b 0.3 mmol of ketone and 0.15 mmol of aldehyde in 0.50 ml of DMSO.

| Entry | Mol % Catalyst | Reaction Time | Solvent | Dehydrated product yield % | Aldol yield % |
|---|---|---|---|---|---|
| 1 | 20 | 21.5 hr | DMSO | 93 | |
| 2 | 20 | 21.5 hr | DMF | 71 | 28 |
| 3 | 20 | 21.5 hr | $CH_2Cl_2$ | 43 | 54 |
| 4 | 20 | 21.5 hr | $CHCl_3$ | 37 | 61 |
| 5 | 20 | 21.5 hr | 1,4-Dioxane | 33 | 65 |
| 6 | 20 | 21.5 hr | EtOAc | 32 | 66 |
| 7 | 20 | 21.5 hr | Isopropanol | 32 | 53 |
| 8 | 20 | 21.5 hr | THF | 31 | 68 |
| 9 | 20 | 21.5 hr | $CH_3CN$ | 31 | 47 |

Reaction conditions: A mixture of aldehyde (0.15 mmol), ketone (0.30 mmol) and catalyst IVa in 0.5 mL of anhydrous DMSO was vigorously stirred for a certain period of time. The endpoint of the reaction was monitored by TLC. The resulting mixture was then directly purified by silica gel chromatography and fractions were collected and concentration in vacuo to produce a solid or clear oil.

The effect of catalyst loading on the reaction efficiency was next evaluated (Table 14B). It was found that the use of 20 mol % of pyrrolidine imide IVa was optimal to ensure high reaction efficiency (93% yield) while maintaining a reasonable reaction time (entry 1).

TABLE 14B

Effect of Catalyst loading:

0.3 mmol of ketone and 0.15 mmol of aldehyde in 0.50 ml of DMSO.

| Entry | Mol % catalyst | Reaction Time | % yield |
|---|---|---|---|
| 1 | 20 | 21.5 hr | 93 |
| 2 | 10 | 7 days | 70 |
| 3 | 5 | 7 days | 31 |

Having established optimal reaction conditions, the generality of the process was probed (Table 14C). The reaction between cyclopentanone (0.15 mL) and an aldehyde (0.3 mmol) in DMSO (0.5 mL) at room temperature in the presence of 20 mol % pyrrolidine imide IVa was conducted. The processes proceeded smoothly and stereoselectively to afford (E) α,β-unsaturated ketones in good yields (59-94%). The pyrrolidine imide IVa promoted reactions were applicable to a variety of aldehydes with different structure features including aromatic (Table 10C, entries 1-3) and aliphatic (entries 6-13). It was found that electronic and steric effects on the reactions were very limited (Table 14C, entries 2-3). For example, benzaldehydes having electron-donating (entry 2) and withdrawing groups (entry 3) afforded products both in high yields (94 and 93% respectively). The variations in side chains of aliphatic aldehydes (entries 5-8) resulted in comparable reaction yields (82, 61 and 69%, respectively).

TABLE 14C

Synthesis of α,β-Unsaturated Cyclopentanones[a]

| entry | product | t (h) | % yield[b] |
|---|---|---|---|
| 1 | | 10 | 84 |

TABLE 14C-continued

Synthesis of α,β-Unsaturated Cyclopentanones[a]

cyclopentanone + H(C=O)R →(IVa, 20 mol %, DMSO, RT)→ 2-(R-methylene)cyclopentanone

| entry | product | t (h) | % yield[b] |
|---|---|---|---|
| 2 | 2-(4-methoxybenzylidene)cyclopentanone | 40 | 94 |
| 3 | 2-(4-nitrobenzylidene)cyclopentanone | 21.5 | 93 |
| 4 | 2-(4-bromobenzylidene)cyclopentanone | 40 | 88 |
| 5 | 2-(1-naphthylmethylene)cyclopentanone | 132 | 85 |
| 6 | 2-(cyclohexylmethylene)cyclopentanone | 40 | 82 |
| 7 | 2-(cyclopentylmethylene)cyclopentanone | 6 | 61 |
| 8 | 2-(2-methylpentylidene)cyclopentanone | 72 | 69 |
| 9 | 2-(3-methylbutylidene)cyclopentanone | 47 | 71 |
| 10 | 2-(n-C$_5$H$_{11}$-methylene)cyclopentanone | 47 | 79 |
| 11 | 2-(n-C$_6$H$_{13}$-methylene)cyclopentanone | 47 | 64 |
| 12 | 2-(n-C$_7$H$_{15}$-methylene)cyclopentanone | 47 | 59 |
| 13[c] | 2-(3-methoxypropylidene)cyclopentanone | 107 | 66 |

[a]Reaction conditions: a mixture of aldehyde (0.15 mmol), ketone (0.30 mmol), and catalyst (0.03 mmol) in 0.5 mL of anhydrous DMSO was vigorously stirred. The resulting mixture was then directly purified by silica gel chromatography to provide a solid or clear oil.
[b]Isolated yield.
[c]Ratio of 5:1 for ketone to aldehyde was used.

The catalyst IVa catalyzed reactions were tolerant of not only cyclic ketones, but also acylic systems (Table 14D). When the same reaction conditions were employed for reactions of acetone with p-nitrobenzaldehyde in 2:1 molar ratio in DMSO, a relatively low reaction yield (61%, table 14D, entry 1) was obtained. However, when acetone was used as a solvent and reagent, significant improvement for the reaction was made with a much higher yield (95%, entry 2). Consequently, the reactions between acetone and aldehydes (0.15 mmol) were carried out in acetone (0.5 mL) in the presence of 20 mol % catalyst IVa. The reactions were general to both aromatic and aliphatic aldehydes and the α,β-unsaturated ketones were produced in good yields. Unfortunately, under the same reaction conditions, reactions with other ketone substrates proceeded very slowly in low yields and a larger amount of the unreacted starting materials were recovered.

TABLE 14D

Synthesis of α, β-Unsaturated Acetones

[Reaction scheme: Acetone + R-CHO → α,β-unsaturated ketone, Catalyst, RT]

0.15 mmol of aldehyde in 0.50 ml of Acetone.

| Entry | R = | Reaction Time | % yield |
|---|---|---|---|
| 1 | 4-nitrophenyl | 10 hr | 95 |
| 2 | 4-chlorophenyl | 46 hr | 89 |
| 3 | isobutyl (branched) | 46 hr | 41 |
| 4 | cyclohexyl | 46 hr | 60 |
| 5 | n-butyl (linear alkyl) | 46 hr | 67 |

Mannich Reactions of Ketones, Amines and Aldehydes

Figure 11:
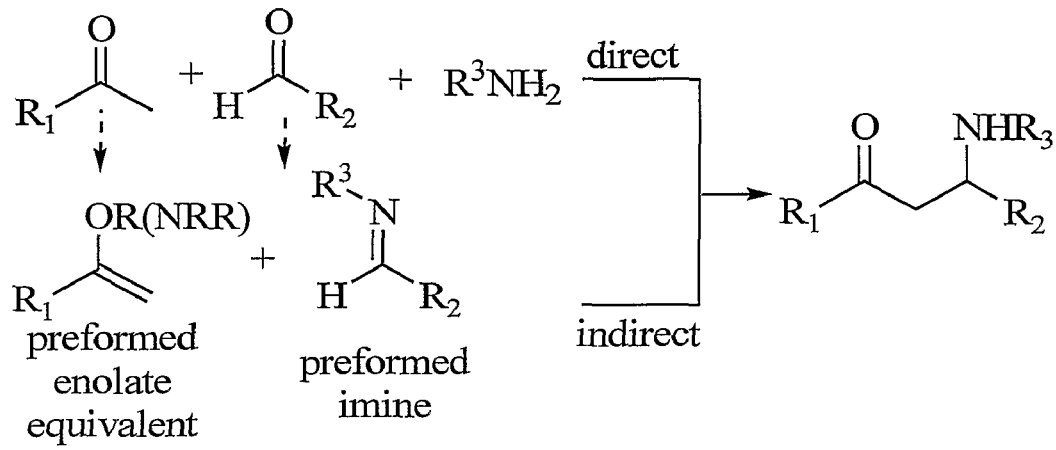
FIGS. 11-13 show three component Mannich reactions.

A multicomponent reaction (MCR), in which three or more reactants combine to generate products represents an economical approach in organic synthesis.[68, 130, 131] One of the classic three component reactions is the Mannich reaction (FIG. 11), which allows for the efficient one step construction of versatile nitrogen-containing molecules from readily available simple ketones, aldehydes and amines.[68] Therefore, tremendous efforts have been made on developing this reaction. Both the direct method with unmodified ketone donors and the indirect method utilizing preformed enolate equivalents have been described,[68, 132] and a number of organometallics-catalyzed asymmetric Mannich reactions have been reported. However, most of these methods rely on indirect approaches requiring preformed enolate equivalents and/or preformed imines. Direct three-component Mannich reactions are more efficient and economical, but are rare, particular in the catalytic enantioselective format. Recently, List discovered the first examples of direct, L-proline-catalyzed, three-component Mannich reaction of ketones, aldehydes and amines.[133-136] With this study as precedent, we plan to explore the use of our organocatalysts for promoting direct, three-component Mannich reactions. To the best of our knowledge, the proposed study represents the first example of the Mannich reaction using a small organic molecule as a catalyst other than L-proline.

Figure 12:
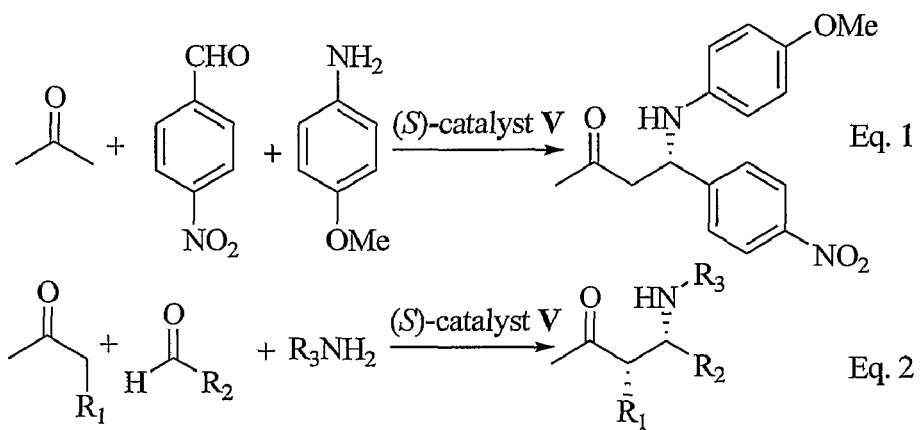

Based on our previously demonstrated Mannich-type reactions of α-imino esters with ketones, we propose the organocatalyst V and others could facilitate the direct three-component Mannich reactions in the same way as does proline (FIG. 12). In a preliminary study, we will investigate a reaction between acetone, 4-nitrobenzaldehyde and p-methoxyaniline in the presence of 30 mol % V in DMSO (FIG. 12, Eq. 1). The enantio- and/or diastereoselectivity of the reaction will be determined by chiral HPLC and $^1$H NMR, respectively. As described for other reaction types, further efforts will focus on optimizing reaction conditions to improve yields and enantio- and diastereoselectivity. The scope of the reactions with variations of ketones, aldehydes and amines will be examined (FIG. 12, Eq. 2). If the result of catalyst V catalyzed the reaction turns out to be poor, other pyrrolidine amides/sulfonamides will be screened and evaluated.

Figure 13:
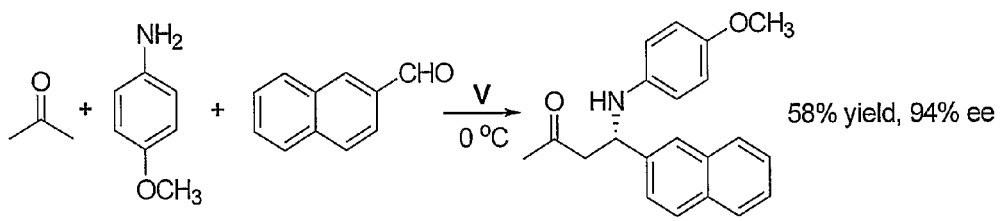

In another Mannich reaction, this time of acetone, p-methoxyanisidine and 2-naphthaldehyde, the desired single enantiomer product was obtained in up to 94% yield by using 20% mole catalyst V at 0° C. only for 4.5 hours. The reaction scheme for this reaction is set forth in FIG. 13.

Mukaiyama-Michael Addition of Silyl Enol Ethers to Alpha Beta-Unsaturated Aldehydes to Produce 1,5-Dicarbonyl Compounds A great deal of effort in asymmetric organocatalysis has been directed towards a single reaction by using simple achiral molecules. However, much less attention has been paid to multistep, sequential reactions, which can produce more structurally diversified, polyfunctional molecules in a short, economical way.[147-149] Here we designed a novel sequential Mannich-type, tandem Mukaiyama aldol-cyclization reaction protocol which could result in highly stereoselective formation of α,β,γ-substituted adipic acids 8 and piperidinecarboxylic acid derivatives 9 (FIG. 13).[150] Specifically, we plan to employ our organocatalyst pyrrolidine trifluoromethanesulfonamide V for asymmetric Mannich-type reactions of α-imino esters with aldehydes to give enantioselective α-amino acid aldehydes 6 (the study that has been proposed in i of this section). The aldehydes 6 will serve as starting materials for reaction with a second aldehyde through a crossed aldol reaction. There are two challenging issues to be answered for the crossed aldol reaction, as mentioned previously. First, the nonequivalent aldehydes must selectively partition into two discrete components, a nulceophilic donor and an electrophilic acceptor, to achieve a good level of chemo-selectivity.[139] The second is how to control stereoselectivity of the reaction. We envision that a Lewis acid promoted Mukaiyama aldol reaction can provide a solution to both issues.[150-153] An enol silyl ether 7 derived from an ester or thioester serves as donor and an aldehyde containing Mannich-type reaction adduct 6 serves as acceptor. A Lewis acid such as $TiCl_4$ and $MgBr_2$ is used to (1) activate the carbonyl group of the aldehyde acceptor and (2) serve as a "chiral auxiliary" by coordination of the metal with the carbonyl group and amino group of the substrate to induce a chrial environment (FIG. 13).[154-156] Such a chiral complex (9) can only allow the enol to attack from the β-face of the aldehyde stereoselectively to give a product 8 with a newly formed (S) stereogenic center. The adduct ethyl ester 8 will undergo spontaneous intramolecular lactamization to furnish a cyclic product 10. The diastereoselectivity of the Mukaiyama aldol reaction will be determined by $^1$H NMR and the absolute configuration of the newly generated chiral center can be determined by converting the product to a known compound, (2S, 3S,4R)-3-ethyl-4-hydroxy-2-piperidinecarboxylic acid.[157] Once the optimal reaction conditions are established, the scope of the reaction between the aldehydes and enols will be evaluated to determine the generality of the reactions. It should be noted that the reaction can be applied in the synthesis of biologically important polyhydroxypiperidines.

Figure 14:
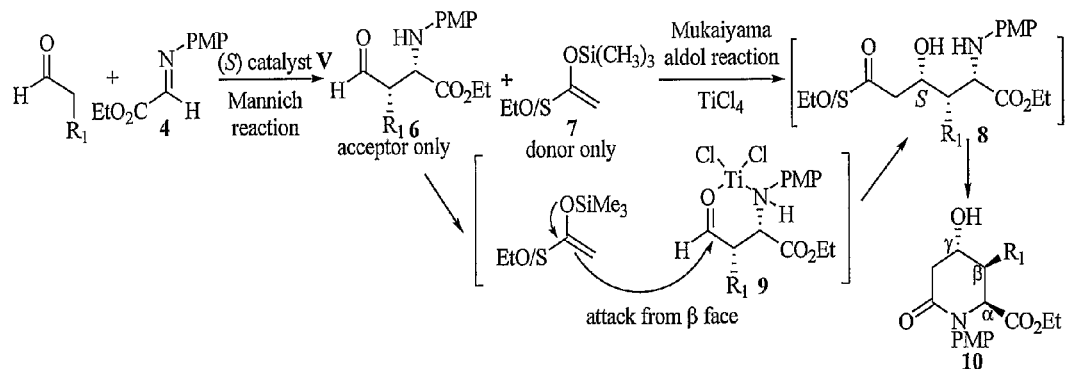
FIG. 14 shows a Mukaiyama Alcol-cyclization reaction.

Chiral pyrrolidine and pyrrolidinone derivatives have been shown to be effective organocatalysts for the asymmetric reactions.[7] Consequently, in initial exploratory efforts, directed at the development of chiral amine-catalyzed asymmetric Michael addition reactions, we screened five chiral pyrrolidines and pyrrolidinones (FIG. 14). These substances were used by ours and others as catalysts for the different versions of the Michael addition reactions.[5,8-10] Reaction of 1-phenyl-1-(trimethylsilylox)ethylene 1a with trans-cinnamaldehyde 2a and 20 mol % chiral imidazolidinone I in $CH_2Cl_2$ at room temperature (rt) in the presence of 2,4-dinitrobenzenesulfonic acid (DNBA) (20 mol %) proceeded very slowly in low yield (14%, 12 h) (Table 14, entry 1). A survey of solvents revealed that the reaction media had a significant effect on the rate of this process (Table 14, entries 1-5).[11] For example, the reactions carried out in i-PrOH and t-BuOH gave higher yields (58% and 55%, respectively, Table 1, entries 2 and 4). More importantly, reactions in these solvents were highly enantioselective (87% ee in t-BuOH and 76% ee in i-PrOH). The major enantiomer of product, 1,5-diketoaldehyde 3a, has the R configuration.[12] By lowing the temperature to 0° C. for reaction in i-PrOH, both the enantioselectivity (86% ee) and the yield (68%) were significantly improved (Table 14, entry 3). Optimization studies showed that a solvent system consisting of 5:1 (v/v) mixture of t-BuOH and i-PrOH at 0° C. was ideal for this process.

TABLE 15

The Results of Exploratory Studies of Catalytic Asymmetric Mukaiyama-Michael Addition Reactions of Silyl Enol Ether and trans-Cinnamaldehyde[a]

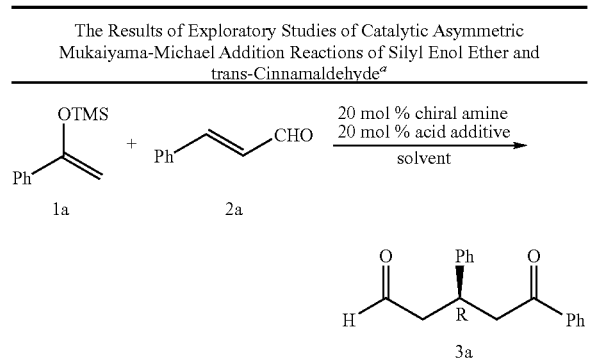

| entry | catalyst | Solvent | t (° C.) | yield (%)[b] | ee (%)[c] |
|---|---|---|---|---|---|
| 1 | I + DNBA | $CH_2Cl_2$ | rt | 14 | —[d] |
| 2 | I + DNBA | i-PrOH | rt | 58 | 76 |
| 3 | I + DNBA | i-PrOH | 0 | 68 | 86 |
| 4 | I + DNBA | i-PrOH | rt | 55 | 87 |
| 5 | I + DNBA | mixture[e] | 0 | 60 | 90 |
| 6 | I + HCl | mixture[e] | 0 | <10 | —[d] |
| 7 | I + TFA | mixture[e] | 0 | —[d] | —[d] |
| 8 | I + DNBA[f] | mixture[e] | 0 | 75 | 90 |
| 9 | II + DNBA | mixture[e] | 0 | 40 | 47 |
| 10 | III + DNBA | mixture[e] | 0 | 16 | 83[g] |
| 11 | IV + DNBA | mixture[e] | 0 | —[d] | —[d] |
| 12 | V + DNBA | mixture[e] | 0 | —[d] | —[d] |

[a]Unless otherwise specified, the reaction was carried out with 5 equiv. of 1a and 1 equiv. of 2a in the presence of 20 mol % chiral amine and acid (20 mol %) in 0.5 mL solvent at rt or 0° C. for 12 h.
[b]Isolated yield after chromatographic purification.
[c]Determined by chiral HPLC analysis (Chiralpak AS-H, hexane/2-propanol = 90:10).
[d]Not determined.
[e]a mixture of t-BuOH/i-PrOH (5:1 v/v) used.
[f]30 mol % I and 30 mol % DNBA used.
[g](S) Configuration.

An acid additive is required for this reaction, in which an aldiminium ion serves as a key intermediate.[5] Evaluation of three acids revealed that strong acids, such as HCl and TFA, caused decomposition of silyl ether 1a. In contrast, 1a tolerated DNBA (Table 15, entries 5-7), and subsequently the acid was used in further studies of this process.

Studies showed that the catalytic activities of five organocatalysts I-V, differed significantly (Table 15, entries 5 and 9-12). Under identical reaction conditions (0° C. in t-BuOH and i-PrOH (5/1, v/v) with DNBA), reaction of silylenol ether 1a with trans-cinnamaldehyde 2a catalyzed by I afforded adduct 3a with excellent enantioselectivity (90% ee) and good yield (60%, Table 15, entry 5). Moreover, increasing the loading of I up to 30 mol % significantly improves the yield of this reaction without sacrificing enantioselectivity (75% yield, 90% ee, entry 8). However, the reaction promoted by catalyst II, which has a similar structure to I, took place with a much lower enantioselectivity (47% ee, entry 9). Interestingly, a highly enantioselective reaction (83% ee, entry 10) occurred when our pyrrolidine trifluoromethanesulfonamide catalyst V was used, but, unfortunately the rate of this process was very low. L-Proline III and diamine IV did not serve to catalyze the formation of product 3a even after a 12 h period (entries 11-12).

Having established the optimal reaction conditions, we next probed the generality of this asymmetric catalytic variant of the Mukaiyama-Michael addition reaction with a variety of silyl ethers 1 and α,β-unsaturated aldehydes 2 (Table 16). The results showed that the reactions took place efficiently (56-87%) and high to excellent levels of enantioselectivity (85-97%) with all of the silyl enol ethers and unsaturated aldehyde were achieved. As revealed by inspecting the results given in Table 16, high to excellent enantioselectivities were obtained with silyl ethers that possess both electron-withdrawing (4-Br, Table 16, entry 2) and electron-donating substituents (4-Me and 4-MeO, Table 16, entries 3-4). It was noted that reactions with electron-withdrawing group substituted aldehydes tended to give lower enantioselectivities (e.g., 4-Br, 86% ee, entry 2), whereas those with electron-donating group substituted substrates (4-Me and 4-MeO, entries 3-4) proceeded with higher enantioselectivities (95 and 97% ee).

TABLE 16

Catalytic Asymmetric Mukaiyama-Michael Addition of Silyl Enol Ethers 1 to Unsaturated Aldehydes 2[a]

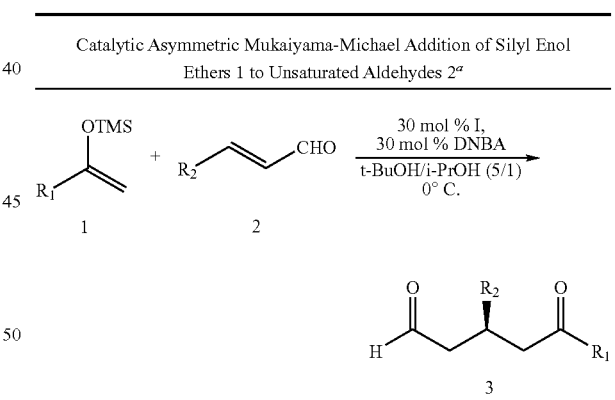

| Entry | $R_1$ | $R_2$ | yield (%)[b] | ee (%)[c] |
|---|---|---|---|---|
| 1 | Ph | Ph | 75 | 90 |
| 2 | 4-BrC$_6$H$_4$ | Ph | 58 | 86 |
| 3 | 4-MeC$_6$H$_4$ | Ph | 62 | 95 |
| 4 | 4-MeOC$_6$H$_4$ | Ph | 56 | 97 |
| 5[c] | 4-MeC$_6$H$_4$ | 4-FC$_6$H$_4$ | 71 | 92 |
| 6 | 4-MeOC$_6$H$_4$ | 4-FC$_6$H$_4$ | 63 | 95 |
| 7* | Ph | 4-CNC$_6$H$_4$ | 59 | 90 |
| 8 | 4-MeOC$_6$H$_4$ | 4-CNC$_6$H$_4$ | 61 | 94 |
| 9 | 4-MeOC$_6$H$_4$ | 4-MeOC$_6$H$_4$ | 63 | 90 |
| 10 | 4-MeC$_6$H$_4$ | Me | 60 | 87 |

TABLE 16-continued

Catalytic Asymmetric Mukaiyama-Michael Addition of Silyl Enol Ethers 1 to Unsaturated Aldehydes 2[a]

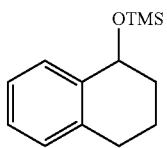

| Entry | $R_1$ | $R_2$ | yield (%)[b] | ee (%)[c] |
|---|---|---|---|---|
| 11[d,e] | ![OTMS-tetralone] OTMS | Ph | 87 | 85 |

[a]See footnote in Table 1.
[b]Isolated yield after chromatographic purification.
[c]Determined by chiral HPLC analysis (Chiralpak AS-H or Chialcel OJ-H).
[d]Reaction run at –20° C.
[e]dr determined by $^1$H NMR.

Significant structural variation in the α,β-unsaturated aldehydes was tolerated in this reaction, which occurred efficiently independent of the nature of substituents on the phenyl ring (Table 15, entries 5-9, 59-71% yields, 90-95% ee). In all cases, excellent levels (≧90% ee) of enantioselectivity were observed. Moreover, based on preliminary results, it appeared that catalytic process was applicable to β-alkyl substituted α,β-unsaturated aldehydes (e.g., acerloin) and cyclic (e.g., tetralone) silylenol ethers (entries 10 and 11, 60% yield, 87% ee and 87% yield and 85% ee, respectively). In the latter case, two stereogenic centers were produced in the reaction with high enantioselectivity (85% ee) and diastereoselectivity (30:1 dr) (Table 15, entry 11).[13]

In summary, we have developed a catalytic variant of the asymmetric Mukaiyama-Michael addition reaction between silyl enol ethers and α,β-unsaturated aldehydes. The reactions are effectively catalyzed by the organocatalyst I, affording synthetically useful 1,5-dicarbonyl compounds in high yields and high to excellent levels of enantioselectivity.

Synthesis of Useful Building Blocks, Biologically Active Compounds, and Natural Products.

An important goal in organic synthesis is to develop efficient synthetic methods and apply them for the preparation of biologically useful molecules. Accordingly, having demonstrated the feasibility of the above-described organocatalytic asymmetric transformations, we propose to prepare a variety of structure-diversified molecules including useful building blocks, biologically active compounds, and natural products. In the application, we will demonstrate that the utility of these transformations, which can be used to produce optically pure, complex molecules in a very efficient, practical way from simple starting materials and in a highly stereocontrolled fashion. The synthetic targets we are interested in include chiral pyrrolidine derivatives and natural products, which have been shown to possess a broad spectrum of structural diversities and biological activities, and chiral amino alcohols, which are important moieties in a number of biologically active molecules and natural products with a variety of biological interests.

1. Michael addition reactions employed for asymmetric synthesis of: (i) a potent $H_3$ agonist Sch 50971; (ii) novel conformationally rigid γ-aminobutyric acid (GABA) analogues; (iii) CCR5 antagonists as anti-HIV agents; (iv) Ro 15-8081, a potent dual analgesic-antidepressant agent; (v) the "privileged" structure benzopyrano[3,4-c]pyrrole scaffold; and (vi) natural products montanine-type Amaryllidaceae alkaloids.

(i) Two-Step Synthesis of Sch 50971.

Figure 16:
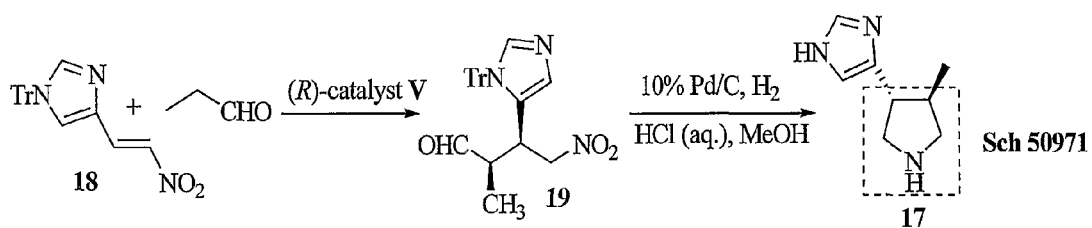
FIGS. 16-24 show the synthesis of a number of intermediates or final products which utilize organocatalysts according to the present invention.

The potent $H_3$ agonist Sch 50971 (17) has been identified with potential use for the treatment of a variety of diseases including obesity, Alzheimer's disease, and attention deficient/hyperactivity (FIG. 16).[165-169] This compound was prepared by applying Evan's auxiliary controlled Michael addition as a key step.[165] However, only 88% de was achieved and therefore an additional crystallization was needed in order to get a more optical pure material. We believe that the (R) organocatalyst V can be used to catalyze the asymmetric Michael addition reaction of nitroolefin 18 to propionaldehyde, with high enantio- and diastereoselectivities and thus provide optically pure key intermediate 19 (FIG. 16). Using a known synthetic sequence we developed, Sch 50971 can be produced from 19 in a one-pot, 3-step reaction. [170] In the transformation, reduction of the nitro group in 19 by hydrogenation in the presence of 10% Pd/C in a mixture of HCl aqueous solution and MeOH will give an amine, which then reacts with the aldehyde group to form an enamine with the formation of a five membered ring.[170] Finally, the generating enamine will be reduced in situ by Pd-catalyzed hydrogenation and afford the final product pyrrolidine Sch 50971 (17) in a HCl salt form.

(ii) Three-Step Synthesis of Novel Conformationally Rigid γ-Aminobutyric Acid (GABA) Analogues.

Figure 17:
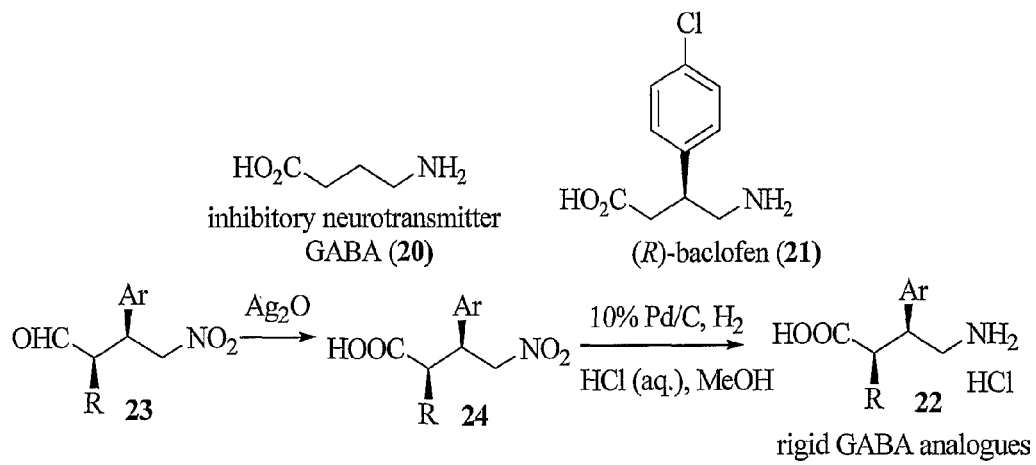

GABA (20) is an inhibitory neurotransmitter in the central nervous system and it operates through ionotropic ($GABA_A$ and $GABA_C$) as well as G protein-coupled ($GABA_B$) receptors.[171, 172] Its analogues have been designed for elucidating the biological functions of GABA receptors and serving as therapeutic agents for the treatment of neurodegenerative diseases. (R)-Baclofen (21) is the only clinically useful selective $GABA_B$ agonist (FIG. 17).[173] There is a tremendous biological and therapeutic interest in developing selective agonists, partial agonists, and antagonists for these receptors.[174] Toward this end, we plan to design novel conformationally rigid GABA analogues 22 using GABA as a lead compound. We propose to introduce functional groups at the α and β positions of GABA. Such modifications would constrain their conformation and could result in selective and potent ligands with preference for binding to GABA receptors. Organic synthesis is of primary importance in this work since these compounds possess two chiral centers. We envision that the novel GABA analogues can be efficiently synthesized in 3 steps, as illustrated in FIG. 17. The key step is the highly stereo-controlled asymmetric Michael addition reactions of aldehydes to trans-β-nitrostyrenes to give the intermediates 23 in a complete stereocontrol. Transformation of the aldehyde 23 to a carboxylic acid 24 by $Ag_2O$ mediated oxidation and the nitro group to an amine by Pd-catalyzed hydrogenation will furnish the final products 22. Their biological activities and selectivities to GABA receptors will be evaluated.

(iii) Synthesis of CCR5 Antagonists as Potent Anti-HIV Agents.

Figure 18:
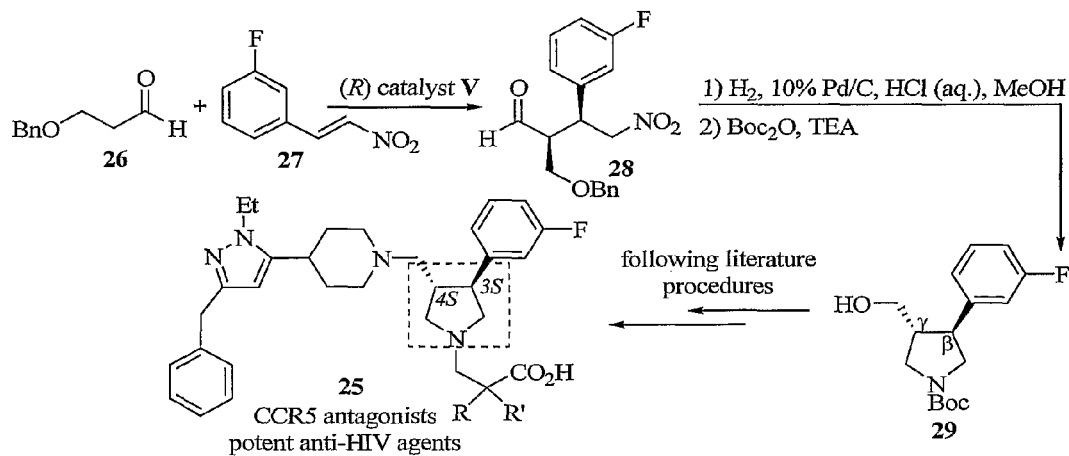

Recently, scientists in Merck have identified 3-(pyrrolodin-1-yl)propionic acid derivatives 25 as novel potent CCR5 antagonists, which can be developed as new anti-HIV agents (FIG. 18).[175-178] In addition to their high pharmacological activities, they also have favorable pharmacokinetics such as good bioavailability and low clearance rates. As a result, this new type of promising compounds will attract considerable synthetic interest in developing a facile, stereoselective synthetic route for their preparation. The key for their synthesis is how to effectively construct the β,γ-substituted pyrrolidine core 29, which consist of two chiral centers with absolute (3S, 4S) configurations. As reported in the literature, the optically pure compound was obtained by using a chiral auxiliary-based resolution.[178] We propose that the organocatalytic asymmetric Michael addition reaction of aldehydes to β-nitrostyrenes as a key step can provide the pyrrolidine core in three steps in a highly stereo-controlled manner (FIG. 18). Asymmetric Michael addition of aldehyde 26 to m-fluoro-β-nitrostyrene 27 in the presence of (R) organocatalyst pyrrolidine trifluoromethanesulfonamide V should afford product aldehyde 28 in high enantio- and diastereoselectivity with high yields. Conversion of nitro aldehyde 28 to a cyclic pyrrolidine 29 in a one-pot reaction will be straightforward by using the established procedures.[170] Protection of the amino group by Boc will provide the key intermediate 29, which can serve as a starting material for preparation of the CCR5 antagonist by following the literature procedures. [178]

(iv) Synthesis of Ro 15-8081, a Potent Dual Analgesic-Antidepressant.

Ro 15-8081 (30), developed by Roche, is a potent dual analgesic-antidepressant agent that inhibits the re-uptake of norepinephrine and of serotonin. It currently is in clinical trials (FIG. 19).[179, 180] A lengthy racemic synthesis has been described.[181, 182] To our knowledge, no study has been reported for its asymmetric preparation so far. However, the synthesis of optically active Ro 15-8081 is considerable challenging since it possesses 3 chiral centers and multiple functional groups.

Figure 19:
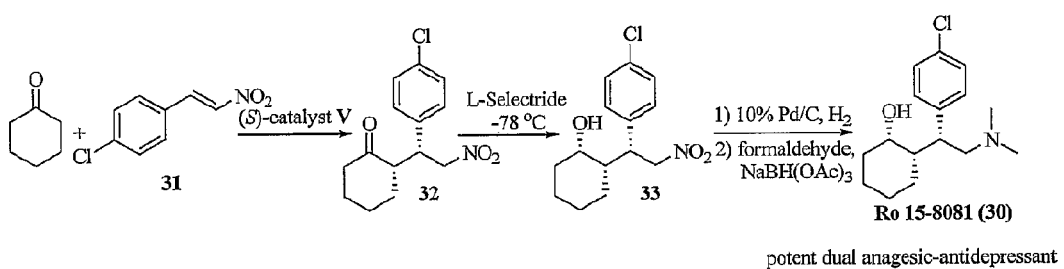

We propose a 4-step synthetic route to construct this molecule (FIG. 19). The key step is the (S) organocatalyst I promoted, asymmetric Michael addition reaction of cyclohexanone with trans-4-chloro-β-nitrostyrene 31. It is expected that by using the highly stereoselective Michael addition, adduct 32 can be formed. Facially selective reduction of the ketone by L-Selectride should give the alcohol 33 with absolute (S) configuration as a product.[81] Finally, reduction of the nitro group by Pd-catalyzed hydrogenation and then reductive amination with formaldehyde using NaBH(OAc)$_3$ as a reducing agent should afford Ro 15-8081 (30) in high yield.

(v) Synthesis of the "Privileged" Structure Benzopyrano[3,4-c]pyrrole Scaffold.

The tricyclic benzopyrano[3,4-c]pyrrole scaffold 35 is considered a "privileged" structure, where the attachment of different functional groups have led to a variety of biologically active molecules towards different targets (FIG. 20). [183-188] These benzopyrano[3,4-c]pyrrole derivatives 36 have shown high potency and selectivity as antagonists for dopamine $D_{3f}$[183] and α-1 adreno receptors,[184, 185] as dual α2/5-HT2c antagonists,[186] as dual $α_vβ_3/α_vβ_5$ integrin antagonists[187], and as selective protein kinase C (PKC) inhibitors.[188] Therefore, these compounds have paramount potentials to serve as effective tools for elucidating biological functions of the neurotransmitter receptors, integrins and PKC, and develop as drugs for the treatment of central nervous system disorders (CNS) disorders, such as Parkinson's disease, obesity, cognition disorder, anxiety depression, psychosis, schizophrenia, sleep disorders, sexual disorders, migraine, conditions associate with cephalic pain, and social phobias.[183-188] In addition, they can also potentially serve as potent agents for the treatment of benign prostatic hyperplasia, bladder outlet obstruction, neurogenic bladder, uterine smooth muscle contraction, as well as cancers.[183-188] As a result, their broad spectrum of therapeutic applications demand an efficient approach to their synthesis. Although several methods have been developed, they lack synthetic efficiency and give poor stereoselectivity.[183-188] It is realized that the synthesis of the benzopyrano[3,4-c]pyrrole structure is of considerable synthetic challenge since it possesses two chiral centers in the fused tricyclic system with multiple functionalities.

Figure 20:
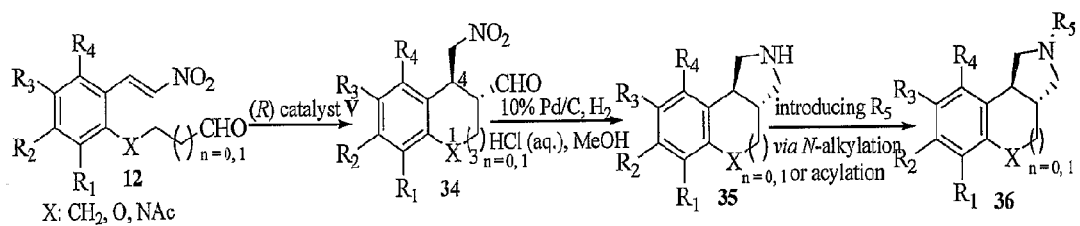

We propose an intramolecular asymmetric Michael conjugation reaction, which can lead to a simple, 2-step synthesis of the tricyclic benzopyrano[3,4-c]pyrrole scaffold 35 from trans-β-nitrostyrene aldehydes 12 (FIG. 20). This method can allow for building the two chiral centers at the same time, catalyzed by the (R) organocatalyst I. In the study of the intramolecular Michael addition reaction, we will demonstrate the feasibility of this methodology (see the proposed study in Specific Aim 2). (R) pyrrolidine trifluoromethanesulfonamide V should provide the product 34 with two newly formed stereogenic centers (3R, 4S) in a complete stereocontrol, whereas employing (S)-V, its enantiomers can be accessed selectively as well with the formation of a five or six-membered ring. Under the same reaction conditions used previously, a one pot reaction using the Pd-catalyzed hydrogenation can afford the pyrrolidines 35, which will be employed for introducing the $R_5$ moieties through N-alkylation or acylation to give the target molecules 36.

(vi) Synthesis of the Key Intermediate 37, which can Lead to the Total Synthesis of Montanine Alkaloids.

Figure 21:
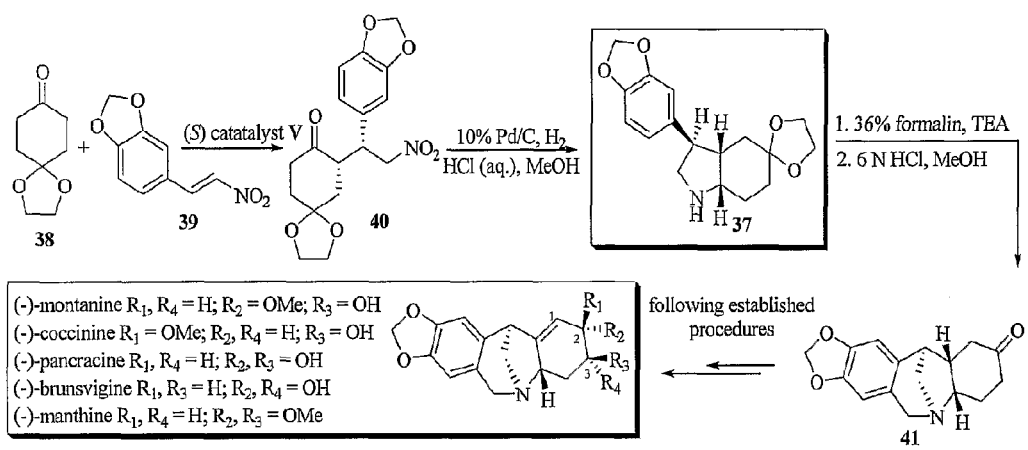

The montanine-type alkaloids belong to a subclass of Amaryllidaceae alkaloids that share the core structural feature of the 5,11-methanomorphantridine ring system and differ primarily in the configurations of stereocenters and the type of oxygen substitution patterns at C-2 and C-3 (FIG. 21).[189-192] Because of their unique pentacyclic ring structure and promising pharmacological potentials, these alkaloids have attracted tremendous synthetic interests. Hoshino et al. reported the first total synthesis of racemic montanine, coccinine, pancracine, brunsvigine, and O-acetylmontanine, using reductive cyclization as a key step to assemble the pentacyclic unit.[193-196] Overman and Shim developed an elegant total synthesis of racemic pancracine employing an aza-Cope rearrangement and Mannich cyclization.[197, 198] Weinreb and Jin reported an enantioselective synthesis of (−)-coccinine and (−)-pancracine via a concerted ene reaction of allenylsilane imines.[199] Total synthesis of (+)-coccinine, a nonnatural enantiomer of (−)-coccinine was reported by Pearson and Lian who undertook cycloaddition of a 2-azaallyl anion.[200] Sha and co-workers reported the first total synthesis of (−)-brunsvigine via anionic cyclization of the Weinreb amide intermediate as a key step.[201] Ikeda et al. reported a formal total synthesis of racemic pancracine based on α-carbonyl radical cyclization.[202, 203] In this approach, the key intermediate 37 was prepared in 9 steps.[202, 203] We envision that the same intermediate 37 can be synthesized in only 2 steps from readily available starting materials by using (S) organocatalyst I catalyzed asymmetric Michael addition reaction as a key step (FIG. 21). The synthetic entry to the 5,11-methanomorphantridine skeleton, which can finally lead to the synthesis of these Amaryllidaceae alkaloids, is remarkably concise and fully stereocontrolled.

The proposed two-step synthesis of the intermediate 37 is described in FIG. 21. The synthesis starts from both commercially available starting materials 1,4-cyclohexanedione mono-ethylene ketal 38 and 3,4-methylenedioxy-trans-β-nitrostyrene 39. Asymmetric Michael addition reaction between these two substances is carried out in the presence of 20 mol % (S) pyrrolidine trifluoromethanesulfonamide V. This reaction affords the adduct 40 with a complete (R, R)-stereocontrol because a model study has demonstrated that an excellent level of enantio- (97% ee) and diastereoselectivity (50:1 dr) and high yield (96%) of the reaction between cyclohexanone and trans-β-nitrostyrene has been achieved. With this compound 40 in hand, conversion to the pyrrolidine stereoselectively by a one-pot reaction will produce the key intermediate 37. The one-pot reaction, which has been developed previously, will be applied for the formation of the pyrrolidine ring 37. The nitro group can be reduced to amine by Pd-catalyzed hydrogenation, and then intramolecular cyclization of the carbonyl group with the amine will give an enamine. The resulting enamine can be facial selectively reduced to an amine by hydrogenation from less the hindered α-face to give 37. Following the established procedures,[202] compound 37 is subjected to the Pictet-Spengler cyclization to give 41, with concomitant deprotection of the ethylene acetal. The syntheses of (−)-pancracine, (−)montaine, and (−)coccinine can be accomplished by following literature procedures since compound 41 has already been converted to these alkaloids but in a racemic form.[203]

2. Mannich-type reaction applied for asymmetric synthesis of (i) (+) polyoxamic acid (42), the key component of natural products polyoxins and (ii) an amino lactone 46 that will lead to the total synthesis of natural products (−)-funebrine and (−)-funebral.

(i) Synthesis of (+) Polyoxamic Acid 42, the Key Component of Natural Products Polyoxins.

Figure 22:
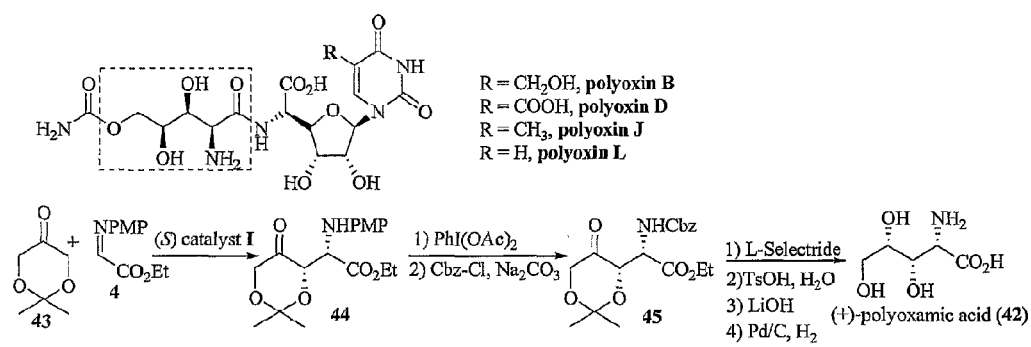

Polyoxins are a group of peptidyl nucleoside antibiotics isolated from the culture broth of *Streptomyces cacoi* (FIG. 22).[204] The characteristic structural features of polyoxins include a unique ribofuranosyl α-amino acid nucleoside and polyoxamic acid 42 and they are connected through an amide linkage. The members of the polyoxin family differ from each other in the substitution on the pyrimidine bases (FIG. 22). They are potent chitin synthase (CS) inhibitors and therefore can prevent the biosynthesis of chitin, an essential component of the fungal cell wall structure.[205, 206] Because CS is absent in mammals, the inhibition of CS by polyoxins has been recognized as a promising strategy for the development of antifungal therapeutics. Consequently, the syntheses of these molecules and their analogues are of great synthetic and biological interests.[204] In the total synthesis of polyoxins, [207-209] the preparation of the component (+)-polyoxamic acid 42 presents a considerable synthetic challenge due to the presence of three consecutive stereogenic centers. Several synthetic approaches to the amino acid 42 have been reported, but long, tedious sequences are required.[210-218]

In the course of the study directed toward the development of stereoselective Mannich-type reactions of ketones with α-imino esters, we have described conditions, where excellent enantio- and diastereoselectivities have been achieved. [48] This method can be employed to the synthesis of enantiomerically pure polyoxamic acid 42 in 6 steps from readily available starting materials (FIG. 22). The key step is the asymmetric Mannich-type reaction of 1,3-bis-benzyloxy-propan-2-one 43 with α-imino ethyl ester 4. It is expected that high stereoselectivity can be obtained in the simultaneous creation of two adjacent stereogenic centers with the desired absolute (S, S) configuration in 44. Facile oxidative deprotection of the MPM group by PhI(OAc)$_2$ [219] and in situ reprotection of amino group by Cbz give product 45. The facially selective reduction of ketone group in 45 by using the bulky reducing reagent L-Selectride should afford a new (S) stereogenic center with high diastereoselectivity, because L-Selectride can only attack from less hindered β-face.[81] Finally, removing the protecting groups ketals, ethyl ester, and Cbz will provide the final product (+)-polyoxamic acid (42).

(ii) Synthesis of Amino Lactone 46 That Will Lead to the Total Synthesis of Natural Products (−)-Funebrine and (−)-Funebral.

Figure 23:
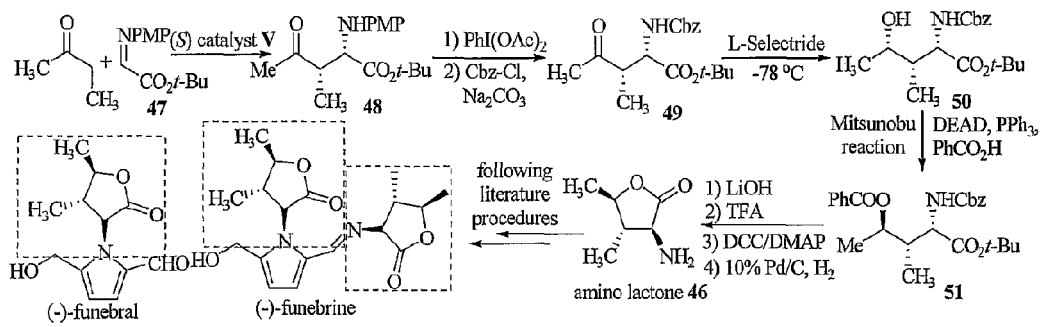

Using a similar synthetic strategy, the key component amino lactone 46 in the natural products (−)-funebrine and (−)-funebral can be synthesized efficiently (FIG. 23). (−)-Funebrine and (−)-funebral were first isolated from fragrant flowers of Quarabribea funebris in 1986.[220] They consist of a unique pyrrole moiety with one or two amino lactones 46 attached. Their unique structural features and wide range of biological activities, recently have attracted synthetic interests in their syntheses.[221-223] We anticipate that the asymmetric Mannich-type reaction can serve as an efficient and key step for the preparation of the amino lactone 46, which will finally lead to the synthesis of these two structurally related natural products. The (S) pyrrolidine sulfonamide V that promotes the Mannich-type reaction of 2-butanone with α-imino t-butyl ester 47 should result in highly stereoselective product 48. Conversion to a Cbz protected amino group can be achieved by oxidation and protection using the same procedures developed earlier. It should be noted that, in this case, the carboxyl group is protected as a t-butyl ester instead of ethyl ester because the t-butyl ester can prevent the lactonization when the carbonyl group is reduced by L-Selectride to an alcohol 50. Inversion of (S) to the desired (R) configuration for the hydroxyl group in 50 can be achieved via an Mitsunobu reaction.[224] Deprotection of the benzoyl group by LiOH-catalyzed hydrolysis and the t-butyl group by TFA gives a hydroxy acid, which undergoes an intramolecular lactonization by treatment with DCC in the presence of catalytic amount of DMAP. Removal of the Cbz group by Pd-catalyzed hydrogenation provides the amino lactone 46. With the lactone 46 in hand, the synthesis of (−)-funebrine and (−)-funebral is straightforward following the literature procedures.[221]

3. Sequential Mannich-Type, Tandem Mukaiyama Adol-Cyclization Reactions: Three-Step Synthesis of Azasugars.

Because of their ability to mimic sugars and to competitively and selectively inhibit glycosidases and glycotransferases, polyhydroxylated piperidines (azasugars) and their synthetic analogues have attracted a great deal of attention in recent years (FIG. 24).[225-227] They have tremendous potential as mechanistic probes and chemotherapeutic agents for a widening number of disease such as diabetes, cancer, AIDS, hepatitis, Gaucher's disease and influenza.[225, 228] Included among the natural product azasugars, which are highly potent inhibitors of glycosidase, are 1-deoxygalactstatin (52),[229] and isogalactofagomine (53)(FIG. 24).[230, 231] Their biological and therapeutic importance has attracted considerable synthetic interest.[226, 232-240] However, most of the reported methodologies are lengthy and poorly stereoselective. Here we propose a 3-step approach, which can result in their synthesis highly enantioselectively. With the demonstration of the novel Mannich-type, tandem Mukaiyama aldol-cyclization reactions (see the proposed work in Specific Aim 2), we plan to employ the reaction for the preparation of azasugars (52, 53) and their analogues 54, 55 from simple starting materials (FIG. 25). In the proposed synthesis, the first step is the highly stereoselective (S) pyrrolidine sulfonamide I promoted Mannich-type reaction of aldehyde 56 and α-imino ester 4, which will produce amino ester 57 with formation of two (S, S) chiral centers. Then Lewis acid (TiCl$_4$)-mediated Mukaiyama aldol reaction with 58, followed by a spontaneous cyclization and reduction will form an azasugar.

Figure 24:
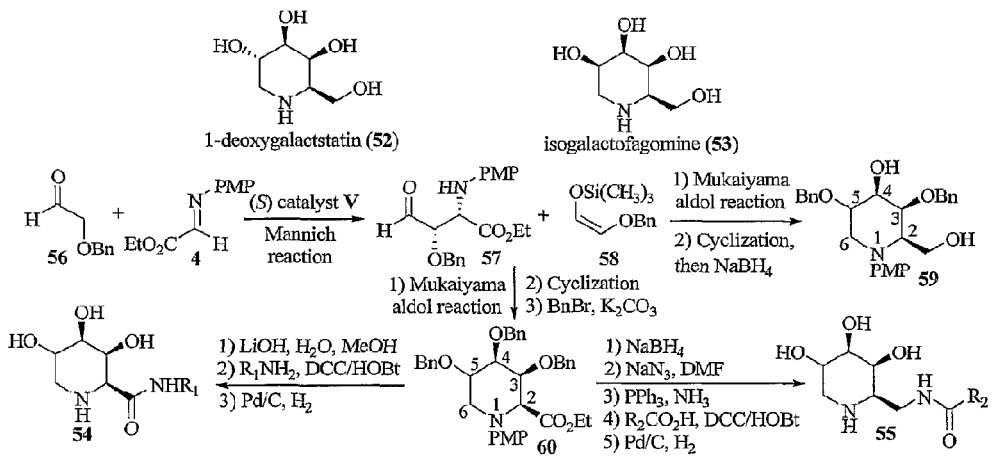

It is expected that during these transformations, the stereochemistry at position 4 in 59 and 60 should be fully controlled by the chiral Lewis acid-amino acid aldehyde complex.[241] Other Lewis acids such as MgBr$_2$ and solvents will be examined as well since recent studies have shown that these factors have a significant effect on the sterereoslectivity. [241] Using this approach, natural products 1-deoxygalactstatin (52), and isogalactofagomine (53) could be prepared from 59 by deprotection of Bn (PhCH$_2$) and PMP (p-MeOC$_6$H$_4$) groups. The stereochemistry in position 5 will be determined by $^1$H NMR comparison with the corresponding spectroscopy data for 1-deoxygalactostatin (52), and isogalactofagomine (53). We are also interested in extending the methodology to the synthesis of their analogues 54, 55 (FIG. 24). In these analogues, the focus of this effort will be placed on the modification of position 2 with incorporation of amines or carboxylic acids through amides.[235]

The following examples are provided to further describe the present invention. The examples are meant to provide context to the present invention and are not meant to limit the invention in any way.

EXAMPLES

α-Aminoxylation Reactions

General Information: Commercial chemicals and reagents were used as received, unless otherwise stated. Burdick & Jackson HPLC grade hexane and i-propanol were used for HPLC analysis. Merck 60 silica gel was used for column chromatography, and Whatman silica gel plates with fluorescence F$_{254}$ were used for thin-layer chromatography (TLC) analysis. $^1$H and $^{13}$C NMR spectra were recorded on the Broker Advance 500 and tetramethylsilane (TMS) was used as a reference. Data for $^1$H are reported as follows: chemical shift in ppm and multiplicity (s=singlet, d=doublet, t=triplet, q=quartet, m=multiplet). Data for $^{13}$C NMR are reported as ppm. Mass Spectra were obtained from the University of Arizona Mass Spectra Facility. High performance liquid chromatography (HPLC) was performed on Shimadzu SCL-10A VP chromatographs using Chiralpak AD and Chiralpak AS-H columns.

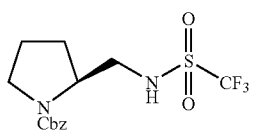

(S)-2-(trifluoro methane sulfonylamino methyl)-1-N-Cbz-pyrrolidine. To a solution of (S)-2-Aminomethyl-1-N-Cbz-pyrrolidine (2.0 g, 8.55 mmol) and TEA (1.43 mL, 10.3 mmol) in 40 mL of CaH$_2$ dried CH$_2$Cl$_2$ was added trifluoromethanesulfonic anhydride (1.6 mL, 9.4 mmol) dropwisely by a syringe pump over 1 h at 0° C. under N$_2$. The resulting solution was stirred for 4.5 h at rt, then diluted with 80 mL of CH$_2$Cl$_2$ and washed with 50 mL of 1N HCl aqueous solution. The organic layer was dried over MgSO$_4$, and concentrated in vacuo. Flash chromatography (Ethyl Acetate/Hexane=1/7) afforded a colorless oil in 76% yield (2.38 g, 6.50 mmol). [α]$_D$ −27.7 (c 1.0, CHCl$_3$); $^1$H NMR (500 MHz, CDCl$_3$): δ 7.68 (s, 1H), 7.10-7.39 (m, 5H), 5.15 (q, 2H), 3.98-4.09 (m, 1H), 3.24-3.57 (m, 4H), 2.12 (m, 1H), 1.88 (m, 2H), 1.67 (m, 1H); $^{13}$C NMR (125 MHz, CDCl$_3$): δ 157.7, 136.2, 128.8, 128.6, 128.5, 128.3, 68.0, 58.1, 49.9, 47.5, 30.0, 24.1. HRMS (FAB) calcd for C$_{14}$H$_{18}$F$_3$N$_2$O$_4$S (M+1) m/z 367.0939. Found 367.0928.

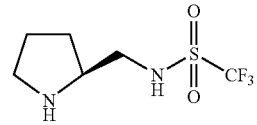

(S)-2-(trifluoro methane sulfonylamino methyl)-pyrrolidine. (Catalyst V) A solution of (S)-2-(trifluoromethane sulfonylamino methyl)-1-N-Cbz-pyrrolidine (0.794 g, 2.17 mmol) in 15 mL MeOH was hydrogenated in the presence of 10% Pd/C (0.16 g) with a H$_2$ balloon at rt for 5 h. The catalyst was filtered through a pad of celite and washed with 2×20 mL of MeOH. The filtrate was concentrated in vacuo to give a white solid (>95% purity) in 93% yield (0.469 g, 2.02 mmol). The product was recrystallized in MeOH to give a crystal, which was used for catalyzing reactions. [α]$_D$ +10.5 (c 1.0, CH$_3$OH); $^1$H NMR (500 MHz, CD$_3$OD): δ 3.47 (m, 1H), 3.08-3.28 (m, 4H), 1.86-2.02 (m, 3H), 1.61-1.68 (m, 1H); $^{13}$C NMR (125 MHz, CD$_3$OD): δ 123.5 (q, J=325 Hz), 122.2, 63.7, 46.4, 28.5, 24.7. HRMS (FAB) calcd for C$_6$H$_{12}$F$_3$N$_2$O$_2$S (M+1) m/z 233.0572. Found 233.0580.

General Procedure for α-Aminoxylation of Aldehyde: To a vial containing aldehyde (0.261 mmol), catalyst V (0.043 mmol) and 0.5 mL of anhydrous DMSO was added a solution of nitrosobenzene (0.217 mmol) in 0.5 mL of anhydrous DMSO by syringe pump over 30-60 min at room temperature. The mixture was vigorously stirred for another 30 min after addition. The endpoint of the reaction was monitored by TLC and the color change from light blue to orange generally. The reaction mixture was then poured into a suspension of NaBH$_4$ (0.868 mmol) in 0.3 mL of anhydrous ethanol. After 45 min, the reaction was treated with brine (5 mL), then the solution was extracted with ethyl acetate (3×5 mL). The combined extracts were dried over MgSO$_4$, filtered, and concentrated in vacuo. The resulting residue was then purified by silica gel chromatography and fractions were collected and concentrated in vacuo to provide the product. The enantioselectivity was determined by chiral HPLC analysis.

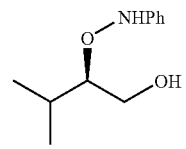

(R)-3-Methyl-2-(N-phenyl-aminooxy)-butan-1-ol (3e). This follows the procedure of Zhong, G. Angew. Chem., Int. Engl. 2003, 42, 4247. Prepared according to the general procedure from isovaleraldehyde (28 μL, 0.26 mmol) for 1.5 h to provide the title compound as a slightly yellow oil (34 mg, 81% yield) after silica gel chromatography (EtOAc/Hexane=1/8.5). $^1$H NMR (500 MHz, CDCl$_3$): δ 7.27 (m, 2H), 6.98 (m, 3H), 3.87 (m, 2H), 3.75 (m, 1H), 2.03 (m, 1H), 1.04 (d, 3H, J=6.5 Hz), 1.00 (d, 3H, J=6.5 Hz); $^{13}$C NMR (125 MHz, CDCl$_3$): δ 148.5, 129.3, 122.9, 115.3, 88.9, 64.1, 29.0, 18.9, 18.8; HPLC (Chirapak AD, i-Propanol/Hexane=4/96, flow rate 1.0 mL/min, λ=254 nm): t$_{minor}$=15.6 min,

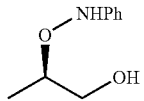

(R)-2-(N-Phenyl-aminooxy)-propan-1-ol (3f): Prepared according to the general procedure from propionaldehyde (19 μL, 0.262 mmol) for 2.0 h to provide the title compound as a slightly yellow oil (24 mg, 66% yield) after silica gel chromatography (EtOAc/Hexane=1/7.5). $^1$H NMR (500 MHz, CDCl$_3$): δ 7.27 (m, 2H), 6.98 (m, 3H), 4.14 (m, 1H), 3.75 (m, 2H), 1.26 (d, 3H, J=6.5 Hz); $^{13}$C NMR (125 MHz, CDCl$_3$): δ 148.7, 129.3, 122.7, 114.9, 80.3, 66.8, 15.6; HPLC (Chirapak AD, i-Propanol/Hexane=4/96, flow rate 1.0 mL/min, λ=254 nm): $t_{minor}$=21.90 min, $t_{major}$=25.09 min, [α]$_D$=+26.0 (c=0.4, CHCl$_3$), ee>99% HRMS (FAB) calcd for C$_9$H$_{13}$NO$_2$ m/z 167.0946. Found 167.0943.

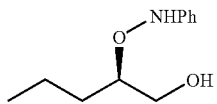

(R)-2-(N-Phenyl-aminooxy)-pentan-1-ol (3 g): Prepared according to the general procedure from valeraldehyde (30 μL, 0.261 mmol) for 1.5 h to provide the title compound as a slightly yellow oil (31 mg, 73% yield) after silica gel chromatography (EtOAc/Hexane=1/8.5). $^1$H NMR (500 MHz, CDCl$_3$): δ 7.28 (m, 2H), 7.00 (m, 3H), 3.98 (m, 1H), 3.86 (dd, 1H, J=12.0, 2.5 Hz), 3.78 (dd, 1H, J=12.0, 6.5 Hz), 1.75-1.4 (m, 4H), 0.97 (t, 3H, J=6.2 Hz); $^{13}$C NMR (125 MHz, CDCl$_3$): δ 148.5, 129.3, 122.8, 115.1, 84.0, 65.8, 32.3, 19.3, 14.5; HPLC (Chirapak AD, i-Propanol/Hexane=4/96, flow rate 1.0 mL/min, λ=254 nm): $t_{minor}$=18.5 min, $t_{major}$=20.8 min, [α]$_D$=+31.4 (c=0.5, CHCl$_3$), ee>99%. HRMS (FAB) calcd for C$_{11}$H$_{18}$NO$_2$ m/z 196.1338 (M+1). Found 196.1340.

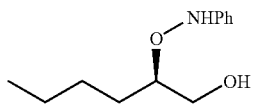

(R)-2-(N-Phenyl-aminooxy)-hexan-1-ol (3h): Prepared according to the general procedure from hexanal (32 μL, 0.262 mmol) for 2.0 h to provide the title compound as a slightly yellow oil (33 mg, 74% yield) after silica gel chromatography (EtOAc/Hexane=1/9). $^1$H NMR (500 MHz, CDCl$_3$): δ 7.28 (m, 2H), 7.01 (m, 3H), 3.98 (m, 1H), 3.86 (dd, 1H, J=12.0, 2.5 Hz), 3.78 (dd, 1H, J=12.0, 6.5 Hz), 1.75-1.20 (m, 6H), 0.92 (t, 3H, J=7.0 Hz); $^{13}$C NMR (125 MHz, CDCl$_3$): δ 148.6, 129.3, 122.8, 115.2, 84.2, 65.8, 29.9, 28.1, 23.0, 14.2; HPLC (Chirapak AD, i-Propanol/Hexane=4/96, flow rate 1.0 mL/min, λ=254 nm): $t_{minor}$=16.7 min, $t_{major}$=20.1 mm, [α]$_D$=+26.0 (c=0.5, CHCl$_3$), ee>99%. HRMS (FAB) calcd for C$_{12}$H$_{19}$NO$_2$ m/z 209.1416. Found 209.1416.

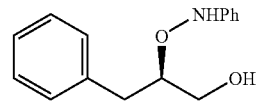

(R)-3-Phenyl-2-(N-phenyl-aminooxy)-propan-1-ol (3i): Prepared according to the general procedure from hydrocinnamaldehyde (35 μL, 0.261 mmol) for 2.0 h to provide the title compound as a slightly yellow oil (44 mg, 79% yield) after silica gel chromatography (EtOAc/Hexane=1/8.5). $^1$H NMR (500 MHz, CDCl$_3$): δ 7.33-7.18 (m, 7H), 7.03 (t, 1H, J=7.0 Hz), 6.87 (d, 2H, J=8.0 Hz), 4.17 (m, 1H), 3.87 (dd, 1H, J=12.0, 2.5 Hz), 3.75 (dd, 1H, J=12.0, 5.5 Hz), 3.06 (dd, 1H, J=13.8, 7.0 Hz), 2.84 (dd, 1H, J=13.8, 7.0 Hz); $^{13}$C NMR (125 MHz, CDCl$_3$): δ 148.5, 138.0, 129.3, 128.9, 128.7, 126.7, 122.7, 115.0, 85.2, 64.6, 36.7; HPLC (Chirapak AD, i-Propanol/Hexane=4/96, flow rate 1.0 mL/min, λ=254 nm): $t_{minor}$=31.8 min, $t_{major}$=42.7 min, [α]$_D$=+39.1 (c=0.5, CHCl$_3$), ee>99%.

General Procedure for α-Aminoxylation of Ketone: To a vial containing ketone (0.43 mmol), catalyst V (0.043 mmol) and 0.5 mL of anhydrous DMSO was added a solution of nitrosobenzene (0.215 mmol) in 0.5 mL of anhydrous DMSO by syringe pump over 10-60 min at room temperature. After 0.25-2.0 h of vigorous stirring, the reaction was quenched by addition of saturated aqueous NH$_4$Cl (5 mL) and the aqueous phase was extracted with EtOAc (3×10 mL). The combined organic layers were dried over MgSO$_4$, and the solvent was removed under reduced pressure. The crude product was purified by silica gel column chromatography to afford product.

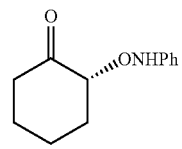

(R)-2-(N-Phenyl-aminooxy)-cyclohexanone (3a). This follows the procedure set forth in Hayashi, et al., *Angew. Chem., Int. Engl.* 2004, 43, 1112; and Bøgevig, et al., *Angew. Chem., Int. Engl.* 2004, 43, 1109. Prepared according to the general procedure from cyclohexanone (22 μL, 0.216 mmol) for 20 min to provide the title compound as a slightly yellow solid (19 mg, 84% yield) after silica gel chromatography (EtOAc/Hexane=1/9.5). $^1$H NMR (CDCl$_3$): δ 7.78 (brs, 1H), 7.25 (m, 2H), 6.94 (m, 3H), 4.40 (dd, 1H, J=6.0 Hz), 2.34-2.58 (m, 3H), 1.96-2.10 (m, 2H), 1.60-1.86 (m, 3H); $^{13}$C NMR: δ 210.1, 148.3, 129.1, 122.3, 114.6, 86.5, 41.1, 32.7, 27.5, 24.0; HPLC (Chiralpak AD, i-Propanol/Hexane=10/90, flow rate 0.5 mL/min, λ=242 nm): $t_{minor}$=22.4 min, $t_{major}$=26.5 min, [α]$_D$=+122.4 (c=1.0, CHCl$_3$) [Lit$^{(4)}$. [α]$_D$=+111.3 (c=0.15, CHCl$_3$)], ee>99%. HRMS (FAB) calcd for C$_{12}$H$_{15}$NO$_2$ m/z 205.1103. Found 205.1113.

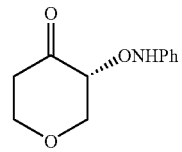

(R)-3-(N-Phenyl-aminooxy)-tetrahydro-pyran-4-one (3b): Prepared according to the general procedure from tetrahydro-4H-pyran-4-one (40 μL, 0.43 mmol) for 3.0 h to provide the title compound as a white solid (38 mg, 86% yield) after silica gel chromatography (EtOAc/Hexane=1/10). $^1$H NMR (CDCl$_3$): δ 7.26-7.29 (m, 2H), 6.92-7.00 (m, 3H), 4.50-4.54 (m, 1H), 4.42-4.46 (m, 1H), 4.20-4.23 (m, 1H), 3.69-3.75 (m, 2H), 2.67-2.74 (m, 1H), 2.56-2.60 (m, 1H); $^{13}$C NMR: δ 205.4, 147.9, 129.2, 122.9, 115.0, 83.7, 70.3, 68.4, 42.6; HPLC (Chiralpak AS-H, i-Propanol/Hexane=8/92, flow rate 1.0 mL/min, λ=242 nm): $t_{minor}$=37.8 min, $t_{major}$=33.6 min, $[α]_D$=+44.2 (c=0.5, CHCl$_3$), ee>99%. HRMS (FAB) calcd for C$_{11}$H$_{13}$NO$_3$ m/z 207.0895. Found 207.0888.

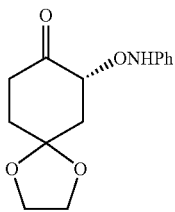

(R)-7-(N-Phenyl-aminooxy)-2,3-dioxa-spiro[4.5]decan-8-one (3c): Prepared according to the general procedure from 1,4-Cyclohexanedione mono-ethylene ketal (36 μL, 0.345 mmol) for 2.0 h to provide the title compound as a slightly yellow solid (53 mg, 94% yield) after silica gel chromatography (EtOAc/Hexane=1/10). $^1$H NMR (CDCl$_3$): δ 7.24-7.29 (m, 2H), 6.90-6.97 (m, 3H), 4.65 (dd, 1H, J=6.5 Hz), 4.0-4.15 (m, 4H), 2.64-2.76 (m, 1H), 2.40-2.53 (m, 2H), 2.20 (t, 1H, J=7.5 Hz), 1.95-2.07 (m, 2H); $^{13}$C NMR: δ 208.6, 147.9, 128.8, 122.1 114.4, 107.5, 82.6, 64.7, 39.6, 35.9, 34.3; HPLC (Chiralpak AS-H, i-Propanol/Hexane=8/92, flow rate 1.0 mL/min, λ=242 nm): $t_{minor}$=31.5 min, $t_{major}$=32.7 min, $[α]_D$=+75.7 (c=0.7, CHCl$_3$), ee=98%. HRMS (FAB) calcd for C$_{14}$H$_{17}$NO$_4$ m/z 263.1158. Found 263.1167.

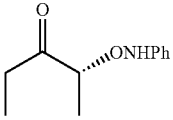

(R)-2-(N-Phenyl-aminooxy)-pentan-3-one (3d): Prepared according to the general procedure from 3-pentanone (67 mg, 0.43 mmol) for 2.0 h to provide the title compound as a slightly yellow solid (24 mg, 71% yield) after silica gel chromatography (EtOAc/Hexane=1/9). $^1$H NMR (CDCl$_3$): δ 7.25-7.28 (m, 2H), 6.93-6.98 (m, 3H), 4.48 (q, 1H, J=7.0 Hz), 2.54 (q, 2H, J=7.0 Hz), 1.42 (d, 3H, J=7.0 Hz), 1.10 (t, 3H, J=7.0 Hz); $^{13}$C NMR (CDCl$_3$): δ 211.9, 148.2, 129.2, 122.6, 114.7, 84.3, 31.8, 16.1, 7.6; HPLC (Chiralpak AS-H, i-Propanol/Hexane=3/97, flow rate 1.0 mL/min, λ=242 nm): $t_{minor}$=16.3 min, $t_{major}$=15.1 min, $[α]_D$=+54.8 (c=0.5, CHCl$_3$) [Lit.[4]. $[α]_D$=+57.7 (c=2.1, CHCl$_3$)], ee=97%. HRMS (FAB) calcd for C$_{11}$H$_{15}$NO$_2$ m/z 193.1103. Found 193.1105.

Mannich-Type Reactions of Ketones and Aldehydes with α-Imino Ester

General Procedure for the Catalytic Asymmetric Reaction Between N-PMP Protected α-Imino Ethyl Glyoxylates and Ketones.

To a vial containing ketone (1.72 mmol), catalyst V (0.0172 mmol, 4 mg) and anhydrous DMSO (0.5 mL) was added a solution of N-PMP-protected α-imino ethyl glyoxylate (0.172 mmol, 36 mg) in anhydrous DMSO (0.5 mL) at room temperature. The mixture was vigorously stirred for 2-20 h at room temperature. The endpoint of reactions was monitored by TLC. Following aqueous work-up with half-saturated ammonium chloride solution (10 mL) and extraction with ethyl acetate (3×10 mL), the organic layer was dried over anhydrous MgSO4, filtered, and concentrated. The resulting residue was then purified by silica gel chromatography. The enantioselectivity was determined by chiral HPLC analysis.

Ethyl (2S)-2-(4-methoxyphenylamino)-4-oxo-pentanoate: Prepared according to the general procedure from N-PMP-protected α-imino ethyl glyoxylate (0.172 mmol) for 2.0 h to provide compound as clear oil (42 mg, 91% yield) after silica gel chromatography (EtOAc/Hexane=1/6). $^1$H NMR (500 MHz, CDCl$_3$): δ 6.76 (d, 2H, J=9.0 Hz), 6.66 (d, 2H, J=9.0 Hz), 4.33 (t, 1H, J=5.5 Hz), 4.18 (q, 2H, J=7.5 Hz), 3.74 (s, 3H), 2.97 (d, 2H, J=5.5 Hz), 2.18 (s, 3H), 1.23 (t, 3H, J=7.5 Hz); $^{13}$C NMR (125 MHz, CDCl$_3$): δ 206.1, 173.1, 153.5, 140.5, 116.2, 115.1, 61.7, 55.9, 54.6, 46.0, 30.6, 14.3; HPLC (Chirapak AD, i-Propanol/Hexane=3/97, flow rate 1.0 mL/min, λ=254 nm): $t_{minor}$=41.8 min, $t_{major}$=45.9 min; $[α]_D$=−15.3 (c=2.5, CHCl$_3$) [Lit.[1] $[α]_D$=−15.5 (c=0.4, CHCl$_3$)], ee>99%.

Ethyl (2S, 3S)-2-(4-methoxyphenylamino)-3-methyl-4-oxo-pentanoate: Prepared according to the general procedure from N-PMP-protected α-imino ethyl glyoxylate (0.172 mmol) for 11 h to provide title compound as clear oil (40 mg, 84% yield) after silica gel chromatography (EtOAc/Hexane=1/6). $^1$H NMR (500 MHz, CDCl$_3$): δ 6.76 (d, 2H, J=9.0 Hz), 6.65 (d, 2H, J=9.0 Hz), 4.31 (d, 1H, J=6.0 Hz), 4.10-4.20 (m, 2H), 3.74 (s, 3H), 3.02 (m, 1H), 2.23 (s, 3H), 1.17-1.27 (m, 6H); $^{13}$C NMR (125 MHz, CDCl$_3$): δ 209.4, 173.0 153.4, 141.0, 116.0, 115.0, 61.6, 59.8, 55.9, 49.5, 28.7, 14.4, 12.5; HPLC (Chirapak AS-H, i-Propanol/Hexane=10/90, flow rate 1.0 mL/min, λ=254 nm): $t_{minor}$=18.1 min, $t_{major}$=13.1 min; $[α]_D$=−76.6 (c=0.5, CHCl3) [Lit. (1) $[α]_D$=−71.3 (c=1.0, CHCl$_3$)], ee=97%.

Ethyl (2S, 3S)-2-(4-methoxyphenylamino)-3-methyl-4-oxo-hexanoate: Prepared according to the general procedure from N-PMP-protected α-imino ethyl glyoxylate (0.172 mmol) for 20 h to provide title compound as clear oil (42.0 mg, 83% yield) after silica gel chromatography (EtOAc/Hexane=1/6). $^1$H NMR (500 MHz, CDCl$_3$): δ 6.77 (d, 2H, J=9.0 Hz), 6.64 (d, 2H, J=9.0 Hz), 4.30 (d, 1H, J=6.5 Hz), 4.10-4.20 (m, 2H), 3.88 (brs, 1H), 3.74 (s, 3H), 3.03 (m, 1H), 2.54 (m, 2H), 1.18-1.25 (m, 6H), 1.04 (t, 3H, J=7.0 Hz); $^{13}$C NMR (125 MHz, CDCl$_3$): δ 212.1, 173.1, 153.3, 141.0, 116.0, 115.0, 61.5, 60.0, 55.9, 48.7, 34.6, 14.4, 12.8, 7.8; HPLC (Chirapak AS-H, i-Propanol/Hexane=2/98, flow rate 1.0 mL/min, λ=254 nm): $t_{minor}$=25.8 min, $t_{major}$=22.4 min; $[α]_D$=−53.4 (c=1.0, CHCl$_3$), ee=97%.

Ethyl (2S, 3S)-2-(4-methoxyphenylamino)-2-(2'-oxocyclohex-1'-yl)-acetate: Prepared according to the general procedure from N-PMP-protected α-imino ethyl glyoxylate (0.086 mmol) for 3.5 h to provide title compound as clear oil (24 mg, 90% yield) after silica gel chromatography (EtOAc/Hexane=1/6.5). $^1$H NMR (500 MHz, CDCl$_3$): δ 6.73-6.78 (m, 4H), 4.23 (d, 1H, J=5.0 Hz), 4.12-4.18 (m, 2H), 3.74 (s, 3H), 2.82 (m, 1H), 1.66-2.48 (m, 8H), 1.22 (t, 3H, J=7.0 Hz); $^{13}$C NMR (125 MHz, CDCl$_3$): δ 210.2, 173.6, 153.3, 141.2, 116.4, 115.0, 61.4, 58.4, 56.0, 53.8, 42.0, 29.8, 27.0, 25.0, 14.3; HPLC (Chirapak AS-H, i-Propanol/Hexane=10/90, flow rate 1.0 mL/min, λ=254 nm): $t_{minor}$=20.2 min, $t_{major}$=16.6 min; $[\alpha]_D$=−43.5 (c=0.6, CHCl$_3$) [Lit.[(1)] $[\alpha]_D$=−40.3 (c=2.0, CHCl$_3$)], ee=96%.

Ethyl (2S, 3S)-2-(4-Methoxy-phenylamino)-2-(4-oxo-tetrahydro-pyran-3-yl)-acetate: Prepared according to the general procedure from N-PMP-protected α-imino ethyl glyoxylate (0.172 mmol) for 9.0 h to provide the title compound as clear oil (44 mg, 83% yield) after silica gel chromatography (EtOAc/Hexane=1/5). $^1$H NMR (500 MHz, CDCl$_3$): δ 6.78 (d, 2H, J=9.0 Hz), 6.72 (d, 2H, J=8.5 Hz), 4.26 (d, 1H, J=6.5 Hz), 4.08-4.20 (m, 4H), 4.02 (dd, 1H, J=11.5, 8.0 Hz), 3.88-3.93 (m, 1H), 3.74 (s, 3H), 2.91 (dd, 1H, J=14.0, 6.0 Hz), 2.60 (m, 2H), 1.22 (t, 3H, J=7.0 Hz); $^{13}$C NMR (125 MHz, CDCl$_3$): δ 206.1, 172.8, 153.6, 140.9, 116.5, 115.1, 69.8, 68.3, 61.7, 56.9, 55.9, 54.7, 42.3, 14.3; HPLC (Chirapak AS-H, i-Propanol/Hexane=45/55, flow rate 1.0 mL/min, λ=254 nm): $t_{minor}$=10.0 min, $t_{major}$=11.8 min; $[\alpha]_D$=−66.5 (c=1.0, CHCl$_3$), ee=96%.

Ethyl (2S, 3S)-2-(4-Methoxy-phenylamino)-2-(8-oxo-1,4-dioxa-spiro[4.5]dec-7-yl)-acetate: Prepared according to the general procedure from N-PMP-protected α-imino ethyl glyoxylate (0.172 mmol) for 3.5 h to provide the title compound as clear oil (49 mg, 78% yield) after silica gel chromatography (EtOAc/Hexane=1/5). $^1$H NMR (500 MHz, CDCl$_3$): δ 6.74-6.78 (m, 4H), 4.29 (d, 1H, J=4.5 Hz), 4.10-4.20 (m, 2H), 4.01-4.06 (m, 4H), 3.74 (s, 3H), 3.12-3.19 (m, 1H), 2.62-2.69 (m, 1H), 2.47 (dt, 1H, J=15.0, 4.5 Hz), 2.11-2.21 (m, 2H), 2.03 (dd, 2H, J=11.0, 4.0 Hz), 1.22 (t, 3H, J=7.0 Hz); $^{13}$C NMR (125 MHz, CDCl$_3$): δ 208.8, 173.3, 153.5, 141.1, 116.6, 115.0, 107.6, 65.0, 64.9, 61.5, 58.2, 55.9, 49.9, 38.3, 36.5, 34.0, 14.4; HPLC (Chirapak AS-H, i-Propanol/Hexane=45/55, flow rate 1.0 mL/min, λ=254 nm): $t_{minor}$=11.9 min, $t_{major}$=21.1 min; $[\alpha]_D$=−68.0 (c=1.0, CHCl$_3$), ee=96%.

Ethyl (2S, 3S)-2-(4-methoxy-phenylamino)-3-Acetyl-hex-5-enoate: Prepared according to the general procedure from N-PMP-protected α-imino ethyl glyoxylate (0.172 mmol) for 4.0 h to provide title compound as clear oil (45 mg, 88% yield) after silica gel chromatography (EtOAc/Hexane=1/9). $^1$H NMR (500 MHz, CDCl$_3$): δ 6.77 (d, 2H, J=9.0 Hz), 6.63 (d, 2H, J=8.5 Hz), 5.73-5.80 (m, 1H), 5.08-5.13 (m, 2H), 4.22 (d, 1H, J=6.5 Hz), 4.13-4.19 (m, 2H), 3.95 (brs, 1H), 3.74 (s, 3H), 3.08 (dd, 1H, J=13.5, 7.0 Hz), 2.52-2.55 (m, 2H), 2.21 (s, 3H), 1.21 (t, 3H, J=7.0 Hz); $^{13}$C NMR (125 MHz, CDCl$_3$): δ 209.2, 172.9, 153.3, 140.7, 134.9, 118.1, 115.8, 115.0, 61.6, 58.7, 55.9, 55.0, 32.6, 30.5, 14.3; HPLC (Chirapak AD, i-Propanol/Hexane=10/90, flow rate 1.0 mL/min, λ=254 nm): $t_{minor}$=9.5 min, $t_{major}$=10.9 min; $[\alpha]_D$=−55.0 (c=0.7, CHCl$_3$), ee=96%.

Ethyl (2S, 3S)-2-(4-methoxy-phenylamino)-3-Hydroxy-4-oxo-pentanoate: Prepared according to general procedure from N-PMP-protected α-imino ethyl glyoxylate (0.086 mmol) for 12 h to provide title compound as clear oil (18 mg, 74% yield) after silica gel chromatography (EtOAc/Hexane=1/4). $^1$H NMR (500 MHz, CDCl$_3$): δ 6.77 (d, 2H, J=9.0 Hz), 6.62 (d, 2H, J=9.0 Hz), 4.64 (d, 1H, J=1.0 Hz), 4.46 (d, 1H, J=1.5 Hz), 4.19-4.26 (m, 2H), 4.08 (brs, 1H), 3.88 (brs, 1H), 3.74 (s, 3H), 2.31 (s, 3H), 1.24 (t, 3H, J=7.0 Hz); $^{13}$C NMR (125 MHz, CDCl$_3$): δ 206.2, 171.0, 153.7, 140.4, 116.3, 115.1, 77.0, 62.0, 59.7, 55.9, 25.1, 14.4; HPLC (Chirapak AD, i-Propanol/Hexane=10/90, flow rate 1.0 mL/min, λ=254 nm): $t_{minor}$=17.6 min, $t_{major}$=19.8 min; $[\alpha]_D$=+24.5 (c=0.7, CHCl$_3$) [Lit.[(1)] $[\alpha]_D$=+24.3 (c=0.6, CHCl$_3$)], ee>99%.

General Procedure for the Catalytic Asymmetric Reaction Between N-PMP Protected α-Imino Ethyl Glyoxylates and Aldehydes To a vial containing aldehyde (0.258 mmol), catalyst V (0.0086 mmol, 2 mg) and anhydrous 1,4 Dioxane (0.5 mL) was added a solution of N-PMP-protected α-imino ethyl glyoxylate (0.172 mmol, 36 mg) in anhydrous 1,4 Dioxane (0.5 mL) at room temperature. The mixture was vigorously stirred for 6.0-8.5 h at room temperature. The endpoint of the reaction was monitored by TLC. Following aqueous work-up with half-saturated ammonium chloride solution (10 mL) and extraction with ethyl acetate (3×10 mL), the organic layer was dried by anhydrous MgSO$_4$, filtered, concentrated. The resulting residue was then purified by silica gel chromatography and fractions concentrated in vacuo to provide the product. The enantioselectivity was determined by chiral HPLC analysis.

Ethyl (2S, 3S)-3-formyl-4-methyl-2-p-tolylamino-pentanoic acid ethyl ester: Prepared according to the general procedure from N-PMP-protected α-imino ethyl glyoxylate (0.172 mmol) for 6.5 h to provide title compound as clear oil (43 mg, 86% yield) after silica gel chromatography (EtOAc/Hexane=1/7.5). $^1$H NMR (500 MHz, CDCl$_3$): δ 9.78 (d, 1H, J=3.0 Hz), 6.77 (d, 2H, J=12.5 Hz), 6.66 (d, 2H, J=12.0 Hz), 4.32 (d, 1H, J=7.0 Hz), 4.16 (dq, 2H, J=7.0 Hz, 1.5 Hz), 3.74 (s, 3H), 2.55 (m, 1H), 2.31 (m, 1H), 1.22 (t, 3H, J=7.0 Hz), 1.16 (d, 3H, J=7.0 Hz), 1.03 (d, 3H, J=7.0 Hz); $^{13}$C NMR (125 MHz, CDCl$_3$): δ 203.8, 172.9, 153.4, 140.4, 116.0, 115.1, 61.6, 59.8, 57.3, 55.9, 26.5, 21.1, 20.0, 14.3; HPLC (Chiralpak AS-H, i-Propanol/Hexane=10/90, flow rate 1.0 mL/min, λ=254 nm): $t_{minor}$=18.3 min, $t_{major}$=11.3 min; $[\alpha]_D$=−44.4 (c=2.0, CHCl$_3$), ee=97%; HRMS calcd for C$_{16}$H$_{23}$NO$_4$ (M+Na$^+$) 316.1519. Found 316.1502.

Ethyl (2S, 3S)-3-formyl-2-p-tolylamino-hexanoic acid ethyl ester: Prepared according to the general procedure from N-PMP-protected α-imino ethyl glyoxylate (0.172 mmol) for 6.0 h to provide title compound as clear oil (45 mg, 88% yield) after silica gel chromatography (EtOAc/Hexane=1/9). $^1$H NMR (500 MHz, CDCl$_3$): δ 9.71 (s, 1H), 6.77 (d, 2H, J=9.0 Hz), 6.65 (d, 2H, J=9.0 Hz), 4.34 (d, 1H, J=5.0 Hz), 4.18 (m, 2H), 3.96 (m, 1H), 3.74 (s, 3H), 2.73 (m, 1H), 1.86 (m, 1H), 1.59 (m, 1H), 1.48-1.30 (m, 2H), 1.23 (t, 3H, J=7.0 Hz), 0.94 (t, 3H, J=7.5 Hz); $^{13}$C NMR (125 MHz, CDCl$_3$): δ 202.8, 172.6, 153.6, 140.7, 116.4, 115.1, 61.8, 58.7, 55.9, 53.8, 27.5, 21.0, 14.4, 14.2; HPLC (Chiralpak AS-H, i-Propanol/Hexane=10/90, flow rate 1.0 mL/min, λ=254 nm): $t_{minor}$=17.1 min, $t_{major}$=12.6 min; $[\alpha]_D$=−44.0 (c=0.5, CHCl$_3$), ee=97%; HRMS calcd for C$_{16}$H$_{23}$NO$_4$ (M+Na$^+$) 316.1519. Found 316.1539.

Ethyl (2S, 3S)-3-formyl-2-p-tolylamino-heptanoic acid ethyl ester: Prepared according to the general procedure from N-PMP-protected α-imino ethyl glyoxylate (0.172 mmol) for 6.5 h to provide title compound as clear oil (43 mg, 85% yield) after silica gel chromatography (EtOAc/Hexane=1/9). $^1$H NMR (500 MHz, CDCl$_3$): δ 9.74 (d, 1H, J=4.0 Hz), 6.76 (d, 2H, J=9.0 Hz), 6.66 (d, 2H, J=9.0 Hz), 4.34 (d, 1H, J=5.0 Hz), 4.18 (m, 2H), 3.96 (m, 1H), 3.74 (s, 3H), 2.73 (m, 1H), 1.87 (m, 1H), 1.61 (m, 1H), 1.43-1.32 (m, 5H), 1.23 (3H, J=7.5 Hz), 0.90 (t, 3H, J=7.0 Hz); $^{13}$C NMR (125 MHz, CDCl$_3$): δ 202.8, 172.6, 153.6, 140.7, 116.4, 115.1, 61.7, 58.7, 55.9, 54.0, 29.9, 25.1, 22.8, 14.4, 14.0; HPLC (Chiralpak AS-H, i-Propanol/Hexane=2/98, flow rate 1.0 mL/min, λ=254 nm): $t_{minor}$=15.8 min, $t_{major}$=12.1 min; $[\alpha]_D$=−32.4 (c=0.5, CHCl$_3$), ee=96%; HRMS calcd for C$_{17}$H$_{25}$NO$_4$ (M+Na$^+$) 330.1676. Found 330.1662.

Ethyl (2S, 3S)-3-formyl-2-p-tolylamino-octanoic acid ethyl ester: Prepared according to the general procedure from N-PMP-protected α-imino ethyl glyoxylate (0.172 mmol) for 7.5 h to provide the title compound as clear oil (48 mg, 87% yield) after silica gel chromatography (EtOAc/Hexane=1/10). $^1$H NMR (500 MHz, CDCl$_3$): δ 9.71 (d, 1H, J=1.5 Hz), 6.76 (d, 2H, J=8.5 Hz), 6.65 (d, 2H, J=9.0 Hz), 4.34 (d, 1H, J=5.0 Hz), 4.19 (m, 2H), 3.96 (m, 1H), 3.74 (s, 3H), 2.72 (m, 1H), 1.87 (m, 1H), 1.61 (m, 1H), 1.43-1.27 (m, 6H), 1.24 (t, 3H, J=7.0 Hz), 0.88 (t, 3H, J=6.5 Hz); $^{13}$C NMR (125 MHz, CDCl$_3$): δ 202.9, 172.6, 153.6, 140.7, 116.4, 115.1, 61.8, 58.7, 55.9, 54.0, 31.9, 27.4, 25.4, 22.6, 14.4, 14.2; HPLC (Chirapak AS-H, i-Propanol/Hexane=10/90, flow rate 1.0 mL/min, λ=254 nm): $t_{minor}$=14.1 min, $t_{major}$=10.7 min; $[α]_D$=−21.5 (c=1.4, CHCl$_3$) [Lit.$^{(1)}$ $[α]_D$=−22.1 (c=0.7, CH$_2$Cl$_2$)], ee=96%; HRMS calcd for C$_{18}$H$_{27}$NO$_4$ (M+Na$^+$) 344.1832. Found 344.1848.

Ethyl (2S, 3S)-3-formyl-2-p-tolylamino-nonanoic acid ethyl ester: Prepared according to the general procedure from N-PMP-protected α-imino ethyl glyoxylate (0.172 mmol) for 7.0 h to provide title compound as clear oil (49 mg, 84% yield) after silica gel chromatography (EtOAc/Hexane=1/10). $^1$H NMR (500 MHz, CDCl$_3$): δ 9.74 (s, 1H), 6.77 (d, 2H, J=8.5 Hz), 6.65 (d, 2H, J=9.0 Hz), 4.34 (d, 1H, J=4.5 Hz), 4.18 (m, 2H), 3.74 (s, 3H, J=1H), 1.87 (m, 1H), 1.61 (m, 3H), 1.42-1.27 (m, 6H), 1.24 (t, 3H, J=7.5 Hz), 0.88 (t, 3H, J=7.0 Hz); $^{13}$C NMR (125 MHz, CDCl$_3$): δ 202.9, 172.6, 153.6, 140.7, 116.4, 115.1, 61.8, 58.7, 55.9, 54.0, 31.7, 29.4, 27.7, 25.4, 22.8, 14.4, 14.2; HPLC (Chiralpak AS-H, i-Propanol/Hexane=10/90, flow rate 1.0 mL/min, λ=254 nm): $t_{minor}$=12.8 min, $t_{major}$=9.4 min; $[α]_D$=−27.2 (c=0.5, CHCl$_3$), ee=96%; HRMS calcd for C$_{19}$H$_{29}$NO$_4$ (M+Na$^+$) 358.1989. Found 358.1987.

Ethyl (2S, 3S)-3-formyl-2-p-tolylamino-decanoic acid ethyl ester: Prepared according to the general procedure from N-PMP-protected α-imino ethyl glyoxylate (0.172 mmol) for 8.5 h to provide title compound as clear oil (49 mg, 81% yield) after silica gel chromatography (EtOAc/Hexane=1/10). $^1$H NMR (500 MHz, CDCl$_3$): δ 9.71 (d, 1H, J=2.0 Hz), 6.77 (d, 2H, J=9.0 Hz), 6.65 (d, 2H, J=9.0 Hz), 4.34 (d, 1H, J=5.0 Hz), 4.18 (m, 2H), 3.94 (bs, 1H), 3.74 (s, 3H), 2.71 (m, 1H), 1.87 (m, 1H), 1.61 (m, 2H), 1.43-1.25 (m, 9H), 1.24 (t, 3H, J=7.5 Hz), 0.88 (t, 3H, J=7.0 Hz); $^{13}$C NMR (125 MHz, CDCl$_3$): δ 202.9, 172.6, 153.6, 140.7, 116.3, 115.1, 61.8, 58.7, 55.9, 54.0, 32.0, 29.7, 29.2, 27.7, 25.4, 22.8, 14.4, 14.3; HPLC (Chirapak AS-H, i-Propanol/Hexane=10/90, flow rate 1.0 mL/min, λ=254 nm): $t_{minor}$=11.8 min, $t_{major}$=8.6 min; $[α]_D$=−20.0 (c=0.5, CHCl$_3$), ee=97%; HRMS calcd for C$_{20}$H$_{31}$NO$_4$ (M+Na$^+$) 372.2145. Found 372.2123.

Ethyl (2S, 3S)-3-formyl-2-p-tolylamino-undecanoic acid ethyl ester: Prepared according to the general procedure from N-PMP-protected α-imino ethyl glyoxylate (0.172 mmol) for 4.0 h to provide title compound as clear oil (57 mg, 91% yield) after silica gel chromatography (EtOAc/Hexane=1/10). $^1$H NMR (500 MHz, CDCl$_3$): δ 9.74 (d, 1H, J=2.0 Hz), 6.77 (d, 2H, J=12.5 Hz), 6.65 (d, 2H, J=12.5 Hz), 4.34 (d, 1H, J=5.0 Hz), 4.18 (m, 2H), 3.74 (s, 3H), 2.71 (m, 1H), 1.87 (m, 1H), 1.61 (m, 2H), 1.47-1.25 (m, 11H), 1.24 (t, 3H, J=7.5 Hz), 0.88 (t, 3H, J=7.0 Hz); $^{13}$C NMR (125 MHz, CDCl$_3$): δ 202.9, 172.6, 153.6, 140.7, 116.4, 115.1, 61.7, 58.7, 55.9, 54.0, 32.0, 29.7, 29.5, 29.4, 27.7, 25.4, 22.8, 14.4, 14.3; HPLC (Chiralpak AS-H, i-Propanol/Hexane=10/90, flow rate 1.0 mL/min, λ=254 nm): $t_{minor}$=10.5 min, $t_{major}$=7.7 min; $[α]_D$=−34.2 (c=0.5, CHCl$_3$), ee=97%; HRMS calcd for C$_{21}$H$_{33}$NO$_4$ (M+Na$^+$) 386.2302. Found 386.2311.

Ethyl (2S, 3S)-3-benzyl-4-oxo-2-p-tolylamino-butyric acid ethyl ester: Prepared according to the general procedure from N-PMP-protected α-imino ethyl glyoxylate (0.172 mmol) for 7.0 h to provide the title compound as clear oil (46 mg, 78% yield) after silica gel chromatography (EtOAc/Hexane=1/14). $^1$H NMR (500 MHz, CDCl$_3$): δ 9.77 (d, 1H, J=1.0 Hz), 7.34-7.18 (m, 6H), 6.73 (d, 2H, J=9.0 Hz), 6.51 (d, 2H, J=9.0 Hz), 4.30 (d, 1H, J=4.5 Hz), 4.14 (m, 3H), 3.73 (s, 3H), 3.25 (m, 1H), 3.12 (m, 1H), 2.97 (m, 1H), 1.23 (t, 3H, J=7.0 Hz); $^{13}$C NMR (125 MHz, CDCl$_3$): δ 202.0, 172.3, 153.5, 140.3, 138.2, 129.4, 129.0, 127.1, 116.1, 115.1, 61.9, 57.6, 55.9, 55.7, 31.8, 14.4; HPLC (Chirapak AS-H, i-Propanol/Hexane=10/90, flow rate 1.0 mL/min, λ=254 nm): $t_{minor}$=28.2 min, $t_{major}$=19.8 min; ee=96%; HRMS calcd for C$_{20}$H$_{23}$NO$_4$ (M+Na$^+$) 364.1519. Found 364.1518.

Michael Addition Reactions of Aldehydes to Nitrostyrenes

General Information: Commercial reagents were used as received, unless otherwise stated. Merck 60 silica gel was used for chromatography, and Whatman silica gel plates with fluorescence F$_{254}$ indicator were used for thin-layer chromatography (TLC) analysis. $^1$H and $^{13}$C NMR spectra were recorded on Broker Advance 500, and tetramethylsilane (TMS) was used as a reference. Data for $^1$H are reported as follows: chemical shift (ppm), and multiplicity (s=singlet, d=doublet, t=triplet, q=quartet, m=multiplet). Data for $^{13}$C NMR are reported as ppm. Mass Spectra were obtained from the Ohio State University Mass Spectral facility.

Procedures for Preparation of Pyrrolidine Trifluoromethanesulfonamide Organocatalyst V.

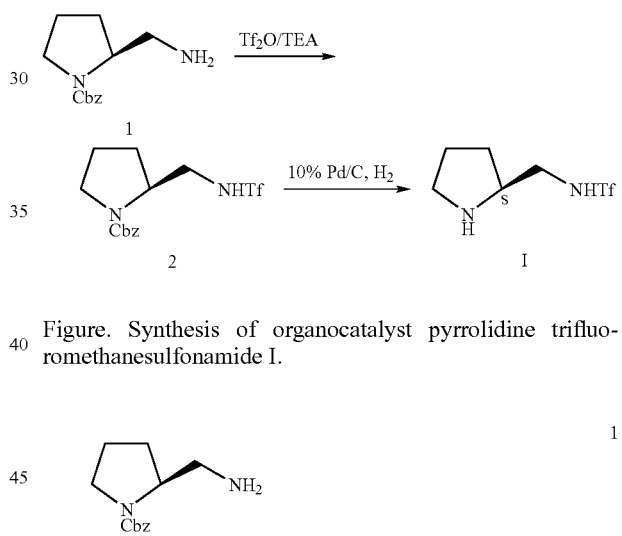

Figure. Synthesis of organocatalyst pyrrolidine trifluoromethanesulfonamide I.

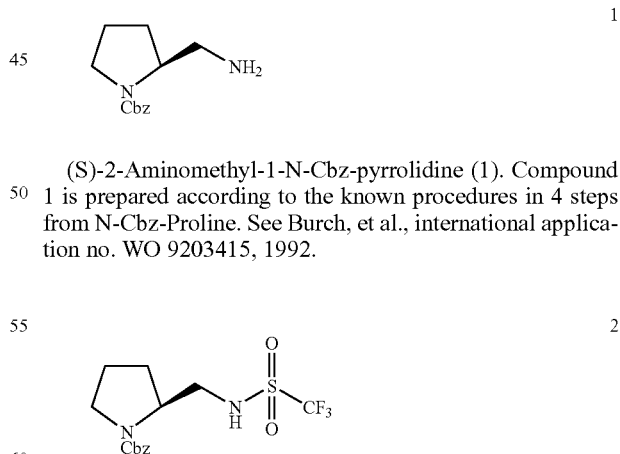

(S)-2-Aminomethyl-1-N-Cbz-pyrrolidine (1). Compound 1 is prepared according to the known procedures in 4 steps from N-Cbz-Proline. See Burch, et al., international application no. WO 9203415, 1992.

(S)-2-(Trifluoromethanesulfonylaminomethyl)-1-N-Cbz-pyrrolidine (2). To a solution of (S)-2-aminomethyl-1-N-Cbz-pyrrolidine (2.0 g, 8.55 mmol) and TEA (1.43 mL, 10.3 mmol) in 40 mL of CaH$_2$ dried CH$_2$Cl$_2$ was added trifluoromethanesulfonic anhydride (1.6 mL, 9.4 mmol) dropwisely by a syringe pump over 1 h at 0° C. under N$_2$. The resulting solution was stirred for 4.5 h at room temperature, then diluted with 80 mL of $CH_2Cl_2$ and washed with 50 mL of 1N HCl aqueous solution. The organic layer was dried over $MgSO_4$, and concentrated in vacuo. Flash chromatography (Ethyl Acetate/Hexane=1/7) afforded a colorless oil in 76% yield (2.38 g, 6.50 mmol). $[\alpha]_D^{25}$ −27.7 (c=1.0 in $CHCl_3$); $^1$H NMR (500 MHz, $CDCl_3$, TMS): δ=7.68 (s, 1H; Ph), 7.10-7.39 (m, 5H; Ph), 5.15 (m, 2H; $CH_2$), 3.98-4.09 (m, 1H; CH), 3.24-3.57 (m, 4H; CH and $CH_2$), 2.12 (m, 1H; CH), 1.88 (m, 2H; $CH_2$), 1.67 (m, 1H; CH); $^{13}$C NMR (125 MHz, $CDCl_3$, TMS): δ=157.7, 136.2, 128.8, 128.6, 128.5, 128.3, 68.0, 58.1, 49.9, 47.5, 30.0, 24.1; HRMS (FAB) calcd for $C_{14}H_{18}F_3N_2O_4S$ (M+1) m/z 367.0939, found 367.0928.

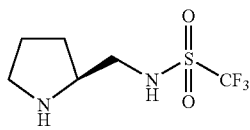

I (S)-2-(trifluoromethane sulfonylamino methyl)-pyrrolidine (V). A solution of (S)-2-(trifluoromethanesulfonylamino methyl)-1-N-Cbz-pyrrolidine (0.794 g, 2.17 mmol) in 15 mL of MeOH was hydrogenated in the presence of 10% Pd/C (0.16 g) with a $H_2$ balloon at room temperature for 5 h. The catalyst was filtered through a pad of celite and washed with 2×20 mL of MeOH. The filtrate was concentrated in vacuo to give a white solid (>95% purity) in 93% yield (0.469 g, 2.02 mmol). The product was crystallized in MeOH to give a crystal, which was used for catalyzing reactions. $[\alpha]_D^{25}$+10.5 (c=1.0 in $CH_3OH$); $^1$H NMR (500 MHz, $CD_3OD$, TMS): δ=3.47 (m, 1H; CH), 3.08-3.28 (m, 4H; CH and $CH_2$), 1.86-2.02 (m, 3H; CH and $CH_2$), 1.61-1.68 (m, 1H; CH); $^{13}$C NMR (125 MHz, $CD_3OD$, TMS): δ=123.5 (q, $^2$J (C, F)=325 Hz), 122.2, 63.7, 46.4, 28.5, 24.7; HRMS (FAB) calcd for $C_6H_{12}F_3N_2O_2S$ (M+1) m/z 233.0572. Found 233.0580.

Typical/general Procedure for Michael Addition Reaction: To a vial containing iso-butyraldehyde (0.20 mL, 2.19 mmol), and 1.0 mL of dry isopropyl alcohol was added catalyst pyrrolidine sulfonamide I (10 mg, 0.044 mmol) at 0° C. The mixture was vigorously stirred for 15 min, and then trans-β-nitrostyrene (33 mg, 0.219 mmol) was added. After 4.5 d stirring, TLC analysis indicated completion of the reaction. After reaction mixture was concentrated under reduced pressure, the resulting residue was then purified by silica gel chromatography (ethyl acetate/hexane=1/30 to 1/5) and fractions were collected and concentrated in vacuo to provide a clear oil (41 mg, 0.186 mmol, 85%). Relative and absolute configurations of the products were determined by comparison with the known $^1$H NMR, $^{13}$C NMR, chiral HPLC analysis, and optical rotation values.

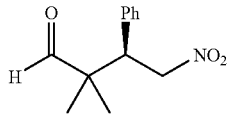

(R)-2,2-Dimethyl-4-nitro-3-phenylbutanal This compound was prepared according to the typical procedure, as described above in 85% yield. $^1$H NMR (500 MHz, $CDCl_3$, TMS): δ=9.53 (s, 1H; CHO), 7.35-7.19 (m, 5H; Ph), 4.85 (dd, $^2$J (H, H)=13.0 Hz, $^3$J (H, H)=11.5 Hz, 1H; CH), 4.69 (dd, $^2$J (H, H)=13.0 Hz, $^3$J (H, H)=4.0 Hz, 1H; CH), 3.78 (dd, $^3$J (H, H)=11.5 Hz, $^3$J (H, H)=4.0 Hz, 1H; CH), 1.14 (s, 3H; $CH_3$), 1.01 (s, 3H; $CH_3$); $^{13}$C NMR (125 MHz, $CDCl_3$, TMS): δ=204.4, 135.6, 129.3, 128.9, 128.4, 76.5, 48.7, 48.4, 21.9, 19.1; HPLC (Chiralpak AS-H, i-Propanol/Hexane=10/90, flow rate 0.5 mL/min, λ=254 nm): $t_{minor}$=22.2 min, $t_{major}$=23.0 min, ee=90%.

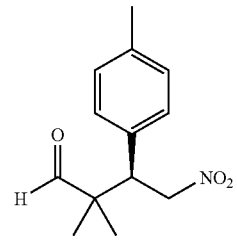

(R)-2,2-Dimethyl-4-nitro-3-p-tolylbutanal: This compound was prepared according to the typical procedure, as described above in 67% yield. $^1$H NMR (500 MHz, $CDCl_3$, TMS): δ=9.53 (s, 1H; CHO), 7.13 (d, $^3$J (H, H)=8.0 Hz, 2H; Ph), 7.07 (d, $^3$J (H, H)=8.0 Hz, 2H; Ph), 4.82 (dd, $^2$J (H, H)=12.5 Hz, $^3$J (H, H)=11.5 Hz, 1H; CH), 4.67 (dd, $^2$J (H, H)=13.0 Hz, $^3$J (H, H)=4.0 Hz, 1H; CH), 3.74 (dd, $^3$J (H, H)=11.5 Hz, $^3$J (H, H)=4.0 Hz, 1H; CH), 2.32 (s, 3H; $CH_3$), 1.13 (s, 3H; $CH_3$), 1.00 (s, 3H; $CH_3$); $^{13}$C NMR (125 MHz, $CDCl_3$, TMS): δ=204.6, 138.1, 132.4, 129.6, 129.1, 76.6, 48.4, 21.8, 21.2, 19.1; HPLC (Chiralcel OD-H, i-Propanol/Hexane=20/80, flow rate 1.0 mL/min, λ=254 nm): $t_{minor}$=15.1 min, $t_{major}$=10.4 min; $[\alpha]_D$=+25.4 (c=0.5 in $CHCl_3$), ee=90%.

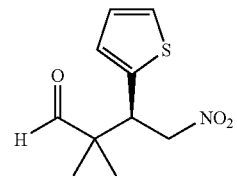

(R)-2,2-Dimethyl-4-nitro-3-(thiophen-2-yl)butanal: This compound was prepared according the typical procedure, as described above in 75% yield. $^1$H NMR (500 MHz, $CDCl_3$, TMS): δ=9.54 (s, 1H; CHO), 7.26-6.92 (m, 3H; Ph), 4.73-4.67 (m, 2H; $CH_2$), 4.14 (dd, $^2$J (H,H)=10.8 Hz, $^3$J (H, H)=4.0 Hz, 1H; CH), 1.21 (s, 3H; $CH_3$), 1.09 (s, 3H; $CH_3$); $^{13}$C NMR (125 MHz, $CDCl_3$, TMS): δ=192.8, 138.1, 129.6, 129.2, 125.2, 59.9, 30.9, 25.7, 24.2; HPLC (Chiralcel OD-H, i-Propanol/Hexane=20/80, flow rate 1.0 mL/min, λ=254 nm): $t_{minor}$=19.8 min, $t_{major}$=11.4 min; $[\alpha]_D$=+54.1 (c=1.0 in $CHCl_3$), ee=89%.

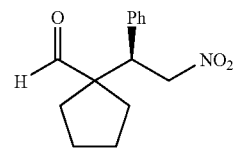

1-((R)-2-Nitro-1-phenylethyl)cyclopentanecarbaldehyde: This compound was prepared according the typical procedure, as described above in 89% yield. $^1$H NMR (500 MHz, $CDCl_3$, TMS): δ=9.49 (s, 1H; CHO), 7.33-7.19 (m, 5H; Ph), 4.96 (dd, $^2$J (H, H)=13.5 Hz, $^3$J (H, H)=11.5 Hz, 1H; CH), 4.70 (dd, $^2$J (H, H)=13.5 Hz, $^3$J (H, H)=4.0 Hz, 1H; CH), 3.70 (dd, $^3$J (H, H)=11.5 Hz, $^3$J (H, H)=4.0 Hz, 1H; CH), 2.07-2.02

(m, 1H; CH), 1.90-1.86 (m, 1H; CH), 1.68-1.51 (m, 6H); $^{13}$C NMR (125 MHz, CDCl$_3$, TMS): δ=204.6, 136.6, 129.019, 129.002, 128.3, 77.6, 60.5, 49.5, 32.8, 31.7, 25.0, 24.9; HPLC (Chiralcel OD-H, i-Propanol/Hexane=20/80, flow rate 1.0 mL/min, λ=254 nm): t$_{minor}$=14.6 min, t$_{major}$=10.5 min; [α]$_D$=−7.2 (c=3.8 in CHCl$_3$), ee=93%.

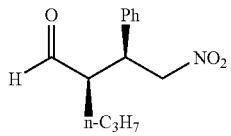

(R)-2-[(S)-2-Nitro-1-phenylethyl]pentanal: This compound was prepared according the typical procedure, as described above in 99% yield. $^1$H NMR (500 MHz, CDCl$_3$, TMS): δ=9.71 (d, $^3$J (H, H)=3.0 Hz, 1H; CHO), 7.35-7.17 (m, 5H; Ph), 4.72-4.63 (m, 2H), 3.80-3.75 (m, 1H; CH), 2.73-2.68 (m, 1H; CH), 1.49-1.11 (m, 4H), 0.80 (t, $^3$J (H, H)=7.5 Hz, 3H; CH$_3$); $^{13}$C NMR (125 MHz, CDCl$_3$, TMS): δ=203.4, 137.0, 129.3, 128.4, 128.2, 78.6, 54.0, 43.4, 29.7, 20.0, 14.1; HPLC (Chiralcel OD-H, i-Propanol/Hexane=20/80, flow rate 1.0 mL/min, λ=254 nm): t$_{minor}$=10.9 min, t$_{major}$=12.9 min; [α]$_D$=+51.2 (c=0.5 in CHCl$_3$), ee=97%.

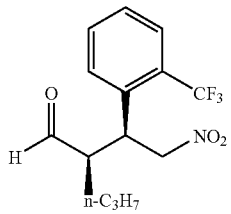

(R)-2-[(S)-1-(2-(Trifluoromethyl)phenyl)-2-nitroethyl] pentanal: This compound was prepared according the typical procedure, as described above in 63% yield. $^1$H NMR (500 MHz, CDCl$_3$, TMS): δ=9.76 (d, $^3$J (H, H)=3.0 Hz, 1H; CHO), 7.73 (d, $^3$J (H, H)=80 Hz, 1H; Ph), 7.59 (t, $^3$J (H, H)=7.5 Hz, 1H; Ph), 7.45 (t, $^3$J (H, H)=8.0 Hz, 1H; Ph), 7.37 (d, $^3$J (H, H)=7.5 Hz, 1H; CH), 4.80 (dd, $^2$J (H, H)=13.0 Hz, $^3$J (H, H)=7.5 Hz, 1H; CH), 4.66 (dd, $^2$J (H, H)=13.0 Hz, $^3$J (H, H)=5.0 Hz, 1H; CH), 4.17-4.14 (m, 1H; CH), 2.95-2.93 (m, 1H; CH), 1.60-1.20 (m, 4H), 0.81 (t, $^3$J (H, H)=7.5 Hz, 3H; CH$_3$); $^{13}$C NMR (125 MHz, CDCl$_3$, TMS): δ=203.0, 136.3, 132.6, 129.4 (q), 128.0, 126.9, 125.1, 123.0, 77.8, 54.0, 38.6, 30.3, 20.1, 13.9; HPLC (Chiralcel OD-H, i-Propanol/Hexane=20/80, flow rate 1.0 mL/min, λ=254 nm): t$_{minor}$=8.6 min, t$_{major}$=10.1 min; [α]$_D$=+31.4 (c=1.0 in CHCl$_3$), ee=94%.

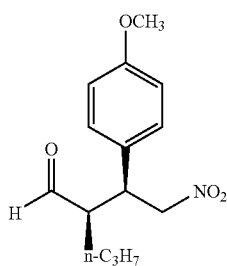

(R)-2-[(S)-1-(4-Methoxyphenyl)-2-nitroethyl]pentanal This compound was prepared according the typical procedure, as described above in 86% yield. $^1$H NMR (500 MHz, CDCl$_3$, TMS): δ=9.69 (d, $^3$J (H, H)=3.0 Hz, 1H; CHO), 7.08 (d, $^3$J (H, H)=8.5 Hz, 2H; Ph), 6.86 (d, $^3$J (H, H)=8.5 Hz, 2H; Ph), 4.66 (dd, $^2$J (H, H)=13.0 Hz, $^3$J (H, H)=5.0 Hz, 1H; CH), 4.60 (dd, $^2$J (H, H)=13.0 Hz, $^3$J (H, H)=10.0 Hz, 1H; CH), 3.78 (s, 3H; CH$_3$), 3.75-3.71 (m, 1H; CH), 2.66-2.65 (m, 1H; CH), 1.49-1.29 (m, 4H), 0.80 (t, $^3$J (H, H)=7.5 Hz, 3H; CH$_3$); $^{13}$C NMR (125 MHz, CDCl$_3$, TMS): δ=203.6, 159.4, 129.2, 128.7, 114.7, 78.8, 55.4, 54.1, 42.6, 29.6, 20.0, 14.1; HPLC (Chiralcelk OD-H, i-Propanol/Hexane=10/90, flow rate 1.0 mL/min, λ=254 nm): t$_{minor}$=18.4 min, t$_{major}$=21.5 min; [α]$_D$=+41.7 (c=2.0 in CHCl$_3$), ee=99%.

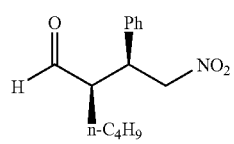

(R)-2-[(S)-2-Nitro-1-phenylethyl]hexanal This compound was prepared according the typical procedure, as described above in 94% yield. $^1$H NMR (500 MHz, CDCl$_3$, TMS): δ=9.71 (d, $^3$J (H, H)=3.0 Hz, 1H; CHO), 7.36-7.17 (m, 5H; Ph), 4.73-4.62 (m, 2H), 3.80-3.75 (m, 1H; CH), 2.72-2.67 (m, 1H; CH), 1.53-1.11 (m, 6H), 0.78 (t, $^3$J (H, H)=7.0 Hz, 3H; CH$_3$); $^{13}$C NMR (125 MHz, CDCl$_3$, TMS): δ=203.5, 137.0, 129.3, 128.4, 128.2, 78.6, 54.1, 43.4, 28.7, 27.2, 26.7, 13.8; HPLC (Chiralcel OD-H, i-Propanol/Hexane=20/80, flow rate 1.0 mL/min, λ=254 nm): t$_{minor}$=10.4 min, t$_{major}$=11.8 min; [α]$_D$=+52.4 (c=0.5 in CHCl$_3$), ee=99%.

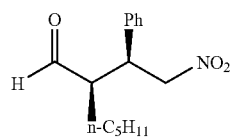

(R)-2-((S)-2-Nitro-1-phenylethyl)heptanal This compound was prepared according the typical procedure, as described above in 91% yield. $^1$H NMR (500 MHz, CDCl$_3$): δ=9.70 (d, $^3$J (H, H)=3.0 Hz, 1H; CHO), 7.36-7.17 (m, 5H; Ph), 4.73-4.62 (m, 2H; CH$_2$), 3.80-3.75 (m, 1H; CH), 2.72-2.67 (m, 1H; CH), 1.53-1.08 (m, 8H), 0.80 (t, $^3$J (H, H)=7.5 Hz, 3H; CH$_3$); $^{13}$C NMR (125 MHz, CDCl$_3$, TMS): δ=203.4, 137.0, 129.3, 128.4, 128.2, 78.7, 54.1, 43.4, 31.8, 27.5, 26.3, 22.4, 14.0; HPLC (Chiralcel OD-H, i-Propanol/Hexane=20/80, flow rate 1.0 mL/min, λ=254 nm): t$_{minor}$=9.7 min, t$_{major}$=11.0 min; [α]$_D$=+59.0 (c=2.0, CHCl$_3$), ee=97%.

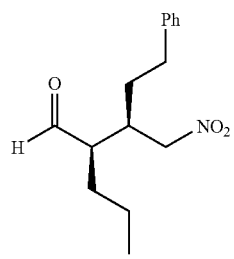

(R)-2-((S)-1-nitro-4-phenylbutan-2-yl)pentanal: This compound was prepared according the typical procedure, as described above in 76% yield. $^1$H NMR (500 MHz, CDCl$_3$, TMS): δ=9.67 (s, 1H; CHO), 7.31-7.14 (m, 5H; Ph), 4.53 (dd, $^2$J (H, H)=12.5 Hz, $^3$J (H, H)=7.0 Hz, 1H; CH); 4.46 (dd, $^2$J (H, H)=12.5 Hz, $^3$J (H, H)=6.5 Hz, 1H; CH), 2.69-2.61 (m, 3H), 2.55-2.50 (m, 1H; CH), 1.80-1.65 (m, 3H), 1.45-1.30 (m, 3H), 0.94 (t, $^3$J (H, H)=6.5 Hz, 3H; CH$_3$); $^{13}$C NMR (125 MHz, CDCl$_3$, TMS): δ=202.9, 140.4, 128.6, 128.1, 126.3, 52.0, 36.5, 33.0, 30.9, 27.5, 20.7, 14.0. HPLC (Chiralcel OD-H, i-Propanol/Hexane=8/92, flow rate 0.5 mL/min, λ=254 nm), t$_{major}$=40.5 min, t$_{minor}$=44.2 min; ee=22%.

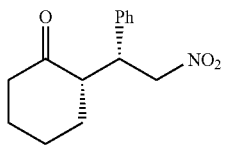

(S)-2-[(R)-2-Nitro-1-phenylethyl]cyclohexanone This compound was prepared according the typical procedure, as described above in 96% yield. $^1$H NMR (500 MHz, CDCl$_3$, TMS): δ=7.34-7.16 (m, 5H; Ph), 4.94 (dd, $^2$J (H, H)=12.5 Hz, $^3$J (H, H)=4.5 Hz, 1H; CH), 4.63 (dd, $^2$J (H, H)=12.5 Hz, $^3$J (H, H)=10.0 Hz, 2H; CH$_2$), 3.78-3.74 (m, 1H; CH), 2.75-2.64 (m, 1H; CH), 2.47-2.30 (m, 2H; CH$_2$), 2.10-2.00 (m, 1H; CH), 1.77-1.55 (m, 3H), 1.26-1.22 (m, 1H; CH); $^{13}$C NMR (125 MHz, CDCl$_3$, TMS): δ=212.1, 138.0, 129.1, 128.4, 128.0, 79.1, 52.7, 44.1, 42.9, 33.4, 28.7, 25.2; HPLC (Chiralpak AS-H, i-Propanol/Hexane=25/75, flow rate 1.0 mL/min, λ=254 nm): t$_{minor}$=7.9 min, t$_{major}$=12.2 min; [α]$_D$=−17.3 (c=2.0 in CHCl$_3$), ee=97%.

α-Selenylation Reactions of Aldehydes and Ketones

General. All reactions were performed under aerobic atmosphere. Commercial, anhydrous (HPLC grade) CH$_2$Cl$_2$ was used directly for reactions without further purification. HPLC grade EtOAc and hexanes were used for column chromatography. Column chromatography was performed with silica gel (230-400 mesh size). TLC plates with F$_{254}$ indicator were used for monitoring reactions. The combined organic layers were dried over MgSO$_4$. Solvents were evaporated under reduced pressure. All yields given refer to as isolated yields. $^1$H NMR was recorded on a 500 MHz and $^{13}$C on a 125 MHz spectrometer. HRMS experiment was performed on a high resolution magnetic sector spectrometer. Tetramethylsilane (TMS) was used as a reference for $^1$H NMR experiments. Data for $^1$H are reported as follows: chemical shift (ppm), and multiplicity (s=singlet, d=doublet, t=triplet, q=quartet, m=multiplet). Data for $^{13}$C NMR are reported as ppm.

General Procedure A for α-Selenenylation of Aldehyde (Table 9, Entries 1-10): To a vial containing aldehyde (0.25 mmol), 0.5 mL of anhydrous CH$_2$Cl$_2$ and catalyst L-prolinamide 1 (0.005 mmol) was added N-(phenylseleno)phthalimide (0.3 mmol) at room temperature. After 10 min, reaction mixture was treated with water (5 mL), then the solution was extracted with ethyl acetate (3×5 mL). The combined extracts were dried over MgSO$_4$, filtered, and concentrated in, vacuo. The resulting residue was then purified by silica gel chromatography, eluting with EtOAc/Hexane to afford a clear oil.

2-(Phenylseleno)propanal: The reaction was carried out following the general procedure to provide a clear oil (45 mg, 81%). $^1$H NMR (500 MHz, CDCl$_3$): δ 9.45 (d, 1H, J=3.0 Hz), 7.51 (d, 2H, J=7.0 Hz), 7.35 (t, 1H, J=7.5 Hz), 7.29 (t, 2H, J=7.5 Hz), 3.71 (dq, 1H, J=7.0, 3.0 Hz), 1.46 (d, 3H, J=7.0 Hz); $^{13}$C NMR (125 MHz, CDCl$_3$): δ 193.7, 136.3, 129.5, 129.1, 125.9, 46.8, 13.6. HRMS (EI) calcd for C$_9$H$_{10}$OSe (M$^+$) 213.9891, obsd 213.9909.

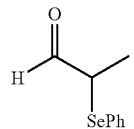

2-(Phenylseleno)butyraldehyde: The reaction was carried out following the general procedure to provide a clear oil (49 mg, 83%). $^1$H NMR (500 MHz, CDCl$_3$): δ 9.41 (d, 1H, J=3.5 Hz), 7.51 (d, 2H, J=7.0 Hz), 7.34 (t, 1H, J=7.5 Hz), 7.28 (t, 2H, J=7.5 Hz), 3.71 (dt, 1H, J=7.5, 3.5 Hz), 1.91-1.83 (m, 1H), 1.75-1.58 (m, 1H), 1.08 (t, 3H, J=7.5 Hz); $^{13}$C NMR (125 MHz, CDCl$_3$): δ 193.3, 136.1, 129.5, 129.0, 126.1, 54.9, 21.3, 12.8. HRMS (EI) calcd for C$_{10}$H$_{12}$OSe (M$^+$) 228.0048, obsd 228.0065.

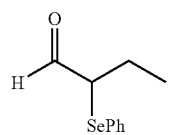

2-(Phenylseleno)pentanal: The reaction was carried out following the general procedure to provide a clear oil (53 mg, 85%). $^1$H NMR (500 MHz, CDCl$_3$): δ 9.39 (d, 1H, J=3.5 Hz), 7.51 (d, 2H, J=7.0 Hz), 7.33 (t, 1H, J=7.5 Hz), 7.28 (t, 2H, J=7.5 Hz), 3.61 (dt, 1H, J=7.5, 3.5 Hz), 1.79-1.78 (m, 1H), 1.70-1.67 (m, 1H), 1.65-1.42 (m, 2H), 0.95 (t, 3H, J=7.5 Hz); $^{13}$C NMR (125 MHz, CDCl$_3$): δ 193.3, 136.0, 129.5, 129.0, 126.2, 52.9, 29.9, 21.4, 13.9. HRMS (EI) calcd for C$_{11}$H$_{14}$OSe (M$^+$) 242.0204, obsd 242.0191.

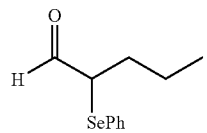

3-Methyl-2-(Phenylseleno)butyraldehyde: The reaction was carried out following the general procedure to provide a clear oil (55 mg, 88%). $^1$H NMR (500 MHz, CDCl$_3$): δ 9.36 (d, 1H, J=5.0 Hz), 7.51 (d, 2H, J=7.0 Hz), 7.32 (t, 1H, J=7.5 Hz), 7.28 (t, 2H, J=7.5 Hz), 3.61 (dd, 1H, J=9.0, 5.0 Hz), 2.12-2.05 (m, 1H), 1.20 (d, 3H, J=6.5 Hz), 1.09 (d, 3H, J=7.0 Hz); $^{13}$C NMR (125 MHz, CDCl$_3$): δ 192.8, 135.6, 129.5, 128.8, 127.0, 62.1, 27.4, 21.5 21.3. HRMS (EI) calcd for C$_{11}$H$_{14}$OSe (M$^+$) 242.0204, obsd 242.0191.

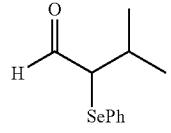

2-(Phenylseleno)hexanal: The reaction was carried out following the general procedure to provide a clear oil (50 mg, 78%). $^1$H NMR (500 MHz, CDCl$_3$): δ 9.38 (d, 1H, J=3.5 Hz), 7.50 (d, 2H, J=7.0 Hz), 7.33 (t, 1H, J=7.0 Hz), 7.28 (t, 2H, J=7.5 Hz), 3.61 (dt, 1H, J=7.5, 3.5 Hz), 1.87-1.80 (m, 1H), 1.71-1.64 (m, 1H), 1.54-1.48 (m, 1H), 1.43-1.30 (m, 3H), 0.90 (t, 3H, J=7.5 Hz); $^{13}$C NMR (125 MHz, CDCl$_3$): δ 193.3, 136.0, 129.5, 129.0, 126.2, 53.1, 30.3, 27.6, 22.6, 14.1. HRMS (EI) calcd for $C_{12}H_{16}OSe$ ($M^+$) 256.0361, obsd 256.0323.

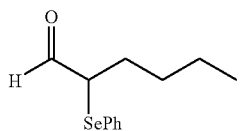

2-(Phenylseleno)heptanal: The reaction was carried out following the general procedure to provide a clear oil (58 mg, 86%). $^1$H NMR (500 MHz, CDCl$_3$): δ 9.38 (d, 1H, J=4.0 Hz), 7.50 (dd, 2H, J=8.0, 1.0 Hz), 7.35-7.26 (m, 3H), 3.60 (dt, 1H, J=7.0, 4.0 Hz), 1.86-1.80 (m, 1H), 1.78-1.63 (m, 1H), 1.55-1.45 (m, 1H), 1.46-1.36 (m, 1H), 1.35-1.26 (m, 4H), 0.89 (t, 3H, J=7.0 Hz); $^{13}$C NMR (125 MHz, CDCl$_3$): δ 193.3, 136.0, 129.5, 129.0, 126.0, 53.2, 31.6, 27.9, 27.8, 22.6, 14.1. HRMS (EI) calcd for $C_{13}H_{18}OSe$ (M+) 270.0517, obsd 270.0527.

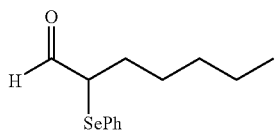

2-(Phenylseleno)octanal: The reaction was carried out following the general procedure to provide a clear oil (67 mg, 95%). $^1$H NMR (500 MHz, CDCl$_3$): δ 9.38 (d, 1H, J=3.5 Hz), 7.50 (d, 2H, J=7.5 Hz), 7.33 (t, 1H, J=7.5 Hz), 7.28 (t, 2H, J=7.5 Hz), 3.60 (dt, 1H, J=7.0, 3.5 Hz), 1.86-1.79 (m, 1H), 1.71-1.66 (m, 1H), 1.58-1.47 (m, 1H), 1.45-1.25 (m, 7H), 0.88 (t, 3H, J=7.0 Hz); $^{13}$C NMR (125 MHz, CDCl$_3$): δ 193.3, 136.0, 129.5, 129.0, 126.2, 53.2, 31.8, 29.1, 28.1, 27.9, 22.7, 14.2. HRMS (EI) calcd for $C_{14}H_{20}OSe$ ($M^+$) 284.0674, obsd 284.0685.

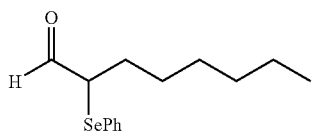

2-(Phenylseleno)nonanal: The reaction was carried out following the general procedure to provide a clear oil (67 mg, 91%). $^1$H NMR (500 MHz, CDCl$_3$): δ 9.38 (d, 1H, J=4.0 Hz), 7.50 (d, 2H, J=7.0 Hz), 7.33 (t, 1H, J=7.5 Hz), 7.28 (t, 2H, J=7.0 Hz), 3.60 (dt, 1H, J=7.0, 3.5 Hz), 1.86-1.79 (m, 1H), 1.71-1.64 (m, 1H), 1.57-1.47 (m, 1H), 1.43-1.36 (m, 1H), 1.35-1.26 (m, 8H), 0.88 (t, 3H, J=7.0 Hz); $^{13}$C NMR (125 MHz, CDCl$_3$): δ 193.3, 136.0, 129.5, 129.0, 126.2, 53.2, 31.9, 29.4, 29.2, 28.2, 27.8, 22.8, 14.3. HRMS (EI) calcd for $C_{15}H_{22}OSe$ ($M^+$) 298.0830, obsd 298.0807.

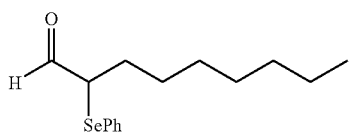

2-(Phenylseleno)decanal:[4] The reaction was carried out following the general procedure to provide a clear oil (67 mg, 84%). $^1$H NMR (500 MHz, CDCl$_3$): δ 9.38 (d, 1H, J=4.0 Hz), 7.50 (d, 2H, J=7.0 Hz), 7.33 (t, 1H, J=7.5 Hz), 7.28 (t, 2H, J=7.5 Hz), 3.60 (dt, 1H, J=7.0, 4.0 Hz), 1.86-1.79 (m, 1H), 1.71-1.64 (m, 1H), 1.57-1.47 (m, 1H), 1.43-1.37 (m, 1H), 1.31-1.25 (m, 10H), 0.88 (t, 3H, J=7.0 Hz); $^{13}$C NMR (125 MHz, CDCl$_3$): δ 193.3, 136.0, 129.5, 129.0, 126.2, 53.2, 32.0, 29.5, 29.4, 29.3, 28.2, 27.8, 22.8, 14.3. HRMS (EI) calcd for $C_{16}H_{24}OSe$ ($M^+$) 312.0987, obsd 312.0974.

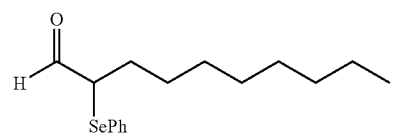

3-Phenyl-2-(Phenylseleno)propionaldehyde: The reaction was carried out following the general procedure to provide a clear oil (60 mg, 80%). $^1$H NMR (500 MHz, CDCl$_3$): δ 9.47 (d, 1H, J=4.0 Hz), 7.49 (d, 2H, J=7.5 Hz), 7.35 (t, 1H, J=7.0 Hz), 7.31-7.19 (m, 7H), 3.90-3.87 (m, 1H), 3.23 (dd, 1H, J=14.0, 8.0 Hz), 3.00 (dd, 1H, J=14.0, 6.5 Hz); $^{13}$C NMR (125 MHz, CDCl$_3$): δ 129.4, 138.5, 136.3, 129.6, 129.2, 128.8, 127.1, 126.0, 53.7, 34.3. HRMS (EI) calcd for $C_{15}H_{14}OSe$ ($M^+$) 290.0204, obsd 290.0183.

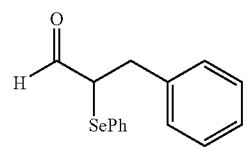

General Procedure B for α-Selenenylation of Aldehyde (Table 9, Entries 11 and 12): To a vial containing an aldehyde (0.25 mmol), and 0.5 mL of anhydrous CH$_2$Cl$_2$ was added catalyst L-prolinamide I (0.005 mmol) at room temperature. The mixture was vigorously stirred for 0.5 h in the presence of 4 Å molecule sieves (40 mg). Then N-(phenylseleno)phthalimide (0.3 mmol) was added. After 0.5 h, the molecule sieves were removed by filtrating paper and then the filtrate was treated with water (5 mL), the solution was extracted with ethyl acetate (3×5 mL). The combined extracts were dried over MgSO$_4$, filtered, and concentrated iii vacuo. The resulting residue was then purified by silica gel chromatography, eluting with EtOAc/Hexane (1/40) to provide a clear oil.

2-Methyl-2-(Phenylseleno)propionaldehyde: The reaction was carried out following the general procedure to provide a clear oil (45 mg, 76%). $^1$H NMR (500 MHz, CDCl$_3$): δ 9.26 (s, 1H), 7.49 (d, 2H, J=7.0 Hz), 7.39 (t, 1H, J=7.5 Hz), 7.30 (t, 2H, J=8.0 Hz), 1.44 (s, 6H); $^{13}$C NMR (125 MHz, CDCl$_3$): δ 193.7, 138.0, 129.7, 129.3, 126.3, 53.6, 21.7. HRMS (EI) calcd for $C_{10}H_{12}OSe$ ($M^+$) 228.0048, obsd 228.0065.

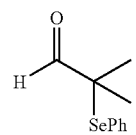

1-(Phenylseleno)cyclohexanecarbaldehyde: The reaction was carried out following the general procedure to provide a clear oil (56 mg, 81%). $^1$H NMR (500 MHz, CDCl$_3$): δ 9.18 (s, 1H), 7.47 (d, 2H, J=7.0 Hz), 7.37 (t, 1H, J=7.5 Hz), 7.30 (t, 2H, J=7.5 Hz), 1.92-1.88 (m, 2H), 1.76-1.71 (m, 4H), 1.56-1.53 (m, 1H), 1.45-1.23 (m, 3H); $^{13}$C NMR (125 MHz, CDCl$_3$): δ 192.8, 138.1, 129.6, 129.2, 125.2, 59.9, 30.9, 25.7, 24.2. HRMS (EI) calcd for C$_{13}$H$_{16}$OSe (M+) 268.0361, obsd 268.0336.

General Procedure for α-Selenenylation of Ketones (Table 10, entries 1-14): To a vial containing ketone (0.3 mmol), and 1.0 mL of anhydrous CH$_2$Cl$_2$ was added catalyst pyrrolidine trifluoromethanesulfonamide I (0.03 mmol) at room temperature. The mixture was vigorously stirred for 1 hr before N-(phenylseleno)phthalimide (0.3 mmol) was added. After 16-48 h, the reaction mixture was treated with water (10 mL), and then the solution was extracted with ethyl acetate (3 □ 10 mL). The combined extracts were dried over MgSO$_4$, filtered, and concentrated in vacuo. The resulting residue was then purified by silica gel chromatography and fractions were collected and concentrated in vacuo to provide a clear oil.

1-(Phenylselanyl)propan-2-one: This compound was prepared according to the general procedure in 69% yield. $^1$H NMR (500 MHz, CDCl$_3$): δ7.55-7.50 (m, 2H), 7.26-7.31 (m, 3H), 3.59 (s, 2H), 2.27 (s, 3H); $^{13}$C NMR (125 MHz, CDCl$_3$): δ 203.7, 33.5, 129.6, 128.9, 128.2, 37.0, 28.2; HRMS (EI) calcd for C$_9$H$_{10}$OSe (M$^+$) 213.9891, obsd 213.9909.

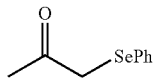

2-(Phenylselanyl)pentan-3-one: This compound was prepared according to the general procedure in 61% yield. $^1$H NMR (500 MHz, CDCl$_3$): δ 7.52 (dd, 2H, J=8.0, 1.0 Hz), 7.37-7.25 (m, 3H), 3.81 (q, 1H, J=7.0 Hz), 2.78 (dq, 1H, J=17.5, 7.0 Hz), 2.50 (dq, 1H, J=17.5, 7.0 Hz), 1.48 (d, 3H, J=7.0 Hz), 1.08 (t, 3H, J=7.5 Hz); $^{13}$C NMR (125 MHz, CDCl$_3$): δ 207.9, 136.0, 129.4, 128.9, 127.4, 45.3, 33.2, 16.7, 8.6; HRMS (EI) calcd for C$_{11}$H$_{14}$OSe (M$^+$) 242.0204, obsd 242.0191.

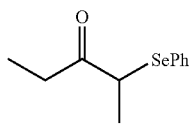

3-(Phenylselanyl)heptan-4-one: This compound was prepared according to the general procedure in 58% yield. $^1$H NMR (500 MHz, CDCl$_3$): δ 7.51 (dd, 2H, J=7.5, 1.0 Hz), 7.35-7.25 (m, 3H), 3.56 (t, 1H, J=7.5 Hz), 2.63 (dt, 1H, J=16.5, 7.5 Hz), 2.49 (dq, 1H, J=16.5, 7.0 Hz), 1.91-1.85 (m, 1H), 1.76-1.70 (m, 1H), 1.65-1.58 (m, 1H), 0.98 (d, 3H, =7.5 Hz), 0.91 (t, 3H, J=7.5 Hz); $^{13}$C NMR (125 MHz, CDCl$_3$): δ 206.6, 135.8, 129.3, 128.7, 127.6, 53.7, 42.6, 23.9, 17.8, 13.9, 13.0; HRMS (EI) calcd for C$_{13}$H$_{18}$OSe (M+) 270.0517, obsd 270.0520.

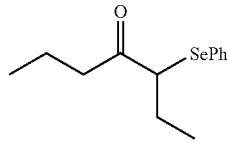

4-Methyl-1-(phenylselanyl)pentan-2-one: This compound was prepared according to the general procedure in 62% yield. $^1$H NMR (500 MHz, CDCl$_3$): δ 7.53 (dd, 2H, J=6.0, 3.0 Hz), 7.29-7.26 (m, 3H), 3.58 (s, 2H), 2.46 (d, 2H, J=7.0 Hz), 2.13-2.08 (m, 1H), 0.89 (d, 6H, J=6.5 Hz); $^{13}$C NMR (125 MHz, CDCl$_3$): δ 205.6, 133.5, 129.5, 129.1, 128.1, 49.9, 36.6, 24.9, 22.7; HRMS (EI) calcd for C$_{12}$H$_{16}$OSe (M$^+$) 256.0361, obsd 256.0323.

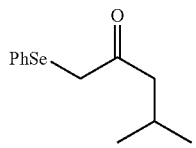

1-(Phenylselanyl)hex-5-en-2-one: This compound was prepared according to the general procedure in 63% yield. $^1$H NMR (500 MHz, CDCl$_3$): δ 7.53 (dd, 2H, J=6.0, 2.0 Hz), 7.35-7.26 (m, 3H), 5.80-5.73 (m, 1H), 5.02-4.90 (m, 2H), 3.59 (s, 2H), 2.68 (t, 2H, J=7.0 Hz), 2.33-2.29 (m, 2H); $^{13}$C NMR (125 MHz, CDCl$_3$): δ 205.1, 137.1, 136.1, 133.6, 129.5, 128.2, 115.6, 40.0, 36.3, 28.2; HRMS (EI) calcd for C$_{12}$H$_{14}$OSe (M$^+$) 254.0204, obsd 254.0280.

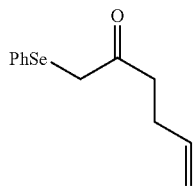

1-Phenyl-2-(phenylselanyl)ethanone: This compound was prepared according to the general procedure in 81% yield. $^1$H NMR (500 MHz, CDCl$_3$): δ 7.88 (dd, 2H, J=8.0, 1.0 Hz), 7.56-7.52 (m, 3H), 7.42 (t, 2H, J=7.5 Hz), 7.29-7.24 (m, 3H), 4.17 (s, 2H); $^{13}$C NMR (125 MHz, CDCl$_3$): δ195.1, 135.6, 134.2, 133.5, 129.4, 129.2, 128.9, 128.8, 128.3, 32.9; HRMS (EI) calcd for C$_{14}$H$_{12}$OSe (M$^+$) 276.0048, obsd 276.0064.

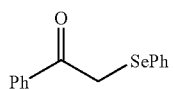

2-(Phenylselanyl)cyclopentanone: This compound was prepared according to the general procedure in 78% yield. $^1$H NMR (500 MHz, CDCl$_3$): δ 7.51 (dd, 2H, J=6.5, 1.5 Hz), 7.34-7.26 (m, 3H), 3.75 (t, 1H, J=7.5 Hz), 2.36-2.28 (m, 2H), 2.22-2.15 (m, 1H), 2.08-1.89 (m, 3H); $^{13}$C NMR (125 MHz, CDCl$_3$): δ 214.7, 135.5, 129.3, 128.6, 128.0, 46.6, 36.5, 30.9, 21.1; HRMS (EI) calcd for C$_{11}$H$_{12}$OSe (M$^+$) 240.0048, obsd 240.0062.

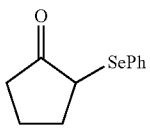

2,2-Dimethyl-5-(phenylselanyl)cyclopentanone: This compound was prepared according to the general procedure in 67% yield. $^1$H NMR (500 MHz, CDCl$_3$): δ 7.61 (dd, 2H, J=6.0, 1.0 Hz), 7.34-7.26 (m, 3H), 3.83 (dd, 1H, J=7.5, 5.0 Hz), 2.32-2.25 (m, 1H), 1.96-1.89 (m, 2H), 1.78-1.73 (m, 1H), 1.03 (s, 3H), 1.02 (s, 3H); $^{13}$C NMR (125 MHz, CDCl$_3$): δ 218.2, 135.6, 129.0, 128.4, 127.9, 45.9, 44.3, 36.6, 27.0, 25.2, 24.4; HRMS (EI) calcd for C$_{13}$H$_{16}$OSe (M$^+$) 268.0361, obsd 268.0343.

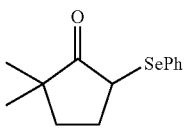

2-(Phenylselanyl)cyclohexanone: This compound was prepared according to the general procedure in 80% yield. $^1$H NMR (500 MHz, CDCl$_3$): δ 7.55 (dd, 2H, J=6.5, 1.5 Hz), 7.31-7.26 (m, 3H), 3.91 (t, 1H, J=5.0 Hz), 2.95 (m, 1H), 2.36-2.28 (m, 1H), 2.27-2.15 (m, 2H), 2.00-1.95 (m, 1H), 1.89-1.69 (m, 3H), $^{13}$C NMR (125 MHz, CDCl$_3$): δ 208.1, 134.8, 129.4, 128.8, 128.3, 51.8, 38.7, 34.2, 27.1, 23.1; HRMS (EI) calcd for C$_{12}$H$_{14}$OSe (M$^+$) 254.0204, obsd 254.0122.

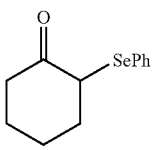

Tetrahydro-3-(phenylselanyl)pyran-4-one: This compound was prepared according to the general procedure in 79% yield. $^1$H NMR (500 MHz, CDCl$_3$): δ 7.54 (dd, 2H, J=9.5, 2.0 Hz), 7.33-7.26 (m, 3H), 4.16-4.03 (m, 3H), 3.96-3.89 (m, 2H), 3.14-3.09 (m, 1H), 2.51-2.47 (m, 1H); $^{13}$C NMR (125 MHz, CDCl$_3$): δ 203.2, 135.0, 129.5, 128.6, 127.8, 73.2, 68.5, 51.3, 40.5; HRMS (EI) calcd for C$_{11}$H$_{12}$O$_2$Se (M$^+$) 255.9997, obsd 255.9974.

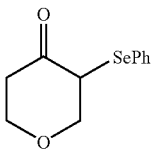

1-Methyl-3-(phenylselanyl)piperidin-4-one: This compound was prepared according to the general procedure in 76% yield. $^1$H NMR (500 MHz, CDCl$_3$): δ 7.54 (dd, 2H, J=9.0, 2.0 Hz), 7.29-7.25 (m, 3H), 3.76 (brs, 1H), 3.33-3.27 (m, 1H), 3.17-3.14 (m, 1H), 2.97-2.88 (m, 2H), 2.50-2.45 (m, 1H), 2.38 (s, 3H), 2.37-2.32 (m, 1H); $^{13}$C NMR (125 MHz, CDCl$_3$): δ 205.3, 134.2, 129.5, 129.4, 128.1, 61.8, 55.7, 50.3, 45.9, 37.7; HRMS (EI) calcd for C$_{12}$H$_{15}$NOSe (M$^+$) 269.0313, obsd 269.0341.

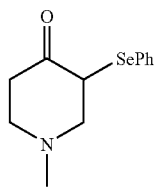

1-Ethylene ketal-3-(phenylselanyl)cyclohexanedin-4-one: This compound was prepared according to the general procedure in 85% yield. $^1$H NMR (500 MHz, CDCl$_3$): δ 7.54 (dd, 2H, J=5.0, 2.0 Hz), 7.28-7.25 (m, 3H), 4.07-3.98 (m, 5H), 3.18-3.12 (m, 1H), 2.50-2.42 (m, 2H), 2.32 (dd, 1H, J=14.5, 6.5 Hz), 2.04 (t, 2H, J=7.0 Hz); $^{13}$C NMR (125 MHz, CDCl$_3$); δ 206.4, 134.5, 129.8, 129.3, 128.2, 107.0, 65.1, 64.9, 48.0, 41.0, 35.3, 34.6; HRMS (EI) calcd for C$_{14}$H$_{16}$O$_3$Se (M$^+$) 312.0259, obsd 312.0260.

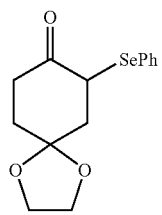

6-(Phenylselanyl)cyclohex-2-enone: This compound was prepared according to the general procedure in 63% yield. $^1$H NMR (500 MHz, CDCl$_3$): δ 7.60 (d, 2H, J=7.0 Hz), 7.33-7.26 (m, 3H), 6.93-6.90 (m, 1H), 6.03 (d, 1H, J=10.0 Hz), 4.03 (t, 1H, J=5.0 Hz), 2.60-2.53 (m, 1H), 2.40-2.16 (m, 3H); $^{13}$C NMR (125 MHz, CDCl$_3$): δ 195.3, 149.4, 135.6, 129.3, 128.6, 128.5, 127.8, 48.0, 29.3, 24.0; HRMS (EI) calcd for C$_{12}$H$_{12}$OSe (M$^+$) 252.0048, obsd 252.0043.

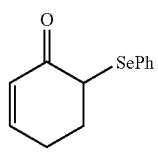

2-(Phenylselanyl)cycloheptanone: This compound was prepared according to the general procedure in 59% yield. $^1$H NMR (500 MHz, CDCl$_3$): ϵ 7.54 (dd, 2H, J=6.0, 2.0 Hz), 7.32-7.26 (m, 3H), 3.80 (dd, 1H, J=11.0, 5.5 Hz), 2.77-2.71 (m, 1H), 2.41-2.37 (m, 1H), 2.32-2.26 (m, 1H), 1.95-1.87 (m, 2H), 1.85-1.80 (m, 1H), 1.67-1.60 (m, 1H), 1.51-1.35 (m, 2H), 1.33-1.21 (m, 1H); $^{13}$C NMR (125 MHz, CDCl$_3$): δ 209.5, 135.2, 129.3, 128.6, 128.5, 52.5, 40.1, 30.7, 30.4, 28.2, 25.9; HRMS (EI) calcd for C$_{13}$H$_{16}$OSe (M$^+$) 268.0361, obsd 268.0342.

α-Sulfenylation Reactions of Aldehydes and Ketones

General Information: Commercial reagents were used as received, unless otherwise stated. Merck 60 silica gel was used for chromatography, and Whatman silica gel plates with fluorescence F$_{254}$ were used for thin-layer chromatography (TLC) analysis. $^1$H and $^{13}$C NMR spectra were recorded on Bruker AC250 and Broker Avance 500, and tetramethylsilane (TMS) was used as a reference. Data for $^1$H are reported as follows: chemical shift (ppm), and multiplicity (s=singlet, d=doublet, t=triplet, q=quartet, m=multiplet). Data for $^{13}$C NMR are reported as ppm. Mass Spectra were obtained from Ohio State University Mass Spectral facility.

General Procedure for α-Sulfenylation of Aldehydes and Ketones (Entry 1-11): To a vial containing aldehyde or ketone (0.5 mmol) in 0.5 mL of anhydrous $CH_3CN$ was added catalyst (S)-2-(trifluoro methane sulfonylamino methyl)-pyrrolidine (0.075 mmol) at room temperature. The mixture was vigorously stirred for 10 min in the presence of 0.1 g 4 Å molecular sieves. Then N-(Phenylthio)-phthalimide (0.25 mmol) was added. The reaction was monitored by TLC. The reaction mixture was treated with water (5 mL) and extracted with $CH_2Cl_2$ (3×5 mL). The combined extracts were dried over $MgSO_4$, filtered, and concentrated in vacuo. The resulting residue was then purified by silica gel chromatography and fractions were collected and concentrated in vacuo to provide a clear oil.

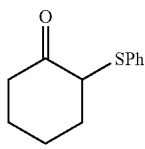

2-Phenylsulfanyl-cyclohexanone (Table 11, Entry 1): This compound was prepared according to the general procedure in 83% yield. $^1$H NMR (250 MHz, $CDCl_3$): δ 7.20-7.42 (m, 5H), 3.83 (t, 1H, J=5.3 Hz), 2.90 (m, 1H), 1.65-2.34 (m, 7H); $^{13}$C NMR (62.5 MHz, $CDCl_3$): δ 207.5, 133.8, 131.8, 129.0, 127.4, 56.4, 39.0, 33.9, 27.3, 22.6. HRMS (EI) exact mass calcd for [M+] ($C_{12}H_{14}OS$) 206.0760. Found 206.0765.

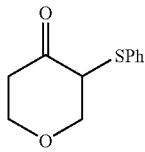

3-Phenylsulfanyl-tetrahydro-pyran-4-one (Table 11, Entry 2): This compound was prepared according to the general procedure in 88% yield. $^1$H NMR (250 MHz, $CDCl_3$): δ 7.41-7.45 (m, 2H), 7.26-7.34 (m, 3H), 4.11-4.18 (m, 1H), 3.85-4.03 (m, 4H), 2.97 (m, 1H), 2.52 (m, 1H); $^{13}$C NMR (62.5 MHz, $CDCl_3$): δ 197.2, 132.7, 132.2, 129.1, 127.8, 72.6, 68.4, 56.6, 41.0. HRMS (EI) exact mass calcd for [M+] ($C_{11}H_{12}O_2S$) 208.0553. Found 208.0553.

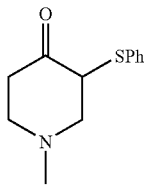

1-Methyl-3-phenylsulfanyl-piperidin-4-one (Table 11, Entry 3): This compound was prepared according to the general procedure in 60% yield. $^1$H NMR (250 MHz, $CDCl_3$): δ 7.40-7.43 (m, 2H), 7.23-7.33 (m, 3H), 3.80 (m, 1H), 3.07 (m, 1H), 2.94 (d, 2H, J=5 Hz), 2.89 (m, 1H), 2.63 (m, 1H), 2.43 (m, 1H), 2.36 (s, 3H); $^{13}$C NMR (62.5 MHz, $CDCl_3$): δ 204.6, 134.0, 131.5, 129.1, 127.4, 61.4, 55.7, 55.2, 45.4, 38.5. HRMS (EI) exact mass calcd for [M+] ($C_{12}H_{15}NOS$) 221.0869. Found 221.0852.

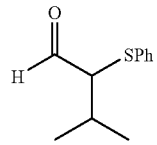

3-Methyl-2-phenylsulfanyl-butyraldehyde (Table 11, Entry 4): This compound was prepared according to the general procedure in 56% yield. $^1$H NMR (250 MHz, $CDCl_3$): δ 9.34 (d, 1H, J=5.4 Hz), 7.22-7.40 (m, 5H), 3.29 (q, 1H, J=5.4 Hz, J=8.5 Hz), 2.10 (m, 1H), 1.19 (d, 3H, J=6.8 Hz), 1.09 (d, 3H, J=6.8 Hz); $^{13}$C NMR (62.5 MHz, $CDCl_3$): δ 195.1, 132.7, 132.2, 129.2, 127.8, 64.5, 27.9, 20.7, 20.0. HRMS (EI) exact mass calcd for [M+] ($C_{11}H_{14}OS$, mono-addition product) 194.0760. Found 194.0743, [M+] ($C_{17}H_{18}OS_2$, bis-addition product) 302.0794. Found 302.0841.

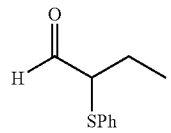

2-Phenylsulfanyl-butyraldehyde (Table 11, Entry 5): This compound was prepared according to the general procedure in 56% yield. $^1$H NMR (500 MHz, $CDCl_3$): δ 9.39 (d, 1H, J=4.0 Hz), 7.22-7.41 (m, 5H), 3.45 (m, 1H), 1.64-1.90 (m, 2H), 1.10 (t, 3H, J=7.5 Hz); $^{13}$C NMR (125 MHz, $CDCl_3$): δ 195.6, 136.8, 133.1, 132.1, 130.1, 129.4, 128.4, 127.8, 58.7, 29.9, 23.8, 21.5, 11.8; HRMS (EI) exact mass calcd for [M+] ($C_{10}H_{12}OS$, mono-addition product) 180.0603. Found 180.0572, [M+] ($C_{16}H_{16}OS_2$, bis-addition product) 288.0637. Found 288.0653.

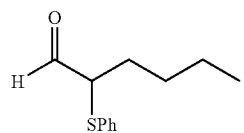

2-Phenylsulfanyl-hexanal (Table 11, Entry 6): This compound was prepared according to the general procedure in 42% yield. $^1$H NMR (250 MHz, $CDCl_3$): δ 9.36 (d, 1H, J=4.3 Hz), 7.26-7.48 (m, 5H), 3.51 (m, 1H), 1.25-1.80 (m, 6H), 0.92 (t, 3H, J=6.8 Hz); $^{13}$C NMR (62.5 MHz, $CDCl_3$): δ 195.3, 132.7, 132.0, 129.1, 128.1, 56.8, 29.0, 27.6, 22.4, 13.8. HRMS (EI) exact mass calcd for [M+] ($C_{12}H_{16}OS$, mono-addition product) 208.0916. Found 208.0923, [M+] ($C_{18}H_{20}OS_2$, bis-addition product) 316.0950. Found 316.1025.

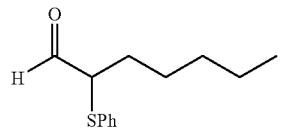

2-Phenylsulfanyl-heptanal (Table 11, Entry 7): This compound was prepared according to the general procedure in 52% yield. $^1$H NMR (250 MHz, CDCl$_3$): δ 9.36 (d, 1H, J=4.3 Hz), 7.22-7.40 (m, 5H), 3.52 (m, 1H), 1.26-1.79 (m, 8H), 0.88 (t, 3H, J=3.3 Hz); $^{13}$C NMR (125 MHz, CDCl$_3$): δ 195.5, 136.7, 134.7, 133.0, 132.2, 130.0, 129.4, 128.3, 101.9, 57.1, 34.6, 31.9, 31.6, 31.3, 29.2, 28.0, 26.8, 23.7, 22.8, 22.6, 14.3, 14.1. HRMS (EI) exact mass calcd for [M+] (C$_{13}$H$_{18}$OS) 222.1073. Found 222.1076.

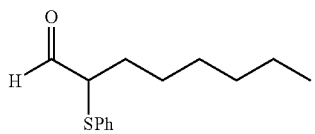

2-Phenylsulfanyl-octanal (Table 11, Entry 8): This compound was prepared according to the general procedure in 66% yield. $^1$H NMR (250 MHz, CDCl$_3$): δ 9.36 (d, 1H, J=4.3 Hz), 7.26-7.40 (m, 5H), 3.52 (m, 1H), 1.29-1.83 (m, 10H), 0.88 (t, 3H, J=6.5 Hz); $^{13}$C NMR (62.5 MHz, CDCl$_3$): δ 195.3, 132.7, 132.0, 129.1, 128.1, 56.8, 31.5, 28.9, 27.9, 26.8, 22.5, 14.0. HRMS (EI) exact mass calcd for [M+] (C$_{14}$H$_{20}$OS) 236.1129. Found 236.1217.

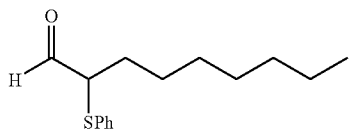

2-Phenylsulfanyl-nonanal (Table 11, Entry 9): This compound was prepared according to the general procedure in 63% yield. $^1$H NMR (250 MHz, CDCl$_3$): δ 9.36 (d, 1H, J=4.3 Hz), 7.26-7.40 (m, 5H), 3.51 (m, 1H), 1.45-1.81 (m, 12H), 0.88 (d, 3H, J=6.8 Hz); $^{13}$C NMR (62.5 MHz, CDCl$_3$): δ 195.3, 132.7, 132.0, 129.1, 128.1, 56.8, 31.7, 29.2, 29.0, 27.9, 26.9, 22.6, 14.0. HRMS (EI) exact mass calcd for [M+] (C$_{15}$H$_{22}$OS) 250.1386. Found 250.1404.

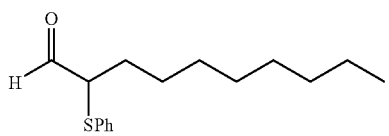

2-Phenylsulfanyl-decanal (Table 11, Entry 10): This compound was prepared according to the general procedure in 57% yield. $^1$H NMR (500 MHz, CDCl$_3$): δ 9.29 (d, 1H, J=4.5 Hz), 7.16-7.42 (m, 5H), 3.44 (m, 1H), 1.16-1.77 (m, 14H), 0.81 (t, 3H, J=6.5 Hz); $^{13}$C NMR (125 MHz, CDCl$_3$): δ 195.5, 191.0, 136.7, 134.7, 133.0, 132.2, 129.4, 129.1, 128.3, 57.0, 32.0, 30.9, 29.6, 29.5, 29.4, 29.2, 28.1, 27.1, 24.2, 22.8, 14.3. HRMS (EI) exact mass calcd for [M+] (C$_{16}$H$_{24}$OS, mono-addition product) 264.1542. Found 264.1534, [M+] (C$_{12}$H$_{28}$OS$_2$, bis-addition product) 372.1576. Found 372.1554.

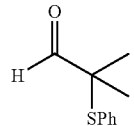

2-Methyl-2-phenylsulfanyl-propionaldehyde (Table 11, Entry 11): This compound was prepared according to the general procedure in 46% yield. $^1$H NMR (500 MHz, CDCl$_3$): δ 9.35 (s, 1H), 7.29-7.40 (m, 5H), 1.33 (s, 6H); $^{13}$C NMR (125 MHz, CDCl$_3$): δ 195.6, 137.1, 130.1, 129.8, 129.2, 55.6, 21.4. HRMS (EI) exact mass calcd for [M+] (C$_{12}$H$_{14}$OS) 206.0760, found 206.0765.

Aldol Condensation Reactions of Ketones and Aldehydes to Produce Alpha Beta Unsaturated Ketones General Information: Commercial reagents were used as received, unless otherwise stated. Merck 60 silica gel was used for chromatography, and Whatman silica gel plates with fluorescence F$_{254}$ were used for thin-layer chromatography (TLC) analysis. $^1$H and $^{13}$C NMR spectra were recorded on Broker Avance 500, and tetramethylsilane (TMS) was used as a reference. Data for $^1$H are reported as follows: chemical shift (ppm), and multiplicity (s=singlet, d=doublet, t=triplet, q=quartet, m=multiplet). Data for $^{13}$C NMR are reported as ppm. Mass Spectra were obtained from Ohio State University Mass Spectral facility.

General Procedure for Aldol Reaction of α,α-Dialkyl Aldehydes to Aryl Aldehydes: A mixture of iso-butyraldehyde (4.0 mmol) and an aryl Aldehyde (0.4 mmol) in the presence of 20 mol % chiral (S) pyrrolidine sulfonamide V was stirred for 1-7 days. Then the crude product was directly purified by silica gel chromatography without workup using a mixture of EtOAc/hexanes (⅕ up to ½) as eluent and fractions were collected and concentrated in vacuo to provide the desired product.

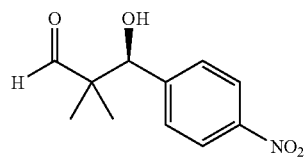

(S)-3-Hydroxy-2,2-dimethyl-3-(4-nitrophenyl)propanal (Table 13, entry 1): Yield: 83%; $^1$H NMR (500 MHz, CDCl$_3$): δ 9.62 (s, 1H), 8.21 (d, 2H, J=8.5 Hz), 7.51 (d, 2H, J=8.0 Hz), 5.05 (s, 1H), 2.87 (s, 1H), 1.07 (s, 3H), 0.99 (s, 3H); $^{13}$C NMR (125 MHz, CDCl$_3$): δ 206.0, 147.8, 147.1, 128.6, 123.3, 76.4, 51.0, 20.1, 15.8; [α]$_D^{25}$=+31.6 (c=1.0, CHCl$_3$); HPLC (Daicel CHIRALPAK AS-H, Hexane/2-PrOH=90:10, flow rate 1.0 mL/min, γ=254 nm); t$_R$=28.98 (major), 32.31 (minor) min.

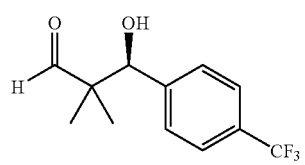

(S)-3-(4-(Trifluoromethyl)phenyl)-3-hydroxy-2,2-dimethylpropanal (Table 13, entry 2): Yield: 83%; $^1$H NIMR (250 MHz, CDCl$_3$): δ 9.61 (s, 1H), 7.59 (d, 2H, J=8.0 Hz), 7.42 (d, 2H, J=8.0 Hz), 4.95 (s, 1H), 2.69 (s, 1H), 1.04 (s, 3H), 0.95 (s, 3H); $^{13}$C NMR (62.5 MHz, CDCl$_3$): δ 206.1, 143.6, 128.1 (q), 127.9, 124.9, 124.8, 76.5, 50.7, 19.9, 15.6; HPLC (Daicel CHIRALPAK AS-H, Hexane/2-PrOH=95:5, flow rate 1.0 mL/min, γ=254 nm); $t_R$=15.53 (major), 16.38 (minor) min. HRMS (EI) exact mass calcd for $[C_{12}H_{13}F_3O_2]^+$: 246.0862. Found 246.0858.

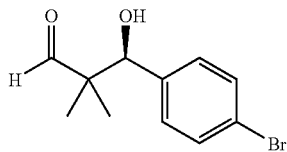

(S)-3-(4-Bromophenyl)-3-hydroxy-2,2-dimethyl-propionaldehyde (Table 13, entry 3): Yield: 94%; $^1$H NMR (250 MHz, CDCl$_3$): δ 9.62 (s, 1H), 7.47 (d, 2H, J=8.4 Hz), 7.18 (d, 2H, J=8.4 Hz), 4.85 (d, 1H, J=1.4 Hz), 2.68 (d, 1H, J=2.4 Hz), 1.03 (s, 3H), 0.95 (s, 3H); $^{13}$C NMR (62.5 MHz, CDCl$_3$): δ 206.3, 138.6, 131.1, 129.1, 121.9, 76.6, 50.7, 19.9, 15.6; $[α]_D^{25}$=+67.0 (c=0.5, CHCl$_3$); HPLC (Daicel CHIRALPAK AS-H, Hexane/2-PrOH=90:10, flow rate 1.0 mL/min, γ=254 nm); $t_R$=11.57 (major), 13.21 (minor) min.

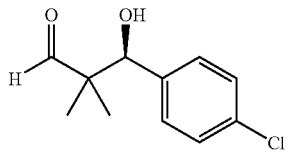

(S)-3-(4-Chlorophenyl)-3-hydroxy-2,2-dimethyl-propionaldehyde (Table 13, entry 4): Yield: 96%; $^1$H NMR (250 MHz, CDCl$_3$): δ 9.63 (s, 1H), 7.32 (d, 2H, J=8.5 Hz), 7.24 (d, 2H, J=8.5 Hz), 4.88 (s, 1H), 2.64 (s, 1H), 1.04 (s, 3H), 0.95 (s, 3H); $^{13}$C NMR (62.5 MHz, CDCl$_3$): δ 206.3, 138.1, 133.8, 128.8, 128.1, 76.5, 50.8, 19.9, 15.7; $[α]_D^{25}$=+25.4 (c=1.0, CHCl$_3$); HPLC (Daicel CHIRALPAK AS-H, Hexane/2-PrOH=90:10, flow rate 1.0 mL/min, γ=254 nm); $t_R$=11.08 (major), 12.78 (minor) min. HRMS (EI) exact mass calcd for $[2C_{11}H_{13}ClO_2+Na]^+$: 447.1100. Found 447.1108.

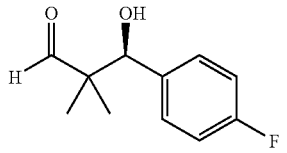

(S)-3-(4-Fluorophenyl)-3-hydroxy-2,2-dimethyl-propionaldehyde (Table 13, entry 5): Yield: 81%; $^1$H NMR (250 MHz, CDCl$_3$): δ 9.63 (s, 1H), 6.99-7.30 (m, 4H), 4.86 (s, 1H), 2.74 (s, 1H), 1.03 (s, 3H), 0.94 (s, 3H); $^{13}$C NMR (62.5 MHz, CDCl$_3$): δ 206.5, 163.4, 161.4, 135.4, 129.1, 129.0, 114.9, 114.7, 76.7, 50.8, 19.9, 15.6; $[α]_D^{25}$=+39.2 (c=1.0, CHCl$_3$); HPLC (Daicel CHIRALPAK AS-H, Hexane/2-PrOH=90:10, flow rate 1.0 mL/min, γ=254 nm); $t_R$=10.84 (major), 12.81 (minor) min. HRMS (EI) exact mass calcd for $[2C_{11}H_{13}FO_2+Na]^+$: 415.1691. Found 415.1675.

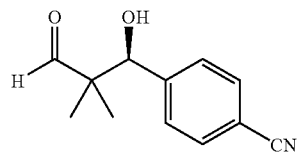

(S)-4-(1-Hydroxy-2,2-dimethyl-3-oxo-propyl)-benzonitrile (Table 13, entry 6): Yield: 95%; $^1$H NMR (250 MHz, CDCl$_3$): δ 9.57 (s, 1H), 7.58 (d, 2H, J=8.2 Hz), 7.39 (d, 2H, J=8.2 Hz), 4.91 (s, 1H), 3.00 (s, 1H), 0.98 (s, 3H), 0.91 (s, 3H); $^{13}$C NMR (62.5 MHz, CDCl$_3$): δ 205.8, 145.2, 131.6, 128.2, 118.5, 111.4, 76.3, 50.7, 19.7, 15.6; $[α]_D^{25}$=+37.1 (c=1.0, CHCl$_3$); HPLC (Daicel CHIRALPAK AS-H, Hexane/2-PrOH=90:10, flow rate 1.0 mL/min, γ=254 nm); $t_R$=29.62 (major), 34.84 (minor) min. HRMS (EI) exact mass calcd for $[2C_{11}H_{13}NO_2+Na]^+$: 429.1785. Found 429.1791.

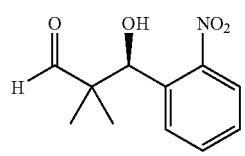

(S)-3-Hydroxy-2,2-dimethyl-3-(2-nitrophenyl)-propionaldehyde (Table 13, entry 7): Yield: 81%; $^1$H NMR (250 MHz, CDCl$_3$): δ 9.54 (s, 1H), 7.76 (q, 2H, $J_1$=8.2 Hz, $J_2$=12.0 Hz), 7.59 (t, 1H, J=7.7 Hz), 7.41 (t, 1H, J=7.7 Hz), 5.79 (d, 1H, J=3.6 Hz), 3.00 (d, 1H, J=3.7 Hz), 0.98 (s, 3H), 0.88 (s, 3H); $^{13}$C NMR (62.5 MHz, CDCl$_3$): δ 205.3, 148.8, 134.5, 132.6, 129.9, 128.6, 124.1, 70.1, 51.4, 19.0, 16.0; $[α]_D^{25}$=+260.9 (c=1.0, CHCl$_3$); HPLC (Daicel CHIRALPAK AS-H, Hexane/2-PrOH=90:10, flow rate 1.0 mL/min, γ=254 nm); $t_R$=15.84 (minor), 16.56 (major) min. HRMS (EI) exact mass calcd for $[C_{11}H_{13}NO_4+Na]^+$: 246.0737. Found 246.0729.

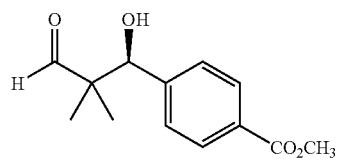

(S)-4-(1-Hydroxy-2,2-dimethyl-3-oxo-propyl)-benzoic acid methyl ester (Table 13, entry 8): Yield: 93%; $^1$H NMR (250 MHz, CDCl$_3$): δ 9.61 (s, 1H), 7.96 (d, 2H, J=8.2 Hz), 7.35 (d, 2H, J=8.2 Hz), 4.92 (s, 1H), 3.88 (s, 3H), 2.80 (s, 1H), 1.01 (s, 3H), 0.93 (s, 3H); $^{13}$C NMR (62.5 MHz, CDCl$_3$): δ 206.1, 166.8, 144.8, 129.7, 129.2, 127.5, 76.8, 52.1, 50.7, 19.9, 15.6; $[α]_D^{25}$=+25.2 (c=0.5, CHCl$_3$); HPLC (Daicel CHIRALPAK AS-H, Hexane/2-PrOH=90:10, flow rate 1.0 mL/min, γ=254 nm); $t_R$=18.89 (major), 24.26 (minor) min. HRMS (EI) exact mass calcd for $[C_{13}H_{16}O_4+MeOH+Na]^+$: 291.1203. Found 291.1199.

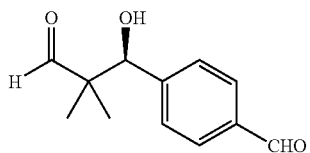

(S)-4-(1-Hydroxy-2,2-dimethyl-3-oxo-propyl)-benzaldehyde (Table 13, entry 9): Yield: 97%; $^1$H NMR (250 MHz, CDCl$_3$): δ 9.98 (s, 1H), 9.64 (s, 1H), 7.84 (d, 2H, J=4.1 Hz), 7.48 (d, 2H, J=4.1 Hz), 4.98 (s, 1H), 3.48 (s, 1H), 1.05 (s, 3H), 0.97 (s, 3H); $^{13}$C NMR (62.5 MHz, CDCl$_3$): δ 206.0, 192.0, 146.6, 135.8, 129.2, 128.1, 76.7, 50.7, 19.8, 15.7; $[\alpha]_D^{25}$=+24.0 (c=0.41, CHCl$_3$); HPLC (Daicel CHIRALPAK AS-H, Hexane/2-PrOH=90:10, flow rate 1.0 mL/min, γ=254 nm); $t_R$=35.63 (major), 40.82 (minor) min. HRMS (EI) exact mass calcd for $[2C_{12}H_{14}O_3+H]^+$: 413.2255. Found 413.2237.

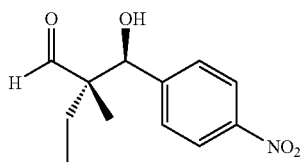

(S, S)-2-[Hydroxy-(4-nitrophenyl)methyl]-2-methyl-butyraldehyde (Table 13, entry 10): Yield: 85%; $^1$H NMR (250 MHz, CDCl$_3$): δ 9.67 (syn), 9.66 (anti), 8.20 (anti), 8.18 (syn), 7.50 (d, 2H, J=4.3 Hz), 5.10 (anti), 5.02 (syn), 2.83 (brs, 1H), 1.36-1.67 (m, 2H), 1.01 (anti) and 1.05 (syn) (s, 3H), 0.86-0.91 (m, 3H); $[\alpha]_D^{25}$=+14.3 (c=0.3, CHCl$_3$); HPLC (Daicel CHIRAL DECIAL OJ-H, Hexane/2-PrOH=95:5, flow rate 1.0 mL/min, γ=254 nm); $t_R$=43.65 (major syn-isomer), $t_R$=47.75 (minor syn-isomer), $t_R$=57.75 (minor anti-isomer), $t_R$=64.66 (major anti-isomer).

Dehydration Reactions of Ketones and Aldehydes to Produce Alpha, Beta-Unsaturated Ketones General Information: Commercial reagents were used as received, unless otherwise stated. Merck 60 silica gel was used for chromatography, and Whatman silica gel plates with fluorescence F$_{254}$ were used for thin-layer chromatography (TLC) analysis. $^1$H and $^{13}$C NMR spectra were recorded on Broker Advance 500, and tetramethylsilane (TMS) was used as a reference. Data for $^1$H are reported as follows: chemical shift (ppm), and multiplicity (s=singlet, d=doublet, t=triplet, q=quartet, m=multiplet). Data for $^{13}$C NMR are reported as ppm.

Preparation of Catalyst I

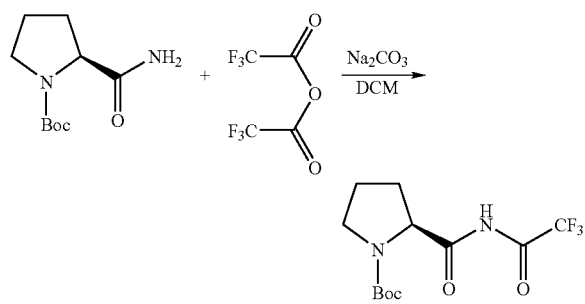

(S)-tert-Butyl 2-(2,2,2-trifluoroacetylcarbamoyl)pyrrolidine-1-carboxylate. To a solution of (S)-tert-butyl 2-carbamoylpyrrolidine-1-carboxylate (1165 mg, 5.44 mmol) and sodium carbonate (577 mg, 5.44 mmol) in 21 mL of dichloromethane at 0° C. was added dropwise trifluoroacetic anhydride (1.55 mL, 11.1 mmol) for 30 min. The resulting mixture was stirred at room temperature for 45 min. The precipitate was filtered off. The resulting residue was then purified by silica gel chromatography (EtOAc/Hexane=1/7) and fractions were collected and concentrated in vacuo to provide product as a clear oil in 68% yield (1.15 g, 3.70 mmol).

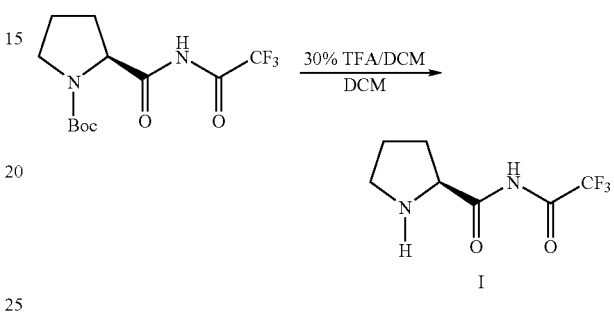

(S)—N-(2,2,2-Trifluoroacetyl)pyrrolidine-2-carboxamide (I). A solution of trifluoroacetic acid (14 mL) in 48 mL of dichloromethane was added dropwise in 45 min into a stirring mixture of (S)-tert-butyl 2-(2,2,2-trifluoroacetylcarbamoyl) pyrrolidine-1-carboxylate (1.15 g, 3.70 mmol) and 28 mL of dichloromethane at room temperature. The solution was stirred for 2 h at room temperature, and the volatiles were removed under reduced pressure. The remaining viscous product was treated with ethyl ether (3×20 mL) to provide a white solid in 57% yield. (441 mg, 2.10 mmol). $^1$H NMR (500 MHz, CD$_3$OD): δ 4.57 (t, 1H, J=7.5 Hz), 3.36-3.24 (m, 2H), 2.39-2.33 (m, 1H), 2.21-2.14 (m, 1H), 2.12-1.97 (m, 2H). $^{13}$C NMR (125 MHz, CD$_3$OD): δ 163.5, 163.3, 163.0, 162.7, 121.6, 119.3, 116.9, 116.5, 114.6, 47.9, 47.0, 31.2, 24.5.

General Procedure for Synthesis of α,β-Unsaturated Cyclopentanones: A mixture of aldehyde (0.15 mmol), ketone (0.30 mmol) and catalyst I (0.03 mmol) in 0.5 mL of anhydrous DMSO was vigorously stirred for 6-132 hr. The endpoint of the reaction was monitored by TLC. The resulting mixture was then directly purified by silica gel chromatography and fractions were collected and concentrated in vacuo to provide a solid or clear oil.

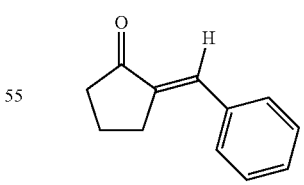

(E)-2-Benzylidenecyclopentanone: This compound was prepared according to the general procedure in 84% yield. $^1$H NMR (500 MHz, CDCl$_3$): δ 7.53 (d, 2H, J=7.45 Hz), 7.43-7.34 (m, 4H), 2.98 (dt, 2H, J=7.2, 2.65 Hz), 2.40 (t, 2H, J=7.9 Hz), 2.07-2.00 (m, 2H). $^{13}$C NMR (125 MHz, CDCl$_3$): δ 207.8, 136.1, 135.6, 132.3, 130.5, 129.3, 128.7, 37.7, 29.3, 20.2.

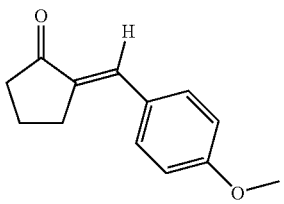

(E)-2-(4-Methoxybenzylidene)cyclopentanone: This compound was prepared according to the general procedures in 94% yield. $^1$H NMR (500 MHz, CDCl$_3$): δ 7.49 (d, 2H, J=8.7 Hz), 7.35 (t, 1H, J=2.6 Hz), 6.94 (d, 2H, J=8.8 Hz), 3.84 (s, 3H, 2.95 (dt, 2H, J=7.3 Hz, 2.6 Hz), 2.38 (t, 2H, J=7.9 Hz), 2.06-1.99 (m, 2H. $^{13}$C NMR (125 MHz, CDCl$_3$): δ 207.8, 160.6, 133.7, 132.2, 132.1, 128.3, 114.2, 55.3, 37.7, 29.2, 20.1.

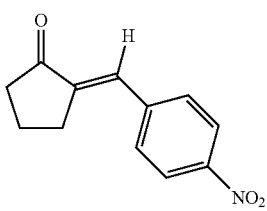

(E)-2-(4-Nitrobenzylidene)cyclopentanone: This compound was prepared according to the general procedure in 93% yield. $^1$H NMR (500 MHz, CDCl$_3$): δ 8.27 (d, 2H, J=8.7 Hz), 7.67 (d, 2H, J=8.7 Hz), 7.39 (t, 1H, J=2.6 Hz), 3.01 (dt, 2H, J=7.2, 2.7 Hz), 2.46 (t, 2H, J=7.9 Hz), 2.13-2.06 (m, 2H), $^{13}$C NMR (125 MHz, CDCl$_3$): δ 207.3, 147.5, 141.9, 139.8, 130.8, 129.3, 123.9, 37.7, 29.4, 20.0.

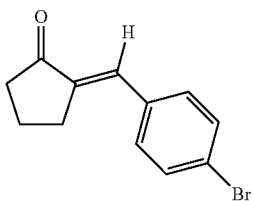

(E)-2-(4-Bromobenzylidene)cyclopentanone: This compound was prepared according to the general procedure in 88% yield. $^1$H NMR (500 MHz, CDCl$_3$): δ 7.54 (d, 2H, J=8.3 Hz), 7.38 (d, 2H, J=8.3 Hz), 7.30 (t, 1H, J=2.4 Hz), 2.93 (dt, 2H, J=7.2, 2.4 Hz), 2.40 (t, 2H, J=7.9 Hz), 2.08-2.01 (m, 2H). $^{13}$C NMR (125 MHz, CDCl$_3$): δ 207.5, 136.7, 134.5, 131.9, 131.8, 130.9, 123.6, 37.7, 29.3, 20.1.

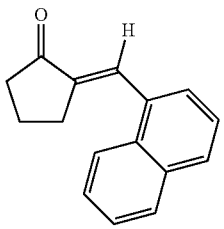

(E)-2-(1-Naphthylidene)cyclopentanone: This compound was prepared according to the general procedure in 85% yield. $^1$H NMR (500 MHz, CDCl$_3$): δ 8.14-8.12 (m, 2H), 7.88-7.84 (m, 2H), 7.60-7.47 (m, 4H), 2.90 (dt, 2H, J=7.1 Hz, 2.6 Hz), 2.46 (t, 2H, J=7.8 Hz), 2.03-1.96 (m, 2H). $^{13}$C NMR (125 MHz, CDCl$_3$): δ 207.4, 138.4, 133.6, 132.4, 132.3, 129.6, 128.9, 128.7, 126.9, 126.6, 126.2, 125.1, 124.0, 38.2, 29.6, 20.5.

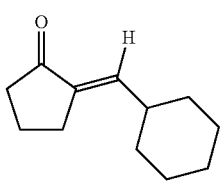

(E)-2-(Cyclohexylmethylidene)cyclopentanone: This compound was prepared according to the general procedure in 82% yield. $^1$H NMR (500 MHz, CDCl$_3$): δ 6.39 (d, 1H, J=9.6 Hz), 2.61 (dt, 2H, J=7.2 Hz, 2.0 Hz), 2.32 (t, 2H, J=7.7 Hz), 2.16 (m, 1H), 1.93 (m, 2H), 1.76-1.64 (m, 5H), 1.34-1.14 (m, 5H). $^{13}$C NMR (125 MHz, CDCl$_3$): δ 207.8, 140.9, 135.2, 38.8, 38.5, 31.6, 26.6, 25.8, 25.5, 19.8.

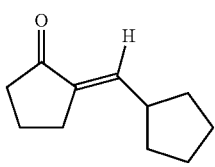

(E)-2-(Cyclopentylmethylidene)cyclopentanone: This compound was prepared according to the general procedure in 61% yield. $^1$H NMR (500 MHz, CDCl$_3$): δ 6.48 (dt, 1H, J=9.7 Hz, 2.5 Hz), 2.64-2.55 (m, 3H), 2.31 (t, 2H, J=7.9 Hz), 1.96-1.89 (m, 2H), 1.87-1.33 (m, 8H). $^{13}$C NMR (125 MHz, CDCl$_3$): δ 207.2, 141.0, 135.5, 40.3, 38.4, 32.7, 26.6, 25.4, 19.7.

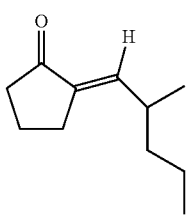

(E)-2-(2-Methylpentylidene)cyclopentanone: This compound was prepared according to the general procedure in 69% yield. $^1$H NMR (500 MHz, CDCl$_3$): δ 6.34 (dt, 1H, J=10.2 Hz, 2.5 Hz), 2.62-2.57 (m, 2H), 2.33 (t, 2H, J=7.9 Hz), 1.97-1.90 (m, 2H), 1.40-1.20 (m, 5H), 1.01 (d, 3H, J=6.7 Hz), 0.87 (t, 3H, J=7.2 Hz). $^{13}$C NMR (125 MHz, CDCl$_3$): δ 207.6, 141.9, 135.7, 38.9, 38.6, 34.3, 26.8, 20.6, 19.9, 19.8, 14.1.

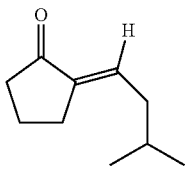

(E)-2-(3-Methylbutylidene)cyclopentanone: This compound was prepared according to the general procedure in 71% yield. ¹H NMR (500 MHz, CDCl₃): δ 6.60-6.55 (m, 1H), 2.58 (dt, 2H, J=7.2, 1.2 Hz), 2.33 (t, 2H, J=7.9 Hz), 2.06-2.02 (m, 2H), 1.96-1.89 (m, 2H), 1.83-1.74 (m, 1H), 0.93 (d, 6H, J=6.7 Hz). ¹³C NMR (125 MHz, CDCl₃): δ 206.9, 137.9, 135.1, 38.8, 38.6, 28.3, 26.9, 22.5, 19.8.

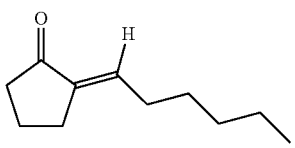

(E)-2-Hexylidenecyclopentanone: This compound was prepared according to the general procedure in 79% yield. ¹H NMR (500 MHz, CDCl₃): δ6.57-6.53 (m, 1H), 2.58 (dt, 2H, J=6.3, 1.4 Hz), 2.33 (t, 2H, J=7.9 Hz), 2.17-2.11 (m, 2), 1.97-1.90 (m, 2H), 1.50-1.43 (m, 2H), 1.34-1.29 (m, 4H), 0.89 (t, 3H, J=6.9 Hz). ¹³C NMR (125 MHz, CDCl₃): δ 207.2, 137.1, 136.4, 38.6, 31.5, 29.6, 28.0, 26.7, 22.4, 19.8, 13.9.

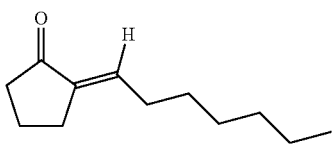

(E)-2-heptylidenecyclopentanone: This compound was prepared according to the general procedure in 64% yield. ¹H NMR (500 MHz, CDCl₃): δ6.58-6.53 (m, 1H), 2.58 (dt, 2H, J=6.0, 1.1 Hz), 2.33 (t, 2H, J=7.9 Hz), 2.14 (q, 2H, J=7.4 Hz), 1.97-1.90 (m, 2H), 1.49-1.42 (m, 2H), 1.35-1.25 (m, 6H), 0.88 (t, 3H, J=6.9 Hz). ¹³C NMR (125 MHz, CDCl₃): δ 207.3, 137.2, 136.4, 38.6, 31.6, 29.7, 29.0, 28.3, 26.7, 22.6, 19.8, 14.0.

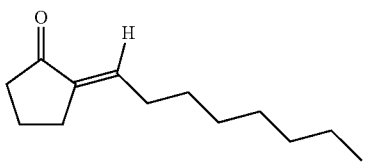

(E)-2-Octylidenecyclopentanone: This compound was prepared according to the general procedure in 55% yield. ¹H NMR (500 MHz, CDCl₃): δ 6.57-6.53 (m, 1H), 2.58 (dt, 2H, J=6.0, 1.1 Hz), 2.33 (t, 2H, J=7.9 Hz), 2.14 (q, 2H, J=7.4 Hz), 1.97-1.90 (m, 2H), 1.47-1.42 (m, 2H), 1.35-1.25 (m, 8H), 0.88 (t, 3H, J=6.8 Hz). ¹³C NMR (125 MHz, CDCl₃): δ 207.2, 137.2, 136.4, 38.6, 31.7, 29.6, 29.3, 29.1, 28.4, 26.7, 22.6, 19.8, 14.0.

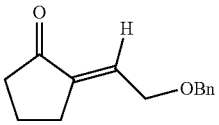

(E)-2-(Benzyloxy)methylene)cyclopentanone: This compound was prepared according to the general procedure in 66% yield. ¹H NMR (500 MHz, CDCl₃): δ 7.38-7.28 (m, 5H), 6.66-6.63 (m, 1H), 4.54 (s, 2H), 4.18 (d, 2H, J=5.9 Hz), 2.60 (dt, 2H, J=7.2, 2.0 Hz), 2.33 (t, 2H, J=7.9 Hz), 1.98-1.91 (m, 2H). ¹³C NMR (125 MHz, CDCl₃): δ 206.9, 138.2, 137.8, 131.1, 128.4, 127.8, 127.7, 72.8, 67.5, 38.1, 27.0, 19.8.

General Procedure for Synthesis of α,β-Unsaturated Acetones: A mixture of aldehyde (0.15 mmol) and catalyst I (0.03 mmol) in 0.5 mL of anhydrous acetone was vigorously stirred for 10 or 46 hr. The endpoint of the reaction was monitored by TLC. The resulting mixture was then purified by silica gel chromatography and fractions were collected and concentrated in vacuo to provide a solid or clear oil.

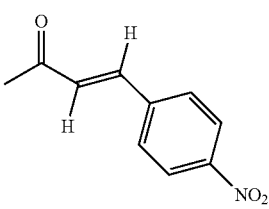

(E)-4-(4-Nitrophenyl)-3-buten-2-one: This compound was prepared according to the general procedure in 95% yield. ¹H NMR (500 MHz, CDCl₃): δ8.26 (d, 2H, J=8.6 Hz), 7.71 (d, 2H, J=8.6 Hz), 7.55 (d, 1H, J=16.3 Hz), 6.83 (d, 1H, J=16.3 Hz), 2.43 (s, 3H). ¹³C NMR (125 MHz, CDCl₃): δ 197.5, 148.5, 140.6, 140.0, 130.3, 128.8, 124.1, 28.0.

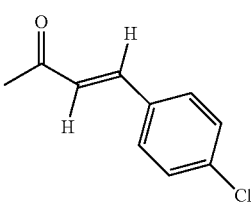

(E)-4-(4-Chlorophenyl)-3-buten-2-one: This compound was prepared according to the general procedure in 89% yield. ¹H NMR (500 MHz, CDCl₃): δ 7.49-7.44 (m, 3H), 7.38 (d, 2H, J=8.5 Hz), 6.69 (d, 1H, J=16.3 Hz, 2.38 (s, 3H). ¹³C NMR (125 MHz, CDCl₃): δ 198.0, 141.8, 136.4, 132.9, 129.4, 129.3, 127.5, 27.7.

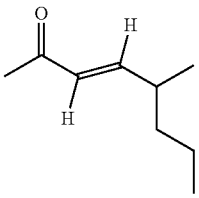

(E)-5-Methyloct-3-en-2-one: This compound was prepared according to the general procedure in 41% yield. ¹H NMR (500 MHz, CDCl₃): δ 6.68 (dd, 1H, J=16.0, 7.9 Hz), 6.03 (d, 1H, J=16.0 Hz), 2.33 (m, 1H), 2.25 (s, 3H), 1.48-1.23 (m, 4H), 1.06 (d, 3H, J=6.7 Hz), 0.90 (t, 3H, J=7.1 Hz). ¹³C NMR (125 MHz, CDCl₃): δ 198.9, 153.8, 129.5, 38.3, 36.5, 26.9, 20.3, 19.4, 14.0.

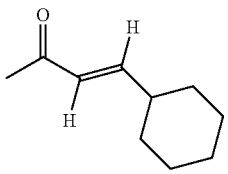

(E)-4-Cyclohexylbut-3-en-2-one: This compound was prepared according to the general procedure in 60% yield. ¹H NMR (500 MHz, CDCl₃): δ 6.73 (dd, 1H, J=16.1, 6.8 Hz), 6.02 (dd, 1H, J=16.1, 1.2 Hz), 2.24 (s, 3H), 2.18-2.11 (m, 1H), 1.79-1.75 (m, 4H), 1.36-1.07 (m, 6H). ¹³C NMR (125 MHz, CDCl₃): δ 199.1, 153.4, 128.8, 40.6, 31.8, 26.8, 25.9, 25.7.

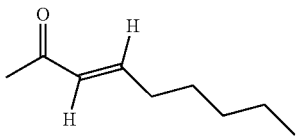

(E)-Non-3-en-2-one: This compound was prepared according to the general procedure in 67% yield. ¹H NMR (500 MHz, CDCl₃): δ 6.84-6.77 (m, 1H), 6.07 (d, 1H, J=15.5 Hz), 2.25-2.20 (m, 5H), 1.51-1.44 (m, 2H), 1.35-1.29 (m, 4H), 0.90 (t, 3H, J=7.0 Hz) ¹³C NMR (125 MHz, CDCl₃): δ 198.7, 148.6, 131.3, 32.4, 31.3, 27.8, 26.8, 22.4, 13.9.

Mukaiyama-Michael Addition of Silyl Enol Ethers to Alpha, Beta-Unsaturated Aldehydes to Produce 1,5-dicarbonyl Compounds General Information: Commercial reagents were used as received, unless otherwise stated. Merck 60 silica gel was used for chromatography, and Whatman silica gel plates with fluorescence F₂₅₄ were used for thin-layer chromatography (TLC) analysis. ¹H and ¹³C NMR spectra were recorded on Broker Avance 500, and tetramethylsilane (TMS) was used as a reference. Data for ¹H are reported as follows: chemical shift (ppm), and multiplicity (s=singlet, d=doublet, t=triplet, q=quartet, m=multiplet). Data for ¹³C NMR are reported as ppm. Mass Spectra were obtained from Ohio State University Mass Spectral facility.

Figure 15:
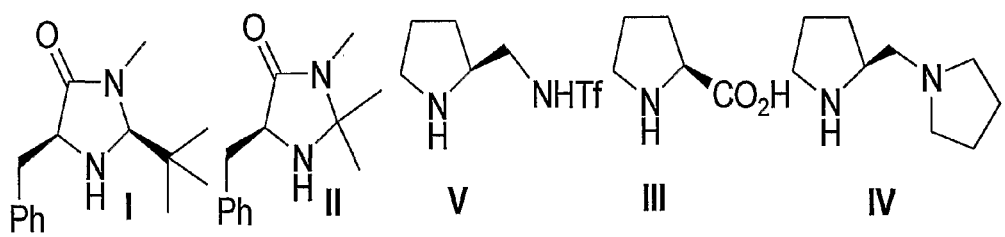
FIG. 15 show certain chiral amine catalysts useful in Mukaiyama-Alcohol cyclization reactions as well as other reactions according to the present invention.

General Procedure for addition of silyl enol ethers to unsaturated aldehydes: A mixture of an aldehyde (1 equiv.) in the presence of 30 mol % chiral amine I (FIG. 15) and DNBA in 0.5 mL of t-BuOH and i-PrOH (5/1, v/v) was stirred at rt for 10 min, then 5 equiv. of silyl enol ether was added and stirred for 4-18 h at rt or 0° C. The solution was concentrated in vacuo. The resulting residue was then purified by silica gel chromatography and fractions were collected and concentrated in vacuo to provide the desired product.

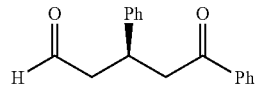

(R)-5-Oxo-3,5-diphenyl-pentanal (entry 1): Yield: 75%; ¹H NMR (500 MHz, CDCl₃): δ 9.62 (s, 1H), 7.83 (d, 2H, J=8.0 Hz), 7.12-7.48 (m, 8H), 3.90 (m, 1H), 3.27 (d, 2H, J=7.0 Hz), 2.71-2.86 (m, 2H); ¹³C NMR (125 MHz, CDCl₃): δ 201.1, 198.1, 143.2, 136.7, 133.2, 128.8, 128.6, 128.0, 127.4, 126.9, 49.5, 44.9, 35.3; $[\alpha]_D^{25}$=+1.4 (c=0.5, CHCl₃); HPLC (Daicel CHIRALPAK AS-H, Hexane/2-PrOH=90:10, flow rate 1.0 my min, γ=254 nm); $t_R$=17.66 (minor), 19.71 (major) min.

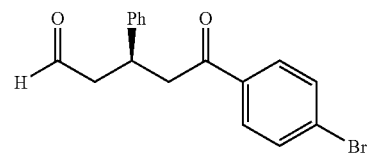

(R)-5-(4-Bromophenyl)-5-oxo-3-phenyl-pentanal (entry 2): Yield: 58%; ¹H NMR (500 MHz, CDCl₃): δ 9.71 (d, 1H, J=1.6 Hz), 7.76 (d, 2H, J=8.6 Hz), 7.57 (d, 2H, J=8.6 Hz), 7.20-7.32 (m, 5H), 3.95 (m, 1H), 3.30 (d, 2H, J=7.0 Hz), 2.79-2.94 (m, 2H); ¹³C NMR (125 MHz, CDCl₃): δ 200.9, 197.1, 142.9, 135.4, 131.9, 129.5, 128.8, 128.4, 127.3, 127.0, 49.5, 44.8, 35.3. $[\alpha]_D^{25}$=+4.7 (c=1.0, CHCl₃); HPLC (Daicel CHIRALPAK AS-H, Hexane/2-PrOH=90:10, flow rate 1.0 ml/min, γ=254 nm); $t_R$=20.99 (minor), 23.84 (major) min.

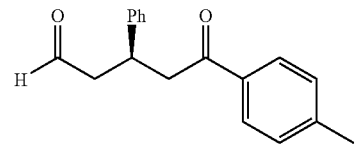

(R)-5-Oxo-3-phenyl-5-p-tolyl-pentanal (entry 3): Yield: 62%; ¹H NMR (500 MHz, CDCl₃): δ 9.69 (s, 1H), 7.81 (d, 2H, J=8.1 Hz), 7.19-7.31 (m, 7H), 3.97 (m, 1H), 3.31 (d, 2H, J=7.3 Hz), 2.77-2.93 (m, 2H), 2.39 (s, 3H); ¹³C NMR (125 MHz, CDCl₃): δ 201.2, 197.7, 144.1, 143.2, 134.3, 129.3, 128.8, 128.1, 127.3, 126.9, 49.5, 44.8, 35.4, 21.6. $[\alpha]_D^{25}$=+4.1 (c=1.0, CHCl₃); HPLC (Daicel CHIRALPAK AS-H, Hexane/2-PrOH=90:10, flow rate 1.0 ml/min, γ=254 nm); $t_R$=16.50 (minor), 17.55 (major) min.

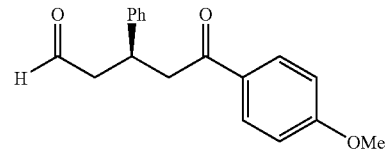

(R)-5-(4-Methoxyphenyl)-5-oxo-3-phenyl-pentanal (entry 4): Yield: 56%; ¹H NMR (500 MHz, CDCl₃): δ 9.70 (s, 1H), 7.89 (d, 2H, J=8.5 Hz), 7.19-7.32 (m, 5H), 6.90 (d, 2H, J=8.5 Hz), 3.96 (m, 1H), 3.85 (s, 3H), 3.28 (d, 2H, J=6.9 Hz), 2.78-2.93 (m, 2H); ¹³C NMR (125 MHz, CDCl₃): δ 201.3, 196.6, 163.6, 143.3, 130.3, 129.8, 128.8, 127.4, 126.9, 113.7, 55.4, 49.5, 44.6, 35.5. $[\alpha]_D^{25}$=+4.0 (c=1.0, CHCl₃); HPLC (Daicel CHIRALPAK AS-H, Hexane/2-PrOH=90:10, flow rate 1.0 ml/min, γ=254 nm); $t_R$=35.75 (minor), 38.15 (major) min.

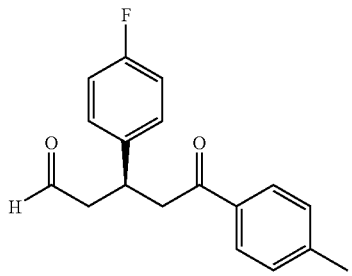

(R)-3-(4-Fluorophenyl)-5-oxo-5-p-tolyl-pentanal (entry 5): Yield: 71%; $^1$H NMR (500 MHz, CDCl$_3$): δ 9.69 (s, 1H), 7.80 (d, 2H, J=8.1 Hz), 7.22-7.26 (m, 4H), 6.98 (t, 2H, J=8.6 Hz), 3.97 (m, 1H), 3.29 (d, 2H, J=7.0 Hz), 2.76-2.93 (m, 2H), 2.40 (s, 3H); $^{13}$C NMR (125 MHz, CDCl$_3$): δ 200.8, 197.5, 162.6, 160.6, 144.2, 138.9, 134.2, 129.3, 128.9, 128.8, 128.1, 115.6, 115.5, 49.7, 44.8, 34.7, 21.6. $[α]_D^{25}$=+2.5 (c=1.0, CHCl$_3$); HPLC (CHIRALCEL OJ-H, Hexane/2-PrOH=90:10, flow rate 1.0 ml/min, γ=254 nm); $t_R$=45.13 (minor), 48.47 (major) min.

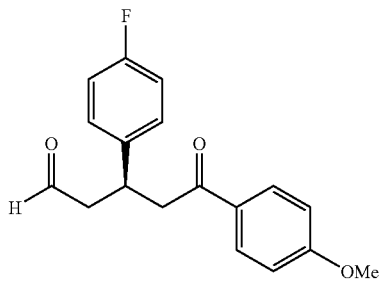

(R)-3-(4-Fluorophenyl)-5-(4-methoxyphenyl)-5-oxo-pentanal (entry 6): Yield: 63%; $^1$H NMR (500 MHz, CDCl$_3$): δ 9.62 (s, 1H), 7.81 (d, 2H, J=9.0 Hz), 7.06 (q, 2H, J=5.4 Hz, J=8.4 Hz), 6.90 (t, 2H, J=8.6 Hz), 6.83 (d, 2H, J=8.8 Hz), 3.88 (m, 1H), 3.18 (d, 2H, J=7.0 Hz), 2.68-2.86 (m, 2H); $^{13}$C NMR (125 MHz, CDCl$_3$): δ 200.9, 196.4, 163.6, 162.5, 160.6, 139.0, 130.3, 129.7, 128.9, 128.8, 115.6, 115.5, 113.7, 55.4, 49.7, 44.5, 34.7. $[α]_D^{25}$=+5.7 (c=1.0, CHCl$_3$); HPLC (Daicel CHIRALPAK AS-H, Hexane/2-PrOH=85:15, flow rate 1.0 ml/min, γ=254 nm); $t_R$=35.05 (major), 42.22 (minor) min.

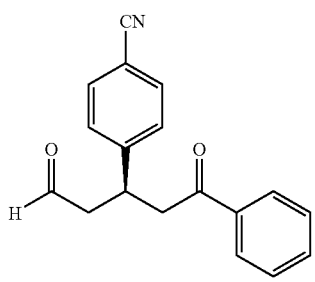

(R)-4-[3-Oxo-1-(2-oxo-ethyl)-3-phenyl-propyl]-benzonitrile (entry 7): Yield: 59%; $^1$H NMR (500 MHz, CDCl$_3$): δ 9.72 (s, 1H), 7.90 (d, 2H, J=7.5 Hz), 7.41-7.60 (m, 7H), 4.05 (m, 1H), 3.38 (m, 2H), 2.85-3.01 (m, 2H); $^{13}$C NMR (125 MHz, CDCl$_3$): δ 199.7, 197.2, 136.3, 133.4, 132.5, 128.7, 128.3, 127.9, 118.6, 110.7, 49.1, 44.0, 35.0. $[α]_D$=+17.4 (c=1.0, CHCl$_3$); HPLC (CHIRALCEL OJ-H, Hexane/2-PrOH=60:40, flow rate 0.7 ml/min, γ=254 nm); $t_R$=37.60 (minor), 41.58 (major) min.

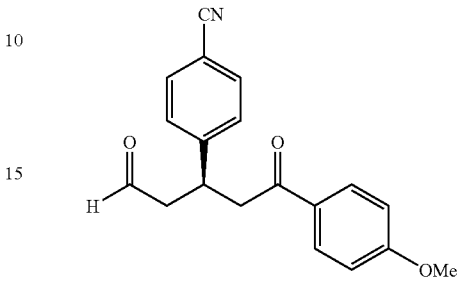

(R)-4-[3-(4-Methoxyphenyl)-3-oxo-1-(2-oxo-ethyl)-propyl]-benzonitrile (entry 8): Yield: 61%; $^1$H NMR (500 MHz, CDCl$_3$): δ 9.71 (s, 1H), 7.88 (d, 2H, J=8.8 Hz), 7.59 (d, 2H, J=8.2 Hz), 7.40 (d, 2H, J=8.2 Hz), 6.91 (d, 2H, J=8.8 Hz), 4.03 (m, 1H), 3.86 (s, 3H), 3.31 (m, 2H), 2.83-3.00 (m, 2H); $^{13}$C NMR (125 MHz, CDCl$_3$): δ 199.8, 195.7, 163.8, 149.0, 132.5, 130.3, 129.5, 128.4, 118.7, 113.8, 110.7, 55.5, 49.2, 43.7, 35.3. $[α]_D^{25}$=+26.4 (c=1.0, CHCl$_3$); HPLC (CHIRALCEL OJ-H, Hexane/2-PrOH=60:40, flow rate 0.7 ml/min, γ=254 nm); $t_R$=71.74 (minor), 92.92 (major) min.

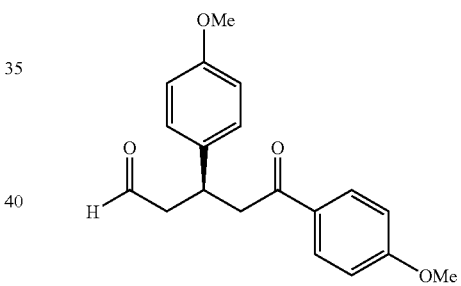

(R)-3,5-Bis-(4-methoxyphenyl)-5-oxo-pentanal (entry 9): Yield: 63%; $^1$H NMR (500 MHz, CDCl$_3$): δ 9.68 (t, 1H, J=1.7 Hz), 7.90 (d, 2H, J=8.9 Hz), 7.18 (d, 2H, J=8.7 Hz), 6.91 (d, 2H, J=8.9 Hz), 6.83 (d, 2H, J=8.7 Hz), 3.92 (m, 1H), 3.85 (s, 3H), 3.77 (s, 3H), 3.25 (d, 2H, J=7.0 Hz), 2.73-2.91 (m, 2H); $^{13}$C NMR (125 MHz, CDCl$_3$): δ 201.4, 196.7, 163.5, 158.3, 135.2, 130.3, 129.9, 128.3, 114.1, 113.7, 55.4, 55.2, 49.7, 44.8, 34.8. $[α]_D^{25}$=+3.6 (c=1.0, CHCl$_3$); HPLC (Daicel CHIRALPAK AS-H, Hexane/2-PrOH=60:40, flow rate 0.7 ml/min, γ=254 nm); $t_R$=59.20 (minor), 68.93 (major) min.

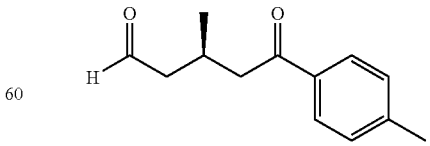

(R)-3-Methyl-5-oxo-5-p-tolyl-pentanal (entry 10): Yield: 60%; $^1$H NMR (500 MHz, CDCl$_3$): δ 9.78 (s, 1H), 7.86 (d, 2H, J=8.1 Hz), 7.26 (d, 2H, J=8.1 Hz), 3.00 (q, 1H, J=6.6 Hz, J=16.4 Hz), 2.88 (q, 1H, J=6.9 Hz, J=16.4 Hz), 2.78 (m, 1H), 2.57 (m, 1H), 2.41 (s, 3H), 2.38 (m, 1H); $^{13}$C NMR (125 MHz, CDCl$_3$): δ 202.0, 198.7, 143.9, 134.4, 129.3, 128.2, 50.5, 44.8, 24.6, 21.6, 20.4. $[α]_D^{25}$=−9.7 (c=1.0, CHCl$_3$); HPLC (CHIRALCEL OJ-H, Hexane/2-PrOH=95:5, flow rate 1.0 ml/min, γ=254 nm); $t_R$=15.73 (minor), 16.93 (major) min.

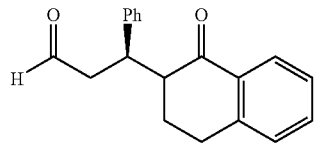

(R)-3-(1,2,3,4-Tetrahydro-1-oxonaphthalen-2-yl)-3-phenylpropanal (entry 11): Yield: 87%; $^1$H NMR (500 MHz, CDCl$_3$): δ 9.67 (m, 1H), 8.05 (d, 1H, J=7.8 Hz), 7.46 (m, 1H), 7.20-7.34 (m, 7H), 4.33 (m, 1H), 2.76-2.95 (m, 5H), 2.08 (m, 1H), 2.1.91 (m, 1H); $^{13}$C NMR (125 MHz, CDCl$_3$): δ 201.8, 201.1, 199.3, 198.3, 143.8, 143.5, 141.5, 141.3, 133.5, 132.7, 132.4, 128.7, 128.4, 127.6, 127.5, 127.0, 126.9, 126.7, 53.7, 52.0, 48.5, 43.5, 38.2, 38.1, 29.3, 27.3, 25.8, 24.3. $[α]_D^{25}$=−39.9 (c=1.0, CHCl$_3$); HPLC (Daicel CHIRALPAK AS-H, Hexane/2-PrOH=90:10, flow rate 1.0 ml/min, γ=254 nm); $t_R$=14.90 (major), 18.24 (minor) min.

REFERENCES

1. Rouhi, A. M. Chiral Business. C. & En. News, 2003, 81, 45-55.
2. Rouhi, A. M. Chiral at Work. C. & En. News, 2003, 81, 56-61.
3. Rouhi, A. M. Chiral Chemistry. C. & En. News, 2004, 82, 47-62.
4. Trost, B. M. Comprehensive Organic Synthesis, 1991, (New York: Pergamon Press).
5. Jacobsen, E. N., Pfaltz, A., and Yamamoto, H. Comprehensive Asymmetric Catalysis I-III, 1999, (New York: Springer).
6. North American Pollution. C & En News, 2004, 82, 8.
7. Anastas, P. T., and Williamson, T. C. Green Chemistry. Designing Chemistry for the Environment, 1996, (Washington, D.C.: the American Chemical Society).
8. Anastas, P. C., and Warner, J. C. Green Chemistry Theory and Practice, 1998, (New York: Oxford University Press).
9. Lancaster, M. Green Chemistry. An Introductory Text, 2002, (Cambridge, UK: The Royal Society of Chemistry).
10. Dalko, P. I., and Moisan, L. Enantioselective Organocatalysis. Angew. Chem. Int. Ed., 2001, 40, 3726-3748.
11. Houk, K. N., and List, B. Asymmetric Organocatalysis. Acc. Chem. Res., 2004, 37, 487-487.
12. List, B. Asymmetric Aminocatalysis. Synlett, 2001, 1675-1686.
13. List, B. Proline-Catalyzed Asymmeric Reactions. Tetrahedron, 2002, 58, 5573-5590.
14. List, B. Enamine Catalysis Is a Powerful Strategy for the Catalytic Generation and Use of Carbanion Equivalents. Acc. Chem. Res., 2004, 37, 548-557.
15. Notz, W., Tanaka, F., and Barbas, C. F., III Enamine-Based Organocatalysis with Proline and Diamines: The Development of Direct Catalytic Asymmetric Aldol, Mannich, Michael, and Diels-Alder Reactions. Acc. Chem. Res., 2004, 37, 580-591.
16. Jarvo, E. R., and Miller, S. J. Amino Acids and Peptides as Asymmetric Organocatalysts. Tetrahedron, 2002, 58, 2481-2495.
17. Miller, S. J. In Search of Peptide-Based Catalysts for Asymmetric Organic Synthesis. Acc. Chem. Res., 2004, 37, 601-610.
18. Lygo, B., and Andrews, B. I. Asymmetric Phase-Transfer Catalysis Utilizing Chiral Quaternary Ammonium Salts: Asymmetric Alkylation of Glycine Imines. Ace. Chem. Res., 2004, 37, 518-525.
19. O'Donnell, M. J. The Enantioselective Synthesis of α-Amino Acids by Phase-Transfer Catalysis with Achiral Schiff Base Esters. Acc. Chem. Res., 2004, 37, 506-517.
20. Horton, D. A., Bourne, G. T., and Smythe, M. L. The Combinatorial Synthesis of Bicyclic Privileged Structures or Privileged Substructures. Chem. Rev., 2003, 103, 893-930.
21. Evans, B. E., Rittle, K. E., Bock, M. G., DiPardo, R. M., Freidinger, R. M., Whitter, W. L., Lundell, G. F., Veber, D. F., Anderson, P. S., Chang, R. S. L., Lotti, V. J., Cerino, D. J., Chen, T. B., Kling, P. J., Kunkel, K. A., Springer, J. P., and Hirshfield, J. Methods for Drug discovery: Development of Potent, Selective, Orally Effective Cholecystokinin Antagonists. J. Med. Chem., 1988, 31, 2235-2346.
22. Plunkett, M. J., and Ellman, J. A. Solid-Phase Synthesis of Structurally Diverse 1,4-Benzodiazepine Derivatives Using the Stille Coupling Reaction. J. Am. Chem. Soc., 1995, 117, 3306-3307.
23. Ahrendt, K. A., Borths, C. J., and MacMillan, D. W. C. New Strategies for Organic Catalysis: The First Highly Enantioselective Organocatalytic Diels-Alder Reaction. J. Am. Chem. Soc., 2000, 122, 4243-4244.
24. Paras, N. A., and MacMillan, D. W. C. New Strategies in Organic Catalysis: The First Enantioselective Organocatalytic Friedel-Crafts Alkylation. J. Am. Chem. Soc., 2001, 123, 4370-4371.
25. Austin, J. F., and MacMillan, D. W. C. Enantioselective Organocatalytic Indole Alkylations. Design of a New and Highly Effective Chiral Amine for Iminium Catalysis. J. Am. Chem. Soc., 2002, 124, 1172-1173.
26. Northrup, A. B., and MacMillan, D. W. C. The First General Enantioselective Catalytic Diels-Alder Reaction with Simple α,β-Unsaturated Ketones. J. Am. Chem. Soc., 2002, 124, 2458-2460.
27. Paras, N. A., and MacMillan, D. W. C. The Enantioselective Organocatalytic 1,4-Addition of Electron-Rich Benzenes to α,β-Unsaturated Aldehydes. J. Am. Chem. Soc., 2002, 124, 7894-7895.
28. Brown, S. P., Goodwin, N. C., and MacMillan, D. W. C. The First Enantioselective Organocatalytic Mukaiyama-Michael Reaction: A Direct Method for the Synthesis of Enantioenriched γ-Butenolide Architecture. J. Am. Chem. Soc., 2003, 125, 1192-1194.
29. Brochu, M. P., Brown, S. P., and MacMillan, D. W. C. Direct and Enantioselective Organocatalytic α-Chlorination of Aldehydes. J. Am. Chem. Soc., 2004, 126, 4108-4109.
30. Halland, N., Hazell, R. G., and Jorgensen, K. A. Organocatalytic Asymmetric Conjugate Addition of Nitroalkanes to α,β-Unsaturated Enones Using Novel Imidazolidine Catalysts. J. Org. Chem., 2002, 67, 8331-8338.
31. Halland, N., Hansen, T., and Jorgensen, K. A. Organocatalytic Asymmetric Michael Reaction of Cyclic 1,3-Dicarbonyl Compounds and α,β-unsaturated Ketones-A Highly Atom-Economic Catalytic One-Step Formation of Optically Active Warfarin Anticoagulant. Angew. Chem. Int. Ed., 2003, 42, 4955-4957.
32. Bernardi, L., Gothelf, A. S., Hazell, R. G., and Jorgensen, K. A. Catalytic Asymmetric Mannich Reactions of Glycine 33. Melchiorre, P., and Jorgensen, K. A. Direct Enantioselective Michael Addition of Aldehydes to Vinyl Ketones Catalyzed by Chiral Amines. J. Org. Chem., 2003, 68, 4151-4157.
34. Cobb, A. J. A., Shaw, D. M., and Ley, S. V. 5-Pyrrolidin-2-yltetrazole: A New, Catalytic, More Soluble Alternative to Proline in an Organocatalytic Asymmetric Mannich-type Reaction. Synlett, 2004, 558-560.
35. Momiyama, N., Torii, H., Saito, S., and Yamamoto, H. O-Nitroso Aldol Synthesis: Catalytic Enantioselective Route to α-Aminooxy Carbonyl Compounds via Enamine Intermediate. Proc. Natl. Acad. Sci. USA, 2004, 101, 5374-5378.
36. Torii, H., Nakadai, M., Ishihara, K., Saito, S., and Yamamoto, H. Asymmetric Direct Aldol Reaction Assisted by Water and a Proline-Derived Tetrazole Catalyst. Angew. Chem. Int. Ed., 2004, 43, 1983-1986.
37. Andrey, O., Alexakis, A., and Bernardinelli, G. Asymmetric Michael Addition of α-Hydroxyketones to Nitroolefins Catalyzed by Chiral Diamine. Org. Lett., 2003, 5, 2559-2561.
38. Nakadai, M., Saito, S., and Yamamoto, H. Diversity-based Strategy for Discovery of Environmentally Benign Organocatalyst: Diamine-Protonic Acid Catalysts for Asymmetirc Direct Aldol Reaction. Tetrahedron, 2002, 58, 8167-8177.
39. Mase, N., Tanaka, F., and Barbas, C. F., III Synthesis of β-Hydroxyaldehydes with Stereogenic Quaternary Carbon Centers by Direct Organocatalytic Asymmetric Aldol Reactions. Angew. Chem. Int. Ed., 2004, 43, 2420-2423.
40. Mase, N., Thayumanavan, R., Tanaka, F., and Barbas, C. F., III Direct Asymmetric Organocatalytic Michael Reactions of α,α-Disubstituted Aldehydes with β-Nitrostyrenes for the Synthesis of Quaternary Carbon-Containing Products. Org. Lett., 2004, 6, 2527-2530.
41. Tang, Z., Jiang, F., Yu, L.-T., Cui, X., Gong, L.-Z., Mi, A.-Q., Jiang, Y.-Z., and Wu, Y.-D. Novel Small Organic Molecules for a Highly Enantioselective Direct Aldol Reaction. J. Am. Chem. Soc., 2003, 125, 5262-5263.
42. List, B., Lerner, R. A., and Barbas, C. F., III Proline-Catalyzed Direct Asymmetric Aldol Reactions. J. Am. Chem. Soc., 2000, 122, 2395-2396.
43. Sakthivel, K., Notz, W., Bui, T., and Barbas, C. F., III Amino Acid Catalyzed Direct Asymmetric Aldol Reactions: A Bioorganic Approach to Catalytic Asymmetric Carbon-Carbon Bond-Forming Reactions. J. Am. Chem. Soc., 2001, 123, 5260-5267.
44. Bordwell, F. G. Equilibrium Acidities in Dimethyl Sulfoxide Solution. Acc. Chem. Res., 1988, 21, 456-463.
45. Bordwell, F. G., Branca, J. C., Hughes, D. L., and Olmstead, W. N. Equilibriums Involving Organic Anions in Dimethyl Sulfoxide and N-Methylpyrrolidin-2-one: Acidities, Ion Pairing, and Hydrogen Bonding. J. Org. Chem., 1980, 41, 3305-3313.
46. Bordwell, F. G., and Algrim, D. Nitrogen Acids. 1. Carboxamides and Sulfonamides. J. Org. Chem., 1976, 41, 2507-2508.
47. Wang, W., Wang, J., Li, H., and Liao, L.-X. An Amine Sulfonamide Molecule as Organocatalyst for Direct and Highly Enantioselective α-Aminoxylation of Aldehydes and Ketones. Tetrahedron Lett., 2004, 45, 7235-7238.
48. Wang, W., Wang, J., and Li, H. Catalysis of Highly Stereoselective Mannich-Type Reactions of Ketones with α-Imino Esters by a Pyrrolidine Sulfonamide. Synthesis of Unnatural α-Amino Acids. Tetrahedron Lett., 2004, 45, 7243-7246.
49. Wang, W., Wang, J., and Li, H. Direct, Highly Enantioselective Pyrrolidine Sulfonamide Catalyzed Michael Addition Reactions of Aldehydes to Nitrostyrenes. Angew. Chem. Int. Ed., 2004, submitted.
50. Wang, W., Wang, J., and Li, H. A Simple and Efficient L-Prolinamide-Catalyzed α-Selenenylation Reactions of Aldehydes. Org. Lett., 2004, 6, 2817-2820.
51. Wang, W., Wang, J., and Li, H. A Direct, Organocatalytic Pyrrolidine Sulfonamide Promoted Ketone α-Selenenylation Reaction. Chem. Commun., submitted.
52. Wang, W., Li, H. Wang, J., and Liao, L.-X. Direct, Organocatalytic α-Sulfenylation of Aldehydes and Ketones. Tetrahedron Lett., 2004, in press.
53. Merino, P., and Tejero, T. Organocatalyzed Asymmetric α-Aminoxylation of Aldehydes and Ketones-An Efficient Access to Enantiomerically Pure α-Hydroxycarbonyl Compounds, Diols, and Even Amino Alcohols. Angew. Chem. Int. Ed., 2004, 43, 2995-2997.
54. Momiyama, N., and Yamamoto, H. Catalytic Enantioselective Synthesis of α-Aminooxy and α-Hydroxyl Ketone Using Nitrosobenzene. J. Am. Chem. Soc., 2003, 125, 6038-6039.
55. Momiyama, N., and Yamaguchi, H. Enantioselective O- and N-Nitroso Aldol Synthesis of Tin Enolates. Isolation of Three BINAP-Silver Complexes and Their Role in Regio- and Enantioselectivity. J. Am. Chem. Soc., 2004, 126, 5360-5361.
56. Brown, F. J., Brochu, M. P., Sinz, C. J., and MacMillan, D. W. C. The Direct and Enantioselective Organocatalytic α-Oxidation of Aldehydes. J. Am. Chem. Soc., 2003, 125, 10808-10809.
57. Zhong, G. A Facile and Rapid Route to Highly Enantiopure 1,2-Diols by Novel Catalytic Asymmetric α-Aminoxylation of Aldehydes. Angew. Chem. Int. Ed., 2003, 42, 4247-4250.
58. Bogevig, A., Sunden, H., and Cordova, A. Direct Catalytic Enantioselective α-Aminoxylation of Ketones: A Stereoselective Synthesis of α-Hydroxy and α,α'-Dihydroxyl Ketones. Angew. Chem. Int. Ed., 2004, 43, 1109-1112.
59. Hayashi, Y., Yamaguchi, J., Sumiya, T., and Shoji, M. Direct Proline-Catalyzed Asymmetric α-Aminoxylation of Ketones. Angew. Chem. Int. Ed., 2004, 43, 1112-1115.
60. Mathew, S. P., Iwamura, H., and Blackmond, D. G. Amplification of Enantiomeric Excess in a Proline-Mediated Reaction. Angew. Chem. Int. Ed., 2004, 43, 3317-3321.
61. Williams, R. M. Synthesis of Optically Active α-Amino Acids, 1989, (Oxford: Pergamon).
62. Williams, R. M. Asymmetric Syntheses of α-Amino Acids. Advances in Asymmetric Synthesis, 1995, 1, 45-94.
63. Duthaler, R. O. Recent Developments in the Stereoselective Synthesis of α-Amino Acids. Tetrahedron, 1994, 50, 1539-1650.
64. Hanessian, S., Mcnaughton-Smith, G., Lombart, H.-G., and Lubell, W. D. Design and Synthesis of Conformationally Constrained Amino Acids as Versatile Scaffolds and Peptide Mimetics. Tetrahedron, 1997, 53, 12789-12854.
65. Kotha, S. The Building Block Approach to Unusual α-Amino Acid Derivatives and Peptides. Acc. Chem. Res., 2003, 36, 342-351.
66. Maruoka, K., and Ooi, T. Enantioselective Amino Acid Synthesis by Chiral Phase-Transfer Catalysis. Chem. Rev., 2003, 103, 3013-3028.

67. Denmark, S. E., and Nicaise, O. J.-C. Alkylation of Imino Groups. In Comprehensive Asymmetric Catalysis, E. N. Jacobsen, A. Pfaltz and H. Yamamoto, eds., 1999, (Heidelberg: Springer), pp. 923-961.
68. Arend, D., Westermann, B., and Risch, N. Modern Variants of the Mannich Reaction. Angew. Chem. Int. Ed., 1998, 37, 1044-1070.
69. Taggi, A. E., Hafez, A. M., and Lectka, T. α-Imino Esters: Versatile Substrates for the Catalytic, Asymmetric Synthesis of α- and β-Amino Acids and β-Lactams. Acc. Chem. Res., 2003, 36, 10-19.
70. Córdova, A. The Direct Catalytic Asymmetric Mannich Reaction. Acc. Chem. Res., 2004, 37, 102-122.
71. Ishitani, H., Ueno, M., and Kobayashi, S. Catalytic Enantioselective Mannich-type Reactions using a Novel Chiral Zirconium Catalyst. J. Am. Chem. Soc., 1997, 119, 7153-7154.
72. Ishitani, H., Ueno, S., and Kobayashi, S. Enantioselective Mannich-type Reactions using a Novel chiral Zirconium Catalyst for the Synthesis of Optically β-Amino Acid Derivatives. J. Am. Chem. Soc., 2000, 122, 8180-8186.
73. Kobayashi, S., Hamada, T., and Manabe, K. The Catalytic Asymmetric Mannich-type Reaction in Aqueous Media. J. Am. Chem. Soc., 2002, 124, 5640-5641.
74. Hagiwara, E., Fujii, A., and Sodeoka, M. Enantioselective Addition of Enol Silyl Ethers to Imines Catalyzed by Palladium Complexes: A Novel Way to Optically Active Acylalanine Derivatives. J. Am. Chem. Soc., 1998, 120, 2474-2475.
75. Fujii, A., Hagiwara, E., and Sodeoka, M. Mechanism of Palladium Complex-Catalyzed Enantioselective Mannich-Type Reaction: Characterization of a Novel Binuclear Palladium Enolate Complex. J. Am. Chem. Soc., 1999, 121, 545-556.
76. Ferraris, D., Young, B., Dudding, T., and Lectka, T. A Novel Synthesis of α-Amino Acid Derivatives through Catalytic, Enantioselective Ene-Reactions of α-Imino Esters. J. Am. Chem. Soc., 1998, 120, 2474-2475.
77. Ferraris, D., Young, B., Cox, C., Dudding, T., Drury, W. J., III, Ryzhkov, L., Taggi, T., and Lectka, T. Catalytic, Enantioselective Alkylation of α-Imino Esters: The Synthesis of Nonnatural α-Amino Acid Derivatives. J. Am. Chem. Soc., 2002, 124, 67-77.
78. Yamasaki, S., Iida, T., and Shibasaki, M. Direct Catalytic Asymmetric Mannich Reaction of Unmodified Ketones: Cooperative Catalysis of an AlLibis(binaphthoxide) Complex and La(OTf)$_3$.nH$_2$O. Tetrahedron Lett., 1999, 40, 307-310.
79. Trost, B. M., and Terrell, L. M. A Direct Catalytic Asymmetric Mannich-type Reaction to syn-Amino Alcohols. J. Am. Chem. Soc., 2003, 125, 338-339.
80. Juhl, K., Gathergood, N., and Jorgensen, K. A. Catalytic Asymmetric Direct Mannich Reactions of Carbonyl Compounds with α-Imino Esters. Angew. Chem. Int. Ed., 2001, 40, 2995-2997.
81. Córdova, A., Notz, W., Zhong, G., Betancort, J. M., and Barbas, C. F., III A Highly Enantioselective Amino Acid-Catalyzed Route to Functionalized α-Amino Acids. J. Am. Chem. Soc., 2002, 124, 1842-1843.
82. Córdova, A., Watanabe, S., Tanaka, F., Notz, W., and Barbas, C. F., III A Highly Enantioselective Route to Either Enantiomer of Both α- and β-Amino Acid Derivatives. J. Am. Chem. Soc., 2002, 124, 1866-1867.
83. Watanabe, S.-i., Cordova, A., Tanaka, F., and Barbas, C. F., III One-Pot Asymmetric Synthesis of β-Cyanohydroxymethyl α-Amino Acid Derivatives: Formation of Three Contiguous Stereogenic Centers. Org. Lett., 2002, 4, 4519-4522.
84. Córdova, A., and Barbas, C. F., III Direct Organocatalytic Asymmetric Mannich-type Reactions in Aqueous Media: One-Pot Mannich-Allylation Reactions. Tetrahedron Lett., 2003, 44, 1923-1926.
85. Chowdari, N. S., Suri, J. T., and Barbas, C. F., III Asymmetric Synthesis of Quaternary α- and β-Amino Acids and β-Lactams via Proline-Catalyzed Mannich Reactions with Branched Aldehyde Donors. Org. Lett., 2004, 6, 2507-2510.
86. Perlmutter, P. Conjugate Addition Reactions in Organic Synthesis, 1992, (Oxford: Pergamon).
87. Krause, N., and Hoffman-Roder, A. Recent Advances in Catalytic Enantioselective Michael Additions. Synthesis, 2001, 171-196.
88. Berner, O. M., Tedeschi, L., and Enders, D. Asymmetric Michael Additions to Nitroalkenes. Eur. J. Org. Chem., 2002, 1877-1894.
89. Hanessian, S., and Pham, V. Catalytic Asymmetric Conjugate Addition of Nitroalkanes to Cycloalkenones. Org. Lett., 2000, 2, 2975-2978.
90. List, B., Pojarliev, P., and Martin, H. J. Efficient Proline-Catalyzed Michael Additions of Unmodified Ketones to Nitro Olefins. Org. Lett., 2001, 3, 2423-2425.
91. Ender, D., and Seki, A. Proline-Catalyzed Enantioselective Michael Additions of Ketones to Nitrostyrene. Synlett, 2002, 26-28.
92. Betancort, J. M., and Barbas, C. F., III Catalytic Direct Asymmetric Michael Reactions: Taming Naked Aldehyde Donors. Org. Lett., 2001, 3, 3737-3740.
93. Betancort, J. M., Sakthivel, K., Thayumanavan, R., and Barbas, C. F., III Catalytic Enantioselective Direct Michael Addition of Ketones to Alkylidene Malonates. Tetrahedron Lett., 2001, 42, 4441-4444.
94. Betancort, J. M., Sakthivel, K., Thayumanavan, R., Tanaka, F., and Barbas, C. F., III Catalytic Direct Asymmetric Michael Reactions: Addition of Unmodified Ketone and Aldehyde Donors to Alkylidene Malonates and Nitro Olefins. Synthesis, 2004, 1509-1521.
95. Alexakis, A., and Andrey, O. Diamine-Catalyzed Asymmetric Michael Additions of Aldehydes and Ketones to Nitrostyrene. Org. Lett., 2002, 4, 3611-3614.
96. Andrey, O., Vidonne, A., and Alexakis, A. Organocatalytic Michael Addition, a Convenient Tool in Total Synthesis. First Asymmetric Synthesis of (−)-Botryodiplodin. Tetrahedron Lett., 2003, 44, 7901-7904.
97. Halland, N., Aburel, P. S., and Jorgensen, K. A. Highly Enantioselective Organocatalytic Conjugate Addition of Malonates to Acyclic α,β-Unsaturated Enones. Angew. Chem. Int. Ed., 2003, 42, 661-665.
98. Halland, N., Aburel, P. S., and Jorgensen, K. A. Highly Enantio- and Diastereoselective Organocatalytic Asymmetric Domino Michael-Aldol Reaction of β-Ketoesters and α,β-Unsaturated Ketones. Angew. Chem. Int. Ed., 2004, 43, 1272-1277.
99. Zhang, F.-Y., and Corey, E. J. Highly Enantioselective Michael Reactions Catalyzed by a Chiral Quaternary Ammonium Salt. Illustration by Asymmetric Synthesis of (S)-Ornithine and Chiral 2-Cyclohexenones. Org. Lett., 2000, 2, 1097-1100.
100. Okino, T., Hoashi, Y., and Takemoto, Y. Enantioselective Michael Reaction of Malonates to Nitroolefins Catalyzed by Bifunctional Organocatalysts. J. Am. Chem. Soc., 2003, 125, 12672-12673.

101. Li, H., Wang, Y., Tang, L., and Deng, L. Highly Enantioselective Conjugate Addition of Malonate and β-Ketoester to Nitroalkenes: Asymmetric C—C Bond Formation with New Bifunctional Organic Catalysts Based on Cinchona Alkaloids. J. Am. Chem. Soc., 2004, 126, 9906-9907.

102. Ishii, T., Fiujioka, S., Sekiguchi, Y., and Kotsuki, H. A New Class of Chiral Pyrrolidine-Pyridine Conjugate Base Catalysts for Use in Asymmetric Michael Addition Reactions. J. Am. Chem. Soc., 2004, 126, 9558-9559.

103. Back, T. G. Organoselenium Chemistry: A Practical Approach, 1999, (New York: Oxford University Press).

104. Paulmier, C. Selenium Reagents and Intermediates in Organic Synthesis, 1986, (Oxford: Pergamon Press).

105. Trost, B. M. α-Sulfenylated Carbonyl Compounds in Organic Synthesis. Chem. Rev., 1978, 78, 363-382.

106. Trost, B. M. Some Aspects of Organosulfur-Mediated Synthesis Methods. Acc. Chem. Res., 1978, 11, 453-461.

107. Reich, H. J., Renga, J. M., and Reich, I. L. Organoselenium Chemistry. Conversion of Ketones to Enones by Selenoxide syiz Elimination. J. Am. Chem. Soc., 1975, 97, 5434-5447.

108. Trost, B. M., Salzmann, T. N., and Hiroi, K. New Synthetic Reactions. Sulfenylations and Dehydrosulfenylations of Esters and Ketones. J. Am. Chem. Soc., 1976, 98, 4887-4902.

109. Denis, J. N., Dumont, W., and Krief, A. Regiospecific Synthetic Routes to α-Seleno Carbonyl Compounds. Tetrahedron Lett., 1976, 17, 453-456.

110. Sharpless, K. B., Lauer, R. F., and Teranishi, A. Y. Electrophilic and Nucleophilic Organoselenium Reagents. New Routes to α,β-Unsaturated Carbonyl Compounds. J. Am. Chem. Soc., 1973, 95, 6137-6139.

111. Houllemare, D., Ponthieux, S., Outurquin, F., and Paulmier, C. Use of Phenylselenium Trichloride for Simple and Rapid Preparation of α-Phenylselenyl Aldehydes and Ketones. Synthesis, 1997, 101-106.

112. Cossy, J., and Furet, N,N-(Phenylseleno)phthalimide: A Useful Reagent for the α-Selenylation of Ketones and Aldehydes. Tetrahedron Lett., 1993, 34, 7755-7756.

113. Williams, D. R., and Nishitani, K. A Mild Oxidation of Aldehydes to α,β-Unsaturated Aldehydes. Tetrahedron Lett., 1980, 21, 4417-4420.

114. Reich, H. J., Lenga, I. L., and Reich, I. L. Organoselenium Chemistry. α-Phenylseleno Carbonyl Compounds as Precursors for α,β-Unsaturated Ketones and Esters. J. Am. Chem. Soc., 1973, 95, 5813-5815.

115. Clive, D. L. J. Fragmentation of Selenoxides. New Method for Dehydrogenation of Ketones. J. Chem. Soc., Chem. Commun., 1973, 695-696.

116. Ryu, I., Murai, S., Niwa, I., and Sonoda, N. A Convenient Synthesis of α-Phenylseleno Ketones and Aldehydes from Enol Silyl Ethers and Phenylselenenyl Bromide. Synthesis, 1977, 874-876.

117. Trost, B. M., and Massiot, G. S. New Synthetic Reactions. A Chemoselective Approach to Cleavage α to a Carbonyl Group via β-Ketone Sulfides. Preparation of 1,2-Diketones. J. Am. Chem. Soc., 1977, 99, 4405-4412.

118. Groenewegen, P., Kallenberg, H., and van der Gen, A. Aldehyde Enolates III. Direct Sulfenylation and Iodination of Aldehyde Anion. Tetrahedron Lett., 1979, 20, 2817-2820.

119. Coates, R. M., Pigott, H. D., and Ollinger, J. Alkylation and Reduction-Alkylation of α-Phenylthio Ketones and Aldehydes. Tetrahedron Lett., 1974, 15, 3955-3958.

120. Seebach, D., and Teschner, M. Thiation of Lithium Enolates of Aldehydes and Ketones. Tetrahedron Lett., 1973, 14, 5113-5116.

121. Seebach, D., and Teschner, M. Preparation of α-Thiolated Carbonyl Compounds. Chem. Ber., 1976, 109, 1601-1616.

122. Huang, C.-H., Liao, K.-S., De, S. K., and Tsai, Y.-M. α-Sulfenylation of Acylsilanes and Aldehydes with N-(Phenylthio)succinimide. Tetrahedron Lett., 2002, 41, 3911-3914.

123. Asinger, F., Schaefer, W., and Triem, H. Concomitant Action of Elementary Sulfur and Gaseous Ammonia on Ketones. LVII. Action of Sulfur and Ammonia on Propiophenone, Butyrophenone, and Isobutyrophenone. Monatsh. Chem., 1966, 97, 1510-1522.

124. Truce, W. E., and Knospe, R. H. The Preparation of β-Oxo Sulfones by the Claisen Condensation. J. Am. Chem. Soc., 1955, 77, 5063-5067.

125. Murai, S., Kuroki, Y., Hasegawa, K., and Tsutsumi, S. Silyl Alkenyl Ethers as the Synthetic Equivalent of Enols. New Syntheses of β-Keto-sulphides and 1,3-Diketones. Chem. Commun., 1972, 946-947.

126. Kuehen, M. E. Reaction of Enamines with Electrophilic Sulfur Compounds. J. Org. Chem., 1963, 28, 2124-2128.

127. Burch, R. M., Patch, R. J., Shearer, B. G., Perumattam, J. J., and Natalie, K. J., Jr. Preparation of N-Piperidinylmethyl- and N-(Pyrrolidinylmethyl)amino Acid Amides as Protein Kinase C Inhibitors. In WO 9203415, 1992, Nova Pharmaceutical Corp., USA: U.S.A.

128. Brown, H. C., and Heim, P. Diborane as a Mild Reducing Agent for the Conversion of Primary, Secondary, and Tertiary Amides into the Corresponding Amines. J. Am. Chem. Soc., 1964, 86, 3566-3567.

129. Curran, W. V., and Angier, R. B. Selective Borane Reduction of a Trifluoroacetamide Substituent in the Presence of a Carbamate. J. Org. Chem., 1966, 31, 3867-3868.

130. Domling, A., and Ugi, I. Multicomponent Reactions with Isocyanides. Angew. Chem. Int. Ed., 2000, 39, 3168-3210.

131. Zhu, J. Recent Development of the Isonitrile-Based Multicomponent Synthesis of Heterocycles. Eur. J. Org. Chem., 2003, 1133-1144.

132. Kleinmnann, E. F. In Comprehensive Organic Synthesis, Volume 2, B. M. Trost, ed., 1991, (New York: Pergamon Press), Chapter 4.1.

133. List, B. The Direct Catalytic Asymmetric Three-Component Mannich Reaction. J. Am. Chem. Soc., 2000, 122, 9336-9337.

134. List, B., Pojarliev, P., Biller, W. T., and Martin, H. J. The Proline-Catalyzed Direct Asymmetric Three-Component Mannich Reaction: Scope, Optimization, and Application to the Highly Enantioselective Synthesis of 1,2-Amino Alcohols. J. Am. Chem. Soc., 2002, 124, 827-833.

135. Hayashi, Y., Tsuboi, W., Shoji, M., and Suzuki, N. Application of High Pressure Induced by Water-Freezing to the Direct Catalytic Asymmetric Three-Component List-Barbas-Mannich Reaction. J. Am. Chem. Soc., 2003, 125, 11208-11209.

136. Hayashi, Y., Tsuboi, W., Ashimine, I., Urushima, T., Shoji, M., and Sakai, K. The Direct and Enantioselective, One-Pot, Three-Component, Cross-Mannich Reaction of Aldehydes. Angew. Chem., Int. Ed., 2003, 42, 3677-3680.

137. List, B., Pojarliev, P., and Castello, C. Proline-Catalyzed Asymmetric Aldol Reactions between Ketones and α,β-Unsaturated Aldehydes. Org. Lett. 2001, 3, 573-575.

138. Pidathala, D., Hoang, L., Vignola, N., and List, B. Direct Catalytic Asymmetric Enolexo Aldolizations. Angew. Chem. Int. Ed., 2003, 42, 2785-2788.

139. Northrup, A. B., and MacMillan, D. W. C. The First Direct and Enantioselective Cross-Aldol Reaction of Aldehydes. J. Am. Chem. Soc., 2002, 124, 6798-6799.

140. Northrup, A. B., Mangion, I. K., Hettche, F., and MacMillan, D. W. C. Enantioselective Organocatalytic Direct Aldol Reactions of α-Oxyaldehydes: Step One in a Two-Step Synthesis of Carbonydrates. Angew. Chem. Int. Ed., 2004, 43, 2152-22154.

141. Thayumanavan, R., Tanaka, F., and Barbas, C. F., III Direct Organocatalytic Asymmetric Aldol Reactions of α-Amino Aldehydes: Expedient Synthesis of Highly Enantiomerically Enriched anti-β-Hydroxy-α-amino Acids. Org. Lett., 2004, 6, 3541-3544.

142. Pan, Q., Zou, B., Wang, Y., and Ma, D. Diastereoselective Aldol Reaction of N,N-Dibenzyl-α-amino Aldehydes with Ketones Catalyzed by Proline. Org. Lett., 2004, 6, 1009-1012.

143. Zhong, G., Fan, J., and Barbas, C. F., III Amino Alcohol Catalyzed Direct Asymmetric Aldol Reactions: Enantioselective Synthesis of Anti-α-fluoro-β-hydroxy Ketones. Tetrahedron Lett., 2004, 45, 5681-5684.

144. Tang, Z., Jiang, F., Cui, X., Gong, L.-Z., Mi, A.-Q., Jiang, Y.-Z., and Wu, Y.-D. Enantioselective Direct Aldol Reactions Catalyzed by L-Prolinamide Derivatives. Proc. Natl. Acad. Sci. USA, 2004, 101, 5755-5760.

145. Tang, Z., Yang, Z.-H., Cun, L.-F., Gong, L., Mi, A.-Q., and Jiang, Y.-Z. Small Peptides Catalyze Highly Enantioselective Direct Aldol Reactions of Aldehydes with Hydroxyacetone: Unprecedented Regiocontrol in Aqueous Media. Org. Lett., 2004, 6, 2285-2287.

146. Saito, S., Nakadai, M., and Yamamoto, H. Diamine-Protonic Acid Catalysts for Catalytic Asymmetric Aldol Reaction. Synlett, 2001, 1245-1248.

147. Pulici, M., Cervi, G., Martina, K., and Quartieri, F. Use of Multicomponent, Domino, and Other One-pot Syntheses on Solid Phase: Powerful Tools for the Generation of Libraries of Diverse and Complex Compounds. Combinatorial Chemistry and High Throughput Screening, 2003, 6, 693-727.

148. Tietze, L. F., and Modi, A. Multicomponent Domino Reactions for the Synthesis of Biologically Active Natural Products and Drugs. Med. Res. Rev., 2000, 20, 304-322.

149. Tietze, L. F. Domino Reactions in Organic Synthesis. Chem. Rev., 1996, 96, 115-136.

150. Carreira, E. M. Mukaiyama Aldol Reaction. In Comprehensive Asymmetric Catalysis, Volume III, E. N. Jacobsen, A. Pfaltz and H. Yamamoto, eds., 1999, (Berlin, Germany: Springer-Verlag), pp. 997-1165.

151. Mukaiyama, T. The Directed Aldol Reaction. Org. Rea., 1982, 28, 203-331.

152. Mukaiyama, T., Narasaka, K., and Banno, K. New Aldol Type Reaction. Chem. Lett., 1973, 9, 1011-1014.

153. Mukaiyama, T., Banno, K., and Narasaka, K. New Cross-Aldol Reactions. Reactions of Silyl Enol Ethers with Carbonyl Compounds Activated by Titanium Tetrachloride. J. Am. Chem. Soc., 1974, 96, 7503-7509.

154. Evans, D. A., Tedrow, J. S., Shaw, J. T., and Downey, C. W. Diastereoselective Magnesium Halide-Catalyzed anti-Aldol Reactions of Chiral N-Acyloxazolidinones. J. Am. Chem. Soc., 2002, 124, 392-393.

155. Evans, D. A., and McGee, L. R. Aldol Diastereoselection Zirconium Enolates. Product-selective, Enolate Structure Independent Condensations. Tetrahedron Lett., 1980, 21, 3975-3978.

156. Yamamoto, Y., and Maruyama, K. Zirconium Enolate as a New Erythro-Selective Aldol Condensation Reagent. Tetrahedron Lett., 1980, 21, 4607-4610.

157. Esch, P. M., Boska, I. M., Hiemstra, H., De Boer, R. F., and Speckamp, W. N. Tin tetrachloride-Induced n-Cyclizations of Glycine Cation Equivalents to Substituted Pipecolic Acid Derivatives. Tetrahedron, 1991, 47, 4039-4062.

158. Storer, R. I., and MacMillan, D. W. C. Enantioselective Organocatalytic Aldehyde-Aldehyde Cross-Aldol Couplings. The Broad Utility of α-Thioacetal Aldehydes. Tetrahedron, 2004, 60, 7705-7714.

159. Hechavarria Fonseca, M. T., and List, B. Catalytic Asymmetric Intramolecular Michael Reaction of Aldehydes. Angew. Chem. Int. Ed., 2004, 43, 3958-3960.

160. Gibson, S. E., Jones, J. O., McCague, R., Tozer, M. J., and Whitcombe, N. J. A Bromoarene Based Approach to Phenylalanine Analogues Hic and Nic. Synlett S1, 1999, 954-956.

161. Hartman, G. D., Phillips, B. T., and Halczenko, W. Iminium Ion Mediated Cyclizations of 4-Aryl-1,4-dihydropyridines. Bridging with Acetals, Carbonyls, and Thiocarbonyls. J. Org. Chem., 1985, 50, 2423-2427.

162. Barnes, D. M., Ji, J., Fickes, M. G., Fitzgerald, M. A., King, S. A., Morton, H. E., Plagge, F. A., Preskill, M., Wagaw, S. H., Wittenberger, S. J., and Zhang, J. Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram. J. Am. Chem. Soc., 2002, 124, 13097-13105.

163. Bauduin, G., Bondon, D., Pietrasanta, Y., and Pucci, B. Transketalization Reactions. II. Influence of Steric and Electronic Factors on Ketalization Energies. Tetrahedron, 1978, 34, 3269-3274.

164. Mackenzie, A. R., Moody, C. J., and Rees, C. W. Synthesis of the Bacterial Coenzyme Methoxatin. Tetrahedron, 1986, 42, 3259-3268.

165. Aslanian, R., Lee, G., Iyer, R. V., Shih, N.-Y., Piwinski, J. J., Draper, R. W., and McPhail, A. T. An Asymmetric Synthesis of the Novel $H_3$ Agonist (+)-(3R,4R)-3-(4-Imidazolyl)-4-methylpyrrolidine Dihydrochloride (Sch 50971). Tetrahedron: Asymmetry, 2000, 11, 3867-3871.

166. McLeod, R. L., Aslanian, R., Del Prado, M., Duffy, R., Egan, R. W., Kreutner, W., McQuade, R., and Hey, J. A. Sch 50971, an Orally Active Histamine $H_3$ Receptor Agonist, Inhibits Central Neurogenic Vascular Inflammation and Produces Sedation in the Guinea Pig. J. Pharmacol. Exp. Ther., 1998, 287, 43-50.

167. Shih, N.-Y., Aslanian, R., Lupo, A. T., Jr., Orlando, S., Piwinski, J. J., Green, M. J., Ganguly, A. K., West, R., Tozzi, S., Kreutner, W., and Hey, J. A. trans-4-Methyl-3-imidazolyl Pyrrolidine as a Potent, Highly Selective Histamine $H_3$ Receptor Agonist in vivo. Bioorg. Med. Chem. Lett., 1998, 8, 243-248.

168. Kotani, H., Takahashi, K., and Suwa, H. Use of Histamine Receptor $H_3$ and Gene Knockout Mouse for Drug Screening, Diagnosis, and Therapy of Diseases Associated with Body Weight or Food Intake Regulation. In WO 2003004637, 2003, pp. 73, Banyu Pharmaceutical Co., Ltd., Japan: Japan.

169. De Esch, I. J. P., Timmerman, H., Menge, W. M. P. B., and Nederkoorn, P. H. J. A Qualitative Model for the Histamine $H_3$ Receptor Explaining Agonistic and Antagonistic Activity Simultaneously. Archiv der Pharmazie, 2000, 333, 254-260.

170. Wang, W., Xiong, C., and Hruby, V. J. An Efficient Approach to Asymmetric Synthesis of Dipeptide β-Turn Mimetics: Indolizidinone Amino Acids. Tetrahedron Lett., 2001, 42, 3159-3161.
171. Bowery, N. G., Hudson, A. L., and Price, G. W. $GABA_A$ and $GABA_B$ Receptor Site Distribution in the Rat Central Nervous System. Neuroscience, 1987, 20, 365-383.
172. Hill, D. R., and Bowery, N. G. $^3$H-Baclofen and $^3$H-GABA Bind to Bicuculline-Insensitive $GABA_B$ Sites in Rat Brain. Nature (London), 1981, 290, 149-152.
173. Bowery, N. G., Hill, D. R., and Hudson, A. L. [$^3$H](–)Baclofen: An Improved Ligand for $GABA_B$ Sites. Neuropharmacology, 1985, 24, 207-210.
174. Shuto, S., Shibuty, N., Yamada, S., Ohkura, T., Kimura, R., and Matsuda, A. Synthesis of Conformationally Restricted Analogs of Baclofen, a Potent $GABA_B$ Receptor Agonist, by the Introduction of a Cyclopropane Ring. Chem. Pharm. Bull., 1999, 47, 1188-1192.
175. Hale, J. J., Budhu, R. J., Mills, S. G., MacCoss, M., Malkowitz, L., Siciliano, S., Gould, S. L., DeMartino, J. A., and Springer, M. S. 1,3,4-Trisubstitued Pyirolidine CCR Receptor Antagonists. Part 1: Discovery of the Pyrrolidine Scaffold and Determination of its Stereochemical Requirements. Bioorg. Med. Chem. Lett., 2001, 11, 1437-1440.
176. Hale, J. J., Lynch, C. L., Caldwell, C. G., Willoughby, C. A., Kim, D., Shen, D.-M., Mills, S. G., Chapman, K. T., Chen, L., Gentry, A., and MacCoss, M. Preparation of Pyrrolidine Modulators of CCR5 Chemokine Receptor Activity. In WO 2002034716, 2002, pp. 203, Merck & Co., Inc., USA: USA.
177. Hale, J. J., Lynch, C. L., Caldwell, C. G., Willoughby, C. A., Kim, D., Shen, D.-M., Mills, S. G., Chapman, K. T., Chen, L., Gentry, A., Maccoss, M., and Konteatis, Z. D. (2002). Preparation of Substituted Pyrrolidines as Modulators of CCR5 Chemokine Receptor Activity. In US 2002094989, 2002, USA.
178. Lynch, C. L., Hale, J. J., Budhu, R. J., Gentry, A. J., Finke, P. E., Caldwell, C. G., Mills, S. G., MacCoss, M., Shen, D.-M., Chapman, K. T., Malkowitz, L., Springer, M. S., Gould, S. L., DeMartino, J. A., Siciliano, S. J., Cascieri, M. A., Carella, A., Carver, G., Holmes, K., Schaefer, W., Danzeisen, R., Hazuda, D., Kessler, J., Lineberger, J., Miller, M., and Emini, E. CCR5 Antagonist: 3-(Pyrrolidin-1yl)propionic Acid Analogues with Potent Anti-HIV Activity. Org. Lett., 2003, 5, 2473-2475.
179. Bolnot-Delmas, D., Buch, J. P., Zeidler, H., and Dougados, M. Ro 15-8081 in Osteoarthritis of Hip and Knee: A Double-Blind Placebo-Controlled Multicentre Dose-Ranging Study on Analgesia. Pain, 1996, 64, 99-105.
180. Stacher, G., Steinringer, H., Schneider, S., Mittelbach, G., Gaupmann, G., Abatzi, T. A., and Stacher-Janotta, G. Effects of Graded Oral Doses of a New 5-Hydroxytryptamine/Noradrenaline Uptake Inhibitor (Ro 15-8081) in Comparison with 60 mg Codeine and Placebo on Experimentally Induced Pain and Side Effect Profile in Healthy Men. British J. Clinic. Pharmaco., 1987, 24, 627-635.
181. Bemauer, K., and Bruderer, H. Phenylethylamine Derivatives. In EP 138030, 1985, pp. 61, Hoffman-La Roche, F., und Co. A.-G., Switz.: Switzerland.
182. Bos, M., Bukrard, W. P., Moreau, J. L., and Schonholzer, P. 97. Synthesis of Rel-(3RS, 3aSR, 7aSR)-3-(4-Chlorophenyl)-3a,4,5,6,7,7a-hexahydro-1-methylindolin-6-one, the Main Metabolite of the Analgesic Ro 15-8081: A Potent Amine-Uptake Inhibitor. Helvetica Chimica Acta, 1990, 73, 932-939.
183. Dubuffet, T., Newman-Tancredi, A., Cussac, D., Audinot, V., Loutz, A., Millan, M. J., and Lavielle, G. Novel Benzopyrano[3,4-c]pyrrole Derivatives as Potent and Selective Dopamine $D_3$ Receptor Antagonists. Bioorg. Med. Chem. Lett., 1999, 9, 2059-2064.
184. Meyer, M. D., Altenbach, R. J., Basha, F., Carroll, W. A., Drizin, I., Kerwin, J. F., Wendt, M. D., Haight, A. R., and Zhang, W. Preparation of Benzopyranopyrrole and Benzopyranopyridine as alpha-1 Adrenergic Antagonists. In WO 9824791, 1998, pp. 179, Abbott Laboratories, USA: USA.
185. Meyer, M. D., Altenbach, R. J., Basha, F. Z., Carroll, W. A., Drizin, I., Kerwin, J. F., Jr., Wendt, M. D., Haight, A. R., and Zhang, W. Preparation of Benzopyranopyrrolylalkylpyridothienopyrimidine-diones and Related Compounds as α1 Adrenergic Antagonists. In U.S. Pat. No. 6,046,207, 2000, pp. 59: USA.
186. La Vielle, G., Dubuffet, T., Muller, O., Millan, M., Dekeyne, A., and Brocco, M. Preparation of Pyrimidin-4-one Derivatives, their Pharmaceutical Compositions and Use as α2/5-HT2c Double Antagonists. In FR 2823752, 2002, pp. 33, Les Laboratoires Servier, Fr.: France.
187. Luci, D. K., Santulli, R. J., Gauthier, D. A., Tounge, B. A., Ghosh, S., Proost, J. C., Kinney, W. A., De Corte, B., Galemmo, R. A., Jr., Lewis, J. M., Dorsch, W. E., Wagaman, M. W., Damiano, B. P., and Maryanoff, B. E. A Concise Synthesis of an Indenopyrrolidine-Based Dual $α_vβ_3/α_vβ5$ integrin Antagonist. Heterocycles, 2004, 62, 543-557.
188. Etcheberrigaray, R., Qiao, L., Kozikowski, A., and Zhao, L. Preparation of Hydroxymethylazacyclopentindenones as Selective Protein Kinase C Modulators. In WO 2001083449, 2001, pp. 58, Georgetown University, USA: USA.
189. Martin, S. F. In The Alkaloids, Volume 30, A. Brossi, ed., 1987, (San Diego, Calif.: Academic Press), pp. 251-376.
190. Lewis, J. R. Amaryllidaceae and Sceletium Alkaloids. Nat. Prod. Rep., 1993, 10, 291-299.
191. Lewis, J. R. Amaryllidaceae and Sceletium Alkaloids. Nat. Prod. Rep., 1994, 11, 329-332.
192. Zhong, J. Amaryllidaceae and Sceletium Alkaloids. Nat. Prod. Rep., 2003, 20, 606-614.
193. Ishizaki, M., Hoshino, O., and Litaka, Y. A First Total Synthesis of Montanine-type Amaryllidaceae Alkaloids, (±)-Coccinine, (±)-Montanine, and (±)-Pancracine. Tetrahedron Lett., 1991, 32, 7079-7082.
194. Ishizaki, M., Hoshino, O., and Litaka, Y. Total Synthesis of Montanine-type Amaryllidaceae Alkaloids, Which Possess a 5,11-Methanomorphanthridine Ring System, through Cyclization with Sodium Bis(2-methoxyethoxy)aluminum hydride (SMEAH): The First Stereoselective Total Syntheses of (±)-Montanine, (±)-Coccinine, (±)—O-Acetylmontanine, (±)-Pancracine, and (±)-Brunsvigine. J. Org. Chem., 1992, 57, 7285-7295.
195. Ishizaki, M., Kurihara, K., Tanazawa, E., and Hoshino, O. Radical-mediated Synthesis of the 5,11-Methanomorphanthridine Ring System: Formal Total Synthesis of Montanine-type Amaryllidaceae Alkaloids, (±)-Montanine, (±)-Coccinine and (±)-Pancracine. J. Chem. Soc., Perkin Trans. 1, 1993, 101-110.
196. Ishizaki, M., Kurihara, K., Tanazawa, E., and Hoshino, O. Radical-mediated Synthesis of the 5,11-Methanomorphanthridine Ring System: Formal Total Synthesis of Montanine-type Amaryllidaceae Alkaloids, (±)-Montanine, (±)-Coccinine and (±)-Pancracine. J. Chem. Soc., Perkin Trans. 1, 1995, 101-110.

197. Overman, L. E., and Shim, J. Synthesis Applications of Cationic Aza-Cope Rearrangements. 23. First Total Synthesis of Amaryllidaceae Alkaloids of the 5,11-Methano Morphanthridine Type. An Efficient Total Synthesis of (i)-Pancracine. J. Org. Chem., 1991, 56, 5005-5007.

198. Overman, L. E., and Shim, J. Total Synthesis of Amaryllidaceae Alkaloids of the 5,11-Methanomorphanthridine Type. Efficient Total Syntheses of (−)-Pancracine and (±)-Pancracine. J. Org. Chem., 1993, 58, 4662-4672.

199. Jin, J., and Weinreb, S. M. Application of a Stereospecific Intramolecular Allenylsilane Imino Ene Reaction to Enantioselective Total Synthesis of the 5,11-Methanomorphanthridine Class of Amaryllidaceae Alkaloids. J. Am. Chem. Soc., 1997, 119, 5773-5784.

200. Pearson, W. H., and Lian, B. W. Application of the Azaallyl Anion Cycloaddition Method to an Enantioselective Total Synthesis of (+)-Coccinine. Angew. Chem. Int. Ed., 1998, 37, 1724-1726.

201. Sha, C.-K., Hong, A.-W., and Huang, C.-M. Synthesis of Aza Bicyclic Enones via Anionic Cyclization: Application to the Total Synthesis of (−)-Brunsvigine. Org. Lett., 2001, 3, 2177-2179.

202. Ikeda, M., Hamada, M., Yamashita, T., Ikegami, F., Sato, T., and Ishibashi, H. Formal Synthesis of (±)-Pancracine Using Stereoselective Radical Cyclization of N-(2-Cyclohexenyl)-α-aryl-α-(phenylthio)acetamide. Synlett, 1998, 1246-1248.

203. Ikeda, M., Hamada, M., Yamashita, T., Matsui, K., Sato, T., and Ishibashi, H. Stereoselective Synthesis of (3R*, 3aS*, 7aS*)-3-aryloctahydroindol-2-ones Using Radical Cyclization: A Formal Synthesis of (±)-Pancracine. J. Chem. Soc., Perkin Trans. 1, 1999, 1949-1956.

204. Zhang, D., and Miller, M. J. Polyoxins and Nikkomycins: Progress in Synthetic and Biological Studies. Curr. Pharm. Design, 1999, 5, 73-99.

205. Behr, J.-B. Chitin Synthase as an Antifungal Target: Recent Advances. Current Medicinal Chemistry: Anti-Infective Agents, 2003, 2, 173-189.

206. Ruiz-Herrera, J., and San-Blas, G. Chitin Synthesis as a Target for Antifungal Drugs. Current Drug Targets: Infectious Disorders, 2003, 3, 77-91.

207. Ghosh, A. K., and Wang, Y. Total Synthesis of (+)-Polyoxin J. J. Org. Chem., 1999, 64, 2789-2795.

208. Dondoni, A., Franco, S., Junquera, F., Merchan, F. L., Merino, P., and Tejero, T. Applications of Sugar Nitrones in Synthesis: The Total Synthesis of (+)-Polyoxin J. J. Org. Chem., 1997, 62, 5497-5507.

209. Dondoni, A., Junquera, F., Merchan, F. L., Merino, P., and Tejero, T. Total Synthesis of (+)-Polyoxin J. Chem. Commun., 1995, 2127-2128.

210. Tarrade, A., Dauban, P., and Dodd, R. H. Enantiospecific Total Synthesis of (−)-Polyoxamic Acid Using 2,3-Aziridino-γ-lactone Methodology. J. Org. Chem., 2003, 68, 9521-9524.

211. Raghavan, S., and Joseph, S. C. The Sulfinyl Moiety as an Internal Nucleophile. Part 8: Efficient, Stereospecific Synthesis of (+)-Polyoxamic Acid. Tetrahedron Lett., 2003, 44, 6713-6715.

212. Davis, F. A., Prasad, K. R., and Carroll, P. J. Asymmetric Synthesis of Polyhydroxy α-Amino Acids with the Sulfinimine-Mediated Asymmetric Strecker Reaction: 2-Amino 2-Deoxy L-Xylono-1,5-lactone (Polyoxamic Acid Lactone). J. Org. Chem., 2002, 67, 7802-7806.

213. Kim, K. S., Lee, Y. J., Kim, J. H., and Sung, D. K. Synthesis of (+)-Polyoxamic Acid and D-Sorbitol from Simple Achiral Allylic Halides Employing (S, S)-Hydrobenzoin as a Chiral Source. Chem. Commun., 2002, 1116-1117.

214. Pepper, A. G., Procter, G., and Voyle, M. Stereoselective Cycloadditions of Chiral Acyl-nitroso Compounds; Selective Reactions of Ring-Cleaved Cycloadducts Leading to a New Approach to Polyoxamic Acid. Chem. Commun., 2002, 1066-1067.

215. Harwood, L. M., and Robertson, S. M. Double Diastereocontrol in the Synthesis of Enantiomerically Pure Polyoxamic Acid. Chem. Commun., 1998, 2641-2642.

216. Kang, S. H., and Choi, H. Asymmetric Amidation of (2S, 3S)-pent-4-ene-1,2,3-triol. Total Syntheses of (−)-Anisomycin and (+)-Polyoxamic acid. Chem. Commun., 1996, 1521-1522.

217. Trost, B. M., Krueger, A., Bunt, R. C., and Zambrano, J. On the Question of Asymmetric Induction with Acyclic Allylic Substrates. An Asymmetric Synthesis of (+)-Polyoxamic Acid. J. Am. Chem. Soc., 1996, 118, 6520-6521.

218. Banik, B. K., Manhas, M. S., and Bose, A. K. Studies on Lactams. 89. Versatile β-Lactam Synthons: Enantiospecific Synthesis of (−)-Polyoxamic Acid. J. Org. Chem., 1993, 58, 307-309.

219. Porter, J. R., Traverse, J. F., Hoveyda, A. H., and Snapper, M. L. Three-Component Catalytic Asymmetric Synthesis of Aliphatic Amines. J. Am. Chem. Soc., 2001, 123, 10409-10410.

220. Zennie, T. M., Cassady, J. M., and Raffauf, R. F. Funebral, a New Pyrrole Lactone Alkaloid from Quararibea Funebris. S. Nat. Prod., 1986, 49, 695-698.

221. Tamura, O., Iyama, N., and Ishibashi, H. Synthesis of (−)-Funebrine and (−)-Funebral, Using Sequential Transesterification and Intramolecular Cycloaddition of a Chiral Nitrone. J. Org. Chem., 2004, 69, 1475-1480.

222. Dong, Y., Pai, N. N., Ablaza, S. L., Yu, S.-X., Bolvig, S., Forsyth, D. A., and Le Quesne, P. W. Quararibea Metabolites. 4. Total Synthesis and Conformational Studies of (±)-Funebrine and (±)-Funebral. J. Org. Chem., 1999, 64, 2657-2666.

223. Yu, S.-X., and Le Quesne, P. W. Quararibea Metabolites. 3. Total Synthesis of (±)-Funebral, a Rotationally Restricted Pyrrole Alkaloid, Using a Novel Paal-Knorr Reaction. Tetrahedron Lett., 1995, 36, 6205-6208.

224. Dirat, O., Kouklovsky, C., and Langlois, Y. Oxazoline N-Oxide-Mediated [2+3] Cycloadditions. Application to a Synthesis of (−)-Tetrahydrolipstatin. Org. Lett., 1999, 1, 753-755.

225. Asano, N., Nash, R. J., Molyneux, R. J., and Fleet, G. W. J. Sugar-mimic Glycosidase Inhibitors: Natural Occurrence, Biological Activity and Prospects for Therapeutic Application. Tetrahedron: Asymmetry, 2000, 11, 1645-1680.

226. Somsak, L., Nagy, V., Hadady, Z., Docsa, T., and Gergely, P. Glucose Analog Inhibitors of Glycogen Phosphorylases as Potential Antidiabetic Agents: Recent Developments. Curr. Pharm. Design, 2003, 9, 1177-1189.

227. Ganem, B. Inhibitors of Carbohydrate-Processing Enzymes: Design and Synthesis of Sugar-Shaped Heterocycles. Acc. Chem. Res., 1996, 29, 340-347.

228. Butters, T. D., Dwek, R. A., and Platt, F. M. Inhibition of Glycosphingolipid Biosynthesis: Application to Lysosomal Storage Disorders. Chem. Rev., 2000, 100, 4683-4696.

229. Kato, A., Asano, N., Kizu, H., and Matsui, K. Fagomine Isomers and Glycosides from Xanthocercis Zambesiaca. J. Nat. Prod., 1997, 60, 312-314.

230. Sohoel, H., Liang, X., and Bols, M. Isogalactofagomine Lactam. A Neutral Nanomolar Lalactosidase Inhibitor. J. Chem. Soc., Perkin Trans. 1, 2001, 1584-1585.
231. Ichikawa, Y., and Igarashi, Y. An Extremely Potent Inhibitor for β-Galactosidase. Tetrahedron Lett., 1995, 36, 4585-4586.
232. Takahata, H., Banba, Y., Ouchi, H., and Nemoto, H. Concise and Highly Stereocontrolled Synthesis of 1-Deoxygalactonojirimycin and Its Congeners Using Dioxanylpiperidene, a Promising Chiral Building Block. Org. Lett., 2003, 5, 2527-2529.
233. Takahata, H., Banba, Y., Sasatani, M., Nemoto, H., Kato, A., and Adachi, I. Asymmetric Synthesis of 1-Deoxynojirimycin and Its Congeners from a Common Chiral Building Block. Tetrahedron, 2004, 60, 8199-8205.
234. Ouchi, H., Mihara, Y., Watanabe, H., and Takahata, H. A Short and Concise Synthesis of Isofagomine, Homoisofagomine, and 5'-Deoxyisofagomine. Tetrahedron Lett., 2004, 45, 7053-7056.
235. Wu, C.-Y., Chang, C.-F., Chen, J. S.-Y., Wong, C.-H., and Lin, C.-H. Rapid Diversity-oriented Synthesis in Microtiter Plates for in situ Screening: Discovery of Potent and Selective α-Fucosidase Inhibitors. Angew. Chem. Int. Ed., 2003, 42, 4661-4664.
236. Ruttens, B., and Van der Eycken, J. Solid-phase Synthesis of a New Class of Oligosaccharide Analogues Based on Azasugars. Tetrahedron Lett., 2002, 43, 2215-2221.
237. Liu, H., Liang, X., Sohoel, H., Buelow, A., and Bols, M. Noeuromycin, a Glycosyl Cation Mimic that Strongly Inhibits Glycosidases. J. Am. Chem. Soc., 2001, 123, 5116-5117.
238. Zhao, G., Deo, U. C., and Ganem, B. Selective Fowler Reductions: Asymmetric Total Syntheses of Isofagoinine and Other 1-Azasugars from Methyl Nicotinate. Org. Lett., 2001, 3, 201-203.
239. Schuster, M., and Blechert, S. Facile Approach towards Phosphorylated Azasugars as Potential Glycosyl Phosphate Mimics. Tetrahedron: Asymmetry, 1999, 10, 3139-3145.
240. Polt, R., Sames, D., and Chruma, J. Glycosidase Inhibitors: Synthesis of Enantiomerically Pure Aza-sugars from Schiff Base Amino Esters via Tandem Reduction-alkenylation and Osmylation. J. Org. Chem., 1999, 64, 6147-6158.
241. Northrup, A. B., and MacMillan, D. W. C. Two-step Synthesis of Carbohydrates by Selective Aldol Reactions. Science, 2004, 305, 1752-1755.

The invention claimed is:

1. A compound according to the chemical structure(s):

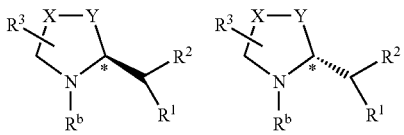

Where X is $CH_2$;
Y is $CH_2$;
$R^b$ is H;
$R^1$ is NHC(=O)R;
$R^2$ is a =O group;
$R^3$ is H or an optionally substituted aryl group;
R is H, an optionally substituted $C_2$-$C_{20}$ alkyl, phenyl group which is optionally substituted with F, Cl or $NO_2$, a p-methylphenyl group, a p-trifluoromethylphenyl group, an optionally substituted 2,6-di($C_1$-$C_4$)alkylphenyl group or an optionally substituted 2,4,6-tri($C_1$-$C_4$) alkylphenyl group where the alkyl groups, if substituted, are $CF_3$ groups,
wherein said compound is free from a metal catalyst.

2. The compound according to claim 1 wherein R is an optionally substituted $C_2$-$C_{12}$ alkyl group, or a phenyl group optionally substituted with F, Cl or $NO_2$.

3. The compound according to claim 1 wherein R is an alkyl group containing at least one electron withdrawing substituent.

4. The compound according to claim 2 wherein R is an alkyl group containing at least one electron withdrawing substituent.

5. The compound according to claim 3 wherein said at least one electron withdrawing substituent is F, Cl or $NO_2$.

6. The compound according to claim 4 wherein said at least one electron withdrawing substituent is F, Cl or $NO_2$.

7. The compound according to claim 4 wherein said alkyl group is a $C_2$-$C_{12}$ alkyl group having at least three electron withdrawing substituents which are F.

8. The compound according to claim 1 wherein R is a phenyl group optionally substituted with F, Cl or $NO_2$.

9. The compound according to claim 1 which is

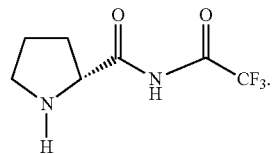

10. The compound according to claim 1 wherein R is a p-methylphenyl group, a p-nitrophenyl group, a p-trifluoromethylphenylgroup, an optionally substituted 2,6-di($C_1$-$C_4$) alkylphenyl group or an optionally substituted 2,4,6-tri($C_1$-$C_4$) alkylphenyl group where the alkyl groups, if substituted, are $CF_3$ groups.

11. A compound according to the chemical structure(s):

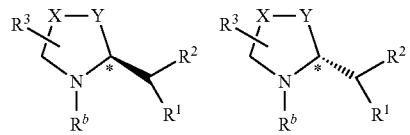

Where X is $CH_2$;
Y is $CH_2$;
$R^b$ is H;
$R^1$ is $NHSO_2R$;
$R^2$ is H or a =O group;
$R^3$ is H or an optionally substituted aryl group;
R is H or an optionally substituted $C_3$-$C_6$ alkyl group
wherein said compound is free from a metal catalyst.

12. The compound according to claim 11 wherein $R^2$ is H.

13. The compound according to claim 11 wherein $R^2$ is =O.

14. The compound according to claim 11 wherein R is an optionally substituted $C_3$-$C_6$ alkyl group.

15. The compound according to claim 14 wherein R is substituted with at least one electron withdrawing substituent.

16. The compound according to claim 15 wherein said at least one electron withdrawing substituent is F, Cl or $NO_2$.

17. The compound according to claim 16 wherein said substituent(s) is F.

18. The compound

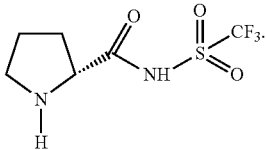

19. The compound

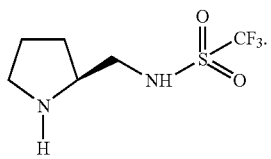

20. The compound

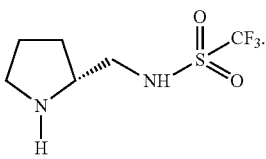

21. A compound according to the chemical structure(s):

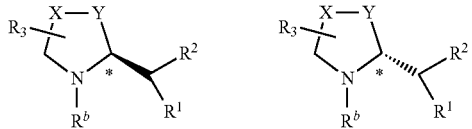

Where X is $CH_2$;
Y is $CH_2$;
$R^b$ is H;
$R^1$ is $NHC(=O)R$;
$R^2$ is H;
$R^3$ is H or an optionally substituted aryl group;
R is H, an optionally substituted $C_2$-$C_{20}$ alkyl group or an aryl group which is substituted with an optionally substituted $C_1$-$C_6$ alkyl, $NO_2$, or CN,
wherein said compound is free from a metal catalyst.

22. The compound according to claim 21 wherein R is a substituted $C_2$-$C_6$ alkyl group.

23. The compound according to claim 22 wherein R which is a p-methylphenyl group, a p-nitrophenyl group, a p-trifluoromethylphenylgroup, an optionally substituted 2,6-di($C_1$-$C_4$) alkylphenyl group or an optionally substituted 2,4,6-tri ($C_1$-$C_4$) alkylphenyl group where the alkyl groups, if substituted, are $CF_3$ groups.

24. A compound according to the chemical structure:

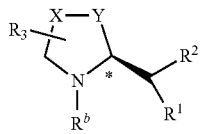 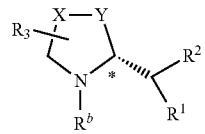

Where X is $CH_2$;
Y is $CH_2$;
$R^b$ is H;
$R^1$ is $NHC(=O)R$;
$R^2$ is H;
$R^3$ is an optionally substituted aryl group; and
R is a substituted methyl group,
wherein said compound is free from a metal catalyst.

25. The compound according to claim 19 wherein R is a trifluoromethyl group.

* * * * *